United States Patent
Makino et al.

(10) Patent No.: US 11,447,743 B2
(45) Date of Patent: Sep. 20, 2022

(54) CELL CULTURE SUBSTRATE COMPRISING FLUORINE-CONTAINING POLYMER ON ITS SURFACE

(71) Applicant: Nippon Shokubai Co., Ltd., Osaka (JP)

(72) Inventors: Tomomi Makino, Suita (JP); Hiroshi Horikawa, Tsukuba (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 15/304,910

(22) PCT Filed: Mar. 17, 2015

(86) PCT No.: PCT/JP2015/057917
§ 371 (c)(1),
(2) Date: Oct. 18, 2016

(87) PCT Pub. No.: WO2015/163043
PCT Pub. Date: Oct. 29, 2015

(65) Prior Publication Data
US 2017/0175078 A1  Jun. 22, 2017

(30) Foreign Application Priority Data

Apr. 22, 2014 (JP) .............. JP2014-088632
Apr. 22, 2014 (JP) .............. JP2014-088634
Apr. 22, 2014 (JP) .............. JP2014-088635
Sep. 5, 2014 (JP) .............. JP2014-181730

(51) Int. Cl.
| | |
|---|---|
| C12N 5/071 | (2010.01) |
| C12N 5/00 | (2006.01) |
| C12M 1/04 | (2006.01) |
| C12M 1/00 | (2006.01) |
| C08G 65/40 | (2006.01) |
| C08G 73/10 | (2006.01) |
| C08J 5/18 | (2006.01) |
| C12M 1/12 | (2006.01) |

(52) U.S. Cl.
CPC ....... *C12N 5/0062* (2013.01); *C08G 65/4043* (2013.01); *C08G 73/105* (2013.01); *C08G 73/1028* (2013.01); *C08G 73/1039* (2013.01); *C08G 73/1071* (2013.01); *C08J 5/18* (2013.01); *C12M 23/20* (2013.01); *C12M 23/24* (2013.01); *C12M 23/26* (2013.01); *C12M 25/02* (2013.01); *C12N 5/0068* (2013.01); *C12N 5/0671* (2013.01); *C08G 73/10* (2013.01); *C08J 2371/10* (2013.01); *C08J 2379/08* (2013.01); *C12N 2513/00* (2013.01); *C12N 2533/30* (2013.01); *C12N 2539/00* (2013.01)

(58) Field of Classification Search
CPC ..... C08G 73/10; C08J 2379/08; C12M 23/24; C12M 23/20; C12N 2539/00; C12N 5/0068
See application file for complete search history.

(56) References Cited

U.S. PATENT DOCUMENTS

| | | | |
|---|---|---|---|
| 3,873,423 A | 3/1975 | Munder et al. | |
| 5,902,747 A | 5/1999 | Nemser et al. | |
| 6,372,808 B1 * | 4/2002 | Kanada | C08J 9/28 521/64 |
| 2004/0125266 A1 | 7/2004 | Miyauchi et al. | |
| 2005/0095699 A1 | 5/2005 | Miyauchi et al. | |
| 2005/0153438 A1 | 7/2005 | Shirasu et al. | |
| 2010/0133192 A1 | 6/2010 | Liu et al. | |
| 2011/0142806 A1 * | 6/2011 | Scott-Carnell | C12N 11/08 424/93.7 |

FOREIGN PATENT DOCUMENTS

| | | |
|---|---|---|
| EP | 0890636 | 1/1999 |
| EP | 1988152 | 11/2008 |
| JP | 63-198972 | 8/1988 |
| JP | 1128083 | 2/1999 |
| JP | 2005218444 | 8/2005 |
| JP | 3761676 | 3/2006 |
| JP | 4159103 | 10/2008 |
| JP | 2009-213716 | * 9/2009 |
| JP | 2009213716 | 9/2009 |

(Continued)

OTHER PUBLICATIONS

Maenosono et al A Transparent Polyimide Film as a Biological Cell Culture Sheet with Microstructures, Journal of Biomaterials and Nanobiotechnology, 2014, 5, 17-23, Published Online on Jan. 2014.*

(Continued)

*Primary Examiner* — Gregory Listvoyb
(74) *Attorney, Agent, or Firm* — McCarter & English, LLP

(57) ABSTRACT

This invention provides a cell culture substrate comprising on its surface a fluorine-containing polymer that enables three-dimensional tissue culture. The cell culture substrate of the invention has a surface at least a part of which is composed of a resin composition comprising a fluorine-containing polymer having one or more fluorine atoms in a repeating unit and exhibits the oxygen gas permeability of 219 cm$^3$ (STP)/(m$^2$·24 h·atm) or higher. Three-dimensional tissue can be formed via cell culture with the use of the cell culture substrate of the invention.

13 Claims, 24 Drawing Sheets
(11 of 24 Drawing Sheet(s) Filed in Color)

(56) References Cited

FOREIGN PATENT DOCUMENTS

| | | |
|---|---|---|
| JP | 4897192 | 3/2012 |
| JP | 2012-521872 | 9/2012 |
| JP | 2014-030405 | 2/2014 |
| JP | 2014083783 | 5/2014 |
| JP | 2014210404 | 11/2014 |
| JP | 2015017232 | 1/2015 |
| WO | 2010/110994 | 9/2010 |
| WO | 2012/170878 | 12/2012 |
| WO | 2014/209701 | 12/2014 |

OTHER PUBLICATIONS

Nica et al Surface Properties and Blood Compatibility of Some Aliphatic/Aromatic Polyimide Blends, Polymer Engineering and Science, 2012, 10, 1-10, published on Oct. 2012.*

Richardson et al "Polyimides as biomaterials: preliminary biocompatibility testing", Biomaterials 1993, pp. 627-635, vol. 14 No. 6, published on Aug. 1993.*

Prichard et al Adult adipose-derived stem cell attachment to biomaterials, Biomaterials 28 (2007) 936-946, Available online Oct. 30, 2006.*

Supplementary European Search Report based on co-pending European Application No. 15782430.1, dated Feb. 13, 2018—5 Pages.

Avgoustiniatos, E.S., et al., "Commerially Available Gas-Permeable Cell Culture Bags May Not Prevent Anoxia in Cultured or Shipped Islets", Transplantation Proceedings, 2008, vol. 40, pp. 395-400.

Japanese Office Action dated Nov. 20, 2018, pertaining to co-pending Japanese Application No. 2015-053562, 4 Pages.

Japanese Office Action relating to co-pending Japanese Patent Application No. 2015-053557, dated Jan. 8, 2019—3 Pages.

Matsumoto, Norihiro, et al., "Cell Processing on Polyimide Surface Patterned by Rubbing", Polymers for Advanced Technologies, 2008, vol. 19, pp. 1002-1008.

Niwa, M., et al., "Fabrication of an Asymmetric Polyimide Hollow Fiber with a Defect-Free Surface Skin Layer", Journal of Membrane Science, 2000, vol. 171, pp. 253-261.

Niwa, M., et al., "Gas Separation of Asymmetric 6FDA Polyimide Membrane with Oriented Surface Skin Layer", Macromolecules, 2001, vol. 34, pp. 9039-9044.

International Search Report based on International Application No. PCT/JP2015/067917, dated Jun. 9, 2015—2 Pages.

\* cited by examiner (a)

(b)

(c)

(A)

24-well multiwell cell culture plate (B)

6FDA/TPEQ membrane (C)

Petri dish for suspension cell culture (Nunc)

(D)

24-well plate with ultra-low attachment surface (Corning)

(A) 24-well multiwell cell culture plate (BD Falcon)

(B) Thermally imidized 6FDA/6FAP membrane (A) 24-well multiwell cell culture plate (BD Falcon)

(B) 6FDA/TFMB (C) High-binding 24-well plate with MS pattern (SCIVAX)

(A) Cadherin (B) Actin (C) Cadherin+Actin (A)

(B)

(C)

(A)

(B)

(C)

CELL CULTURE SUBSTRATE COMPRISING FLUORINE-CONTAINING POLYMER ON ITS SURFACE

RELATED APPLICATIONS

This application is a national stage application filed under 35 USC § 371 of PCT/JP2015/057917, filed Mar. 17, 2015, which claims the benefit of Japanese Patent Application No. 2014-088632, filed Apr. 22, 2014, Japanese Patent Application No. 2014-088634, filed Apr. 22, 2014, Japanese Patent Application No. 2014-088635, filed Apr. 22, 2014, and Japanese Patent Application No. 2014-181730, filed Sep. 5, 2014, all of which are incorporated herein, in entirety, by reference.

TECHNICAL FIELD

The present invention relates to a cell culture substrate, a cell culture vessel comprising such substrate, a method of cell culture using such substrate, and a method of formation of three-dimensional tissue from a cell using such substrate.

BACKGROUND ART

Cells constituting organs such as the liver, the pancreas, the skin, and the blood vessels form three-dimensional networks and function in vivo.

In the field of regenerative medicine aimed at restoration of functions of such organs, accordingly, it is necessary that cells constituting such organs be cultured in a manner such that cells can form a three-dimensional network (i.e., three-dimensional culture). The minimal tissue formed by the three-dimensional network of cells is a spheroid. When cells are to be cultured on the surface of a common resin-made cell culture substrate, however, cells spread and grow in planar direction. That is, a three-dimensional network is not formed.

A variety of substrates for three-dimensional culture have heretofore been developed.

For example, Patent Document 1 discloses a cell culture sheet comprising a substrate made of a thermoplastic organic polymer with columnar fine projections that extend from the substrate, which is used for culture by allowing cells to adhere to the columnar fine projections. Also, Patent Document 2 discloses a cell culture construct having a concave-convex structure and serving as a cell-adhering surface, which is composed of a plurality of unit structures each formed in a polygonal shape in a planar direction and having a minimum internal diameter of less than or equal to 3 μm.

Non-Patent Document 1 is focused on excellent biocompatibility of a fluorine-containing polyimide, and it discloses the following. That is, cell culture is conducted on the surface of the 6FDA-6FAP membrane, which is a type of fluorine-containing polyimide, cells two-dimensionally grow on the 6FDA-6FAP membrane with a flat surface, and a spheroid is not formed. When fine irregularities are provided on the surface via rubbing, however, a spheroid is formed. The term "6FDA-6FAP" used therein refers to a polyimide formed via polymerization of an acid dianhydride (i.e., 2,2'-bis(3,4-dicarboxyphenyl)hexafluoropropane dianhydride (6FDA)) and a diamine compound (i.e., 2,2'-bis(4-aminophenyl)hexafluoropropane (6FAP)). The authors of Non-Patent Document 1 disclose in Patent Document 3 the technique described below. That is, vascular endothelial cells are two-dimensionally cultured on a flat 6FDA-6FAP membrane that has not been subjected to rubbing, the cultured cells are transferred onto a gel to form vascular tissue, liver cancer cells are three-dimensionally cultured on a 6FDA-6FAP membrane with an irregular surface that has been subjected to rubbing to form a spheroid, and the resulting vascular tissue is then combined with the resulting spheroid.

Patent Documents 4 to 6 each disclose a fluorine-containing polyimide used for forming a structure with an irregular configuration and a film and a membrane obtained from a resin composition comprising a fluorine-containing polyimide.

Patent Document 7 discloses a technique of preparing a cell culture vessel comprising a gas permeable plastic material. Patent Document 7 is intended to provide a cell culture vessel that does not require an oxygen supply apparatus.

PRIOR ART DOCUMENTS

Patent Documents

Patent Document 1: JP Patent No. 4,897,192
Patent Document 2: JP Patent No. 4,159,103
Patent Document 3: JP 2009-213,716 A
Patent Document 4: JP 2014-83,783 A
Patent Document 5: JP 2014-210,404 A
Patent Document 6: JP 2015-17,232 A
Patent Document 7: JP Patent No. 3,761,676

Non-Patent Documents

Non-Patent Document 1: N. Matsumoto et al., Polymers for Advanced Technologies, 19, 1002, 2008

SUMMARY OF THE INVENTION

Problems to be Solved by the Invention

Cell culture substrates for three-dimensional culture disclosed in Patent Documents 1 and 2 have fine irregularities on their surfaces and thus are capable of three-dimensional culture. Such substrates are problematic in terms of process cost, because it was not easy to provide fine irregularities. When cell culture is to be performed on a substrate surface with fine irregularities, air bubbles are likely to remain on the substrate surface when a liquid medium is applied to the substrate surface. Thus, it is necessary to remove bubbles after a liquid medium has been applied to the substrate surface.

While the cell culture substrates comprising a 6FDA-6FAP membrane (i.e., a fluorine-containing polyimide) subjected to rubbing disclosed in Non-Patent Document 1 and Patent Document 3 can be prepared more easily than the cell culture substrates disclosed in Patent Documents 1 and 2, the cell culture substrates disclosed in Non-Patent Document 1 and Patent Document 3 still suffer from the same problems as those of Patent Documents 1 and 2. Accordingly, there is still scope for improvement.

Accordingly, the present invention is intended to provide a cell culture substrate comprising on its surface a polymer that enables three-dimensional tissue culture.

It should be noted that the vessel disclosed in Patent Document 7 is not aimed at the formation of three-dimensional tissue, and whether or not three-dimensional tissue formation can be achieved with the use of the vessel disclosed in Patent Document 7 is not examined.

Accordingly, the present invention is also intended to provide a cell culture substrate that enables three-dimensional tissue culture, a cell culture vessel comprising such substrate, and a method of cell culture using such substrate.

Means for Solving the Problems

The present inventors surprisingly found that cells could form three-dimensional tissue, such as a spheroid or three-dimensional cell aggregate, on a substrate comprising on its surface a resin composition containing a fluorine-containing polymer having one or more fluorine atoms in a repeating unit and exhibiting oxygen gas permeability of 219 cm$^3$ (STP)/(m$^2$·24 h·atm) or higher.

Specifically, the cell culture substrate according to the present invention has a surface at least a part of which is composed of a resin composition comprising a fluorine-containing polymer having one or more fluorine atoms in a repeating unit, and the oxygen gas permeability of the cell culture substrate is 219 cm$^3$ (STP)/(m$^2$·24 h·atm) or higher.

According to a preferable embodiment of the cell culture substrate, a fluorine-containing polymer comprises at least one type of fluorine-containing polyimide selected from the group consisting of:
(a) a fluorine-containing polyimide having one or more fluorine atoms in a repeating unit and having one or more ether bonds and thioether bonds in total in a polymerization repeating unit constituting the polyimide;
(b) a fluorine-containing polyimide resulting from thermal imidization of polyamide acid and having one or more fluorine atoms in a repeating unit; and
(c) a fluorine-containing polyimide comprising in its main chain a repeating unit represented by Formula (3):

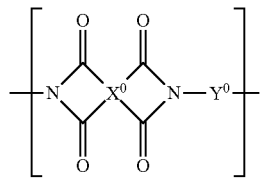

(3)

wherein
X$^0$ represents a tetravalent organic group and Y$^0$ represents a divalent organic group;
X$^0$ and Y$^0$ contain one or more fluorine atoms in total; and
Y$^0$ represents a diamine compound comprising a biphenyl group with each of two benzene rings being substituted with an amino group and the amino group being substituted with a single bond to a nitrogen atom.

According to the embodiment described above, it is preferable that the fluorine content in the resin composition is 1% to 60% by mass, and the degree of imidization is 20% or higher.

According to another preferable embodiment of the cell culture substrate, the fluorine-containing polymer comprises a polymer having a fluorine-containing aromatic ring and having an ether bond in its main chain.

According to the embodiment described above, the fluorine content in the resin composition is preferably 1% to 60% by mass.

Regarding the cell culture substrate according to the present invention, the oxygen gas permeability coefficient of the resin composition is preferably 0.10×10$^{-10}$ cm$^3$ (STP)·cm/(cm$^2$·s·cmHg) or higher.

The present invention also provides a cell culture vessel at least a part of which is composed of the aforementioned cell culture substrate.

Further, the present invention provides a cell culture vessel comprising, in at least in part, a substrate that is provided in a manner such that one surface of the substrate constitutes the bottom of a container portion for containing a cell and medium and the other surface is exposed to the outside of the vessel, wherein the substrate is the cell culture substrate described above and at least a part of the one surface is composed of the resin composition.

The present invention also relates to a method of cell culture comprising a step of culturing cells on the surface of a cell culture substrate composed of the resin composition.

The present invention further relates to a method of cell culture comprising a step of cell culture conducted with the use of a substrate with one surface at least a part of which is composed of a resin composition comprising a fluorine-containing polymer, while cells and a medium are in contact with the one surface of the substrate and oxygen-containing gas is in contact with the other surface of the substrate, wherein the fluorine-containing polymer has one or more fluorine atoms in a repeating unit and the oxygen gas permeability of the substrate is 219 cm$^3$ (STP)/(m$^2$·24 h·atm) or higher.

According to the method of the present invention, the oxygen gas permeability coefficient of the resin composition is preferably 0.10×10$^{-10}$ cm$^3$ (STP)·cm/(cm$^2$·s·cmHg) or higher.

The step of cell culture according to the method of the present invention may comprise a step of three-dimensional cell culture. In the step of three-dimensional cell culture, preferably, the cells are cultured to form a spheroid or three-dimensional cell aggregate.

Hereafter, other embodiments of the present invention are described. It should be noted that the technical idea constituted of any combination of a plurality of aspects or embodiments disclosed herein is within the scope of the present invention.

(1) First Aspect

The present inventors surprisingly found that cells could form three-dimensional tissue, such as a spheroid or three-dimensional cell aggregate, on a substrate comprising on its surface a fluorine-containing polyimide having one or more ether bonds and thioether bonds in total in a polymerization repeating unit (e.g., a polymerization repeating unit derived from acid dianhydride and diamine).

The cell culture substrate according to the first aspect of the present invention has a surface at least a part of which is composed of a polyimide-containing resin composition, wherein the polyimide is a fluorine-containing polyimide having one or more fluorine atoms in a repeating unit and the sum of the ether bonds and the thioether bonds in a polymerization repeating unit constituting the polyimide is at least 1.

In this aspect of the cell culture substrate according to the present invention, however, the polyimide is not at least one type of polyimide selected from the group consisting of:
a polyimide comprising in its main chain the repeating unit as shown in Formula (3), wherein X$^0$ represents a 4,4'-(hexafluoroisopropylidene)diphthalic anhydride residue and Y$^0$ represents a 2,2-bis(4-(4-aminophenoxyl)phenyl) hexafluoropropane residue;
a polyimide comprising in its main chain the repeating unit as shown in Formula (3), wherein X$^0$ represents a 4,4'-(hexafluoroisopropylidene)diphthalic anhydride residue and $Y^0$ represents a bis[4-(4-aminophenoxy)phenyl]sulfone residue; and a polyimide comprising in its main chain the repeating unit as shown in Formula (3), wherein $X^0$ represents a 4,4'-(hexafluoroisopropylidene)diphthalic anhydride residue and $Y^0$ represents a bis[4-(3-aminophenoxy)phenyl]sulfone residue.

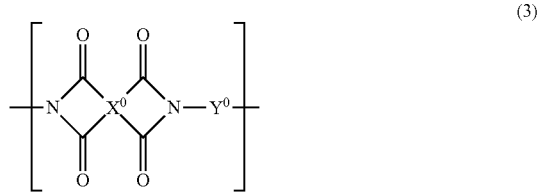

(3)

The cell culture substrate according to the present invention may have a surface at least a part of which is composed of a polyimide-containing resin composition, wherein the polyimide is obtained through the reaction of at least one acid dianhydride with at least one diamine, at least either the acid dianhydride or diamine comprises a fluorine atom in molecules thereof, at least either the acid dianhydride or diamine comprises an ether bond and/or a thioether bond in molecules thereof, and the sum of the ether bonds and the thioether bonds in a polymerization repeating unit derived from the acid dianhydride and the diamine constituting the polyimide is at least 1.

In this aspect of the cell culture substrate according to the present invention, however, the polyimide is not a polyimide obtained through the reaction between 4,4'-(hexafluoroisopropylidene)diphthalic anhydride and 2,2-bis(4-(4-aminophenoxy)phenyl)hexafluoropropane, a polyimide obtained through the reaction between 4,4'-(hexafluoroisopropylidene)diphthalic anhydride and bis[4-(4-aminophenoxy)phenyl]sulfone, or a polyimide obtained through the reaction between 4,4'-(hexafluoroisopropylidene)diphthalic anhydride and bis[4-(3-aminophenoxy)phenyl]sulfone.

A cell culture substrate provided with the features described above has a surface with adequate degrees of flexibility and hydrophobic properties. Thus, cells can form three-dimensional tissue on such surface. In addition, the substrate according to the present invention does not need to have a steric structure on the surface that serves as a scaffold for cells, and it is thus easy to prepare such substrate.

According to a preferable embodiment of the cell culture substrate, the fluorine content in the resin composition is 1% to 60% by mass, and the degree of imidization is 20% or higher.

This embodiment is preferable since it allows three-dimensional tissue to be formed easily on the substrate surface.

The present inventors surprisingly found that cells could form three-dimensional tissue, such as a spheroid or three-dimensional cell aggregate, when culture was conducted with the use of a substrate comprising the polyimide on its surface while providing the substrate at the bottom of a single-well or multi-well plate or a petri dish and, preferably, when cell culture was conducted while bringing cells and a medium into contact with the surface of the substrate comprising the polyimide and bringing oxygen-containing gas such as air into contact with the other surface of the substrate, in addition to with the upper surface of the medium. This has led to the completion of the present invention.

Accordingly, the present invention relates to a cell culture vessel at least a part of which is composed of the aforementioned cell culture substrate.

The cell culture vessel according to the present invention has a surface provided with adequate degrees of flexibility and hydrophobic properties. With the use thereof, accordingly, cell growth and formation of three-dimensional tissue, such as a spheroid or three-dimensional cell aggregate, are likely to proceed. When cell culture is conducted while bringing cells and a medium into contact with the polyimide-containing surface of the substrate and bringing oxygen-containing gas such as air into contact with the other surface of the substrate, in addition to with the upper surface of the medium, cell growth and formation of three-dimensional tissue, such as a spheroid or three-dimensional cell aggregate, are likely to proceed.

The present invention also relates to a method of cell culture comprising a step of culturing cells on the surface of a cell culture substrate.

The present invention further relates to a method of cell culture comprising a step of three dimensionally culturing cells on the surface of the substrate at least a part of which is composed of a polyimide-containing resin composition, wherein the polyimide is a fluorine-containing polyimide having one or more fluorine atoms in a repeating unit, and the sum of the ether bonds and the thioether bonds in a polymerization repeating unit constituting the polyimide is at least 1.

The present invention also relates to a method of cell culture comprising a step of three dimensionally culturing cells on the surface of the substrate at least a part of which is composed of a polyimide-containing resin composition, wherein the polyimide is obtained through the reaction of at least one acid dianhydride with at least one diamine, at least either the acid dianhydride or diamine comprises a fluorine atom in molecules thereof, at least either the acid dianhydride or diamine comprises an ether bond and/or a thioether bond in molecules thereof, and the sum of the ether bonds and the thioether bonds in a polymerization repeating unit derived from the acid dianhydride and the diamine constituting the polyimide is at least 1.

According to the method of the present invention, cell culture and formation of three-dimensional tissue, such as a spheroid or three-dimensional cell aggregate, can be carried out via simple procedures.

(2) Second Aspect

Examples of methods for obtaining a polyimide via imidization of polyamide acid include a method in which polyamide acid is imidized in the presence of an imidization catalyst (i.e., chemical imidization) and a method in which polyamide acid is heated for imidization (i.e., thermal imidization). Polyimides used in the experiments disclosed in Non-Patent Document 1 and Patent Document 3 were obtained via chemical imidization involving the use of a tertiary amine compound as an imidization catalyst.

The present inventors found that, surprisingly, three-dimensional culture could be carried out on a flat surface of the 6FDA-6FAP membrane produced via thermal imidization while three-dimensional culture could not be carried out on a flat surface of the 6FDA-6FAP membrane produced via chemical imidization disclosed in Non-Patent Document 1 and Patent Document 3. In addition, they found that it would be difficult to carry out three-dimensional culture on a flat surface when a tertiary amine compound used as an imidization catalyst remained on the 6FDA-6FAP membrane.

The cell culture substrate according to the second aspect of the present invention comprises a surface at least a part of which is composed of a polyimide-containing resin composition, wherein the polyimide is a fluorine-containing polyimide resulting from thermal imidization of polyamide acid and having one or more fluorine atoms in a repeating unit.

The cell culture substrate of the present invention may comprise a surface at least a part of which is composed of a polyimide-containing resin composition, wherein the polyimide is obtained via thermal imidization of polyamide acid resulting from polymerization of at least one acid dianhydride and at least one diamine, and at least either the acid dianhydride or diamine comprises a fluorine atom in molecules thereof.

Regarding a cell culture substrate provided with the features described above, fluorinated polyimide is prepared via thermal imidization, which does not require the use of an imidization catalyst. Thus, a substrate surface can be free from an imidization catalyst, which may disturb three-dimensional culture, and cells can form three-dimensional tissue on such surface. In addition, the substrate according to the present invention does not need to have a steric structure on such surface that serves as a scaffold for cells, and it is thus easy to prepare such substrate.

According to a preferable embodiment of the cell culture substrate, the fluorine content in the resin composition is 1% to 60% by mass, and the degree of imidization is 20% or higher.

This embodiment is preferable since it allows three-dimensional tissue to be formed easily on the substrate surface.

According to a preferable embodiment of the cell culture substrate, the polyamide acid is subjected to thermal imidization in the absence of a tertiary amine compound.

According to this embodiment, a tertiary amine compound is not present on the substrate surface, and cells can thus form three-dimensional tissue on such surface.

In addition, the cell culture substrate of the present invention may have a surface at least a part of which is composed of a polyimide-containing resin composition, wherein the polyimide is a fluorine-containing polyimide resulting from thermal imidization of polyamide acid and having one or more fluorine atoms in a repeating unit, and the amount of the tertiary amine compound in the resin composition is 0.030% by mass or less relative to the total amount of the polyimide and the remaining polyamide acid in the resin composition.

The cell culture substrate according to another embodiment of the present invention may have a surface at least a part of which is composed of a polyimide-containing resin composition, wherein the polyimide is obtained through the reaction of at least one acid dianhydride with at least one diamine, the amount of the tertiary amine compound in the resin composition is 0.030% by mass or less relative to the total amount of the polyimide and the remaining polyamide acid in the resin composition, and at least either the acid dianhydride or diamine comprises a fluorine atom in molecules thereof.

According to the present invention, the amount of the tertiary amine compound remaining in the resin composition that would disturb three-dimensional culture is sufficiently low. Thus, three-dimensional culture can be carried out.

According to a preferable embodiment of the cell culture substrate, the fluorine content in the resin composition is 1% to 60% by mass, and the degree of imidization is 20% or higher.

This embodiment is preferable since it allows three-dimensional tissue to be formed easily on the substrate surface.

The present inventors surprisingly found that cells could form three-dimensional tissue, such as a spheroid or three-dimensional cell aggregate, when culture was conducted with the use of a substrate comprising the polyimide on its surface while providing the substrate at the bottom of a single-well or multi-well plate or a petri dish and, preferably, when cell culture was conducted while bringing cells and a medium into contact with the surface of the substrate comprising the polyimide and bringing oxygen-containing gas such as air into contact with the other surface of the substrate, in addition to with the upper surface of the medium. This has led to the completion of the present invention.

Accordingly, the present invention relates to a cell culture vessel at least a part of which is composed of the aforementioned cell culture substrate.

The cell culture vessel according to the present invention has a surface provided with adequate degrees of flexibility and hydrophobic properties. With the use thereof, accordingly, cell growth and formation of three-dimensional tissue, such as a spheroid or three-dimensional cell aggregate, are likely to proceed. When cell culture is conducted while bringing cells and a medium into contact with the polyimide-containing surface of the substrate and bringing oxygen-containing gas such as air into contact with the other surface of the substrate, in addition to with the upper surface of the medium, cell growth and formation of three-dimensional tissue, such as a spheroid or three-dimensional cell aggregate, are likely to proceed.

The present invention also relates to a method of cell culture comprising culturing cells on the surface of a cell culture substrate.

The present invention further relates to a method of cell culture comprising a step of three dimensionally culturing cells on the surface of a cell culture substrate.

According to the method of the present invention, cell culture and formation of three-dimensional tissue, such as a spheroid or three-dimensional cell aggregate, can be carried out via simple procedures.

The present invention also relates to a method for producing a cell culture substrate comprising a film made of a polyimide-containing resin composition on at least a part of its surface, which comprises:

a step of forming a membrane of a solution of polyamide acid containing one or more fluorine atoms in molecules thereof dissolved in a solvent; and a step of heating the membrane to imidize polyamide acid in the membrane, thereby forming the film.

The present invention further relates to a method for producing a cell culture substrate comprising a film made of a polyimide-containing resin composition on at least a part of its surface, which comprises:

a step of forming a membrane of a solution of polyamide acid dissolved in a solvent, wherein the polyamide acid is obtained via polymerization of at least one acid dianhydride with at least one diamine, and wherein at least either the acid dianhydride or diamine comprises a fluorine atom in molecules thereof; and a step of heating the membrane to imidize polyamide acid in the membrane, thereby forming the film.

According to this method, a cell culture substrate having a surface that is free from an imidization catalyst, which may disturb three-dimensional culture, can be produced.

According to a preferable embodiment of the method described above, the solution does not contain a tertiary amine compound.

According to this embodiment, a cell culture substrate having a surface that is free from a tertiary amine compound, which may disturb three-dimensional culture, can be produced.

(3) Third Aspect

The present inventors surprisingly found that cells could form three-dimensional tissue, such as a spheroid or three-dimensional cell aggregate, on a substrate comprising a polyimide, which is obtained through the reaction between acid dianhydride and diamine, which is aromatic diamine of a specific structure, on its surface.

According to the third aspect of the present invention, the cell culture substrate has a surface at least a part of which is composed of a polyimide-containing resin composition, wherein the polyimide is a fluorine-containing polyimide comprising in its main chain a repeating unit represented by Formula (3):

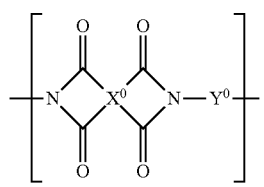

(3)

wherein $X^0$ represents a tetravalent organic group and $Y^0$ represents a divalent organic group;

$X^0$ and $Y^0$ contain one or more fluorine atoms in total; and $Y^0$ represents a diamine compound comprising a biphenyl group with each of two benzene rings being substituted with an amino group and the amino group being substituted with a single bond to a nitrogen atom.

Also, the cell culture substrate of the present invention has a surface at least a part of which is composed of a polyimide-containing resin composition, wherein the polyimide is obtained through the reaction of at least one acid dianhydride with at least one diamine. A diamine compound comprising a biphenyl group with each of two benzene rings being substituted with an amino group is within the scope of the diamine, and at least either the acid dianhydride or diamine comprises a fluorine atom in molecules thereof.

Cells can form three-dimensional tissue on the surface of a cell culture substrate provided with the features described above. In addition, the substrate according to the present invention does not need to have a steric structure on the surface that serves as a scaffold for cells, and it is thus easy to prepare such substrate.

According to a preferable embodiment of the cell culture substrate, the fluorine content in the resin composition is 1% to 60% by mass, and the degree of imidization is 20% or higher.

This embodiment is preferable since it allows three-dimensional tissue to be formed easily on the substrate surface.

The present inventors surprisingly found that cells could form three-dimensional tissue, such as a spheroid or three-dimensional cell aggregate, when culture was conducted with the use of a substrate comprising the polyimide on its surface while providing the substrate at the bottom of a single-well or multi-well plate or a petri dish and, preferably, when cell culture was conducted while bringing cells and a medium into contact with the surface of the substrate comprising the polyimide and bringing oxygen-containing gas such as air into contact with the other surface of the substrate, in addition to with the upper surface of the medium. This has led to the completion of the present invention.

Accordingly, the present invention relates to a cell culture vessel at least a part of which is composed of the aforementioned cell culture substrate.

The cell culture vessel according to the present invention has a surface provided with adequate degrees of flexibility and hydrophobic properties. With the use thereof, accordingly, cell growth and formation of three-dimensional tissue, such as a spheroid or three-dimensional cell aggregate, are likely to proceed. When cell culture is conducted while bringing cells and a medium into contact with the polyimide-containing surface of the substrate and bringing oxygen-containing gas such as air into contact with the other surface of the substrate, in addition to with the upper surface of the medium, cell growth and formation of three-dimensional tissue, such as a spheroid or three-dimensional cell aggregate, are likely to proceed.

The present invention also relates to a method of cell culture comprising a step of culturing cells on the surface of a cell culture substrate.

The present invention further relates to a method of cell culture comprising a step of three dimensionally culturing cells on the surface of a cell culture substrate.

According to the method of the present invention, cell culture and formation of three-dimensional tissue, such as a spheroid or three-dimensional cell aggregate, can be carried out via simple procedures.

(4) Fourth Aspect

The present inventors surprisingly found that cells could form three-dimensional tissue, such as a spheroid or three-dimensional cell aggregate, when culture was conducted with the use of a substrate comprising a fluorine-containing polyimide on its surface and comprising a resin composition with high oxygen gas permeability while bringing cells and a medium into contact with the surface of the substrate comprising the polyimide and bringing oxygen-containing gas such as air into contact with the other surface of the substrate, in addition to with the upper surface of the medium. This has led to the completion of the present invention.

The fourth aspect of the present invention relates to a cell culture vessel comprising, in at least in part, a substrate that is provided in a manner such that one surface of the substrate constitutes the bottom of a container portion for containing a cell and medium and the other surface is exposed to the outside of the vessel, wherein at least a part of the one surface of the substrate is composed of a polyimide-containing resin composition, the polyimide is a fluorine-containing polyimide having one or more fluorine atoms in a repeating unit, and the oxygen gas permeability of the substrate is 219 cm$^3$ (STP)/(m$^2$·24 h·atm) or higher.

With the use of the cell culture vessel according to the present invention, oxygen is easily supplied to the cells through the bottom surface of the substrate from the outside of the vessel, in addition to the usual oxygen supply through the upper surface of the medium. Thus, cell growth and formation of three-dimensional tissue, such as a spheroid or three-dimensional cell aggregate, are likely to proceed.

In the cell culture vessel of the present invention, the oxygen gas permeability coefficient of the resin composition is more preferably $0.10 \times 10^{-10}$ cm$^3$ (STP)·cm/(cm$^2$·s·cmHg) or higher.

In the cell culture vessel according to this embodiment of the present invention, a larger quantity of oxygen is easily supplied to cells, and cell growth and formation of three-dimensional tissue, such as a spheroid or three-dimensional cell aggregate, are likely to proceed.

In the cell culture vessel according to the present invention, more preferably, the fluorine content in the resin composition is 1% to 60% by mass, and the degree of imidization is 20% or higher.

According to this embodiment, cells can form three-dimensional tissue more easily on the substrate surface of the cell culture vessel according to the present invention.

The present invention also relates to a method of cell culture comprising a step of cell culture conducted with the use of a substrate having one surface at least a part of which is composed of a polyimide-containing resin composition, while keeping cells and a medium in contact with the one surface of the substrate and oxygen-containing gas in contact with the other surface of the substrate, wherein the polyimide is a fluorine-containing polyimide having one or more fluorine atoms in a repeating unit, and the oxygen gas permeability of the substrate is 219 cm$^3$ (STP)/(m$^2$·24 h·atm) or higher.

According to the method of cell culture of the present invention, oxygen is easily supplied to the cells through the bottom surface of the substrate, in addition to the usual oxygen supply through the upper surface of the medium. Thus, cell growth is likely to proceed.

According to the method of cell culture of the present invention, more preferably, the oxygen gas permeability coefficient of the resin composition is $0.10 \times 10^{-10}$ cm$^3$ (STP)·cm/(cm$^2$·s·cmHg) or higher.

In the method of cell culture according to this embodiment of the present invention, a larger quantity of oxygen is easily supplied to cells, and cell growth is likely to proceed.

According to the method of cell culture of the present invention, more preferably, the fluorine content in the resin composition is 1% to 60% by mass, and the degree of imidization is 20% or higher.

In the method of cell culture according to this embodiment of the present invention, cell growth is more likely to proceed.

In the method of cell culture according to the present invention, more preferably, the step described above is a step of three-dimensional cell culture. In the step of three-dimensional cell culture, more preferably, the cells are cultured to form a spheroid or three-dimensional cell aggregate.

According to the method of cell culture according to a more preferable embodiment of the present invention, cell culture and formation of three-dimensional tissue, such as a spheroid or three-dimensional cell aggregate, can be carried out via simple procedures.

The present invention also relates to a cell culture substrate having a surface at least a part of which is composed of a polyimide-containing resin composition, wherein the polyimide is a fluorine-containing polyimide having one or more fluorine atoms in a repeating unit, and the oxygen gas permeability of the substrate is 219 cm$^3$ (STP)/(m$^2$·24 h·atm) or higher.

With the use of the cell culture substrate of the present invention, oxygen is easily supplied to the cells through the substrate, in addition to the usual oxygen supply through the upper surface of the medium. Thus, cell growth is likely to proceed.

Regarding the cell culture substrate of the present invention, more preferably, the oxygen gas permeability coefficient of the resin composition is $0.10 \times 10^{-10}$ cm$^3$ (STP)·cm/(cm$^2$·s·cmHg) or higher.

Regarding the cell culture substrate according to this embodiment of the present invention, a larger quantity of oxygen is easily supplied to cells, and cell growth is likely to proceed.

Regarding the cell culture substrate of the present invention, more preferably, the fluorine content in the resin composition is 1% to 60% by mass, and the degree of imidization is 20% or higher.

According to this embodiment, cells can form three-dimensional tissue more easily on the surface of the cell culture substrate according to the present invention.

The fluorine-containing polyimide used in the present invention is typically a polyimide obtained through the reaction of at least one acid dianhydride with at least one diamine, and at least either the acid dianhydride or diamine comprises a fluorine atom in molecules thereof.

(5) Fifth Aspect

The present inventors surprisingly found that cells could form three-dimensional tissue, such as a spheroid or three-dimensional cell aggregate, on a substrate comprising on its surface a fluorine-containing polymer having a fluorine-containing aromatic ring and an ether bond in its main chain.

Accordingly, the fifth aspect of the present invention relates to a cell culture substrate with at least a part of its surface being composed of a resin composition comprising a fluorine-containing polymer, such fluorine-containing polymer being a polymer having a fluorine-containing aromatic ring and comprising an ether bond in its main chain.

Cells can form three-dimensional tissue on the surface of the cell culture substrate provided with the features described above. In addition, the substrate according to the present invention does not need to have a steric structure on the surface that serves as a scaffold for cells, and it is thus easy to prepare such substrate.

According to a preferable embodiment of the cell culture substrate, the oxygen gas permeability is 219 cm$^3$ (STP)/(m$^2$·24 h·atm) or higher.

According to a preferable embodiment of the cell culture substrate, the oxygen gas permeability coefficient of the resin composition is $0.10 \times 10^{-10}$ cm$^3$ (STP) cm/(cm$^2$·s·cmHg) or higher.

According to the embodiment described above, a larger quantity of oxygen is easily supplied to cells, and cell growth and formation of three-dimensional tissue, such as a spheroid or three-dimensional cell aggregate, are likely to proceed.

According to a preferable embodiment of the cell culture substrate, the fluorine content in the resin composition is 1% to 60% by mass.

This embodiment is preferable since it allows three-dimensional tissue to be formed easily on the substrate surface.

According to a preferable embodiment of the cell culture substrate, the fluorine-containing polymer is fluorine-containing aryl ether ketone polymer comprising a repeating unit represented by Formula (II-1):

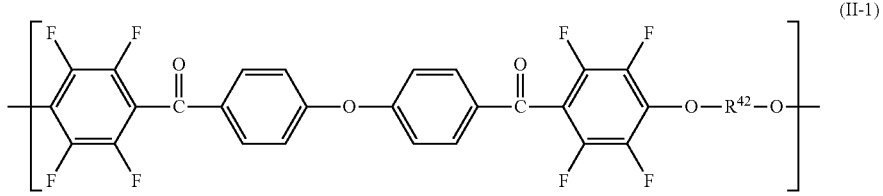

wherein $R^{42}$ has any of the structures represented by formulae shown below.

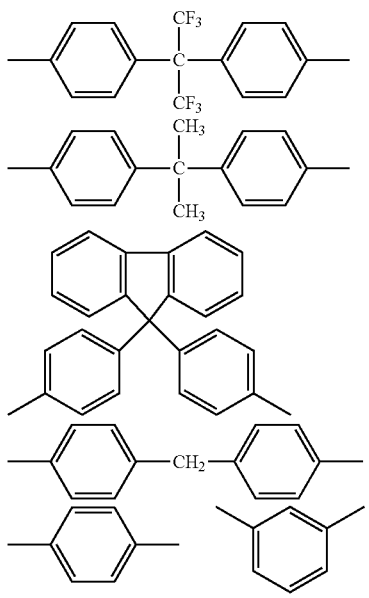

According to this embodiment, the cell culture substrate of the present invention can provide a transparent scaffold to which cells can adequately adhere and on which three-dimensional tissue can be formed. In addition, a larger quantity of oxygen is easily supplied to cells, and cell growth and three-dimensional tissue formation are likely to proceed.

The present inventors surprisingly found that cells could form three-dimensional tissue, such as a spheroid or three-dimensional cell aggregate, when cell culture was conducted with the use of a substrate comprising a fluorine-containing polymer on one surface of the substrate and a resin composition with high oxygen gas permeability while keeping cells and a medium in contact with the one surface of the substrate containing the fluorine-containing polymer and keeping oxygen-containing gas such as air in contact with the other surface of the substrate, in addition to with the upper surface of the medium. This has led to the completion of the present invention.

Accordingly, the present invention relates to a cell culture vessel comprising, in at least in part, a substrate that is provided in a manner such that one surface of the substrate constitutes the bottom of a container portion for containing a cell and medium and the other surface is exposed to the outside of the vessel, wherein the substrate is the cell culture substrate described above.

With the use of the cell culture vessel according to the present invention, oxygen is easily supplied to the cells through the bottom surface of the substrate from the outside of the vessel, in addition to the usual oxygen supply through the upper surface of the medium. Thus, cell growth and formation of three-dimensional tissue, such as a spheroid or three-dimensional cell aggregate, are likely to proceed.

The present invention also relates to a method of cell culture comprising a step of culturing cells on the surface of a cell culture substrate composed of the resin composition.

The present invention further relates to a method of cell culture comprising a step of culturing cells with the use of a substrate, at least a part of one of the surfaces being composed of a resin composition comprising a fluorine-containing polymer, while cells and a medium are in contact with one of the surfaces of the substrate and oxygen-containing gas is in contact with the other surface of the substrate, wherein the fluorine-containing polymer has a fluorine-containing aromatic ring and comprises an ether bond in its main chain.

According to the method of cell culture of the present invention, oxygen is easily supplied to the cells through the bottom surface of the substrate, in addition to the usual oxygen supply through the upper surface of the medium. Thus, cell growth is likely to proceed.

According to a preferable embodiment of the method described above, the step of cell culture is a step of three-dimensional cell culture.

According to a preferable embodiment of the method described above, the step of three-dimensional cell culture is a step of culturing the cells to form a spheroid or three-dimensional cell aggregate.

According to the method of the present invention, cell culture and formation of three-dimensional tissue, such as a spheroid, can be carried out via simple procedures.

The term "resin composition" used in the present invention may be used interchangeably with the term "resin." In general, a fluorine-containing polymer is composed of numerous fluorine-containing polymer molecules of different polymerization degrees. Thus, resin containing a fluorine-containing polymer is referred to as a "resin composition." In the present invention, the "resin composition" or "resin" may or may not contain other components in an amount that would not adversely affect the effects of the present invention. Components or common additives used for polymerization can be used as other components in an amount that would not adversely affect the effects of the present invention.

Effects of the Invention

The surface of the cell culture substrate of the present invention that serves as a scaffold for cells is composed of a particular resin composition. Thus, cells can be three-dimensionally cultured.

According to the present invention, in addition, three-dimensional tissue, such as a spheroid or three-dimensional cell aggregate, can be prepared from cells.

BRIEF DESCRIPTION OF THE DRAWINGS

The patent application file contains at least one drawing executed in color. Copies of this patent or patent application publication with color drawing(s) will be provided by the Office upon request and payment of the necessary fee.

FIG. 4-1 shows an embodiment of the cell culture vessel according to the present invention.

FIG. 4-2 shows another embodiment of the cell culture vessel according to the present invention: wherein (a) schematically shows a vertical cross section of the cell culture vessel 100; and (b) illustrates a method of cell culture conducted with the use of the cell culture vessel 100.

EMBODIMENTS FOR CARRYING OUT THE INVENTION

1. Fluorine-Containing Polymer

Figure 1:
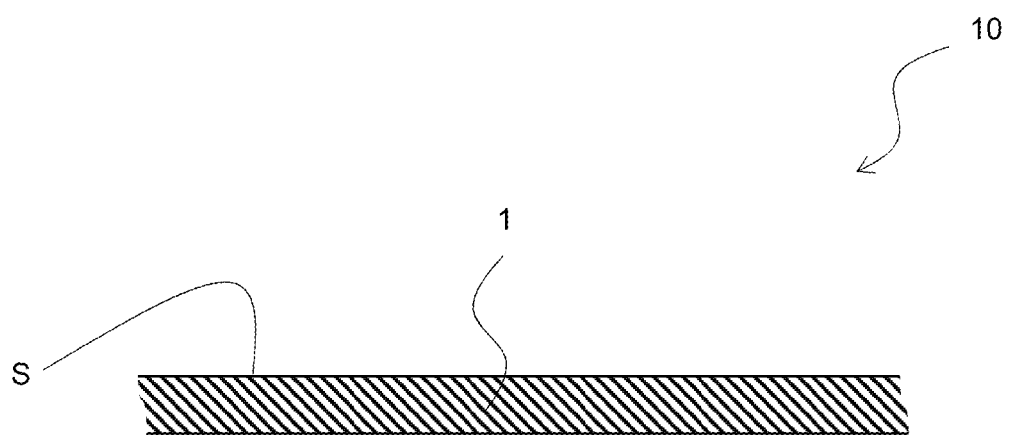
FIG. 1 schematically shows a cross section of a film 1 composed of a resin composition of the cell culture substrate according to the first embodiment of the present invention, which is cut along the plane that is vertical to the main surface of the film 1.

The cell culture substrate according to the present invention involves the use of a fluorine-containing polymer having one or more fluorine atoms in a repeating unit. Specific embodiments of the fluorine-containing polymer are described below.

1.1 Fluorine-Containing Polyimide

The polyimide used in the present invention is a fluorine-containing polyimide having one or more fluorine atoms in a repeating unit. A typical example is a fluorine-containing polyimide obtained through the reaction between at least one acid dianhydride and at least one diamine.

According to an embodiment, polymerization repeating units constituting the polyimide (e.g., polymerization repeating units derived from acid dianhydride and diamine) comprise ether bonds and/or thioether bonds. It is preferable that at least either acid dianhydride or diamine comprise ether bonds and/or thioether bonds in the molecules. The total number of ether bonds and thioether bonds in the polymerization repeating units constituting the polyimide (e.g., polymerization repeating units derived from acid dianhydride and diamine) is at least 1. While the maximal number thereof is not particularly limited, such number is preferably 6 or lower, more preferably 5 or lower, and further preferably 4 or lower. A polyimide comprising the number of ether bonds and thioether bonds within the range described above has an adequate degree of flexibility. Thus, three-dimensional cell culture can be carried out.

While the ether bond is a bond represented by —O—, according to the present invention, the number of ether bonds does not include the number of bonds in the —O— region in an acid anhydride group (i.e., the —C(O)—O—C(O)— region) of the acid dianhydride.

The number of the ether bonds and the thioether bonds can be determined on the basis of the number of ether bonds and thioether bonds in a compound comprising such ether bonds and/or thioether bonds in molecules thereof and the reaction molar ratio of the compound comprising such bonds. While an example of a calculation method is described below, it should be noted that the method is not limited to the method described below.

(1) When an acid dianhydride comprising 2 ether bonds in molecules thereof is allowed to react with diamine not comprising any ether bonds or thioether bonds in molecules thereof at a molar ratio of 1:1 to obtain a polyamide acid, thereby resulting in polyimide, the total number of ether bonds and thioether bonds is 2 (i.e., 2×1+0×1=2). When an acid dianhydride not comprising any ether bonds or thioether bonds in molecules thereof is allowed to react with diamine comprising 2 ether bonds in molecules thereof at a molar ratio of 1:1 to obtain a polyamide acid composition and then obtain polyimide therefrom, the total number of bonds is calculated in the same manner, and such number is 2.

(2) When an acid dianhydride comprising 2 ether bonds in molecules thereof is allowed to react with diamine comprising an ether bond in molecules thereof at a molar ratio of 1:1 to obtain a polyamide acid, thereby resulting in polyimide, the total number of ether bonds and thioether bonds is 3 (i.e., 2×1+1×1=3). When an acid dianhydride comprising an ether bond in molecules thereof is allowed to react with diamine comprising 2 ether bonds in molecules thereof at a molar ratio of 1:1 to obtain a polyamide acid, thereby resulting in polyimide, the total number of bonds is calculated in the same manner, and such number is 3.

(3) When an acid dianhydride "a" comprising 2 ether bonds in molecules thereof, an acid dianhydride "b" not comprising any ether bonds or thioether bonds in molecules thereof, and diamine comprising an ether bond in molecules thereof are allowed to react with each other at a molar ratio of 0.5:0.5:1.0 to obtain a polyamide acid, thereby resulting in polyimide, the total number of ether bonds and thioether bonds is 2 (i.e., 2×0.5+0×0.5+1×1=2).

(4) When an acid dianhydride comprising 2 ether bonds in molecules thereof, diamine "a" comprising an ether bond in molecules thereof, and diamine "b" comprising 2 ether bonds in molecules thereof are allowed to react with each other at a molar ratio of 1:0.5:0.5 to obtain a polyamide acid, thereby resulting in polyimide, the total number of ether bonds and thioether bonds is 3.5 (i.e., 2×1.0+1×0.5+2×0.5=3.5).

As described above, the reaction molar ratio of the starting materials is determined to adjust the sum of all acid dianhydrides and the sum of all diamines to equivalent levels.

The polyimide used in the present invention is a fluorine-containing polyimide containing a fluorine atom. A fluorine-containing polyimide is preferably prepared with the use of at least one compound containing a fluorine atom in molecules thereof as acid dianhydride or diamine. The fluorine content in a resin composition constituting the substrate surface containing the polyimide according to the present invention is 1% to 60% by mass, preferably 5% to 60% by mass, more preferably 10% to 60% by mass, and further preferably 15% to 50% by mass. The fluorine content described above may be attained when acid dianhydride and/or diamine comprise(s) one or more fluorine atoms. On the substrate surface composed of the resin composition with such fluorine content, cells are able to easily form three-dimensional tissue.

At least either the acid dianhydride or diamine contains a fluorine atom. It is not preferable that such fluorine atom be quenched as a result of amidation or imidization between acid dianhydride and diamine.

According to another embodiment, it is not preferable that ether bonds and/or thioether bonds or the fluorine atom within at least either the acid dianhydride or diamine be quenched as a result of amidation or imidization between acid dianhydride and diamine. Specifically, the polyimide preferably comprises in its main chain (which is also referred to as a "main chain backbone") a constitutive unit comprising ether bonds and/or thioether bonds and the fluorine atom derived from the acid dianhydride and/or diamine compound.

Polyimide may be obtained via imidization of a polyamide acid obtained via polymerization of at least one acid dianhydride with at least one diamine. The resin composition constituting the surface of the substrate of the present invention serving as the scaffold for cells may comprise, in its part thereof, polyamide acid, in addition to polyimide. A compound exhibiting an imidization degree of 0% is referred to as "polyamide acid," and a compound exhibiting an imidization degree exceeding 0% is referred to as "polyimide" herein.

In the present invention, polyimide having a fluorine atom is occasionally referred to as a "fluorine-containing polyimide," and its precursor; i.e., polyamide acid, is occasionally referred to as a "fluorine-containing polyamide acid." Also, the "fluorine-containing polyamide acid" used herein is occasionally referred to as a "polyamide acid," the "fluorine-containing aromatic polyamide acid" is referred to as an "aromatic polyamide acid," the "fluorine-containing polyimide" is referred to as a "polyimide," and a "fluorine-containing aromatic polyimide" is occasionally referred to as an "aromatic polyimide."

According to a particular embodiment, a resin composition constituting the surface of the substrate of the present invention serving as the scaffold for cells may comprise, at least in part, polyamide acid, in addition to polyimide. A compound exhibiting an imidization degree of 0% is referred to as "polyamide acid," and a compound exhibiting an imidization degree exceeding 0% is referred to as "polyimide" herein.

The polyimide of the present invention, which may be obtained with the use of a compound represented by Formula (1) as acid dianhydride and a compound represented by Formula (2) as diamine, comprises in its main chain (the main chain backbone) a repeating unit represented by Formula (3).

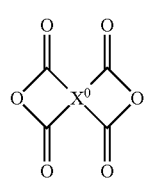
(1)

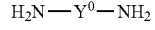
(2)

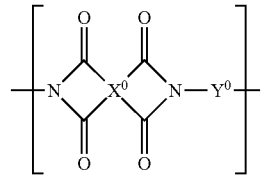
(3)

In Formulae (1) to (3), $X^0$ represents an acid dianhydride residue, which is a tetravalent organic group, $Y^0$ represents a diamine compound residue, which is a divalent organic group, and $X^0$ and $Y^0$ contain one or more fluorine atoms in total.

According to another embodiment, in Formulae (1) to (3), $X^0$ represents an acid dianhydride residue, which is a tetravalent organic group, $Y^0$ represents a diamine compound residue, which is a divalent organic group, $X^0$ and $Y^0$ contain one or more ether bonds and thioether bonds in total, and $X^0$ and $Y^0$ contain one or more fluorine atoms in total.

Fluorine-containing polyimide in the resin composition used in the present invention may be prepared by any method, provided that it has a repeating unit represented by Formula (3), and it is not limited to the fluorine-containing polyimide resulting from the reaction between the acid dianhydride represented by Formula (1) and the diamine represented by Formula (2). It is apparent to a person skilled in the art that, in the "polyimide obtained through the reaction of at least one acid dianhydride with at least one diamine" in the present invention, acid dianhydride may be in the form of an acid dianhydride derivative and diamine may be in the form of a diamine derivative.

Polyimide can be prepared via two-stage synthesis or one-stage synthesis as described in the examples.

According to two-stage synthesis of polyimide, polyamide acid is synthesized as a precursor, and polyamide acid is converted into polyimide acid. Polyamide acid as a precursor may be a polyamide acid derivative. Examples of polyamide acid derivatives include polyamide acid derivatives such as polyamide acid salt, polyamide acid alkyl ester, polyamide acid amide, and bis-methylidene pyromellitid, polyamide acid silyl ester, and polyamide acid isoimide.

Examples of techniques for one-stage synthesis of polyimide that can be employed include those involving the use of a solvent, such as melt-polymerization at high temperature, the isocyanate method, the tetracarboxylic acid dithioanhydride method, and a method involving the use of ionic liquid. Examples of other one-stage synthesis techniques include a polymerization method from nylon-salt-type monomers, solid-phase polymerization at high temperature, solid-phase polymerization at high-temperature and high pressure, and solid-phase polymerization in water.

In the present invention, an "acid dianhydride residue" may be any tetravalent organic group that constitutes the structure described above, and it is not necessary that a residue be formed via the reaction of acid dianhydride. Also, the "diamine compound residue" may be a divalent organic group constituting such structure, and it is not necessary that a residue be formed via the reaction of a diamine compound.

1.1.1. Fluorine-Containing Polyamide Acid

A polyimide comprising a repeating unit represented by Formula (3) can be obtained via imidization of polyamide acid resulting from the reaction of the acid dianhydride represented by Formula (1) and the diamine represented by Formula (2), and the polyamide acid comprises the repeating unit represented by Formula (4) in its main chain (the main chain backbone).

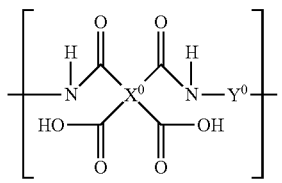

(4)

The number of repeating units represented by Formula (4) contained in molecules thereof of polyamide acid is preferably 1 to 1,300, and it is more preferably 1 to 1,000.

The molecular weight of the polyamide acid is preferably 1,000 to 1,000,000, and it is more preferably 5,000 to 700,000 in terms of weight average molecular weight. When the molecular weight is within such range, gelling does not take place at the time of polymerization, polymerization and film formation can be easily carried out because of low viscosity, and adequate degrees of thermal stability and membrane strength can be expected. The weight average molecular weight is further preferably 10,000 to 500,000.

The weight average molecular weight can be determined via gel permeation chromatography (GPC) with the use of the calibration curve of the standard polystyrene, as in the case of the examples described below.

According to a particular embodiment, the polyamide acid preferably exhibits a value of 0.05 or higher in the unit represented by Formula (4) (i.e., (the total atomic weight of oxygen and sulfur associated with ether bonds and/or thioether bonds)/(the total molecular weight of the unit)=0.05 or higher). Such value is more preferably 0.07 or higher. Thus, an adequate degree of flexibility can be imparted to the resulting surface.

The polyamide acid is preferably aromatic polyamide acid or aliphatic polyamide acid, and more preferably aromatic polyamide acid. Hereafter, preferable embodiments of polyamide acid are described.

1.1.1.1. Specific Examples of Aromatic Polyamide Acid

Aromatic acid dianhydride is a compound represented by Formula (1), wherein $X^0$ includes an aromatic group, and aromatic diamine is a compound represented by Formula (2), wherein $Y^0$ includes an aromatic group. Aromatic polyamide acid is polyamide acid resulting from polymerization of at least one acid dianhydride with at least one diamine, acid dianhydride used for polymerization at least comprises the acid dianhydride represented by Formula (1), wherein $X^0$ includes an aromatic group, and diamine used for polymerization at least comprises the diamine represented by Formula (2), wherein $Y^0$ includes an aromatic group. In fluorine-containing aromatic polyamide acid, either or both $X^0$ derived from acid dianhydride and $Y^0$ derived from diamine contained in the polymerization repeating unit represented by Formula (4) has at least one fluorine atom and at least one aromatic ring structure.

According to a preferable embodiment of aromatic polyamide acid, polyamide acid is obtained via polymerization of at least one acid dianhydride with at least one diamine, wherein the acid dianhydride used for the polymerization comprises at least an acid dianhydride represented by Formula (1), wherein $X^0$ represents a group represented by Formula ($E^1$):

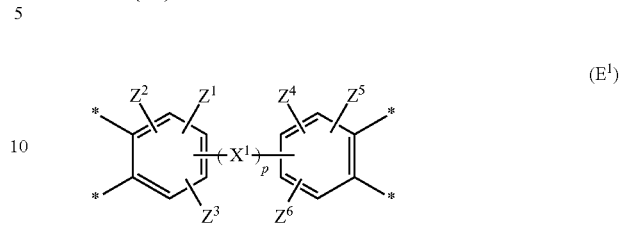

($E^1$)

and the diamine used for the polymerization comprises at least a diamine represented by Formula (2), wherein $Y^0$ is a group represented by $Y^1$ described below. The polyamide acid preferably comprises a polymerization unit represented by Formula (I) below:

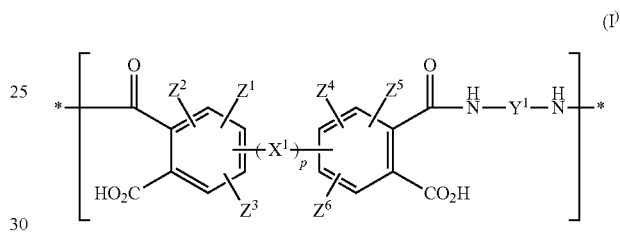

(I)

wherein $X^1$ represents a divalent organic group and $Y^1$ represents a divalent organic group having an aromatic group.

$Z^1$, $Z^2$, $Z^3$, $Z^4$, $Z^5$, and $Z^6$ each independently represent either a hydrogen atom, fluorine atom, chlorine atom, bromine atom, or iodine atom, and at least one of $X^1$, $Y^1$, $Z^1$, $Z^2$, $Z^3$, $Z^4$, $Z^5$, and $Z^6$ comprises at least one fluorine atom.

According to a particular embodiment, at least either $X^1$ or $Y^1$ comprises one or more ether bonds and/or thioether bonds in its main chain. When $X^1$ comprises ether bonds and/or thioether bonds, an oxygen atom or sulfur atom is present in $X^1$ at a site at which $X^1$ binds to a ring-membered carbon atom of at least one of the two benzene rings located adjacent to $X^1$, and ether bonds and/or thioether bonds may be formed between the ring-membered carbon atom and an atom in $X^1$ adjacent to the oxygen or sulfur atom of $X^1$. Alternatively, $X^1$ may represent —O— or —S— and ether bonds and/or thioether bonds may be formed between ring-membered carbon atoms of the two adjacent benzene rings.

The term "main chain" refers to a chain comprising the largest number of atoms connected to each other in a single polymer molecule.

p is 0 or 1.

In Formulae (I) and ($E^1$), when p is 0, $X^1$ does not exist, and benzene rings located on the right and on the left of $X^1$ are directly bound to each other. When p is 1, benzene rings located on the right and on the left of $X^1$ are bound to each other through $X^1$.

Specifically, $X^1$ represents at least one member selected from the group consisting of an alkylene group, an arylene group, an aryleneoxy group, an arylenethio group, —O—, and —S—. Among them, at least one member selected from the group consisting of an alkylene group, an arylene group, an aryleneoxy group, and an arylenethio group is preferable, at least one member selected from the group consisting of an alkylene group, an aryleneoxy group, and an arylenethio group is more preferable, and at least one member selected from the group consisting of an alkylene group and an aryleneoxy group is further preferable. Such groups may be substituted with halogen atoms (e.g., fluorine atoms).

An example of an alkylene group represented by $X^1$ can be at least one member selected from the group consisting of —$C(CA_3)_2$- and —$C(CA_3)_2$—$C(CA_3)_2$-. In such formulae, "A" independently represents a hydrogen atom or fluorine atom, and all "A"s preferably represent fluorine atoms. Among the alkylene groups as examples of $X^1$, —$C(CA_3)_2$— in which all As represent fluorine atoms; that is, —$C(CF_3)_2$—, is preferable. Such fluorine-substituted alkylene group has a bulky structure, and the contact angle becomes enlarged. Accordingly, performance for prevention of substances from becoming attached to an organism is improved, and three-dimensional culture is facilitated. When $Y^1$ does not include a fluorine atom, it is particularly preferable that the alkylene group is a fluorine-substituted alkylene group.

Examples of arylene groups represented by $X^1$ include one or more members selected from the following group:

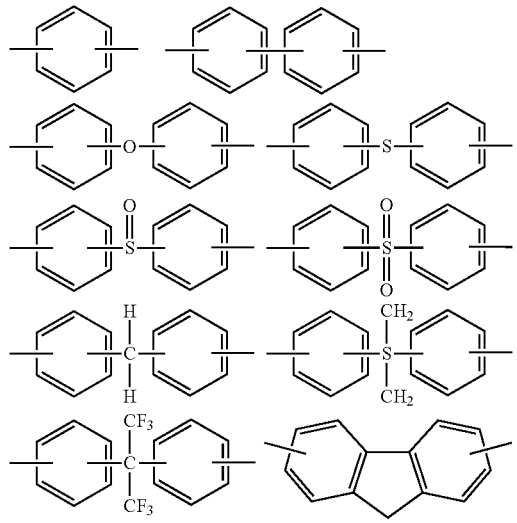

Examples of aryleneoxy groups represented by $X^1$ include one or more members selected from the following group:

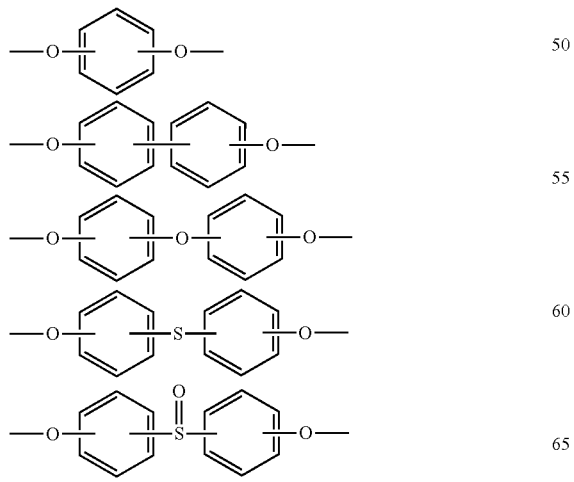

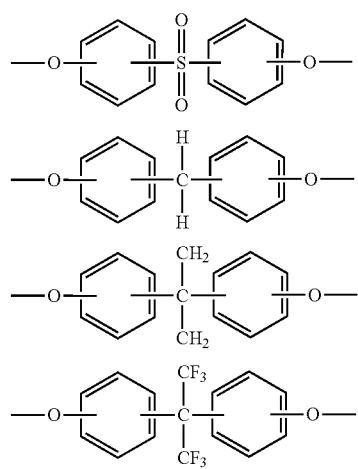

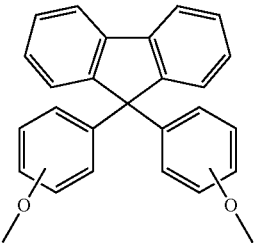

Examples of arylenethio groups represented by $X^1$ include one or more members selected from the following group:

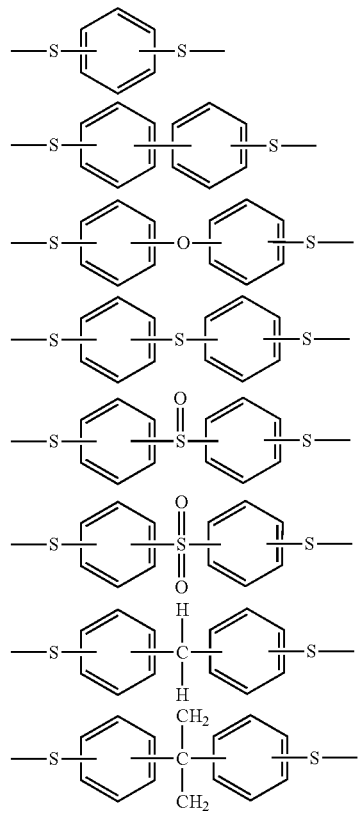

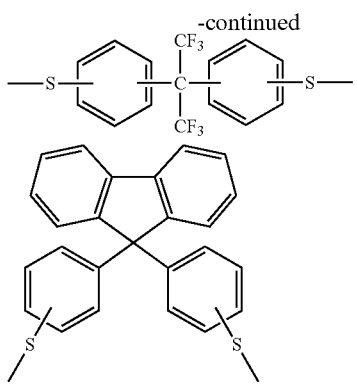

The examples of $X^1$; that is, an arylene group, an aryleneoxy group, and an arylenethio group, may be each independently substituted with at least one member selected from the group consisting of a halogen atom (e.g., a fluorine atom, a chlorine atom, a bromine atom, or an iodine atom, with the fluorine atom or chlorine atom being preferable and the fluorine atom being more preferable), a methyl group, and a trifluoromethyl group. The number of such substituents may be greater than 1, and substituents of the same type or different types may be employed in such a case. Preferable substituents for the arylene group, the aryleneoxy group, and the arylenethio group are the fluorine atom and/or trifluoromethyl group, with the fluorine atom being the most preferable. When $Y^1$ does not include a fluorine atom, the arylene group, the aryleneoxy group, and the arylenethio group are preferably substituted with at least one fluorine atom.

The arylene group, the aryleneoxy group, or the arylenethio group as the example of $X^1$ is preferably at least one member selected from the following group:

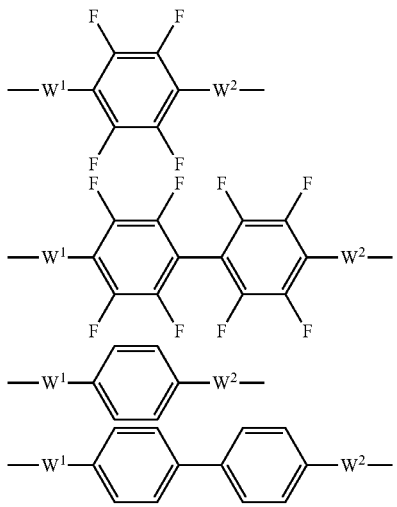

wherein $W^1$ and $W^2$ each independently represents an oxygen atom or sulfur atom.

In such a case, $W^1$ and $W^2$ are preferably the same atoms. That is, both $W^1$ and $W^2$ are preferably oxygen atoms or sulfur atoms, and both $W^1$ and $W^2$ are more preferably oxygen atoms.

According to a particular embodiment, a divalent organic group having an aromatic group represented by $Y^1$ is not particularly limited. Examples thereof include a group comprising a benzene ring and a group comprising two or more benzene rings bound to each other via the carbon, oxygen, or sulfur atom or directly bound to each other. A specific example is at least one member selected from the following group:

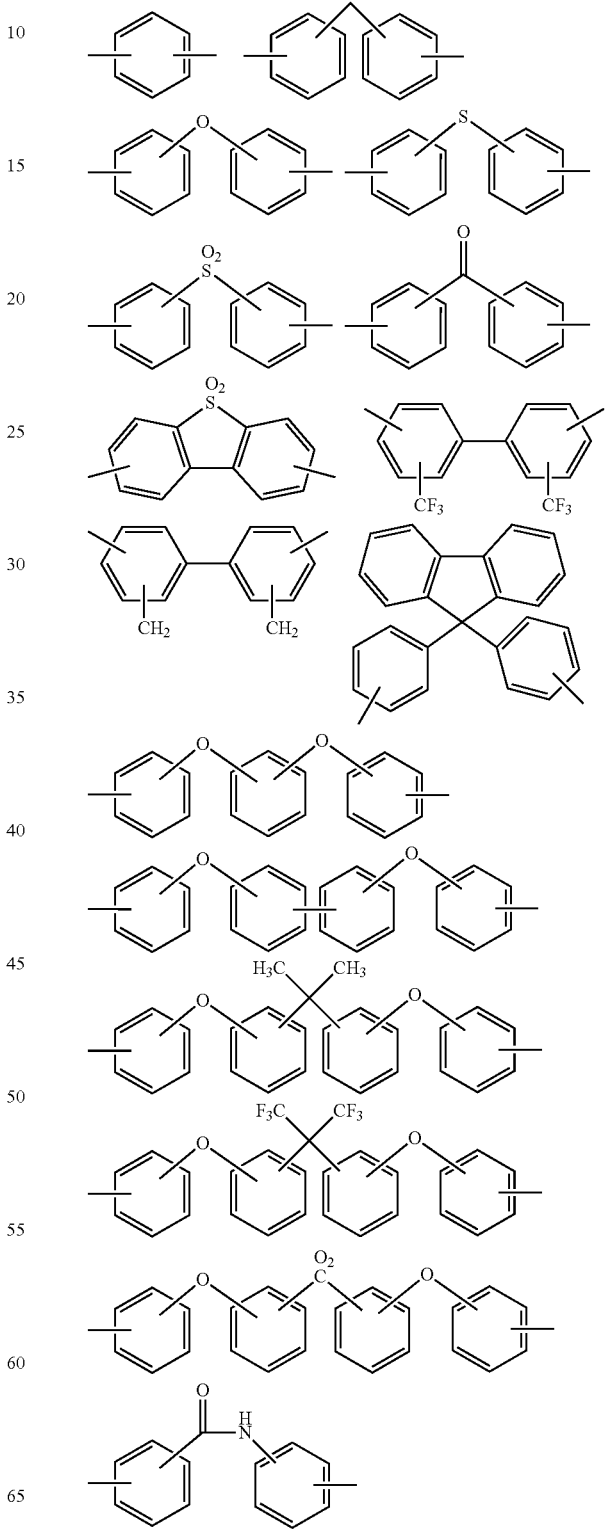

-continued

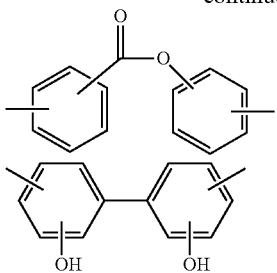

According to a particular embodiment, the divalent organic group having an aromatic group, which is an example of $Y^1$, may be substituted with at least one member selected from the group consisting of a halogen atom (e.g., a fluorine atom, a chlorine atom, a bromine atom, or an iodine atom, with the fluorine atom or chlorine atom being preferable and the fluorine atom being more preferable), a methyl group, an ethyl group, and a trifluoromethyl group, if possible. The substituent is more preferably at least one member selected from the group consisting of a halogen atom, a methyl group, and a trifluoromethyl group. The number of such substituents may be greater than 1, and substituents of the same type or different types may be employed in such a case. When $X^1$ does not include a fluorine atom, in particular, substituents for the divalent organic group having an aromatic ring group are preferably the fluorine atom and/or the trifluoromethyl group, with the fluorine atom being the most preferable.

According to a particular embodiment, another group represented by $Y^1$ is preferably a divalent organic group represented by Formula (5).

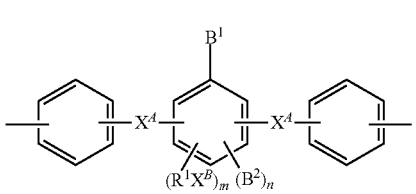

(5)

In Formula (5), $B^1$ represents $CF_3$ or CN. Each $B^2$, any or all of which may be the same or different, represents H, F, Cl, Br, or I. $R^1$ represents a halogen-substituted alkyl group comprising 1 to 20 carbon atoms. Each $X^A$, any or all of which may be the same or different, represents O or S. $X^B$ represents O or S. n represents the number of $B^2$s, and it is an integer from 0 to 2. m represents the number of substitution for a group represented by $R^1X^B$, which is an integer from 1 to 3. The sum of n and m is 3.

According to a particular embodiment, diamine represented by Formula (2), wherein $Y^0$ represents $Y^1$ and $Y^1$ is a group represented by Formula (5), is taught in International Publication WO 2010/150908.

According to a particular embodiment, in Formula (5), $R^1$ represents a halogen-substituted alkyl group. The halogen-substituted alkyl group is a group resulting from substitution of at least a part of the hydrogen atom bound to the carbon atom constituting an alkyl group with the halogen atom, the structure thereof is not particularly limited, and it may be in any form of linear, branched, or cyclic alkyl group. Alternatively, a halogen-substituted alkyl group may comprise an ether bond in it.

In the above embodiment, the halogen atom is preferably the fluorine atom (F), the chlorine atom (Cl), the bromine atom (Br), or the iodine atom (I), and the alkyl group may be substituted with two or more such atoms. $R^1$ preferably represents a fluorine-substituted alkyl group having 1 to 20 carbon atoms.

According to a particular embodiment, $R^1$ more preferably has 2 to 18 carbon atoms, and further preferably 3 to 15 carbon atoms.

An example of a particularly preferable group represented by $R^1$ is at least one member selected from the groups represented by the chemical formulae shown below.

$CF_3-(CF_2)_7-(CH_2)_2-$ $CF_3-(CF_2)_9-(CH_2)_2-$ $CF_3-(CF_2)_2-CH_2-$ $CF_3-(CF_2)_3-CH_2-$ $CHF_2-(CF_2)_7-CH_2-$ $(CF_3)_2-CF(CF_2)_2-(CH_2)_2-$ $CF_3CH_2-$ $HCF_2CH_2-$ $F(CF_2)_2CH_2-$ $CHF_2CF_2CH_2-$ $(CF_3)_2CH-$ $CF_3CH_2CH_2-$ $H(CF_2)_2CH_2-$ $Cl(CF_2)_2CH_2-$ $(CF_3)C(CH_3)H-$ $F(CF_2)_3CH_2-$ $F(CF_2)_2(CH_2)_2-$ $CF_3CHFCF_2CH_2-$ $CF_3(CH_2)_3-$ $F(CF_2)_2C(CH_3)H-$ $CF_3C(CH_3)_2-$ $CH_3C(CF_3)_2-$ $(CF_3)_4C-$ $(CF_3)_2C(CCl_3)-$ $F(CF_2)_4CH_2-$ $F(CF_2)_3(CH_2)_2-$ $F(CF_2)_2(CH_2)_3-$ $CF_3(CH_2)_4-$ $(CF_3)_2CFCH_2CH_2-$ $(CF_3)_2C(CH_3)CH_2-$

H(CF$_2$)$_4$CH$_2$—

Cl(CF$_2$)$_4$CH$_2$—

Br(CF$_2$)$_2$(CH$_2$)$_3$—

CF$_3$CH$_2$CH(CH$_3$)CH$_2$—

CF$_3$CF(OCF$_3$)CH$_2$CH$_2$—

(CF$_3$)$_2$CHOCH$_2$CH$_2$—

F(CF$_2$)$_3$C(CH$_3$)H—

F(CF$_2$)$_5$CH$_2$—

F(CF$_2$)$_4$(CH$_2$)$_2$—

F(CF$_2$)$_3$(CH$_2$)$_3$—

F(CF$_2$)$_2$(CH$_2$)$_4$—

(CF$_3$)$_2$CF(CH$_2$)$_3$—

(CF$_3$)$_3$CCH$_2$CH$_2$—

CF$_3$CF(OCF$_3$)(CH$_2$)$_3$—

F(CF$_2$)$_{30}$CF(CF$_3$)CH$_2$—

H(CF$_2$)$_5$CH$_2$—

F(CF$_2$)$_2$C(CH$_3$)$_2$—

CF$_3$CHFCF$_2$C(CH$_3$)$_2$—

F(CF$_2$)$_6$CH$_2$—

F(CF$_2$)$_5$(CH$_2$)$_2$—

F(CF$_2$)$_4$(CH$_2$)$_3$—

(CF$_3$)$_2$CF(CF$_2$)$_2$(CH$_2$)$_2$—

(CF$_3$)$_2$CFCHFCF(CF$_3$)CH$_2$—

CF$_3$CF$_2$CF(CF$_3$)(CH$_2$)$_3$—

H(CF$_2$)$_6$CH$_2$—

Cl(CF$_2$)$_6$CH$_2$—

F(CF$_2$)$_7$CH$_2$—

F(CF$_2$)$_6$(CH$_2$)$_2$—

F(CF$_2$)$_5$(CH$_2$)$_3$—

F(CF$_2$)$_4$(CH$_2$)$_4$—

F(CF$_2$)$_2$(CH$_2$)$_6$—

F(CF$_2$)$_{30}$CF(CF$_3$)(CH$_2$)$_3$—

(CF$_3$)$_3$C(CH$_2$)$_4$—

H(CF$_2$)$_7$CH$_2$—

F(CF$_2$)$_5$CH$_2$—

F(CF$_2$)$_6$(CH$_2$)$_3$—

(CF$_3$)$_2$CF(CH$_2$)$_6$—

(CF$_3$)$_2$CF(CF$_2$)$_4$(CH$_2$)$_2$—

F(CF$_2$)$_{30}$CF(CF$_3$)CF$_2$OCF(CF$_3$)CH$_2$—

H(CF$_2$)$_8$CH$_2$—

F(CF$_2$)$_4$(CH$_2$)$_6$—

CF$_3$(CF$_2$)$_7$(CH$_2$)$_2$—

F(CF$_2$)$_8$(CH$_2$)$_3$—

(CF$_3$)$_2$CF(CF$_2$)$_6$(CH$_2$)$_2$—

H(CF$_2$)$_{10}$CH$_2$—

F(CF$_2$)$_6$(CH$_2$)$_6$—

F(CF$_2$)$_{10}$(CH$_2$)$_2$—

H(CF$_2$)$_{12}$CH$_2$—

F(CF$_2$)$_8$(CH$_2$)$_6$—

In Formula (5), m is an integer from 1 to 3, and preferably an integer of 2 or 3.

In Formula (5), it is preferable that both $X^4$s represent O or S and it is most preferable that both $X^4$s represent O.

In Formula (5), each $B^2$, any or all of which may be the same or different, represents H, F, Cl, Br, or I, and at least one $B^2$ preferably represents a halogen atom (F, Cl, Br, or I). It is particularly preferable that, in Formula (5), two $B^2$s each represent a halogen atom. Among halogen atoms, a chlorine atom (Cl) or a fluorine atom (F) is preferable, and a fluorine atom (F) is more preferable. It is particularly preferable that, in Formula (5), two $B^2$s each represent a fluorine atom (F). An embodiment in which $B^2$ represents F (i.e., the fluorine atom) is within the scope of preferable embodiments of the present invention.

Other examples of $Y^1$ include divalent groups represented by Formula (D) described in detail in the section "1.1.5.3. Fluorine-containing polyimide comprising biphenyl group" below. More preferably, $Y^1$ represents a divalent group represented by any of Formulae ($D^1$) to ($D^6$).

According to a particular embodiment, $Z^1$, $Z^2$, $Z^3$, $Z^4$, $Z^5$, and $Z^6$, which may be the same or different, are each independently selected from among a hydrogen atom, a fluorine atom, a chlorine atom, a bromine atom, and an iodine atom. When $X^1$ or $Y^1$ does not include a fluorine atom, at least one of $Z^1$, $Z^2$, $Z^3$, $Z^4$, $Z^5$, and $Z^6$ represents the fluorine atom.

According to a particular embodiment, it is sufficient if a main chain of at least either $X^1$ or $Y^1$ comprises ether bonds and/or thioether bonds. More preferably, the main chain of $Y^1$ may comprise ether bonds and/or thioether bonds, and the main chain of $X^1$ may or may not comprise ether bonds and/or thioether bonds.

According to a further preferable embodiment of a repeating unit represented by Formula (I), p is 1, $X^1$ is an alkylene group comprising a fluorine atom, or an aryleneoxy group, which may comprise a fluorine atom, $Z^1$, $Z^2$, $Z^3$, $Z^4$, $Z^5$, and $Z^6$ each independently represent a fluorine atom or hydrogen atom, and $Y^1$ represents the organic group described above.

According to a further preferable embodiment of a repeating unit represented by Formula (I), p is 1, $X^1$ is an alkylene group comprising a fluorine atom, or an aryleneoxy group, which may comprise a fluorine atom, $Z^1$, $Z^2$, $Z^3$, $Z^4$, $Z^5$, and $Z^6$ each independently represent a fluorine atom or hydrogen atom, and $Y^1$ represents an organic group comprising 1 or 2 ether bonds.

According to a further preferable embodiment of a repeating unit represented by Formula (I), $X^1$ is preferably Group x1:

—C(CF$_3$)$_2$—,

Group x2

[chemical structure]

or

Group x3

[chemical structure]

all of $Z^1$, $Z^2$, $Z^3$, $Z^4$, $Z^5$, and $Z^6$ are preferably hydrogen atoms or fluorine atoms, and $Y^1$ is particularly preferably at least one member selected from Groups y1 to y9 shown below:

Group y1

[chemical structure]

Group y2

[chemical structure]

Group y3

[chemical structure]

Group y4

[chemical structure]

Group y5

[chemical structure]

Group y6

[chemical structure]

Group y7

[chemical structure]

Group y8

[chemical structure]

Group y9

[chemical structure]

It should be noted that at least one of $X^1$, $Y^1$, $Z^1$, $Z^2$, $Z^3$, $Z^4$, $Z^5$, and $Z^6$ comprises a fluorine atom.

According to a particular embodiment, when $X^1$ is Group x1 that does not comprise ether bonds, $Y^1$ is limited to Groups y1 to y6 that comprise ether bonds.

According to this embodiment, it is particularly preferable that $Y^1$ be any of y1 to y6.

According to the embodiment above, all of $Z^1$, $Z^2$, $Z^3$, $Z^4$, $Z^5$, and $Z^6$ are preferably hydrogen atoms when $X^1$ is Group x1, and all of $Z^1$, $Z^2$, $Z^3$, $Z^4$, $Z^5$, and $Z^6$ are preferably fluorine atoms when $X^1$ is Group x2 or x3.

According to the embodiment above, it is more preferable that $X^1$ be Group x1.

[chemical structure]

Group x2 is preferably Group x2-1.

[chemical structure]

Group x3 is preferably Group x3-1.

[chemical structure]

Group y1 is preferably Group y1-1:

[chemical structure]

or Group y1-2;

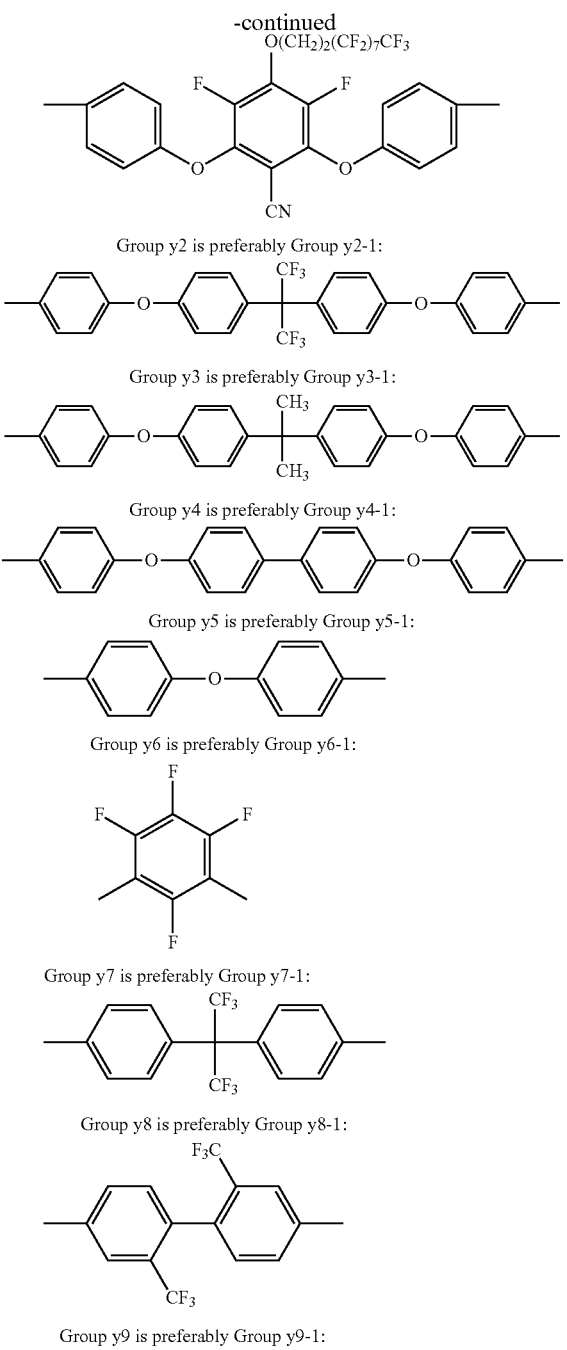

In the acid dianhydrides represented by Formula (1) used for the production of polyamide acids having the structures described above, the proportion of acid dianhydrides represented by a formula in which $X^0$ is a group represented by Formula ($E^1$) is not particularly limited. Other acid dianhydrides can be used in combination, provided that properties of the acid dianhydrides represented by a formula in which $X^0$ is a group represented by Formula ($E^1$) are exerted. When the total amount of acid dianhydride used is 100% by mole, the amount of the acid dianhydride represented by a formula in which $X^0$ is a group represented by Formula ($E^1$) is preferably 25% by mole or more, more preferably 50% by mole or more, further preferably 80% by mole or more, and most preferably 100% by mole. Other acid dianhydrides that can be used are not particularly limited. Examples thereof include acid dianhydride represented by a formula in which $X^0$ is a group represented by Formula ($E^2$) below, acid dianhydride represented by a formula in which $X^0$ is a group represented by Formula ($E^3$) below, and acid dianhydride represented by a formula in which $X^0$ is a group represented by Formula ($E^4$) below. When the total amount of acid dianhydride used is 100% by mole, the total amount of acid dianhydride represented by a formula in which $X^0$ is a group represented by Formula ($E^1$), acid dianhydride represented by a formula in which $X^0$ is a group represented by Formula ($E^2$), acid dianhydride represented by a formula in which $X^0$ is a group represented by Formula ($E^3$), and acid dianhydride represented by a formula in which $X^0$ is a group represented by Formula ($E^4$) is more preferably 90% by mole or more, and most preferably 100% by mole.

In the acid dianhydrides represented by Formula (1) used for the production of polyamide acids having the structures described above according to another particular embodiment, the proportion of acid dianhydrides represented by a formula in which $X^0$ is a group represented by Formula ($E^1$) is not particularly limited. Other acid dianhydrides can be used in combination, provided that properties of the acid dianhydride represented by a formula in which $X^0$ is a group represented by Formula ($E^1$) are exerted. When the total amount of acid dianhydride used is 100% by mole, the amount of the acid dianhydride represented by a formula in which $X^0$ is a group represented by Formula ($E^1$) is preferably 25% by mole or more, more preferably 50% by mole or more, further preferably 80% by mole or more, and most preferably 100% by mole. Other acid dianhydrides that can be used are not particularly limited. Examples thereof include acid dianhydride represented by a formula in which $X^0$ is a group represented by Formula ($E^3$) below and acid dianhydride represented by a formula in which $X^0$ is a group represented by Formula ($E^4$) below. When the total amount of acid dianhydride used is 100% by mole, the total amount of the acid dianhydride represented by a formula in which $X^0$ is a group represented by Formula ($E^1$), the acid dianhydride represented by a formula in which $X^0$ is a group represented by Formula ($E^3$), and acid dianhydride represented by a formula in which $X^0$ is a group represented by Formula ($E^4$) is more preferably 90% by mole or more, and most preferably 100% by mole.

In the diamines represented by Formula (2) used for the production of polyamide acids having the structures described above, the proportion of diamines represented by a formula in which $Y^0$ is $Y^1$ is not particularly limited. Other diamines can be used in combination, provided that properties of the diamine represented by a formula in which $Y^0$ is $Y^1$ are exerted. When the total amount of diamine used is 100% by mole, the amount of the diamine represented by a formula in which $Y^0$ is $Y^1$ is preferably 25% by mole or more, more preferably 50% by mole or more, further preferably 80% by mole or more, and most preferably 100% by mole. Other diamines that can be used are not particularly limited. Examples thereof include diamine represented by a formula in which $Y^0$ is $Y^2$ described below, diamine represented by a formula in which $Y^0$ is $Y^3$ described below, and diamine represented by a formula in which $Y^0$ is $Y^4$ described below. When the total amount of diamine used is 100% by mole, the total amount of the diamine represented by a formula in which $Y^0$ is $Y^1$, the diamine represented by a formula in which $Y^0$ is $Y^2$, the diamine represented by a formula in which $Y^0$ is $Y^3$, and the diamine represented by a formula in which $Y^0$ is $Y^4$ is more preferably 90% by mole or more, and most preferably 100% by mole.

According to another particular embodiment, in the diamines represented by Formula (2) used for the production of polyamide acids having the structures described above, the proportion of diamines represented by a formula in which $Y^0$ is a group represented by Formula (D) is not particularly limited. Other diamines can be used in combination, provided that properties of the diamine represented by a formula in which $Y^0$ is a group represented by Formula (D) are exerted. When the total amount of diamine used is 100% by mole, the amount of the diamine represented by a formula in which $Y^0$ is a group represented by Formula (D) is preferably 25% by mole or more, more preferably 50% by mole or more, further preferably 80% by mole or more, and most preferably 100% by mole.

$X^1$, $Y^1$, $Z^1$, $Z^2$, $Z^3$, $Z^4$, $Z^5$, and $Z^6$ in Formulae (1) and (2) are as defined above with respect to Formula (I).

Alternatively, $X^1$, D, $Z^1$, $Z^2$, $Z^3$, $Z^4$, $Z^5$, and $Z^6$ in Formulae (1) and (2) are as defined above with respect to Formula (I).

1.1.1.2. Aliphatic Polyamide Acid

In the present invention, aliphatic polyamide acid resin can be employed instead of or together with aromatic polyamide acid resin from the viewpoint of coloration.

For example, aliphatic polyamide acid resin is a polymerization product of (1) aromatic diamine with aliphatic acid dianhydride, (2) aliphatic diamine with aromatic acid dianhydride, or (3) aliphatic diamine with aliphatic acid dianhydride. Aliphatic polyamide acid resin preferably comprises aromatic or aliphatic diamine and acid dianhydride, and either or both thereof comprise(s) at least one fluorine atom and at least one aliphatic structure in molecules thereof. The aliphatic polyamide acid resin is preferably at least one type of aliphatic polyamide acid resin comprising the structure shown in any of Formulae (II) to (IV).

Aliphatic polyamide acid represented by Formula (II): Aliphatic polyamide acid is preferably polyamide acid resulting from polymerization of at least one acid dianhydride with at least one diamine, wherein the acid dianhydride used for the polymerization at least comprises acid dianhydride represented by Formula (1) in which $X^0$ is a group represented by Formula ($E^2$),

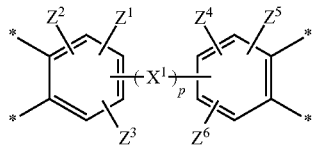

and the diamine used for the polymerization at least comprises diamine represented by Formula (2) in which $Y^0$ is $Y^2$. The polyamide acid preferably comprises a polymerization unit represented by Formula (II):

(II)

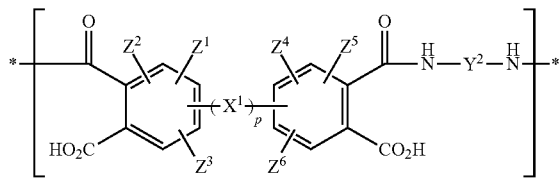

wherein $X^2$ represents a divalent organic group; $Y^2$ represents a divalent organic group having an aliphatic group; $Z^1$, $Z^2$, $Z^3$, $Z^4$, $Z^5$, and $Z^6$ each independently represent either a hydrogen atom, fluorine atom, chlorine atom, bromine atom, or iodine atom; at least one of $X^2$, $Y^2$, $Z^1$, $Z^2$, $Z^3$, $Z^4$, $Z^5$, and $Z^6$ contains one or more fluorine atoms; and p is 0 or 1.

According to a particular embodiment, at least either $X^2$ or $Y^2$ comprises one or more ether bonds and/or thioether bonds in its main chain. When $X^2$ comprises ether bonds and/or thioether bonds, an oxygen atom or sulfur atom is present in $X^2$ at a site at which $X^2$ binds to a ring-membered carbon atom of at least one of the two benzene rings located adjacent to $X^2$, and ether bonds and/or thioether bonds may be formed between the ring-membered carbon atom and an atom in $X^2$ adjacent to the oxygen or sulfur atom of $X^2$. Alternatively, $X^2$ may represent —O— or —S— and ether bonds and/or thioether bonds may be formed between ring-membered carbon atoms of two adjacent benzene rings. The term "main chain" refers to a chain comprising the largest number of atoms connected to each other in a single polymer molecule.

In Formulae (II) and ($E^2$), when p is 0, $X^2$ does not exist, and benzene rings located on the right and on the left of $X^2$ are directly bound to each other. When p is 1, benzene rings located on the right and on the left of $X^2$ are bound to each other through $X^2$.

A divalent organic group represented by $X^2$ can be the same as the group represented by $X^1$ above.

In Formulae (II) and ($E^2$), a divalent organic group having an aliphatic group represented by $Y^2$ is not particularly limited. Examples thereof include a group comprising one alicyclic group, or two or more alicyclic groups bound to each other via a carbon atom, an oxygen atom, or a sulfur atom or directly bound to each other. A specific example is at least one member selected from the following group:

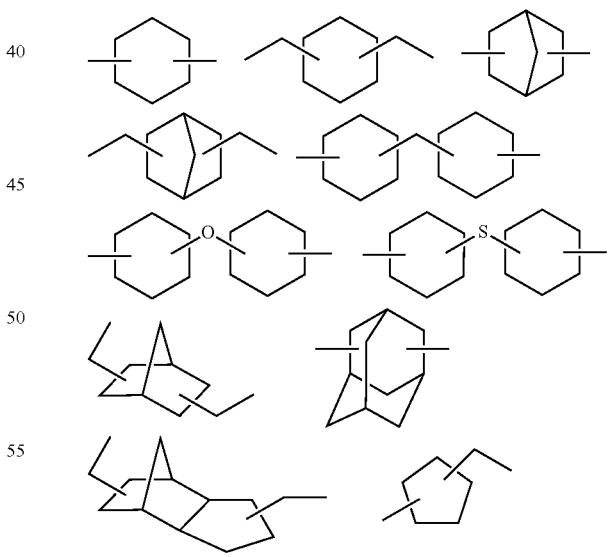

The divalent organic group having an aliphatic group, which is an example of $Y^2$, may be substituted with at least one member selected from the group consisting of a halogen atom (e.g., a fluorine atom, a chlorine atom, a bromine atom, or an iodine atom, with the fluorine atom or chlorine atom being preferable and the fluorine atom being more preferable), a methyl group, and a trifluoromethyl group, if possible. The number of such substituents may be greater than 1, and substituents of the same type or different types may be employed in such a case. When $X^2$ does not include a fluorine atom, in particular, substituents for the divalent organic group having an aliphatic group are preferably the fluorine atom and/or the trifluoromethyl group, with the fluorine atom being the most preferable.

In Formulae (II) and ($E^2$), $Z^1$, $Z^2$, $Z^3$, $Z^4$, $Z^5$, and $Z^6$, which may be the same or different, are each independently selected from among a hydrogen atom, a fluorine atom, a chlorine atom, a bromine atom, and an iodine atom. When either $X^2$ or $Y^2$ does not contain a fluorine atom, at least one of $Z^1$, $Z^2$, $Z^3$, $Z^4$, $Z^5$, and $Z^6$ is a fluorine atom.

At least one of $X^2$, $Y^2$, $Z^1$, $Z^2$, $Z^3$, $Z^4$, $Z^5$, and $Z^6$ preferably comprises one or more fluorine atoms, $X^2$ is preferably an alkylene group containing a fluorine atom, $Y^2$ is preferably the aliphatic group described above, and all of $Z^1$, $Z^2$, $Z^3$, $Z^4$, $Z^5$, and $Z^6$ are more preferably hydrogen atoms.

According to a particular embodiment, it is sufficient for a main chain of at least either $X^2$ or $Y^2$ to comprise ether bonds and/or thioether bonds.

In the acid dianhydrides represented by Formula (1) used for the production of polyamide acids having the structures described above, the proportion of acid dianhydrides represented by a formula in which $X^0$ is a group represented by Formula ($E^2$) is not particularly limited. Other acid dianhydrides can be used in combination, provided that properties of the acid dianhydride represented by a formula in which $X^0$ is a group represented by Formula ($E^2$) are exerted. When the total amount of acid dianhydride used is 100% by mole, the amount of the acid dianhydride represented by a formula in which $X^0$ is a group represented by Formula ($E^2$) is preferably 25% by mole or more, more preferably 50% by mole or more, further preferably 80% by mole or more, and most preferably 100% by mole. Other acid dianhydrides that can be used are not particularly limited. Examples thereof include acid dianhydride represented by a formula in which $X^0$ is a group represented by Formula ($E^1$) above, acid dianhydride represented by a formula in which $X^0$ is a group represented by Formula ($E^3$) below, and acid dianhydride represented by a formula in which $X^0$ is a group represented by Formula ($E^4$) below. When the total amount of acid dianhydride used is 100% by mole, the total amount of acid dianhydride represented by a formula in which $X^0$ is a group represented by Formula ($E^1$), acid dianhydride represented by a formula in which $X^0$ is a group represented by Formula ($E^2$), acid dianhydride represented by a formula in which $X^0$ is a group represented by Formula ($E^3$), and acid dianhydride represented by a formula in which $X^0$ is a group represented by Formula ($E^4$) is more preferably 90% by mole or more, and most preferably 100% by mole.

In the diamines represented by Formula (2) used for the production of polyamide acids having the structures described above, the proportion of diamines represented by a formula in which $Y^0$ is $Y^2$ is not particularly limited. Other diamines can be used in combination, provided that properties of the diamine represented by a formula in which $Y^0$ is $Y^2$ are exerted. When the total amount of diamine used is 100% by mole, the amount of the diamine represented by a formula in which $Y^0$ is $Y^2$ is preferably 25% by mole or more, more preferably 50% by mole or more, further preferably 80% by mole or more, and most preferably 100% by mole. Other diamines that can be used are not particularly limited. Examples thereof include diamine represented by a formula in which $Y^0$ is $Y^1$ described above, diamine represented by a formula in which $Y^0$ is $Y^3$ described below, and diamine represented by a formula in which $Y^0$ is $Y^4$ described below. When the total amount of diamine used is 100% by mole, the total amount of the diamine represented by a formula in which $Y^0$ is $Y^1$, the diamine represented by a formula in which $Y^0$ is $Y^2$, the diamine represented by a formula in which $Y^0$ is $Y^3$, and diamine represented by a formula in which $Y^0$ is $Y^4$ is more preferably 90% by mole or more, and most preferably 100% by mole.

$X^2$, $Y^2$, $Z^1$, $Z^2$, $Z^3$, $Z^4$, $Z^5$, and $Z^6$ in Formulae (1) and (2) are as defined above with respect to Formula (II).

Aliphatic Polyamide Acid Represented by Formula (III):

Aliphatic polyamide acid is preferably polyamide acid resulting from polymerization of at least one acid dianhydride with at least one diamine, wherein the acid dianhydride used for the polymerization at least comprises acid dianhydride represented by Formula (1) in which $X^0$ is a group represented by Formula ($E^3$):

and the diamine used for the polymerization at least comprises diamine represented by Formula (2) wherein $Y^0$ is $Y^3$ or a group represented by Formula (D). Such polyamide acid preferably comprises a polymerization unit as shown in any of Formula (III):

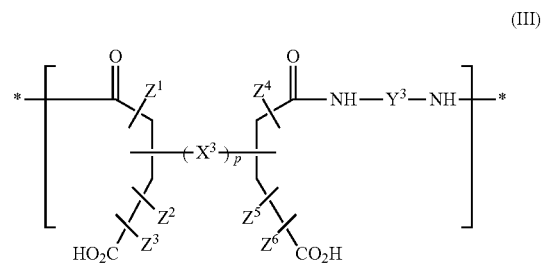

wherein $X^3$ represents a divalent organic group; $Y^3$ represents a divalent organic group having an aliphatic group or an aromatic group; $Z^1$, $Z^2$, $Z^3$, $Z^4$, $Z^5$, and $Z^6$ each independently represent either a hydrogen atom, fluorine atom, chlorine atom, bromine atom, or iodine atom; at least one of $X^3$, $Y^3$, $Z^1$, $Z^2$, $Z^3$, $Z^4$, $Z^5$, and $Z^6$ contains one or more fluorine atoms; and p is 0 or 1.

According to a particular embodiment, at least either $X^3$ or $Y^3$ comprises one or more ether bonds and/or thioether bonds in its main chain. When $X^3$ comprises ether bonds and/or thioether bonds, an oxygen atom or sulfur atom is present at a site in $X^3$ at which $X^3$ binds to a carbon atom of an ethylene group located adjacent to $X^3$, and ether bonds and/or thioether bonds may be formed between the carbon atom of the ethylene group and an atom in $X^3$ adjacent to the oxygen or sulfur atom of $X^3$. Alternatively, $X^3$ may represent —O— or —S— and ether bonds and/or thioether bonds may be formed between carbon atoms of two adjacent ethylene groups. The term "main chain" refers to a chain comprising the largest number of atoms connected to each other in a single polymer molecule.

Alternatively, the polyamide acid preferably comprises a polymerization unit represented by Formula (III):

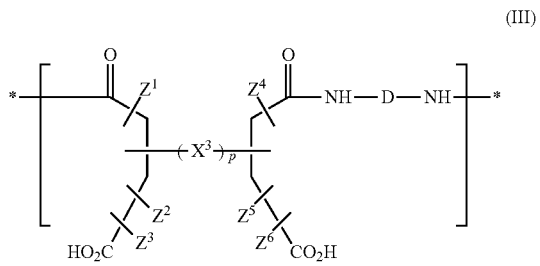
(III)

wherein $X^3$ represents a divalent organic group;

D is at least one type of divalent aromatic group represented by Formula (D) below, it is preferably a divalent aromatic group represented by any of Formulae ($D^1$) to ($D^6$), and it is more preferably a divalent aromatic group represented by Formula ($D^1$);

$Z^1$, $Z^2$, $Z^3$, $Z^4$, $Z^5$, and $Z^6$ each independently represent either a hydrogen atom, fluorine atom, chlorine atom, bromine atom, or iodine atom;

at least one of $X^3$, D, $Z^1$, $Z^2$, $Z^3$, $Z^4$, $Z^5$, and $Z^6$ contains at least one fluorine atom; and p is 0 or 1.

In Formulae (III) and ($E^3$), when p is 0, $X^3$ does not exist, and ethylene groups located on the right and on the left of $X^3$ are directly bound to each other. When p is 1, ethylene groups located on the right and on the left of $X^3$ are bound to each other through $X^3$. A divalent organic group represented by $X^3$ is preferably a divalent organic group having an aliphatic group, and an aliphatic hydrocarbon group having 1 to 40 carbon atoms is particularly preferable. When the organic group comprises two or more ring structures, the organic group has at least one type of structure selected from the group consisting of a polycyclic structure in which rings share one or more bonds, a spirohydrocarbon structure, and a structure in which rings are bound to each other via a binding group, such as in the form of a single bond. The binding group can be, for example, at least one member selected from the group consisting of an ether bond, a thioether group, a ketone group, an ester bond, a sulfonyl group, an alkylene group, an amide group, and a siloxane group, in addition to the single bond. A divalent organic group represented by $X^3$ is preferably at least one member selected from, for example, the following group.

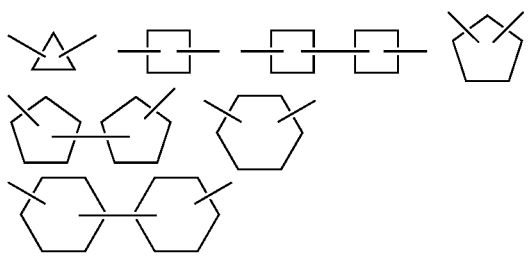

A divalent organic group, which is an example of $X^3$ (when p is 1), may be substituted with at least one member selected from the group consisting of a halogen atom (e.g., a fluorine atom, a chlorine atom, a bromine atom, or an iodine atom, with the fluorine atom or chlorine atom being preferable and the fluorine atom being more preferable), a methyl group, and a trifluoromethyl group. The number of such substituents may be greater than 1, and substituents of the same type or different types may be employed in such a case.

According to a particular embodiment, $Y^3$ represents a divalent organic group having an aliphatic group or an aromatic group, which can be the same group as described with respect to $X^1$, $Y^1$, $Y^2$, or $X^3$.

In Formulae (III) and ($E^3$), $Z^1$, $Z^2$, $Z^3$, $Z^4$, $Z^5$, and $Z^6$, which may be the same or different, are each independently selected from among a hydrogen atom, a fluorine atom, a chlorine atom, a bromine atom, and an iodine atom. When either $X^3$ or $Y^3$ does not contain a fluorine atom, at least one of $Z^1$, $Z^2$, $Z^3$, $Z^4$, $Z^5$, and $Z^6$ is a fluorine atom.

According to a particular embodiment, it is sufficient if a main chain of at least either $X^3$ or $Y^3$ comprises ether bonds and/or thioether bonds.

When either $X^3$ or D does not contain a fluorine atom according to another embodiment, at least one of $Z^1$, $Z^2$, $Z^3$, $Z^4$, $Z^5$, and $Z^6$ is a fluorine atom.

In the acid dianhydrides represented by Formula (1) used for the production of polyamide acids having the structures described above, the proportion of acid dianhydrides represented by a formula in which $X^0$ is a group represented by Formula ($E^3$) is not particularly limited. Other acid dianhydrides can be used in combination, provided that properties of the acid dianhydride represented by a formula in which $X^0$ is a group represented by Formula ($E^3$) are exerted. When the total amount of acid dianhydride used is 100% by mole, the amount of the acid dianhydride represented by a formula in which $X^0$ is a group represented by Formula ($E^3$) is preferably 25% by mole or more, more preferably 50% by mole or more, further preferably 80% by mole or more, and most preferably 100% by mole. Other acid dianhydrides that can be used are not particularly limited. Examples thereof include acid dianhydride represented by a formula in which $X^0$ is a group represented by Formula ($E^1$), acid dianhydride represented by a formula in which $X^0$ is a group represented by Formula ($E^2$), and acid dianhydride represented by a formula in which $X^0$ is a group represented by Formula ($E^4$). When the total amount of acid dianhydride used is 100% by mole, the total amount of the acid dianhydride represented by a formula in which $X^0$ is a group represented by Formula ($E^1$), the acid dianhydride represented by a formula in which $X^0$ is a group represented by Formula ($E^2$), the acid dianhydride represented by a formula in which $X^0$ is a group represented by Formula ($E^3$), and the acid dianhydride represented by a formula in which $X^0$ is a group represented by Formula ($E^4$) is more preferably 90% by mole or more, and most preferably 100% by mole.

In the diamines represented by Formula (2) used for the production of polyamide acids having the structures described above, the proportion of diamines represented by a formula in which $Y^0$ is $Y^3$ is not particularly limited. Other diamines can be used in combination, provided that properties of the diamine represented by a formula in which $Y^0$ is Y3 are exerted. When the total amount of diamine used is 100% by mole, the amount of the diamine represented by a formula in which $Y^0$ is $Y^3$ is preferably 25% by mole or more, more preferably 50% by mole or more, further preferably 80% by mole or more, and most preferably 100% by mole. Other diamines that can be used are not particularly limited. Examples thereof include diamine represented by a formula in which $Y^0$ is $Y^1$, diamine represented by a formula in which $Y^0$ is $Y^2$, and diamine represented by a formula in which $Y^0$ is $Y^4$. When the total amount of diamine used is 100% by mole, the total amount of the diamine represented by a formula in which $Y^0$ is $Y^1$, the diamine represented by a formula in which $Y^0$ is $Y^2$, the diamine represented by a formula in which $Y^0$ is $Y^3$, and the diamine represented by a formula in which $Y^0$ is $Y^4$ is more preferably 90% by mole or more, and most preferably 100% by mole.

$X^3$, $Y^3$, $Z^1$, $Z^2$, $Z^3$, $Z^4$, $Z^5$, and $Z^6$ in Formulae (1) and (2) are as defined above with respect to Formula (III).

In the diamines represented by Formula (2) used for the production of polyamide acids having the structures described above according to another embodiment, the proportion of diamine represented by a formula in which $Y^0$ is a group represented by Formula (D) is not particularly limited. Other diamines can be used in combination, provided that properties of the diamine represented by a formula in which $Y^0$ is a group represented by Formula (D) are exerted. When the total amount of diamine used is 100% by mole, the amount of the diamine represented by a formula in which $Y^0$ is a group represented by Formula (D) is preferably 25% by mole or more, more preferably 50% by mole or more, further preferably 80% by mole or more, and most preferably 100% by mole.

$X^3$, D, $Z^1$, $Z^2$, $Z^3$, $Z^4$, $Z^5$, and $Z^6$ in Formulae (1) and (2) are as defined above with respect to Formula (III).

Aliphatic Polyamide Acid Represented by Formula (IV):

A preferable aliphatic polyamide acid is obtained via polymerization of at least one acid dianhydride with at least one diamine, wherein the acid dianhydride used for the polymerization at least comprises an acid dianhydride represented by Formula (1), wherein $X^0$ represents a group represented by Formula ($E^4$),

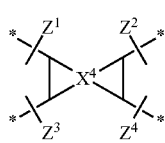

and the diamine used for the polymerization at least comprises diamine represented by Formula (2), wherein $Y^0$ is $Y^4$ described below or a group represented by Formula (D). The polyamide acid preferably comprises a polymerization unit represented by Formula (IV) below:

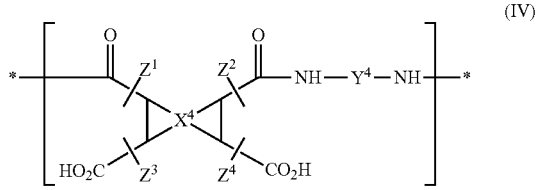

wherein $X^4$ represents a tetravalent organic group comprising an aliphatic group and $Y^4$ represents a divalent organic group having an aliphatic group or an aromatic group; $Z^1$, $Z^2$, $Z^3$, and $Z^4$ each independently represent either a hydrogen atom, fluorine atom, chlorine atom, bromine atom, or iodine atom; and at least one of $X^4$, $Y^4$, $Z^1$, $Z^2$, $Z^3$, and $Z^4$ comprises at least one fluorine atom.

According to a particular embodiment, at least either $X^4$ or $Y^4$ comprises one or more ether bonds and/or thioether bonds in its main chain. When $X^4$ comprises ether bonds and/or thioether bonds, an oxygen atom or sulfur atom is present at a site in $X^4$ at which $X^4$ binds to a carbon atom of an ethylene group located adjacent to $X^4$, and ether bonds and/or thioether bonds may be formed between the carbon atom of the ethylene group and an atom in $X^4$ adjacent to the oxygen or sulfur atom of $X^4$. Alternatively, $X^4$ may represent —O— or —S— and ether bonds and/or thioether bonds may be formed between carbon atoms of two adjacent ethylene groups. The term "main chain" refers to a chain comprising the largest number of atoms connected to each other in a single polymer molecule.

Alternatively, the polyamide acid according to another embodiment preferably comprises a polymerization unit represented by Formula (IV) below:

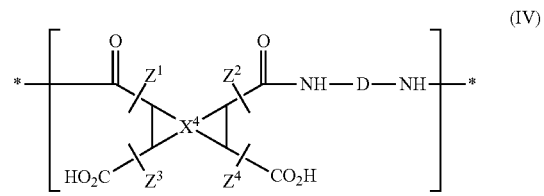

wherein $X^4$ represents a tetravalent organic group comprising an aliphatic group.

D is at least one type of divalent aromatic group represented by Formula (D) below, it is preferably a divalent aromatic group represented by any of Formulae ($D^1$) to ($D^6$), and it is more preferably a divalent aromatic group represented by Formula ($D^1$).

$Z^1$, $Z^2$, $Z^3$, and $Z^4$ each independently represent either a hydrogen atom, fluorine atom, chlorine atom, bromine atom, or iodine atom.

At least one of $X^4$, D, $Z^1$, $Z^2$, $Z^3$, and $Z^4$ contains at least one fluorine atom.

A tetravalent organic group comprising an aliphatic group represented by $X^4$ is preferably an aliphatic hydrocarbon group having 1 to 40 carbon atoms. When the organic group comprises two or more ring structures, the organic group has at least one type of structure selected from the group consisting of a polycyclic structure in which rings share one or more bonds, a spirohydrocarbon structure, and a structure in which rings are bound to each other via a binding group, such as in the form of a single bond. The binding group can be, for example, at least one member selected from the group consisting of an ether bond, a thioether group, a ketone group, an ester bond, a sulfonyl group, an alkylene group, an amide group, and a siloxane group, in addition to the single bond. Specifically, $X^4$ is preferably at least one member selected from the groups shown below. The organic group may be substituted with at least one member selected from the group consisting of a halogen atom (e.g., a fluorine atom, a chlorine atom, a bromine atom, or an iodine atom, with the fluorine atom or chlorine atom being preferable and the fluorine atom being more preferable), a methyl group, and a trifluoromethyl group.

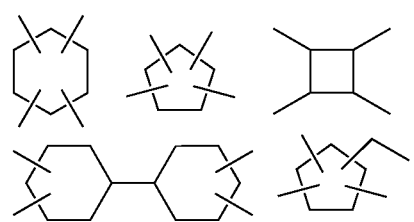

According to a particular embodiment, $Y^4$ is as defined above with respect to $Y^3$.

In Formulae (IV) and ($E^4$), $Z^1$, $Z^2$, $Z^3$, and $Z^4$, which may be the same or different, are each independently selected from among a hydrogen atom, a fluorine atom, a chlorine atom, a bromine atom, and an iodine atom. When either $X^4$ or $Y^4$ does not contain a fluorine atom, at least one of $Z^1$, $Z^2$, $Z^3$, and $Z^4$ is a fluorine atom. According to another embodiment, at least one of $Z^1$, $Z^2$, $Z^3$, and $Z^4$ is a fluorine atom when either $X^4$ or D does not contain a fluorine atom.

According to a particular embodiment, it is sufficient for a main chain of at least either $X^4$ or $Y^4$ to comprise ether bonds and/or thioether bonds.

In the acid dianhydrides represented by Formula (1) used for the production of polyamide acids having the structures described above, the proportion of acid dianhydrides represented by a formula in which $X^0$ is a group represented by Formula ($E^4$) is not particularly limited. Other acid dianhydrides can be used in combination, provided that properties of the acid dianhydride represented by a formula in which $X^0$ is a group represented by Formula ($E^4$) are exerted. When the total amount of acid dianhydride used is 100% by mole, the amount of the acid dianhydride represented by a formula in which $X^0$ is a group represented by Formula ($E^4$) is preferably 25% by mole or more, more preferably 50% by mole or more, further preferably 80% by mole or more, and most preferably 100% by mole. Other acid dianhydrides that can be used are not particularly limited. Examples thereof include the acid dianhydride represented by a formula in which $X^0$ is a group represented by Formula ($E^1$), the acid dianhydride represented by a formula in which $X^0$ is a group represented by Formula ($E^2$), and the acid dianhydride represented by a formula in which $X^0$ is a group represented by Formula ($E^3$). When the total amount of acid dianhydride used is 100% by mole, the total amount of the acid dianhydride represented by a formula in which $X^0$ is a group represented by Formula ($E^1$), the acid dianhydride represented by a formula in which $X^0$ is a group represented by Formula ($E^2$), the acid dianhydride represented by a formula in which $X^0$ is a group represented by Formula ($E^3$), and the acid dianhydride represented by a formula in which $X^0$ is a group represented by Formula ($E^4$) is more preferably 90% by mole or more, and most preferably 100% by mole.

In the diamines represented by Formula (2) used for the production of polyamide acids having the structures described above, the proportion of diamine represented by a formula in which $Y^0$ is $Y^4$ is not particularly limited. Other diamines can be used in combination, provided that properties of the diamine represented by a formula in which $Y^0$ is $Y^4$ are exerted. When the total amount of diamine used is 100% by mole, the amount of the diamine represented by a formula in which $Y^0$ is $Y^4$ is preferably 25% by mole or more, more preferably 50% by mole or more, further preferably 80% by mole or more, and most preferably 100% by mole. Other diamines that can be used are not particularly limited. Examples thereof include diamine represented by a formula in which $Y^0$ is $Y^1$, diamine represented by a formula in which $Y^0$ is $Y^2$, and diamine represented by a formula in which $Y^0$ is $Y^3$. When the total amount of diamine used is 100% by mole, the total amount of the diamine represented by a formula in which $Y^0$ is $Y^1$, the diamine represented by a formula in which $Y^0$ is $Y^2$, the diamine represented by a formula in which $Y^0$ is $Y^3$, and the diamine represented by a formula in which $Y^0$ is $Y^4$ is more preferably 90% by mole or more, and most preferably 100% by mole.

$X^4$, $Y^4$, $Z^1$, $Z^2$, $Z^3$, and $Z^4$ in Formulae (1) and (2) are as defined above with respect to Formula (IV).

In the diamines represented by Formula (2) used for the production of polyamide acids having the structures described above according to another embodiment, the proportion of diamine represented by a formula in which $Y^0$ is a group represented by Formula (D) is not particularly limited. Other diamines can be used in combination, provided that properties of the diamine represented by a formula in which $Y^0$ is a group represented by Formula (D) are exerted. When the total amount of diamine used is 100% by mole, the amount of the diamine represented by a formula in which $Y^0$ is a group represented by Formula (D) is preferably 25% by mole or more, more preferably 50% by mole or more, further preferably 80% by mole or more, and most preferably 100% by mole.

$X^4$, D, $Z^1$, $Z^2$, $Z^3$, and $Z^4$ in Formulae (1) and (2) are as defined above with respect to Formula (IV).

1.1.1.3. Method for Production of Fluorine-Containing Polyamide Acid

The polyamide acid represented by Formula (4) or Formula (I), (II), (III), or (IV), which is a specific example of Formula (4), can be produced through amidation of the aromatic or aliphatic acid dianhydride represented by Formula (1) and the aromatic or aliphatic diamine represented by Formula (2) in a solvent in accordance with a conventional technique. The acid dianhydride and the diamine compound used as starting materials may be adequately selected in accordance with the constitution of the polyamide acid resin of interest.

Examples of aromatic acid dianhydrides represented by Formula (1) include 3,3',4,4'-biphenyltetracarboxylic dianhydride, 2,3,3',4'-biphenyltetracarboxylic dianhydride, 4,4'-oxydiphthalic acid, 4,4'-[(2,3,5,6-tetrafluoro-1,4-phenylene) bis(oxy)]bis(3,5,6-trifluorophthalic anhydride) (10FEDAN), 4,4'-[(1,4-phenylene)bis(oxy)]bis(3,5,6-trifluorophthalic anhydride) (6F4HEDAN), and 4,4'-(hexafluoroisopropylidene)diphthalic anhydride (6FDA).

Examples of aliphatic acid dianhydrides represented by Formula (1) include cyclobutane-1,2,3,4-tetracarboxylic dianhydride, 1-carboxylmethyl-2,3,5-cyclopentanetricarboxylic acid-2,6:3,5-dianhydride, butane-1,2,3,4-tetracarboxylic dianhydride, and cyclohexane-1,2,4,5-tetracarboxylic dianhydride.

Examples of aromatic diamines represented by Formula (2) include p-phenylenediamine, m-phenylenediamine, 2,4-diaminotoluene, 2,5-diaminotoluene, 2,4-diaminoxylene, 2,4-diaminodurene, 4,4'-diaminodiphenylmethane, 4,4'-methylenebis(2-methylaniline), 4,4'-methylenebis(2-ethylaniline), 4,4'-methylenebis(2,6-dimethylaniline), 4,4'-methylenebis(2,6-diethylaniline), 4,4'-diaminodiphenyl ether (ODA), 3,4'-diaminodiphenyl ether, 3,3'-diaminodiphenyl ether, 2,4'-diaminodiphenyl ether, 4,4'-diaminodiphenyl sulfone, 3,3'-diaminodiphenyl sulfone, 4,4'-diaminobenzophenone, 3,3'-diaminobenzophenone, 4,4'-diaminobenzanilide, 4-aminophenyl-4'-aminobenzoate, benzidine, 3,3'-dihydroxybenzidine, 3,3'-dimethoxybenzidine, o-tolidine, m-tolidine, 2,2'-bis(trifluoromethyl)benzidine (TFMB), 1,4-bis(4-aminophenoxy)benzene (TPEQ), 1,3-bis(4-aminophenoxy)benzene (TPER), 1,3-bis(3-aminophenoxy)benzene, 4,4'-bis(4-aminophenoxy)biphenyl (BAPB), bis(4-(3-aminophenoxy)phenyl)sulfone, bis(4-(4-aminophenoxy)phenyl)sulfone, 2,2-bis(4-(4-aminophenoxy)phenyl)propane (BAPP), 2,2-bis(4-(4-aminophenoxyl)phenyl)hexafluoropropane (HFBAPP), 2,2-bis(4-aminophenyl)hexafluoropropane (6FAP), 1,3-diamino-2,4,5,6-tetrafluorobenzene (4FMPD), and 2,6-bis(4-aminophenoxy)-3,5-difluoro-4-(1H,1H,2H,2H-heptadecafluoro-n-decanoxy)benzonitrile (AFDM).

According to a particular embodiment, examples of aromatic diamines represented by Formula (2) include 2,2'-bis(trifluoromethyl)benzidine (TFMB), 2,2'-dimethyl-4.4'-diaminobiphenyl, 3,3'-dihydroxy-4,4'-diaminobiphenyl, O-tolidinesulfone, O-tolidinedisulfonic acid, and 2,2'-dimethoxy-4.4'-diaminobiphenyl.

Examples of aromatic diamines represented by Formula (2) include diamine compounds represented by Formula (IX), which are described in detail in the section "1.1.5.3. Fluorine-containing polyimide having biphenyl group" below, and more preferable examples include diamine compounds represented by Formulae (IX-1) to (IX-6).

Examples of aliphatic diamines represented by Formula (2) include 4,4'-methylenebis(cyclohexylamine), isophorone diamine, 2,5-bis(aminomethyl)bicyclo[2.2.1]heptane, 2,6-bis(aminomethyl)bicyclo[2.2.1]heptane, 3,8-bis(aminomethyl)tricyclo[5.2.1.0]decane, 1,3-diaminoadamantane, 2,2-bis(4-aminocyclohexyl)propane, and 2,2-bis(4-aminocyclohexyl)hexafluoropropane.

Also, aliphatic or aromatic diamine represented by Formula (2) may be at least one compound selected from the compounds shown below.

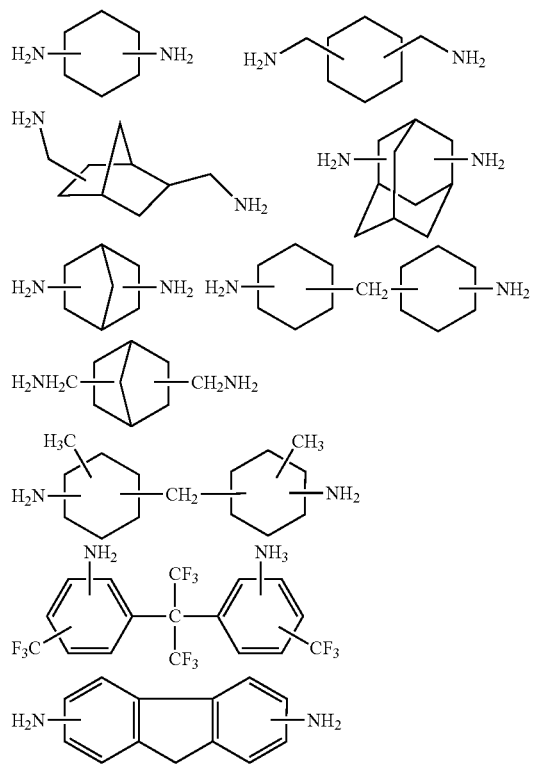

Amidation proceeds by, for example, agitating a solution of acid dianhydride and diamine dissolved in a solvent in an inert gas atmosphere (e.g., nitrogen) at room temperature to prepare a homogenous solution. A solvent may be adequately selected in accordance with acid dianhydride and diamine used as starting materials. After the completion of amidation, the resulting reaction mixture contains polyamide acid in a solvent. Such reaction mixture can be subjected to thermal imidization or chemical imidization without any other processing. Alternatively, the generated polyamide acid may be separated from the reaction mixture, it may be dissolved again in an adequate solvent, and the resultant may then be subjected to thermal imidization or chemical imidization.

It is preferable that amidation be carried out in an organic solvent. The organic solvent is not particularly limited, provided that a reaction of starting materials (i.e., acid dianhydride and diamine) can be efficiently carried out and the solvent is inactive with respect to such starting materials. Examples include: polar solvents, such as N-methylpyrrolidone, N-methyl-2-pyrrolidinone, N,N-dimethylacetamide, N,N-dimethylformamide, tetrahydrofuran, dimethylsulfoxide, sulfolane, methyl isobutyl ketone, acetonitrile, benzonitrile, nitrobenzene, nitromethane, dimethylsulfoxide, acetone, methyl ethyl ketone, isobutyl ketone, and methanol; and non-polar solvents, such as toluene and xylene. Use of a polar solvent is particularly preferable. Such organic solvents may be used alone or in combinations of two or more.

1.1.2. Method for Production of Fluorine-Containing Polyimide

The polyamide acid is subjected to either thermal imidization or chemical imidization to obtain a resin composition containing polyimide.

According to a particular embodiment, the polyamide acid is imidized via heat treatment (i.e., thermal imidization), so as to obtain a polyimide-containing resin composition. Since no catalyst can remain in the polyimide obtained via thermal imidization, such polyimide is more preferably used for cell culture.

At the time of polyamide acid imidization, polyamide acid is not always completely converted into polyimide. The resulting resin composition may comprise polyamide acid and other components, in addition to the polyimide. It is preferable that imidization be performed within the extent of imidization described below.

1.1.2.1. Thermal Imidization

When thermal imidization is performed, for example, the polyamide acid is calcined in the air, preferably in an inert gas atmosphere, such as nitrogen, helium, or argon gas, or in a vacuum, at a temperature of preferably 50° C. to 400° C., and more preferably at 100° C. to 380° C., for preferably 0.1 to 10 hours, and more preferably 0.2 to 5 hours. Thus, a polyimide-containing resin composition can be obtained. The polyamide acid subjected to thermal imidization is preferably dissolved in an adequate solvent. Any solvent can be used, provided that it is possible to dissolve polyamide acid therein, and the solvent described with respect to amidation above can also be used. Examples thereof include: polar solvents, such as N-methylpyrrolidone, N-methyl-2-pyrrolidinone, N,N-dimethylacetamide, N,N-dimethylformamide, tetrahydrofuran, dimethylsulfoxide, sulfolane, methyl isobutyl ketone, acetonitrile, benzonitrile, nitrobenzene, nitromethane, dimethylsulfoxide, acetone, methyl ethyl ketone, isobutyl ketone, and methanol; and non-polar solvents, such as toluene and xylene. Use of a polar solvent is particularly preferable. Such organic solvents may be used alone or in combinations of two or more. As described above, the reaction mixture after the completion of amidation may be subjected to thermal imidization without further processing. While concentration of the polyamide acid in the polyamide acid solution is not particularly limited, it is preferably 5% by weight or more, and more preferably 10% by weight or more, preferably 50% by weight or less, and more preferably 40% by weight or less, from the viewpoint of the polymerizability and the postpolymerization viscosity of the resulting resin composition and ease of handling at the time of film formation or calcination after polymerization.

According to an embodiment, the polyamide acid is preferably subjected to heat treatment in the absence of a tertiary amine compound when thermal imidization is intended.

1.1.2.2. Chemical Imidization

When chemical imidization is performed, polyamide acid can be directly imidized with the use of a cyclodehydration reagent described below in an adequate solvent.

Any cyclodehydration reagent can be used without particular limitation, provided that it can convert polyamide acid into polyimide via chemical cyclodehydration. As such cyclodehydration reagent, use of a tertiary amine compound alone or use of a tertiary amine compound in combination with carboxylic anhydride is preferable, so that imidization can be efficiently carried out.

Examples of tertiary amine compounds include trimethylamine, triethylamine, tripropylamine, tributylamine, pyridine, 1,4-diazabicyclo[2.2.2]octane (DABCO), 1,8-diazabicyclo[5.4.0]undec-7-ene, 1,5-diazabicyclo[4.3.0]non-5-ene, N,N,N',N'-tetramethyldiaminomethane, N,N,N',N'-tetramethylethylenediamine, N,N,N',N'-tetramethyl-1,3-propanediamine, N,N,N',N'-tetramethyl-1,4-phenylenediamine, N,N,N',N'-tetramethyl-1,6-hexanediamine, N,N,N',N'-tetraethylmethylenediamine, and N,N,N',N'-tetraethylethylenediamine. Among them, pyridine, DABCO, and N,N,N',N'-tetramethyldiaminomethane are preferable, with DABCO being more preferable. A single type of tertiary amine or two or more types of tertiary amines may be used.

A tertiary amine compound has a structure in which 3 hydrogen atoms in an ammonia molecule have been substituted with hydrocarbon groups. In the present invention, a structure in which a carbon atom of a carbonyl group (C=O) is bound to a nitrogen atom, such as an imide or amide compound, is excluded from the scope of the tertiary amine compound. In the present invention, specifically, a tertiary amine compound has a structure in which all 3 hydrogen atoms in an ammonia molecule have been substituted with hydrocarbon groups; however, a structure in which a carbon atom of a carbonyl group (C=O) is bound to a nitrogen atom, such as an imide or amide compound, is excluded from the scope of the tertiary amine compound.

Examples of carboxylic anhydrides include acetic anhydride, trifluoroacetic anhydride, propionic anhydride, butyric anhydride, isobutyric anhydride, succinic anhydride, and maleic anhydride. Among them, acetic anhydride and trifluoroacetic anhydride are preferable, with acetic anhydride being more preferable. A single type of carboxylic anhydride or two or more types of carboxylic anhydrides may be used.

A polar solvent that is excellent in terms of solubility is preferable as a solvent that dissolves polyamide acid at the time of chemical imidization. Examples thereof include tetrahydrofuran, N,N-dimethylacetamide, N,N-dimethylformamide, N-methylpyrrolidone, and dimethylsulfoxide. Use of at least one solvent selected from the group consisting of N,N-dimethylacetamide, N,N-dimethylformamide, and N-methylpyrrolidone is particularly preferable, so as to perform a homogenous reaction. When any such solvents are used for amidation, the reaction mixture after amidation can be used for chemical imidization without isolating polyamide acid therefrom.

The polyimide solution can be prepared by mixing the polyamide acid, the cyclodehydration reagent, and the solvent described above. Thus, imidization proceeds and the polyimide solution can be obtained.

Alternatively, a solution of an aromatic polyamide acid and a solution of an aliphatic polyamide acid may be separately prepared, the resulting solutions may be mixed with each other, and aromatic polyimide and aliphatic polyimide may then be subjected to random or alternate polymerization.

The amount of polyamide acid in the mixture containing the polyamide acid, the cyclodehydration reagent, and the solvent may be adequately determined, so that polyimide would not precipitate at room temperature when polyimide is produced. To this end, the amount of polyamide acid mixed is preferably 45% by mass or less, and more preferably 40% by mass or less, relative to the total amount of the polyamide acid, the cyclodehydration reagent, and the solvent by mass. The lower limit of polyamide acid concentration is not particularly limited. For example, the polyamide acid concentration is preferably 5% by mass or more, and more preferably 10% by mass or more. Specific concentrations may be determined on the basis of the results of the preliminary experiment.

The amount of the cyclodehydration reagent in the mixture may be adequately determined in accordance with the amount of polyamide acid. When a tertiary amine is used as a cyclodehydration reagent, for example, the amount thereof is preferably 0.005 equivalents to 0.3 equivalents, and more preferably 0.01 equivalents to 0.2 equivalents, relative to the amide unit in the polyamide acid. When the amount of the tertiary amine is less than 0.005 equivalents, imidization may not sufficiently proceed. When the amount thereof exceeds 0.3 equivalents, however, the catalytic effects become saturated, and economic problems may arise. When carboxylic anhydride is also used as a cyclodehydration reagent, the amount of carboxylic anhydride is preferably 1 equivalent to 20 equivalents, and more preferably 1.1 equivalents to 15 equivalents, relative to the amide unit in the polyamide acid. When the amount of carboxylic anhydride is less than 1 equivalent, an amide bond remains, and the effects as a dehydrating agent may not be sufficiently exerted. When the amount thereof exceeds 20 equivalents, however, the catalytic effects become saturated, and economic problems may arise.

The amount of the solvent in the mixture may be adequately determined, so that the polyamide acid concentration falls within the range described above.

When preparing the polyimide solution, the order in which the polyamide acid, the cyclodehydration reagent, and the solvent are mixed is not particularly limited. For example, the cyclodehydration reagent may be directly added to a mixture of the polyamide acid and the solvent. Alternatively, the cyclodehydration reagent may be dissolved in the solvent, and the resulting mixture may then be added to the polyamide acid. When a mixture of a tertiary amine and carboxylic anhydride is used as the cyclodehydration reagent, the order in which they are mixed is not particularly limited. For example, the tertiary amine and the carboxylic anhydride may be added simultaneously. Alternatively, either thereof may be first added to a mixture of polyamide acid resin and a solvent, following which the mixture is adequately stirred, and the other thereof may then be added thereto.

The polyamide acid, the cyclodehydration reagent, and the solvent are generally mixed preferably at 5° C. to 40° C., and more preferably at 20° C. to 30° C. without heating or cooling. In order to promote imidization, the mixture may be heated at approximately 100° C. or less, according to need.

The duration of mixing the polyamide acid, the cyclodehydration reagent, and the solvent is not particularly limited. When rotation-revolution mixing is performed, mixing proceeds with high efficiency. Thus, the duration of mixing can be, for example, approximately 1 minute to 30 minutes. The specific mixing duration may be determined in accordance with the results of the preliminary experiment. Thereafter, the obtained polyimide may be dissolved and diluted in an organic solvent, such as acetone, from the viewpoint of the removal of a component, such as a cyclodehydration catalyst, therefrom, and the resultant is precipitated again in hydrous methanol, followed by purification. A chemically imidized polyimide is soluble in a solvent. Thus, the purified powdery polyimide may be dissolved in another organic solvent, which was not used at the time of synthesis, so as to prepare a polyimide solution.

1.1.3. Chemical Structure of Fluorine-Containing Polyimide

The resin composition obtained in the manner described above comprises a polyimide having one or more fluorine atoms in a repeating unit. According to an embodiment, the resin composition obtained in the manner described above comprises a polyimide having one or more fluorine atoms and one or more ether bonds and/or thioether bonds in a repeating unit. Such polyimide is more preferably an aromatic polyimide comprising a repeating unit represented by Formula (V) below. On a substrate comprising a polyimide of such a specific structure on the surface thereof, three-dimensional cell culture can be carried out.

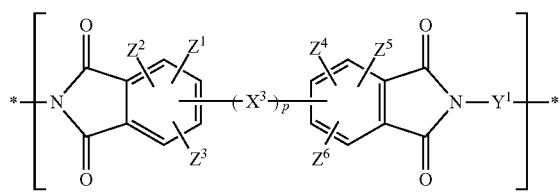
(V)

In Formula (V), definitions and preferable, specific examples of $X^1$, $Y^1$, $Z^1$, $Z^2$, $Z^3$, $Z^4$, $Z^5$, $Z^6$, and p are the same as those described with respect to Formula (I).

The resin composition obtained in the manner described above may comprise an aliphatic polyimide comprising an aliphatic group having one or more fluorine atoms in a repeating unit, and preferably at least one type of aliphatic polyimide comprising a repeating unit represented by any of Formulae (VI) to (VIII) below. According to an embodiment, the resin composition obtained in the manner described above can comprise an aliphatic polyimide comprising an aliphatic group having one or more fluorine atoms and one or more ether bonds and/or thioether bonds in a repeating unit, and preferably at least one type of aliphatic polyimide comprising a repeating unit represented by any of Formulae (VI) to (VIII). On a substrate comprising a polyimide of such a specific structure on the surface thereof, three-dimensional cell culture can be carried out.

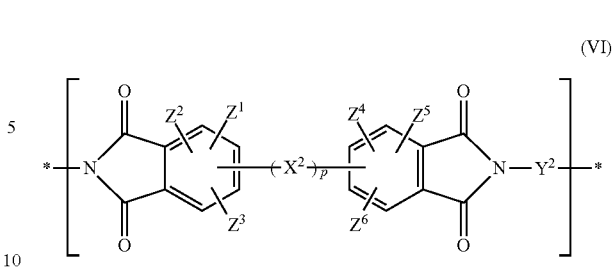
(VI)

In Formula (VI), definitions and preferable, specific examples of $X^2$, $Y^2$, $Z^1$, $Z^2$, $Z^3$, $Z^4$, $Z^5$, $Z^6$, and p are the same as those described with respect to Formula (II).

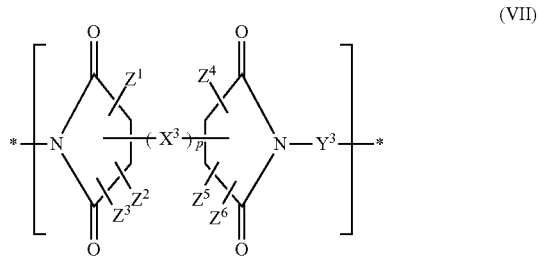
(VII)

In Formula (VII), definitions and preferable, specific examples of $X^3$, $Y^3$, $Z^1$, $Z^2$, $Z^3$, $Z^4$, $Z^5$, and $Z^6$ are the same as those described with respect to Formula (III).

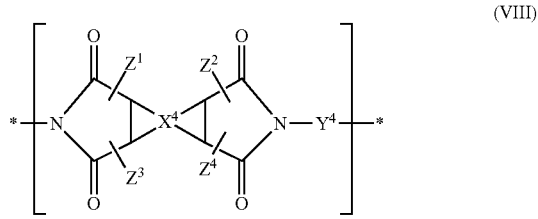
(VIII)

In Formula (VIII), definitions and preferable, specific examples of $X^4$, $Y^4$, $Z^1$, $Z^2$, $Z^3$, and $Z^4$ are the same as those described with respect to Formula (IV).

The polyimide-containing resin composition can adequately comprise various additives that are generally used, according to need, provided that such additives do not adversely affect the effects of the present invention. Examples of such additives include a dispersant, an organic solvent, an inorganic filler, a release agent, a coupling agent, and a flame retardant. Such resin composition is mainly composed of the polyimide and its precursor; that is, an unreacted polyamide acid. The total amount of the polyimide and the polyamide acid is preferably 85% by mass or more, more preferably 90% by mass or more, and most preferably 95% by mass or more, relative to the total amount of the resin composition.

The term "polyimide-containing resin composition" used in the present invention typically refers to a polyimide resin that is obtained via imidization of polyamide acid resulting from polymerization of one or more acid dianhydride and one or more diamine.

The polyimide in the resin composition used in the present invention can comprise a repeating unit represented by Formula (3), regardless of a method of production thereof. In Formula (3) above, $X^0$ and $Y^0$ can be the same as $X^0$ and $Y^0$ of the acid dianhydride, the diamine, and/or the polyamide acid described above. A particularly preferable example of a repeating unit represented by Formula (3) is a structure represented by any of Formulae (V), (VI), (VII), and (VIII) above.

A repeating unit represented by Formula (V) has a structure in which $X^0$ in Formula (3) is a group represented by Formula ($E^1$) and $Y^0$ is $Y^1$. A polyimide comprising a repeating unit represented by Formula (V) may further comprise a repeating unit represented by Formula (V) in which a group represented by Formula ($E^1$) has been substituted with another tetravalent organic group and/or $Y^1$ has been substituted with another divalent organic group. For the convenience of description, the group represented by Formula ($E^1$) and other tetravalent organic groups are collectively referred to as "tetravalent residues," and $Y^1$ and other divalent organic groups are collectively referred to as "divalent residues." A polyimide comprising a repeating unit represented by Formula (V) comprises the group represented by Formula ($E^1$) in an amount that is preferably 25% by mole or more, more preferably 50% by mole or more, further preferably 80% by mole or more, and most preferably 100% by mole, when the total amount of tetravalent residues is designated as 100% by mole. Examples of other tetravalent residues include a group represented by Formula ($E^2$), a group represented by Formula ($E^3$), and a group represented by Formula ($E^4$). When the total amount of tetravalent residues is designated as 100% by mole, the total amount of a group represented by Formula ($E^1$), a group represented by Formula ($E^2$), a group represented by Formula ($E^3$), and a group represented by Formula ($E^4$) is more preferably 90% by mole or more, and most preferably 100% by mole. A polyimide comprising a repeating unit represented by Formula (V) comprises $Y^1$ in an amount that is preferably 25% by mole or more, more preferably 50% by mole or more, further preferably 80% by mole or more, and most preferably 100% by mole, when the total amount of divalent residues is designated as 100% by mole. Examples of other divalent residues include $Y^2$, $Y^3$, and $Y^4$. When the total amount of divalent residues is designated as 100% by mole, the total amount of $Y^1$, $Y^2$, $Y^3$, and $Y^4$ is more preferably 90% by mole or more, and most preferably 100% by mole.

A repeating unit represented by Formula (VI) has a structure in which $X^0$ in Formula (3) is a group represented by Formula ($E^2$) and $Y^0$ is $Y^2$. A polyimide comprising a repeating unit represented by Formula (VI) may further comprise a repeating unit represented by Formula (VI) in which a group represented by Formula ($E^2$) has been substituted with another tetravalent organic group and/or $Y^2$ has been substituted with another divalent organic group. For the convenience of description, the group represented by Formula ($E^2$) and other tetravalent organic groups are collectively referred to as "tetravalent residues," and $Y^2$ and other divalent organic groups are collectively referred to as "divalent residues." A polyimide comprising a repeating unit represented by Formula (VI) comprises the group represented by Formula ($E^2$) in an amount that is preferably 25% by mole or more, more preferably 50% by mole or more, further preferably 80% by mole or more, and most preferably 100% by mole, when the total amount of tetravalent residues is designated as 100% by mole. Examples of other tetravalent residues include a group represented by Formula ($E^1$), a group represented by Formula ($E^3$), and a group represented by Formula ($E^4$). When the total amount of tetravalent residues is designated as 100% by mole, the total amount of a group represented by Formula ($E^1$), a group represented by Formula ($E^2$), a group represented by Formula ($E^3$), and a group represented by Formula ($E^4$) is more preferably 90% by mole or more, and most preferably 100% by mole. A polyimide comprising a repeating unit represented by Formula (VI) comprises $Y^2$ in an amount that is preferably 25% by mole or more, more preferably 50% by mole or more, further preferably 80% by mole or more, and most preferably 100% by mole, when the total amount of divalent residues is designated as 100% by mole. Examples of other divalent residues include $Y^1$, $Y^3$, and $Y^4$. When the total amount of divalent residues is designated as 100% by mole, the total amount of $Y^1$, $Y^2$, $Y^3$, and $Y^4$ is more preferably 90% by mole or more, and most preferably 100% by mole.

A repeating unit represented by Formula (VII) has a structure in which $X^0$ in Formula (3) is a group represented by Formula ($E^1$) and $Y^0$ is $Y^3$. A polyimide comprising a repeating unit represented by Formula (VII) may further comprise a repeating unit represented by Formula (VII) in which a group represented by Formula ($E^3$) has been substituted with another tetravalent organic group and/or $Y^3$ has been substituted with another divalent organic group. For the convenience of description, the group represented by Formula ($E^3$) and other tetravalent organic groups are collectively referred to as "tetravalent residues," and $Y^3$ and other divalent organic groups are collectively referred to as "divalent residues." A polyimide comprising a repeating unit represented by Formula (VII) comprises the group represented by Formula ($E^3$) in an amount that is preferably 25% by mole or more, more preferably 50% by mole or more, further preferably 80% by mole or more, and most preferably 100% by mole, when the total amount of tetravalent residues is designated as 100% by mole. Examples of other tetravalent residues include a group represented by Formula ($E^1$), a group represented by Formula ($E^2$), and a group represented by Formula ($E^4$). When the total amount of tetravalent residues is designated as 100% by mole, the total amount of a group represented by Formula ($E^1$), a group represented by Formula ($E^2$), a group represented by Formula ($E^3$), and a group represented by Formula ($E^4$) is more preferably 90% by mole or more, and most preferably 100% by mole. A polyimide comprising a repeating unit represented by Formula (VII) comprises $Y^3$ in an amount that is preferably 25% by mole or more, more preferably 50% by mole or more, further preferably 80% by mole or more, and most preferably 100% by mole, when the total amount of divalent residues is designated as 100% by mole. Examples of other divalent residues include $Y^1$, $Y^2$, and $Y^4$. When the total amount of divalent residues is designated as 100% by mole, the total amount of $Y^1$, $Y^2$, $Y^3$, and $Y^4$ is more preferably 90% by mole or more, and most preferably 100% by mole.

A repeating unit represented by Formula (VIII) has a structure in which $X^0$ in Formula (3) is a group represented by Formula ($E^4$) and $Y^0$ is $Y^4$. A polyimide comprising a repeating unit represented by Formula (VIII) may further comprise a repeating unit represented by Formula (VIII) in which a group represented by Formula ($E^4$) has been substituted with another tetravalent organic group and/or $Y^4$ has been substituted with another divalent organic group. For the convenience of description, the group represented by Formula ($E^4$) and other tetravalent organic groups are collectively referred to as "tetravalent residues," and $Y^4$ and other divalent organic groups are collectively referred to as "divalent residues." A polyimide comprising a repeating unit represented by Formula (VIII) comprises the group represented by Formula ($E^4$) in an amount that is preferably 25% by mole or more, more preferably 50% by mole or more, further preferably 80% by mole or more, and most preferably 100% by mole, when the total amount of tetravalent residues is designated as 100% by mole. Examples of other tetravalent residues include a group represented by Formula ($E^1$), a group represented by Formula ($E^2$), and a group represented by Formula ($E^3$). When the total amount of tetravalent residues is designated as 100% by mole, the total amount of a group represented by Formula ($E^1$), a group represented by Formula ($E^2$), a group represented by Formula ($E^3$), and a group represented by Formula ($E^4$) is more preferably 90% by mole or more, and most preferably 100% by mole. A polyimide comprising a repeating unit represented by Formula (VIII) comprises $Y^4$ in an amount that is preferably 25% by mole or more, more preferably 50% by mole or more, further preferably 80% by mole or more, and most preferably 100% by mole, when the total amount of divalent residues is designated as 100% by mole. Examples of other divalent residues include $Y^1$, $Y^2$, and $Y^3$. When the total amount of divalent residues is designated as 100% by mole, the total amount of $Y^1$, $Y^2$, $Y^3$, and $Y^4$ is more preferably 90% by mole or more, and most preferably 100% by mole.

1.1.4. Chemical and Physical Properties of Polyimide-Containing Resin Composition

1.1.4.1. Degree of Imidization

The resin composition comprising fluorine-containing polyimide may be heated or treated with a cyclization catalyst when it is subjected to imidization or prepared in the form of a cell culture substrate described below. Thus, the degree of imidization can be improved.

In the present invention, the degree of imidization of the polyimide-containing resin composition constituting the substrate surface is 20% or higher, preferably 25% or higher, more preferably 30% or higher, further preferably 35% or higher, and particularly preferably 40% or higher, preferably 100% or lower, more preferably 99.5% or lower, and further preferably 99% or lower. By adjusting the degree of imidization within such range, the degrees of flexibility and hydrophobicity of the resin composition can be preferably adjusted to levels at which three-dimensional cell culture can be carried out. When the resulting membrane is heated again for the purpose of, for example, sterilization with the use of an autoclave, also, the membrane would not undergo cracking or dimensional change. Thus, the degree of imidization as described above is preferable. The term "degree of imidization" refers to the proportion of amide bonds of polyamide acid converted into imide groups via dehydration condensation in the polyimide obtained through imidization of polyamide acid. The degree of imidization (%) of a certain polyimide resin sample indicates the relative value of the absorbance (i.e., the relative imidization value) measured at a particular imide wavelength (at around 1,370 $cm^{-1}$ in the examples) attained via IR assays on the basis of the relative degree of imidization relative to the relative imidization value of the polyimide resin sample after the final imidization reaction performed at 380° C. for 1 hour, as indicated by 100%. The degree of imidization of polyimide having an aromatic group can be determined in accordance with the method described in the examples. The degree of imidization of polyimide having an aliphatic group can also be determined by the method for assaying imidization via IR spectrometry as described in the examples with the use of "the absorbance at around 1,460 $cm^{-1}$ derived from the C—H deflection" instead of "the absorbance at around 1,500 $cm^{-1}$ derived from the skeletal vibration of the benzene ring" as the reference peak. Via conversion of polyamide acid into polyimide under the imidization conditions described above, the degree of imidization can be adjusted within the range described above. In addition, the degree of imidization described above can be achieved by satisfying the standard (1) described below or, according to need, the standard (2) described below. That is, (1) when the degree of imidization is enhanced via heating, the treatment is carried out at preferably 50° C. to 400° C., and more preferably 100° C. to 380° C., for 0.1 to 10 hours, and more preferably for 0.2 to 5 hours; or (2) when the degree of imidization is enhanced via treatment with a cyclization catalyst, the treatment with a cyclodehydration catalyst may be carried out at room temperature, preferably at 5° C. to 40° C., and more preferably 20° C. to 30° C., over the period of mixing as described above with respect to chemical imidization. After the completion of mixing, the resultant is allowed to stand for preferably 24 hours or longer, and more preferably 48 hours or longer.

1.1.4.2. Water Contact Angle

On the cell culture substrate of the present invention, the water contact angle on the surface composed of a polyimide-containing resin composition (in the form of a film, membrane, plate, or the like) is preferably 70° or more, more preferably 730 or more, and further preferably 75° or more, preferably 115° or less, more preferably 112° or less, and further preferably 110° or less. When the water contact angle is within such range, cells can easily adhere to the substrate surface with adequate strength, and cells can use the surface as the scaffold to form three-dimensional tissue. The contact angle can be determined by measuring the water contact angle at 25° C. with the use of an automated contact angle meter (DM-500, manufactured by Kyowa Interface Science Co., Ltd.).

1.1.4.3. Tensile Modulus of Elasticity

The polyimide-containing resin composition is excellent in flexibility because the polyimide polymerization unit comprises the particular number of ether bonds and/or thioether bonds, and flexibility can be evaluated in terms of the tensile modulus of elasticity. For example, the tensile modulus of elasticity can be 2 GPa or lower. The resin composition exhibiting the tensile modulus of elasticity of 2 GPa or lower is a preferable embodiment of the present invention. Cells can easily form three-dimensional tissue on the surface composed of a flexible resin composition exhibiting the tensile modulus of elasticity within such range. The tensile modulus of elasticity of the resin composition is more preferably 1.5 GPa or lower, and further preferably 1.2 GPa or lower. While the lower limit of the tensile modulus of elasticity is not particularly limited, the tensile modulus of elasticity is preferably 0.3 GPa or higher, and more preferably 0.5 GPa or higher. The tensile modulus of elasticity (GPa) can be determined by the method of dynamic viscoelasticity measurement described in the examples.

1.1.4.4. Molecular Weight of Polyimide

The molecular weight of the polyimide in the resin composition is preferably 1,000 to 1,000,000, and more preferably 5,000 to 700,000, in terms of the weight average molecular weight. When the molecular weight is within such range, gelling would not take place at the time of polymerization, polymerization and film formation can be easily carried out because of low viscosity, and adequate degrees of heat resistance and membrane strength can be imparted and maintained. The weight average molecular weight is further preferably 10,000 to 500,000.

The weight average molecular weight can be measured via gel permeation chromatography (GPC) with the use of the reference polystyrene calibration curve as described in the examples below.

1.1.4.5. Content of Imidization Catalyst

The amount of the imidization catalyst, which is a tertiary amine compound, in the resin composition is preferably 0.030% by mass or less, more preferably 0.015% by mass or less, and further preferably 0.005% by mass or less, relative to the total amount of the polyimide and the remaining polyamide acid in the resin composition. It is most preferable that the imidization catalyst be absent.

Surprisingly, the present inventors found that three-dimensional cell culture could not be performed on a flat surface composed of the resin composition when the amount of the tertiary amine compound in the resin composition is greater than 0.030% by mass relative to the total amount of polyimide and the remaining polyamide acid in the resin composition. They also found that three-dimensional culture could be carried out when such amount was 0.030% by mass or less.

In the present invention, a tertiary amine compound is used as an imidization catalyst, and specific examples thereof are as described above with reference to "imidization catalysts." In the present invention, a structure in which the carbon atom of the carbonyl group (C=O) has been bound to the nitrogen atom, such as an imide compound or amide compound, is excluded from the scope of the tertiary amine compound, as described above. In the present invention, specifically, the tertiary amine compound has a structure in which 3 hydrogen atoms in an ammonia molecule have been substituted with hydrocarbon groups; however, a structure in which a carbon atom in the carbonyl group, such as an imide compound or an amide compound, is excluded from the scope of the tertiary amine compound.

The amount of the tertiary amine compound in the resin composition can be quantified by any method, such as a proton nuclear magnetic resonance spectroscopy ($^1$H-NMR), gas chromatography (GC), or gas chromatography-mass analysis (GC-MS) (SIM). With reference to the results of analysis of an adequate standard sample, the amount relative to the total amount of the polyimide and the remaining polyamide acid in the resin composition can be determined. The total amount of the polyimide and the remaining polyamide acid can be determined based on the values for properties derived from the chemical structure of the group retained after polymerization from among the groups of the acid dianhydride and/or diamine used for producing polyimide.

1.1.5. More Preferable Embodiment of Fluorine-Containing Polyimide

1.1.5.1. Fluorine-Containing Polyimide Comprising Ether Bond and/or Thioether Bond The polyimide used in the present invention is more preferably a fluorine-containing polyimide having one or more fluorine atoms in a repeating unit, and such polyimide comprises a polymerization repeating unit in which the sum of the ether bonds and the thioether bonds is at least 1.

Typically, such polyimide is obtained through the reaction of at least one acid dianhydride with at least one diamine, and at least either the acid dianhydride or diamine comprises a fluorine atom in molecules thereof. At least either the acid dianhydride or diamine comprises ether bonds and/or thioether bonds in molecules thereof, and the polymerization repeating unit derived from the acid dianhydride and the diamine constituting the polyimide comprises one or more ether bonds and thioether bonds in total.

It should be noted that the polyimide of this embodiment is not at least one member selected from the group consisting of:

a polyimide comprising the repeating unit represented by Formula (3) in its main chain (the main chain backbone) wherein $X^0$ represents a 4,4'-(hexafluoroisopropylidene)diphthalic anhydride residue and $Y^0$ represents a 2,2-bis(4-(4-aminophenoxyl)phenyl)hexafluoropropane residue;

a polyimide comprising the repeating unit represented by Formula (3) in its main chain (the main chain backbone) wherein $X^0$ represents a 4,4'-(hexafluoroisopropylidene)diphthalic anhydride residue and $Y^0$ represents a bis[4-(4-aminophenoxy)phenyl]sulfone residue; and a polyimide comprising the repeating unit represented by Formula (3) in its main chain (the main chain backbone) wherein $X^0$ represents a 4,4'-(hexafluoroisopropylidene)diphthalic anhydride residue and $Y^0$ represents a bis[4-(3-aminophenoxy)phenyl]sulfone residue.

The term "4,4'-(hexafluoroisopropylidene)diphthalic anhydride residue" used herein refers to a tetravalent organic group $X^0$ in Formula (1), when the Formula (1) represents 4,4'-(hexafluoroisopropylidene)diphthalic anhydride. The term "2,2-bis(4-(4-aminophenoxyl)phenyl)hexafluoropropane residue" used herein refers to a divalent organic group $Y^0$ in Formula (2), when the Formula (2) represents 2,2-bis(4-(4-aminophenoxyl)phenyl)hexafluoropropane. The term "bis[4-(4-aminophenoxy)phenyl]sulfone residue" used herein refers to a divalent organic group $Y^0$ in Formula (2), when the Formula (2) represents bis[4-(4-aminophenoxy)phenyl]sulfone. The term "bis[4-(3-aminophenoxy)phenyl]sulfone residue" used herein refers to a divalent organic group in Formula (2), when the Formula (2) represents bis[4-(3-aminophenoxy)phenyl]sulfone.

Specifically, it is preferable that the polyimide used in the present invention is not at least one polyimide selected from the group consisting of:

polyimide resulting from the reaction between 4,4'-(hexafluoroisopropylidene)diphthalic anhydride and 2,2-bis(4-(4-aminophenoxyl)phenyl)hexafluoropropane;

polyimide resulting from the reaction between 4,4'-(hexafluoroisopropylidene)diphthalic anhydride and bis[4-(4-aminophenoxy)phenyl]sulfone; and polyimide resulting from the reaction between 4,4'-(hexafluoroisopropylidene)diphthalic anhydride and bis[4-(3-aminophenoxy)phenyl]sulfone.

Regarding the polyimide according to a preferable embodiment described above comprising a repeating unit represented by Formula (I), wherein $X^1$ is selected from among Groups x1, x2, and x3 and $Y^1$ is at least one member selected from among Groups y1, y2, y3, y4, y5, y6, y7, y8, and y9, specifically, when $X^1$ represents Group x1, $Y^1$ is preferably a group other than Group y3, and more preferably at least one member selected from among Groups y1, y2, y4, y5, y6, y7, y8, and y9.

The present inventors surprisingly found that cells could easily form three-dimensional tissue, such as a spheroid or three-dimensional cell aggregate, on a substrate comprising on its surface a fluorine-containing polyimide comprising one or more ether bonds and thioether bonds in total in a polymerization repeating unit (e.g., the polymerization repeating unit derived from acid dianhydride and diamine). The cell culture substrate having such properties has a surface with adequate degrees of flexibility and hydrophobicity. It is thus considered that cells can easily form three-dimensional tissue on such surface. In addition, the substrate according to the present invention does not need to have a steric structure on the surface that serves as a scaffold for cells, and it is thus easy to prepare such substrate.

The total number of ether bonds and thioether bonds in the polymerization repeating unit constituting the polyimide (e.g., the polymerization repeating unit derived from acid dianhydride and diamine) is at least 1. While the upper limit thereof is not particularly limited, the total number is preferably 6 or less, more preferably 5 or less, and further preferably 4 or less. Polyimide comprising the number of ether bonds and thioether bonds within such range has an adequate degree of flexibility. Thus, three-dimensional cell culture can be carried out.

While the ether bond is a bond represented by —O—, according to the present invention, the number of ether bonds does not include the number of bonds in the —O— region in an acid anhydride group (i.e., the —C(O)—O—C(O)— region) of the acid dianhydride.

The number of the ether bonds and the thioether bonds can be determined on the basis of the number of ether bonds and thioether bonds in a compound comprising the ether bonds and/or the thioether bonds in the molecule and the reaction molar ratio of the compound comprising the ether bonds and/or the thioether bonds in the molecule. While an example of a calculation method is described below, it should be noted that the method is not limited to the method described below.

(1) When an acid dianhydride comprising 2 ether bonds in molecules thereof is allowed to react with diamine not comprising any ether bonds or thioether bonds in molecules thereof at a molar ratio of 1:1 to obtain a polyamide acid, thereby resulting in polyimide, the total number of ether bonds and thioether bonds is 2 (i.e., 2×1+0×1=2). When an acid dianhydride not comprising any ether bonds or thioether bonds in molecules thereof is allowed to react with diamine comprising 2 ether bonds in molecules thereof at a molar ratio of 1:1 to obtain a polyamide acid composition and then obtain polyimide therefrom, the total number of bonds is calculated in the same manner; that is, the total number of bonds is 2.

(2) When an acid dianhydride comprising 2 ether bonds in molecules thereof is allowed to react with diamine comprising an ether bond in molecules thereof at a molar ratio of 1:1 to obtain a polyamide acid, thereby resulting in polyimide, the total number of ether bonds and thioether bonds is 3 (i.e., 2×1+1×1=3). When an acid dianhydride comprising an ether bond in molecules thereof is allowed to react with diamine comprising 2 ether bonds in molecules thereof at a molar ratio of 1:1 to obtain a polyamide acid, thereby resulting in polyimide, the total number of bonds is calculated in the same manner, and such number is 3.

(3) When an acid dianhydride "a" comprising 2 ether bonds in molecules thereof, an acid dianhydride "b" not comprising any ether bonds or thioether bonds in molecules thereof, and diamine comprising an ether bond in molecules thereof are allowed to react with each other at a molar ratio of 0.5:0.5:1.0 to obtain a polyamide acid, thereby resulting in polyimide, the total number of ether bonds and thioether bonds is 2 (i.e., 2×0.5+0×0.5+1×1=2).

(4) When an acid dianhydride comprising 2 ether bonds in molecules thereof, diamine "a" comprising an ether bond in molecules thereof, and diamine "b" comprising 2 ether bonds in molecules thereof are allowed to react with each other at a molar ratio of 1:0.5:0.5 to obtain a polyamide acid, thereby resulting in polyimide, the total number of ether bonds and thioether bonds is 3.5 (i.e., 2×1.0+1×0.5+2×0.5=3.5).

As described above, the reaction molar ratio of starting materials is determined to adjust the sums of acid dianhydrides and diamines to equimolar levels.

Ether bonds and/or thioether bonds and a fluorine atom of at least either acid dianhydride or diamine used for producing polyimide is preferably not ether bonds and/or thioether bonds and a fluorine atom that are quenched as a result of amidation or imidization between the acid dianhydride and the diamine. Specifically, the polyimide preferably comprises in its main chain (also referred to as a "main chain backbone") a constitutive unit comprising ether bonds and/or thioether bonds and the fluorine atom derived from the acid dianhydride and/or diamine compound. The polyimide preferably comprises in its main chain (the main chain backbone) a constitutive unit comprising ether bonds and/or thioether bonds and the fluorine atom, regardless of the method of production.

1.1.5.2. Fluorine-Containing Polyimide Obtained Via Thermal Imidization

It is more preferable that the polyimide used in the present invention be obtained via thermal imidization of polyamide acid, which is a fluorine-containing polyimide having one or more fluorine atoms in a repeating unit.

The fluorine-containing polyamide typically results from thermal imidization of polyamide acid obtained through polymerization of at least one acid dianhydride with at least one diamine, and at least either the acid dianhydride or diamine comprises the fluorine atom in the molecule.

A substrate surface composed of a resin composition comprising such fluorine-containing polyimide is prepared via thermal imidization that does not require the use of the imidization catalyst. Thus, the surface can be made free of an imidization catalyst that may inhibit three-dimensional culture, and cells can easily form three-dimensional tissue on such surface.

The conditions described in 1.1.2.1 above can be employed as specific conditions for thermal imidization. It is preferable that polyamide acid be subjected to thermal imidization in the absence of a tertiary amine compound.

Examples of tertiary amine compounds are the same as those exemplified as chemical imidization catalysts in 1.1.2.2 above. A tertiary amine compound has a structure in which 3 hydrogen atoms in an ammonia molecule have been substituted with hydrocarbon groups. In the present invention, a structure in which a carbon atom of a carbonyl group (C=O) is bound to a nitrogen atom, such as an imide or amide compound, is excluded from the scope of the tertiary amine compound. In the present invention, specifically, a tertiary amine compound has a structure in which all 3 hydrogen atoms in the ammonia molecule have been substituted with hydrocarbon groups; however, a structure in which a carbon atom of a carbonyl group (C=O) is bound to a nitrogen atom, such as an imide or amide compound, is excluded from the scope of the tertiary amine compound.

It is more preferable that thermal imidization aimed at obtaining the polyimide be carried out in the absence of tertiary amine and carboxylic anhydride as imidization catalysts. Examples of carboxylic anhydrides are the same as those exemplified in 1.1.2.2 above.

According to a more preferable embodiment of the present invention, the resin composition comprises a fluorine-containing polyimide having one or more fluorine atoms in a repeating unit (e.g., a polyimide resulting from the reaction of at least one acid dianhydride with at least one diamine, with at least either the acid dianhydride or diamine comprising a fluorine atom in molecules thereof), and the amount of the tertiary amine compound in the resin composition is preferably 0.030% by mass or less, more preferably 0.015% by mass or less, and further preferably 0.005% by mass or less, relative to the total amount of the polyimide and the remaining polyamide acid in the resin composition. It is most preferable that the imidization catalyst be absent.

On the surface of the substrate composed of such resin composition comprising fluorine-containing polyimide, the amount of the tertiary amine compound that would disturb three-dimensional culture is sufficiently low. Thus, cells can easily form three-dimensional tissue on such surface.

The amount of the tertiary amine compound in the resin composition can be quantified by any method, such as proton nuclear magnetic resonance spectroscopy ($^1$H-NMR), gas chromatography (GC), or gas chromatography-mass analysis (GC-MS) (SIM). With reference to the results of analysis of an adequate standard sample, the amount relative to the total amount of the polyimide and the remaining polyamide acid in the resin composition can be determined. The total amount of the polyimide and the remaining polyamide acid can be determined based on the values for properties derived from the chemical structure of the group retained after polymerization from among the groups of components used for producing polyimide (e.g., acid dianhydride and/or diamine).

1.1.5.3. Fluorine-Containing Polyimide Having Biphenyl Group

The polyimide used in the present invention is more preferably a polyimide obtained through the reaction of at least one acid dianhydride with at least one diamine, wherein the diamine comprises a diamine compound comprising a biphenyl group with each of its two benzene rings being substituted with an amino group, and wherein at least either the acid dianhydride or diamine comprises a fluorine atom in molecules thereof.

Also, the polyimide used in the present invention is more preferably a fluorine-containing polyimide comprising in its main chain (the main chain backbone) a repeating unit represented by Formula (3), wherein $X^0$ represents a tetravalent organic group and $Y^0$ represents a divalent organic group; $X^0$ and $Y^0$ contain one or more fluorine atoms in total; and $Y^0$ represents a structure of a diamine compound comprising a biphenyl group with each of two benzene rings being substituted with an amino group and the amino group being substituted with a single bond to a nitrogen atom. It is particularly preferable that $Y^0$ represent a group represented by Formula (D) below.

On the surface of the substrate composed of a polyimide-containing resin composition having such properties, cells can easily form three-dimensional tissue. Thus, such substrate is preferable.

In this embodiment of the present invention, as the diamine represented by Formula (2) used for polymerization, a diamine compound (i.e., the diamine) comprising a biphenyl group with each of two benzene rings being substituted with an amino group is used. The hydrogen atom of the biphenyl group may be substituted with another substituent other than the amino group, and it is more preferable that the hydrogen atom be substituted with another substituent other than the amino group. While the number of other substituents is not particularly limited, such number is preferably 1 or 2.

Examples of preferable embodiments of the diamine compounds include compounds represented by Formula (IX):

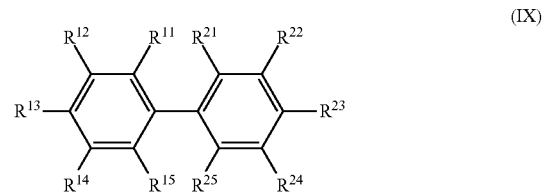

wherein one of $R^{11}$, $R^{12}$, $R^{13}$, $R^{14}$, and $R^{15}$ represents —NH$_2$, 4 other members each independently represent a group selected from the group consisting of a hydrogen atom, an alkyl group having 1 to 6 carbon atoms, an alkoxy group having 1 to 6 carbon atoms, —SO$_3$H, and —OH; one of $R^{21}$, $R^{22}$, $R^{23}$, $R^{24}$, and $R^{25}$ represents —NH$_2$, 4 other members each independently represent a group selected from the group consisting of a hydrogen atom, an alkyl group having 1 to 6 carbon atoms, an alkoxy group having 1 to 6 carbon atoms, —SO$_3$H, and —OH; or $R^{11}$ and $R^{21}$ and/or $R^{15}$ and $R^{25}$ may together form —S(=O)$_2$—.

The alkyl group is preferably an ethyl or methyl group, with a methyl group being particularly preferable.

The alkoxy group is preferably an ethoxy or methoxy group, with a methoxy group being particularly preferable.

All or some hydrogen atoms of the alkyl group may be substituted with a fluorine atom, which is preferably a trifluoromethyl group.

All or some hydrogen atoms of the alkoxy group may be substituted with a fluorine atom, which is preferably a trifluoromethoxy group.

Particularly preferable compounds represented by Formula (IX) are as described below.

Group of Compounds 1:
Compounds represented by Formula (IX) wherein one of $R^1$, $R^{12}$, $R^{13}$, $R^{14}$, and $R^{15}$ represents —NH$_2$, another member is an alkyl group substituted with a fluorine atom having 1 to 6 carbon atoms (preferably a trifluoromethyl group), and the other remaining members are hydrogen atoms; and one of $R^{21}$, $R^{22}$, $R^{23}$, $R^{24}$, and $R^{25}$ represents —NH$_2$, another member is an alkyl group substituted with a fluorine atom having 1 to 6 carbon atoms (preferably a trifluoromethyl group), and the other remaining members are hydrogen atoms;

Group of Compounds 2:
Compounds represented by Formula (IX) wherein one of $R^{11}$, $R^{12}$, $R^{13}$, $R^{14}$, and $R^{15}$ represents —NH$_2$, another member is an alkyl group having 1 to 6 carbon atoms (preferably a methyl group), and the other remaining members are hydrogen atoms; and one of $R^{21}$, $R^{22}$, $R^{23}$, $R^{24}$, and $R^{25}$ represents —NH$_2$, another member is an alkyl group having 1 to 6 carbon atoms (preferably a methyl group), and the other remaining members are hydrogen atoms;

Group of Compounds 3:

Compounds represented by Formula (IX) wherein one of $R^{11}$, $R^{12}$, $R^{13}$, $R^{14}$, and $R^{15}$ represents —$NH_2$, another member is —OH, and the other remaining members are hydrogen atoms; and one of $R^{21}$, $R^{22}$, $R^{23}$, $R^{24}$, and $R^{25}$ represents —$NH_2$, another member is —OH, and the other remaining members are hydrogen atoms;

Group of Compounds 4:

Compounds represented by Formula (IX) wherein $R^{11}$ and $R^{21}$ together form —$S(=O)_2$—, one of $R^{12}$, $R^{13}$, $R^{14}$, and $R^{15}$ represents —$NH_2$, another member is an alkyl group having 1 to 6 carbon atoms, and the other remaining members are hydrogen atoms; and one of $R^{22}$, $R^{23}$, $R^{24}$, and $R^{25}$ represents —$NH_2$, another member is an alkyl group having 1 to 6 carbon atoms, and the other remaining members are hydrogen atoms;

Group of Compounds 5:

Compounds represented by Formula (IX) wherein one of $R^{11}$, $R^{12}$, $R^{13}$, $R^{14}$, and $R^{15}$ represents —$NH_2$, another member is —$SO_3H$, and the other remaining members are hydrogen atoms; and one of $R^{21}$, $R^{22}$, $R^{23}$, $R^{24}$, and $R^{25}$ represents —$NH_2$, another member is —$SO_3H$, and the other remaining members are hydrogen atoms:

Group of Compounds 6:

Compounds represented by Formula (IX) wherein one of $R^{11}$, $R^{12}$, $R^{13}$, $R^{14}$, and $R^{15}$ represents —$NH_2$, another member is an alkoxy group having 1 to 6 carbon atoms (preferably a methoxy group), and the other remaining members are hydrogen atoms; and one of $R^{21}$, $R^{22}$, $R^{23}$, $R^{24}$, and $R^{25}$ represent —$NH_2$, the other is an alkoxy group having 1 to 6 carbon atoms (preferably a methoxy group), and the other remaining members are hydrogen atoms.

In the groups of compounds 1 to 6 above, $R^{13}$ and $R^{23}$ may represent —$NH_2$.

In the group of compounds 1, a compound represented by Formula (IX-1); that is, 2,2'-bis(trifluoromethyl)benzidine (TFMB), is particularly preferable.

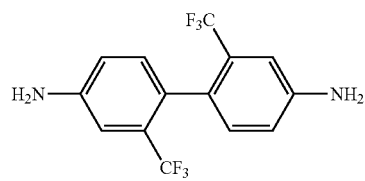

(IX-1)

In the group of compounds 2, a compound represented by Formula (IX-2); that is, 2,2'-dimethyl-4.4'-diaminobiphenyl, is particularly preferable.

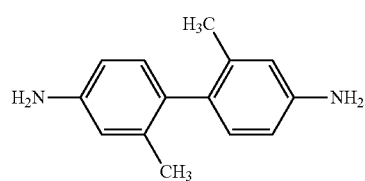

(IX-2)

In the group of compounds 3, a compound represented by Formula (IX-3); that is, 3,3'-dihydroxy-4,4'-diaminobiphenyl, is particularly preferable.

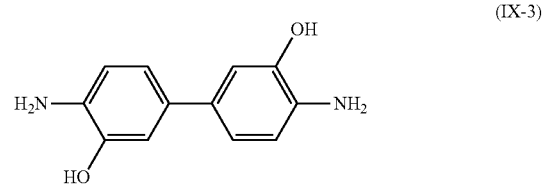 [SMILES: Nc1ccc(-c2ccc(N)c(O)c2)cc1O]

(IX-3)

In the group of compounds 4, a compound represented by Formula (IX-4); that is, O-tolidinesulfone, is particularly preferable.

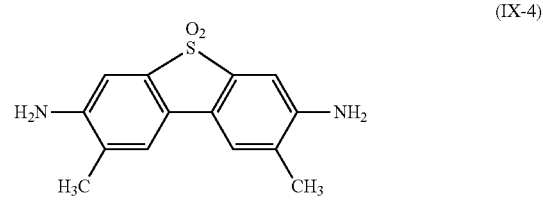 [SMILES: Cc1cc2c(cc1N)S(=O)(=O)c1cc(N)c(C)cc1-2]

(IX-4)

In the group of compounds 5, a compound represented by Formula (IX-5); that is, O-tolidinedisulfonic acid, is particularly preferable.

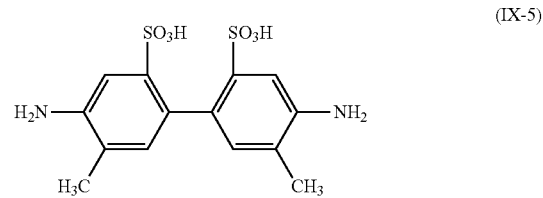 [SMILES: Cc1cc(-c2cc(C)c(N)cc2S(=O)(=O)O)c(S(=O)(=O)O)cc1N]

(IX-5)

In the group of compounds 6, a compound represented by Formula (IX-6); that is, 2,2'-dimethoxy-4.4'-diaminobiphenyl, is particularly preferable.

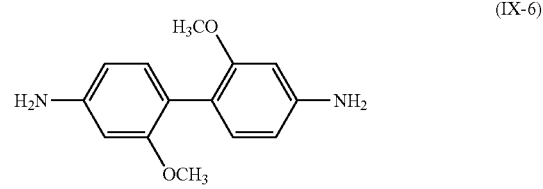 [SMILES: COc1cc(N)ccc1-c1ccc(N)cc1OC]

(IX-6)

Specifically, diamine represented by Formula (2) preferably comprises a diamine in which $Y^0$ is a group represented by Formula (D):

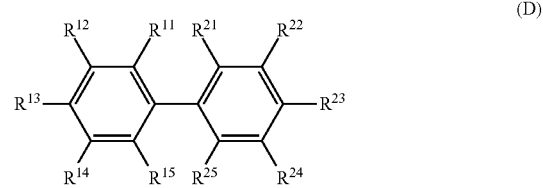

(D)

wherein one of $R^{11}$, $R^{12}$, $R^{13}$, $R^{14}$, and $R^{15}$ is equivalent to —$NH_2$ represented by $R^{11}$, $R^{12}$, $R^{13}$, $R^{14}$, or $R^{15}$ defined with respect to Formula (IX) above, which represents a single bond to a nitrogen atom, and the other remaining members are groups other than —NH$_2$ represented by R$^{11}$, R$^{12}$, R$^{13}$, R$^{14}$, or R$^{15}$ defined with respect to Formula (IX) above, and one of R$^{21}$, R$^{22}$, R$^{23}$, R$^{24}$, and R$^{25}$ is equivalent to —NH$_2$ represented by R$^{11}$, R$^{12}$, R$^{13}$, R$^{14}$, or R$^{15}$ defined with respect to Formula (IX) above, which represents a single bond to a nitrogen atom, and the other remaining members are groups other than —NH$_2$ represented by R$^{21}$, R$^{22}$, R$^{23}$, R$^{24}$, or R$^{25}$ defined with respect to Formula (IX) above. Further, the diamine represented by Formula (2) more preferably comprises a diamine in which Y$^0$ is a group represented by any one of Formulae (D$^1$) to (D$^6$):

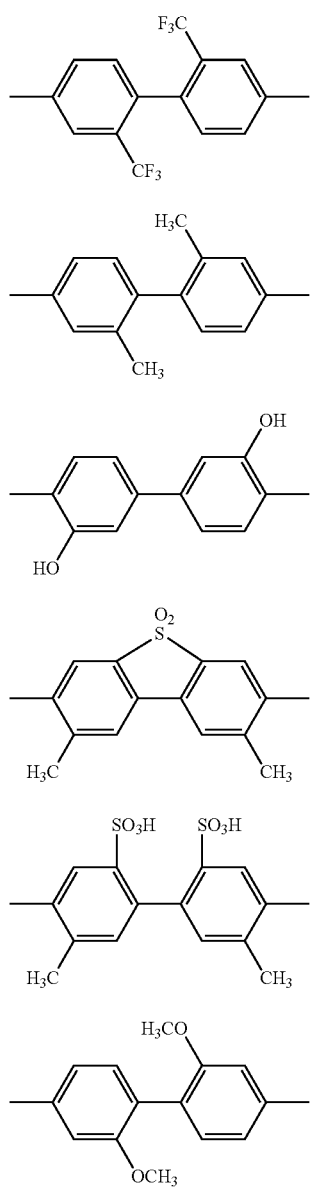

Specifically, Y$^1$ in Formula (I) or Formula (V), Y$^3$ in Formula (III) or Formula (VII), and Y$^4$ in Formula (IV) or Formula (VIII) are each preferably a group represented by Formula (D), and more preferably a group represented by any one of Formulae (D$^1$) to (D$^6$).

1.2. Fluorine-Containing Polymer

Another embodiment of the fluorine-containing polymer used in the present invention is a polymer having a fluorine-containing aromatic ring and in its main chain an ether bond. Preferably, it is a polymer comprising a structure represented by Formula (I-1) below in a repeating unit and an ether bond in its main chain:

(I-1)

wherein at least one of R, R$^{32}$, R$^{33}$, and R$^{34}$ represents a fluorine atom, when R$^{31}$, R$^{32}$, R$^{33}$, or R$^{34}$ does not represent a fluorine atom, R$^{31}$, R$^{32}$, R$^{33}$, and R$^{34}$ each independently represent a hydrogen atom (H), a cyano group (CN), an alkyl group having 1 to 12 carbon atoms, which may be optionally substituted, an alkoxy group having 1 to 12 carbon atoms, which may be optionally substituted, an alkylamino group having 1 to 12 carbon atoms, which may be optionally substituted, an alkylthio group having 1 to 12 carbon atoms, which may be optionally substituted, an aryl group having 6 to 20 carbon atoms, which may be optionally substituted, an aryloxy group having 6 to 20 carbon atoms, which may be optionally substituted, an arylamino group having 6 to 20 carbon atoms, which may be optionally substituted, or an arylthio group having 6 to 20 carbon atoms, which may be optionally substituted.

In Formula (I-1), at least two of R$^{31}$, R$^{32}$, R$^{33}$, and R$^{34}$ preferably represent fluorine atoms. Alternatively, all of R$^{31}$, R$^{32}$, R$^{33}$, and R$^{34}$ may represent fluorine atoms.

The fluorine content in the resin composition used in the present invention is 1% to 60% by mass, preferably 5% to 60% by mass, more preferably 10% to 60% by mass, and further preferably 15% to 50% by mass. On the surface of the substrate composed of a resin composition with such fluorine content, cells can easily form three-dimensional tissue.

1.2.1. Specific Examples of Fluorine-Containing Polymers (1)

A specific example of the fluorine-containing polymer used in the present invention is a fluorine-containing aryl ether ketone polymer represented by Formula (II-2):

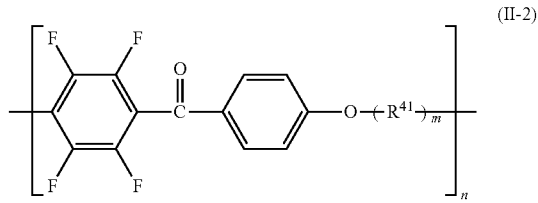

(II-2)

wherein n represents the degree of polymerization, m is the integer 0 or 1, and R$^{41}$ is a group represented by Formula (II-3):

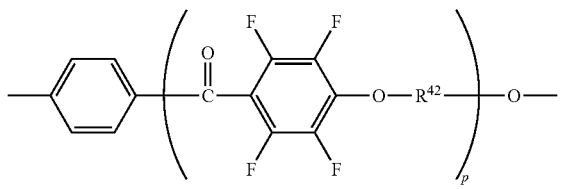

wherein p is the integer 0 or 1, and $R^{42}$ represents a structure represented by any of the formulae shown below.

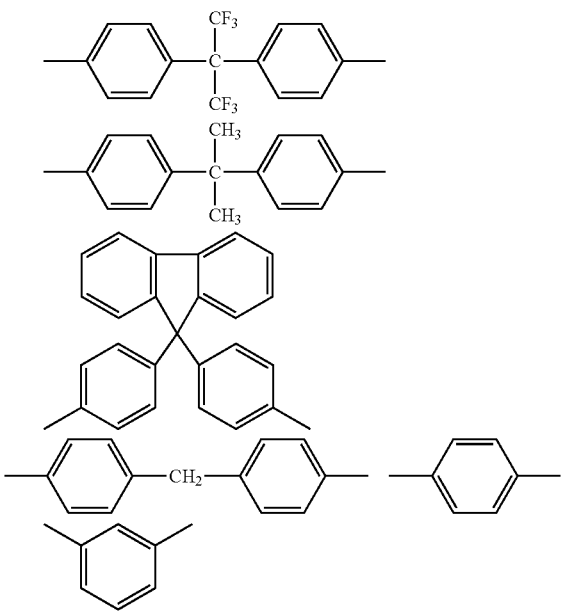

In Formula (II-2), the degree of polymerization (n) is specifically 2 to 5,000, and preferably 5 to 500. According to the present invention, in addition, a fluorine-containing aryl ether ketone polymer may be composed of the same type or different types of repeating units. In the latter case, the repeating unit may be a block or random polymer.

In the present invention, a method for producing a fluorine-containing aryl ether ketone polymer represented by Formula (II-2) is described in detail. According to such description, the fluorine-containing aryl ether ketone polymer represented by Formula (II-2) is considered to comprise a fluorine atom at the terminus at which a benzene ring containing a fluorine atom is present and a hydrogen atom at the terminus at which $R^{41}$ is present. That is, the fluorine-containing aryl ether ketone polymer represented by Formula (II-2) is presumed to be a fluorine-containing aryl ether ketone polymer represented by Formula (II-11):

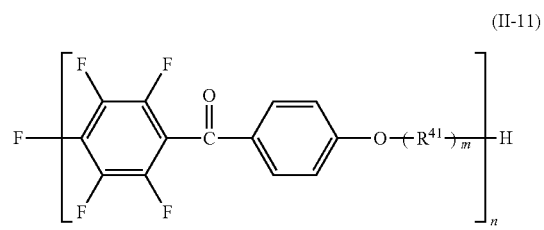

wherein n represents the degree of polymerization, m is the integer 0 or 1, and $R^{41}$ is as defined above.

A polymer represented by Formula (II-2) is, when m is 0, a fluorine-containing aryl ether ketone polymer represented by Formula (II-4):

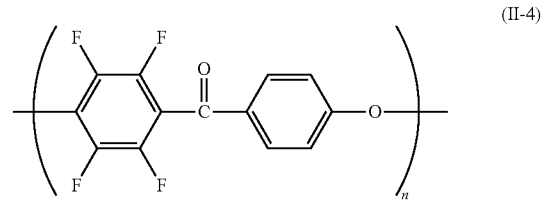

wherein n represents the degree of polymerization.

A polymer represented by Formula (II-2) is, when m is 1 and p is 0, a fluorine-containing aryl ether ketone polymer represented by Formula (II-5):

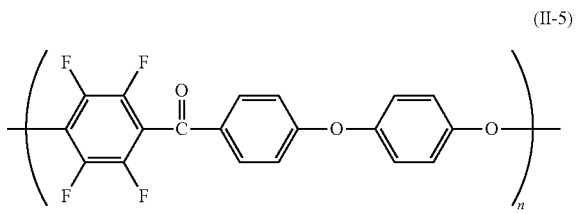

wherein n represents the degree of polymerization.

A polymer represented by Formula (II-2) is, when m is 1 and p is 1, a fluorine-containing aryl ether ketone polymer represented by Formula (II-6):

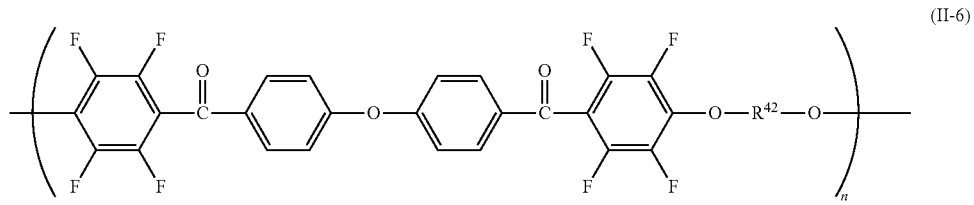

wherein n represents the degree of polymerization, and $R^{42}$ is as defined above. In Formula (II-6), n is preferably 2 to 2000, and more preferably 5 to 200.

According to a preferable embodiment, specifically, a fluorine-containing aryl ether ketone polymer represented by Formula (II-2) is a polymer comprising a repeating unit represented by Formula (II-1):

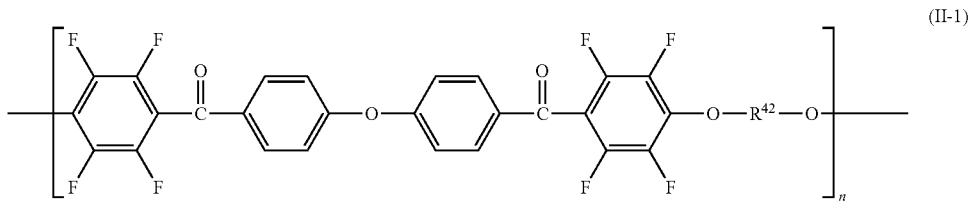

wherein $R^{42}$ is as defined above.

According to a particularly preferable embodiment, a fluorine-containing aryl ether ketone polymer represented by Formula (II-2) is a polymer comprising a repeating unit represented by Formula (II-12):

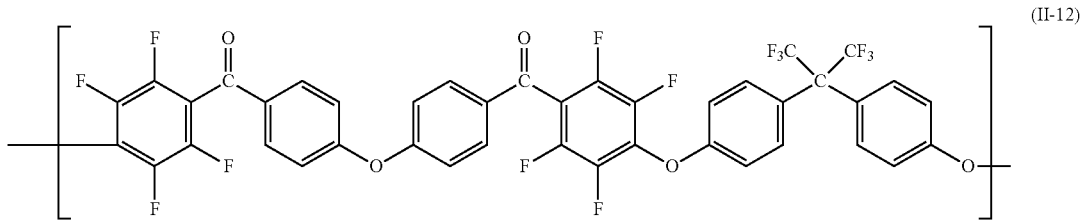

A fluorine-containing aryl ether ketone polymer represented by Formula (II-6):

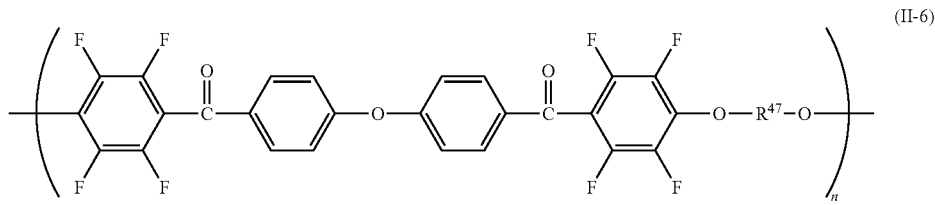

Fluorine-containing aryl ether ketone polymers represented by Formulae (II-3) and (II-4) can be obtained by heating a 2,3,4,5,6-pentafluorobenzoyl compound represented by Formula (II-9) in the presence of a basic compound in an organic solvent:

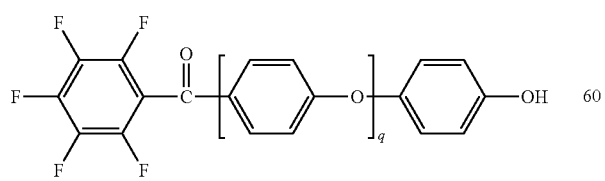

wherein q is the integer 0 or 1.

In the reaction shown above, the reaction temperature is 30° C. to 250° C., and preferably 50° C. to 200° C.

wherein $R^{42}$ is as defined above, and n represents the degree of polymerization, can be obtained by heating 4,4'-bis(2,3,4,5,6-pentafluorobenzoyl)diphenyl ether represented by Formula (II-8):

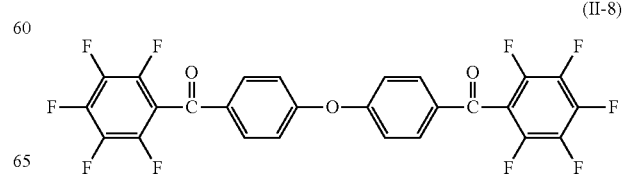

and a divalent phenol compound represented by Formula (II-10):

$$HO-R^{42}-OH \quad (II\text{-}10)$$

wherein $R^{42}$ represents any of the structures shown below:

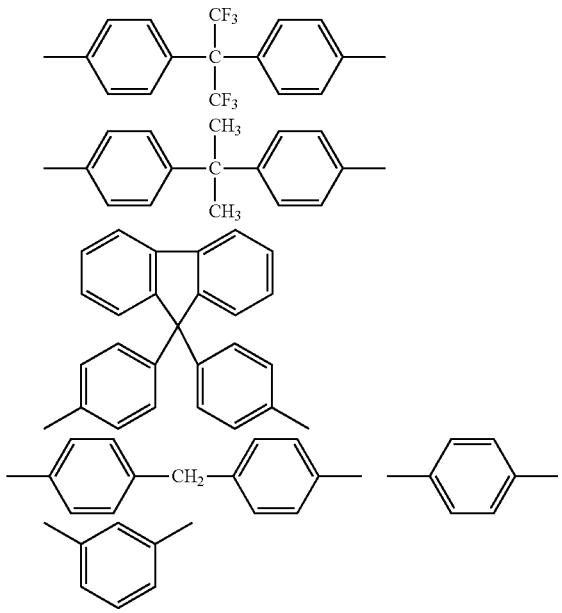

in the presence of a basic compound in an organic solvent.

In the reaction shown above, the reaction temperature is 20° C. to 150° C., and preferably 50° C. to 120° C. By conducting the reaction at such low temperature, side reactions can be suppressed, and the polymer can be prevented from gelling. While the duration of polymerization varies depending on other reaction conditions and starting materials used, it is preferably 1 to 48 hours, and more preferably 2 to 24 hours. While polymerization may be carried out under ordinary pressure or reduced pressure, it is preferably carried out under ordinary pressure from the viewpoint of equipment.

Examples of organic solvents used in the polymerization include: polar solvents, such as N-methylpyrrolidinone, N-methyl-2-pyrrolidinone, N,N-dimethylacetamide, and methanol; and toluene. Such organic solvents may be used alone or in combinations of two or more.

The concentration of the pentafluorobenzoyldiphenyl ether compound in an organic solvent is 5% to 50% by weight, and preferably 10% to 30% by weight.

When toluene or another equivalent solvent is used at the initial stage of the reaction, water, which is a by-product when phenoxide is generated, can be removed as an azeotropic mixture of toluene, regardless of the type of polymerization solvent.

A basic compound used in the present invention captures hydrogen fluoride generated upon polycondensation, so as to promote polycondensation. In the case of polycondensation with the aid of a divalent phenol compound, a phenol compound can be converted into an anion with higher reactivity.

Examples of such basic compounds include potassium carbonate, lithium carbonate, and potassium hydroxide.

The amount of the basic compound used in the present invention is 0.5 to 10 moles, and preferably 0.5 to 5 moles, relative to a mole of the pentafluorobenzoyldiphenyl ether compound used in the case of the polymers represented by Formula (II-3) and Formula (II-4). In the case of the polymer represented by Formula (II-5), such amount is 1 to 20 moles, and preferably 1 to 10 moles, relative to a mole of the pentafluorobenzoyldiphenyl ether compound.

Examples of divalent phenol compounds used in the present invention include 2,2-bis(4-hydroxyphenyl)-1,1,1,3,3,3-hexafluoropropane (hereafter referred to as "6FBA"), bisphenol A (hereafter referred to as "BA"), 9,9-bis(4-hydroxyphenyl)fluorene (hereafter referred to as "HF"), bisphenol F (hereafter referred to as "BF"), hydroquinone (hereafter referred to as "HQ"), and resorcinol (hereafter referred to as "RS"). The amount of the divalent phenol compound used is 0.8 to 1.2 moles, and preferably 0.9 to 1.1 moles, relative to a mole of 4,4'-bis(2,3,4,5,6-pentafluorobenzoyl)diphenyl ether.

For example, 4,4'-bis(2,3,4,5,6-pentafluorobenzoyl)diphenyl ether is allowed to react with a divalent phenol compound (6FBA) in the presence of a basic compound in an organic solvent. Thus, a fluorine-containing aryl ether ketone polymer comprising a repeating unit represented by Formula (II-12) can be produced.

After the completion of polymerization, a solvent is removed from the reaction solution via evaporation or other means, a distillate is washed, according to need, and a polymer of interest is thus obtained. Alternatively, the reaction solution is added to a solvent having a low degree of polymer solubility, so as to allow the polymer to precipitate as a solid, and the precipitate is separated via filtration. Thus, a polymer of interest may be obtained.

1.2.2. Specific Examples of Fluorine-Containing Polymers (2)

Another specific example of a fluorine-containing polymer is a fluorine-containing aryl ester polymer that comprises, as an essential component, a repeating unit represented by Formula (III-1):

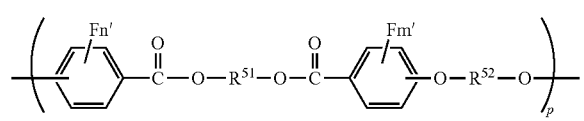

wherein m' and n', both of which may be the same or different, represent the number of fluorine atoms added to the benzene ring, which is an integer from 1 to 4; $R^{51}$ and $R^{52}$, both of which may be the same or different, represent a divalent organic group having 1 to 150 carbon atoms; and p represents the degree of polymerization.

As long as the fluorine-containing aryl ester polymer used in the present invention comprises, as an essential component, the repeating unit represented by Formula (III-1), such polymer may comprise another repeating unit. However, it is preferable that the repeating unit represented by Formula (III-1) be the main component of the repeating unit constituting the fluorine-containing aryl ester polymer. The fluorine-containing aryl ester polymer may comprise a plurality of repeating units represented by Formula (III-1), which may be the same or different. When the polymer is composed of different types of repeating units, it may be, for example, a block or random polymer.

In the repeating unit represented by Formula (III-1), the region of ($-O-R^{52}-O-$) may be bound to any carbon in the ortho position, the meta position, or the para position of a carbon of a benzene ring that forms an ester bond, and such region is preferably bound to a carbon in the ortho position or the para position. In the fluorine-containing aryl ester polymer used in the present invention, a benzene ring comprising a fluorine atom comprises 4 hydrogen atoms, and all or some thereof have been substituted with fluorine atoms. Alternatively, the hydrogen atoms of the benzene ring may be substituted with another substituent, such as a halogen atom other than a fluorine atom or a substituent comprising an alkyl chain. In a benzene ring, accordingly, the total number of hydrogen atoms, fluorine atoms, halogen atoms other than fluorine atoms, and other substituents is 4.

$R^{51}$ and $R^{52}$, both of which may be the same or different, each represent a divalent organic group having 1 to 150 carbon atoms. The divalent organic group preferably has 1 to 50 carbon atoms. The divalent organic group is more preferably a group represented by any of Formulae (8-1) to (8-19) below.

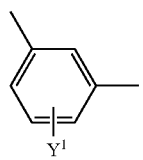
(8-1)

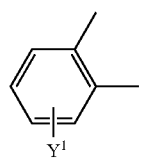
(8-2)

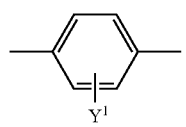
(8-3)

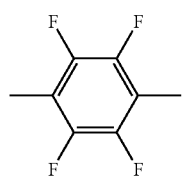
(8-4)

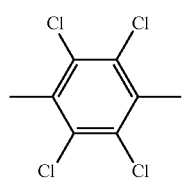
(8-5)

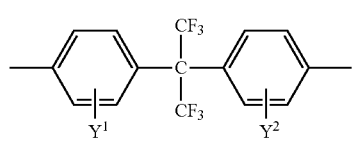
(8-6)

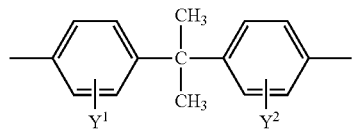
(8-7)

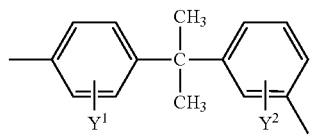
(8-8)

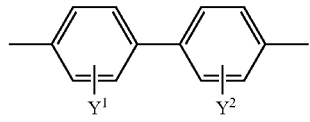
(8-9)

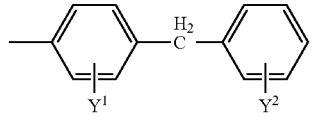
(8-10)

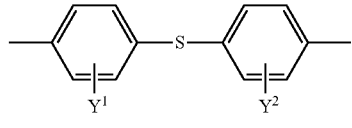
(8-11)

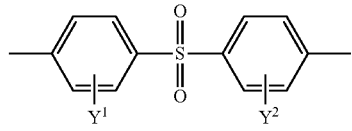
(8-12)

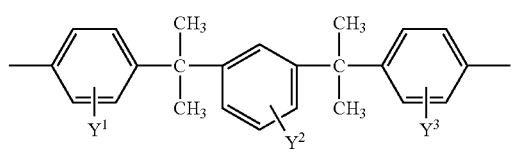
(8-13)

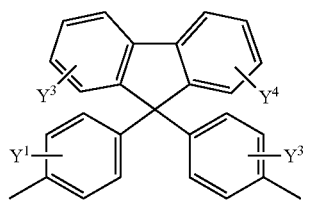
(8-14)

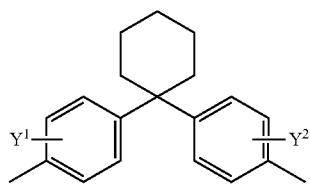
(8-15)

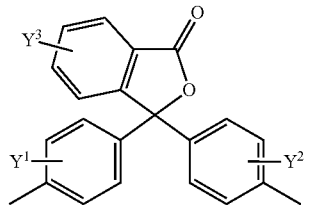
(8-16)

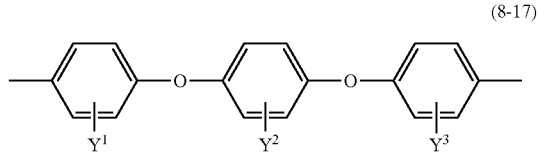
(8-17)

-continued (8-18)
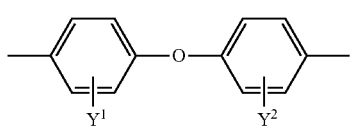

(8-19)
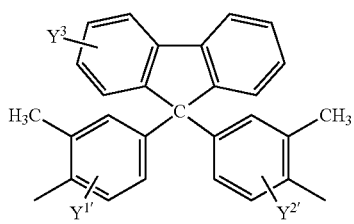

In Formulae (8-1) to (8-19), $Y^1$, $Y^{1'}$, $Y^2$, $Y^{2'}$, $Y^3$, and $Y^4$, which may be the same or different, represent substituents, and a benzene ring comprises from 0 to 4 $Y^1$, $Y^2$, $Y^3$, and $Y^4$ and from 0 to 3 $Y^{1'}$ and $Y^{2'}$ as substituents. Examples of substituents represented by $Y^1$, $Y^{1'}$, $Y^2$, $Y^{2'}$, $Y^3$, and $Y^4$ include halogen atoms and alkyl, alkoxy, alkylamino, alkylthio, aryl, aryloxy, arylamino, and arylthio groups, which may be optionally substituted.

In the fluorine-containing aryl ester polymer used in the present invention, it is preferable that a benzene ring of a group represented by any of Formulae (8-1) to (8-19) have at least one substituent, and that such substituent is an alkyl, alkoxy, or another group having 1 to 30 carbon atoms, which may be optionally substituted, or that the benzene ring is not substituted. It is more preferable that the benzene ring is not substituted. Specifically, the group represented by any of Formulae (8-1) to (8-19) is preferably a group represented by any of Formulae (9-1) to (9-19).

(9-1)
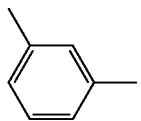

(9-2)
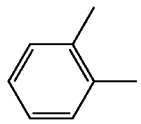

(9-3)
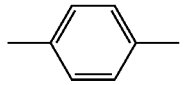

(9-4)
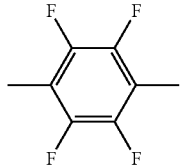

(9-5)
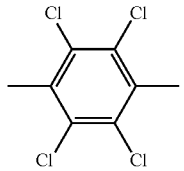

-continued (9-6)
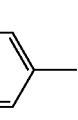

(9-7)
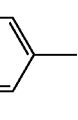

(9-8)
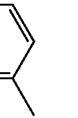

(9-9)

(9-10)

(9-11)

(9-12)

(9-13)
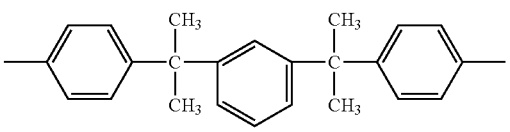

(9-14)
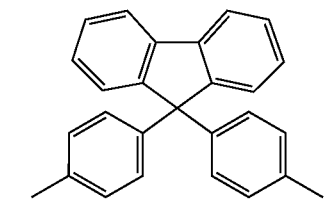

(9-15)
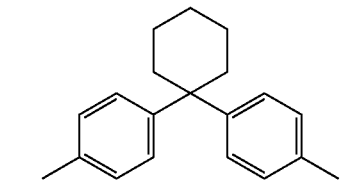

(9-16)
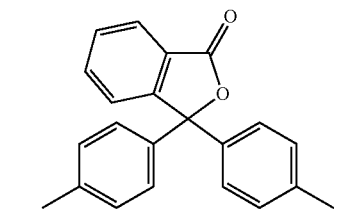

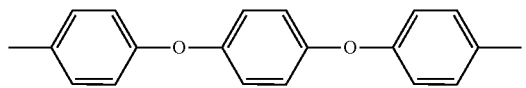
(9-17)

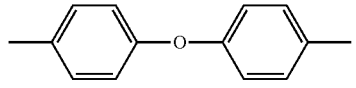
(9-18)

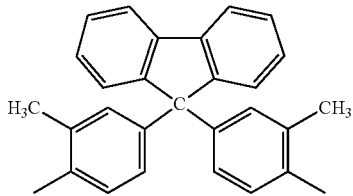
(9-19)

In the fluorine-containing aryl ester polymer used in the present invention, it is preferable that $R^{51}$ in Formula (III-1) represent a structure represented by Formula (9-6) or (9-18) and the benzene ring be not substituted. Specifically, the fluorine-containing aryl ester polymer of the present invention preferably comprises, as an essential component, a repeating unit represented by Formula (III-2):

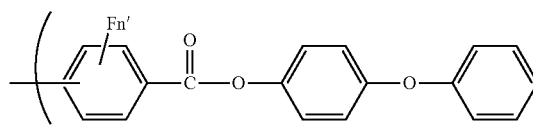
(III-2)

wherein m' and n', both of which may be the same or different, represent the number of fluorine atoms added to the benzene ring, which is an integer from 1 to 4; each $R^{52}$, any or all of which may be the same or different, represents a divalent organic group having 1 to 150 carbon atoms; and p represents the degree of polymerization, and/or a repeating unit represented by Formula (III-3);

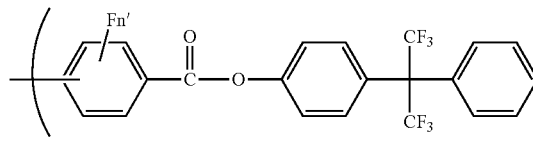
(III-3)

wherein m' and n', both of which may be the same or different, represent the number of fluorine atoms added to the benzene ring, which is an integer from 1 to 4; each $R^{52}$, any or all of which may be the same or different, represents a divalent organic group having 1 to 150 carbon atoms; and p represents the degree of polymerization.

The number average molecular weight (Mn) of the fluorine-containing aryl ester polymer may be adequately determined in accordance with properties of interest. It is preferably 1,000 to 1,000,000, and it is more preferably 3,000 to 500,000. The number average molecular weight can be determined with the use of GPC (HLC-8120GPC, manufactured by Tosoh Corporation), polystyrene as a reference sample, and THF as a developing solvent.

A method for producing a fluorine-containing aryl ester polymer represented by Formula (III-1) is not particularly limited, and such method preferably comprises a step of polymerization of a fluorine-containing ester compound with a dihydroxy compound. From the viewpoint of reaction efficiency, this step is preferably carried out in the presence of a basic catalyst.

Specifically, the fluorine-containing aryl ester polymer represented by Formula (III-1) is preferably produced by the method comprising a step of polymerization of a fluorine-containing ester compound represented by Formula (III-4):

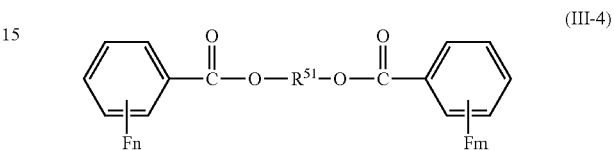
(III-4)

wherein m and n, both of which may be the same or different, represent the number of fluorine atoms added to the benzene ring, which is an integer from 1 to 5; and $R^{51}$ represents a divalent organic group having 1 to 150 carbon atoms, with a dihydroxy compound represented by Formula (III-5):

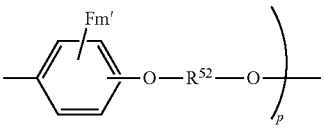
(III-5)

wherein $R^{52}$ represents a divalent organic group having 1 to 150 carbon atoms, in the presence of a basic catalyst.

A fluorine-containing ester compound represented by Formula (III-4) is highly reactive. When producing a polymer with the use of such fluorine-containing ester compound as the starting material as in the case of the method described above, accordingly, various polymerization techniques, such as polymerization in a homogenous system or interfacial polymerization, can be employed without limitation. In addition, polymerization can be carried out at a temperature of 150° C. or less, which is lower than the temperature at which polymerization has been carried out with the use of conventional fluorine-containing compounds.

In the method of production described above, the moiety of (—O—$R^{52}$—O—) derived from the dihydroxy compound may be bound to any carbon in the ortho position, the meta position, or the para position of a carbon of a benzene ring that forms an ester bond, and such moiety is preferably bound to a carbon in the ortho position or the para position. When two or more moieties derived from the dihydroxy

compound are bound to a single benzene ring, a cross-linked structure may occasionally be formed. Since such cross-linked structure causes the resulting polymer to form gel, it is preferable that the number of cross-linked structures be small. In the above method of production, the ease of generating a cross-linked structure varies depending on, for example, reaction temperature, reaction duration, types and concentrations of a solvent or a basic catalyst to be used, the order for introduction of starting materials, or water content in the reaction solution. By optimizing such conditions, accordingly, generation of a cross-linked structure can be inhibited.

In polycondensation carried out via the method of production described above, it is preferable that the amounts of the dihydroxy compound and the fluorine-containing ester compound to be used as starting materials are adequately determined from the viewpoint of the effective use of starting materials and the improved yield of the product. The amount of the dihydroxy compound is preferably 0.8 to 1.2 moles, and more preferably 0.9 to 1.1 moles, relative to a mole of the fluorine-containing ester compound.

In the method of production described above, polycondensation is preferably carried out at 0° C. to 100° C., and more preferably 10° C. to 80° C. The duration of the reaction is preferably 1 to 40 hours, and more preferably 1 to 30 hours. The reaction may be carried out under reduced pressure, ordinary pressure, or increased pressure. From the viewpoint of equipment, the reaction is preferably carried out under ordinary pressure.

In the method of production described above, polycondensation can be carried out with the use of various solvents because of the excellent solubility of the fluorine-containing ester compound in a solvent. Examples of solvents that can be used include: nitriles, such as acetonitrile and benzonitrile; nitros, such as nitrobenzene and nitromethane; ketones, such as acetone, methyl isobutyl ketone (MIBK), methyl ethyl ketone (MEK), and cyclohexanone; halogenated hydrocarbons, such as chloroform, methylene chloride, carbon tetrachloride, chloroethane, dichloroethane, trichloroethane, and tetrachloroethane; aromatic hydrocarbons, such as benzene, toluene, and xylene; hydrocarbons, such as pentane, hexane, cyclohexane, and heptane; ethers, such as diethyl ether, isopropyl ether, tetrahydrofuran (THF), dioxane, diphenyl ether, benzyl ether, and tert-butyl ether; esters, such as methyl formate, ethyl formate, methyl acetate, ethyl acetate, propyl acetate, and isopropyl acetate; N-methyl-2-pyrrolidinone (NMP), dimethylformamide (DMF), dimethylsulfoxide (DMSO), and dimethylacetamide (DMAc). These solvents may be used alone or in combinations of two or more. Among such solvents, acetone, acetonitrile, methyl isobutyl ketone (MIBK), methyl ethyl ketone (MEK), N-methyl-2-pyrrolidinone (NMP), dimethylformamide (DMF), dimethylsulfoxide (DMSO), and dimethylacetamide (DMAc) are particularly preferable. The amount of the solvent may be adequately determined for efficient performance of the reaction. The amount of the fluorine-containing ester compound in the solvent is preferably 1% to 50% by mass, and more preferably 1% to 30% by mass.

A basic compound used for polycondensation in the method of production described above preferably has functions as described below. That is, such basic compound is capable of capturing hydrogen fluoride generated upon polycondensation, thereby promoting polycondensation, and it is capable of converting a dihydroxy compound into an anion with higher reactivity. Examples thereof include calcium carbonate, calcium hydroxide, potassium fluoride, tributylamine, pyridine, potassium carbonate, lithium carbonate, potassium hydroxide, and triethylamine, and such compound can be used alone or in combinations of two or more. The amount of the basic compound used is preferably 0.5 to 20 moles, and more preferably 0.8 to 10 moles, relative to a mole of the fluorine-containing ester compound to be used.

After the completion of the polycondensation, a solvent is removed from the reaction solution via evaporation or other means, a distillate is washed, according to need, and a fluorine-containing aryl ester polymer having a repeating unit represented by Formula (III-1) is thus obtained. Alternatively, the reaction solution is added to a solvent having a low degree of polymer solubility, so as to allow the fluorine-containing aryl ester polymer to precipitate as a solid, and the precipitate is separated via filtration. Thus, a polymer of interest can be obtained.

The fluorine-containing aryl ester polymer according to the present invention is excellent in terms of solubility in a solvent. Thus, such polymer can be shaped into various forms, such as a film or fiber. A shaped article comprising the fluorine-containing aryl ester polymer according to the present invention has high shaping processability because of the excellent solubility in a solvent. In addition, such article is excellent in terms of heat resistance, low hygroscopicity, transparency, weather resistance, water repellency, and electric properties.

1.2.3. Specific Examples of Fluorine-Containing Polymers (3)

According to another embodiment, the fluorine-containing polymer that can be used in the present invention is polycyanoarylether represented by Formula (IV-1):

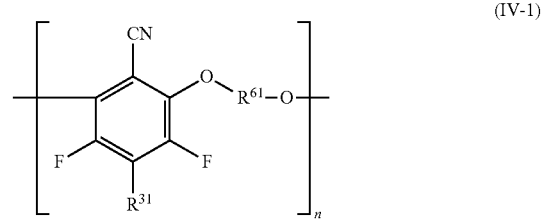

(IV-1)

wherein $R^{31}$ represents an alkyl group having 1 to 12 carbon atoms, which may be optionally substituted, an alkoxy group having 1 to 12 carbon atoms, which may be optionally substituted, an alkylamino group having 1 to 12 carbon atoms, which may be optionally substituted, an alkylthio group having 1 to 12 carbon atoms, which may be optionally substituted, an aryl group having 6 to 20 carbon atoms, which may be optionally substituted, an aryloxy group having 6 to 20 carbon atoms, which may be optionally substituted, an arylamino group having 6 to 20 carbon atoms, which may be optionally substituted, or an arylthio group having 6 to 20 carbon atoms, which may be optionally substituted; $R^{61}$ represents a divalent organic group; and n represents the degree of polymerization.

In Formula (IV-1), $R^{3'}$ represents: an alkyl group having 1 to 12 carbon atoms, which may be optionally substituted, such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, or 2-ethylhexyl, with methyl, ethyl, propyl, or butyl being preferable; an alkoxy group having 1 to 12 carbon atoms, which may be optionally substituted, such as methoxy, ethoxy, propoxy, isopropoxy, butoxy, pentyloxy, hexyloxy, 2-ethylhexyloxy, octyloxy, nonyloxy, decyloxy, undecyloxy, dodecyloxy, furfuryloxy, or allyloxy, with methoxy, ethoxy, propoxy, isopropoxy, or butoxy being preferable; an alkylamino group having 1 to 12 carbon atoms, which may be optionally substituted, such as methylamino, ethylamino, dimethylamino, diethylamino, propylamino, n-butylamino, sec-butylamino, or tert-butylamino, with methylamino, ethylamino, dimethylamino, or diethylamino being preferable; an alkylthio group having 1 to 12 carbon atoms, which may be optionally substituted, such as methylthio, ethylthio, propylthio, n-butylthio, sec-butylthio, tert-butylthio, or iso-propylthio, with methylthio, ethylthio, or propylthio being preferable; an aryl group having 6 to 20 carbon atoms, which may be optionally substituted, such as phenyl, benzyl, phenethyl, o-, m-, or p-tolyl, 2,3- or 2,4-xylyl, mesityl, naphthyl, antolyl, phenantolyl, biphenylyl, benzhydryl, trityl, or pyrenyl, with phenyl or o-, m-, or p-tolyl being preferable; an aryloxy group having 6 to 20 carbon atoms, which may be optionally substituted, such as phenoxy, benzyloxy, hydroxybenzoic acid or a group derived from an ester thereof (e.g., methylester, ethylester, methoxyethylester, ethoxyethylester, furfurylester, or phenyleste; the same applies hereinafter), naphthoxy, o-, m-, or p-methylphenoxy, o-, in-, or p-phenylphenoxy, phenylethynylphenoxy, cresotic acid or a group derived from an ester thereof, with phenoxy or naphthoxy being preferable; an arylamino group having 6 to 20 carbon atoms, which may be optionally substituted, such as anilino, o-, m-, or p-toluidino, 1,2- or 1,3-xylidino, o-, m-, or p-methoxyanilino, anthranilic acid or a group derived from an ester thereof, with anilino or o-, m-, or p-toluidino being preferable; or an arylthio group having 6 to 20 carbon atoms, which may be optionally substituted, such as phenylthio, phenylmethanethio, o-, m-, or p-tolylthio, thiosalicylic acid or a group derived from an ester thereof, with phenylthio being preferable. An aryloxy group, an arylthio group, and an arylamino group, each of which optionally comprise a substituent, are particularly preferable, and a phenoxy group, a phenylthio group, and an anilino group are most preferable as $R^{31}$.

In Formula (IV-1), $R^{31}$ represents an alkyl, alkoxy, alkylamino, alkylthio, aryl, aryloxy, arylamino, or arylthio group having a substituent. In such a case, a substituent that can be used can be adequately selected in accordance with desirable properties of the target object. Examples thereof include, but are not particularly limited to, alkyl groups having 1 to 12 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, and dodecyl; halogen atoms, such as fluorine, chlorine, bromine, and iodine; cyano groups, nitro groups, and carboxyester groups. Methyl and carboxyester groups are particularly preferable.

In Formula (IV-1), $R^{61}$ represents a divalent organic group, such as a group represented by any of formulae shown below.

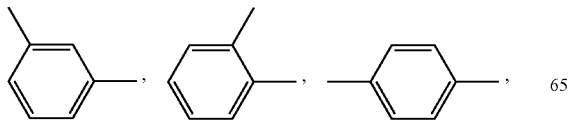

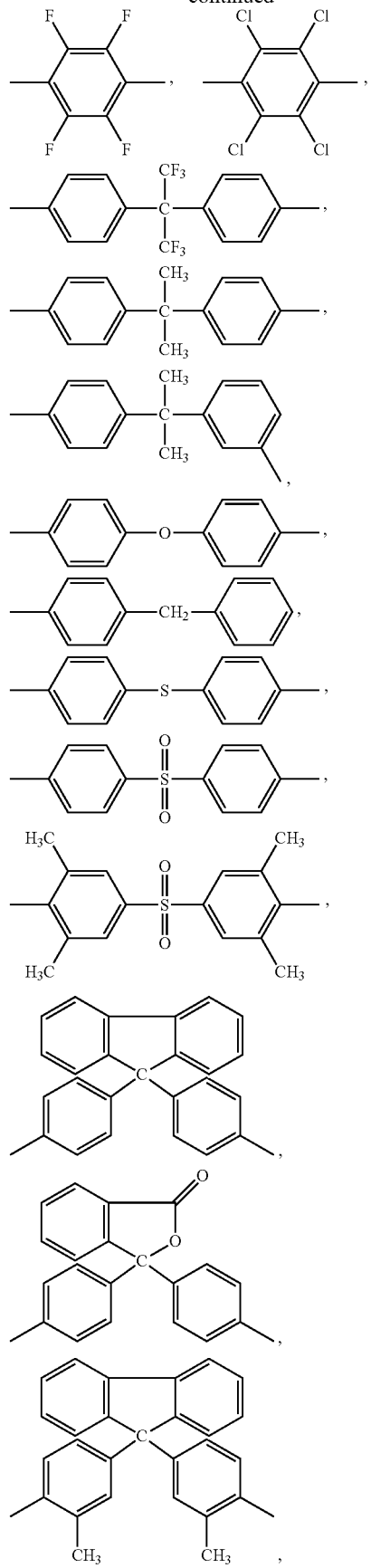

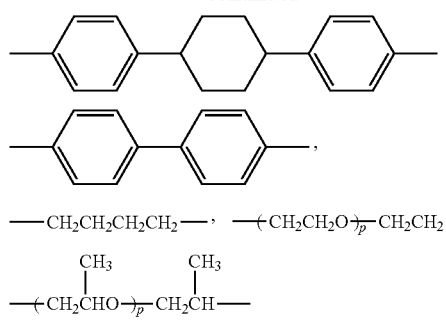
—CH₂CH₂CH₂CH₂—, —(CH₂CH₂O)ₚ-CH₂CH₂—, and
—(CH₂CHO)ₚ-CH₂CH—
       |              |
       CH₃          CH₃
R⁶¹ are preferably divalent organic groups represented by the formulae shown below.
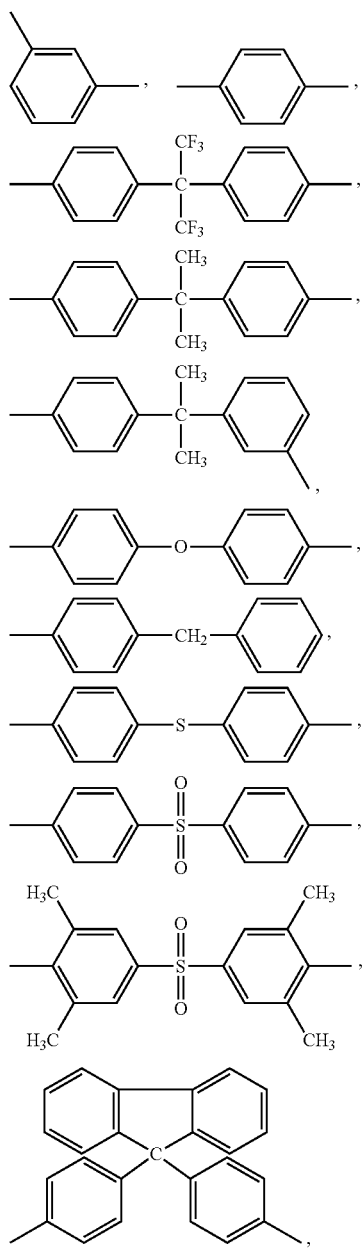
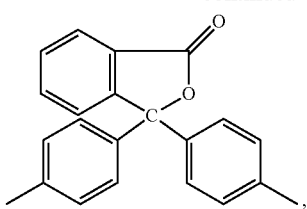
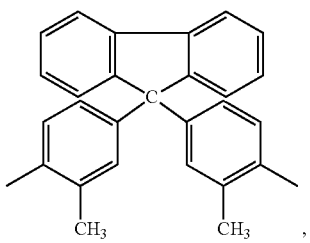
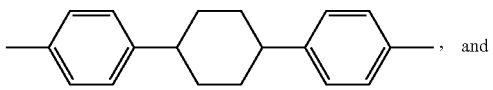
R⁶¹ are particularly preferably divalent organic groups represented by the formulae shown below.
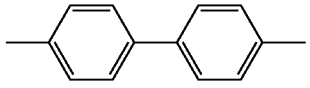
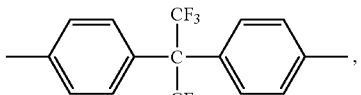
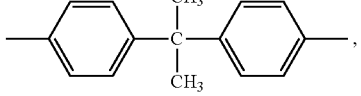
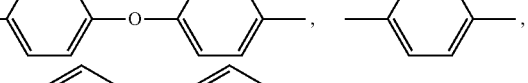
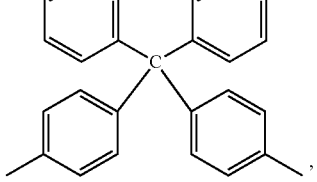
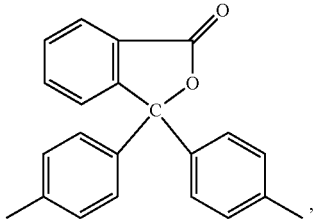

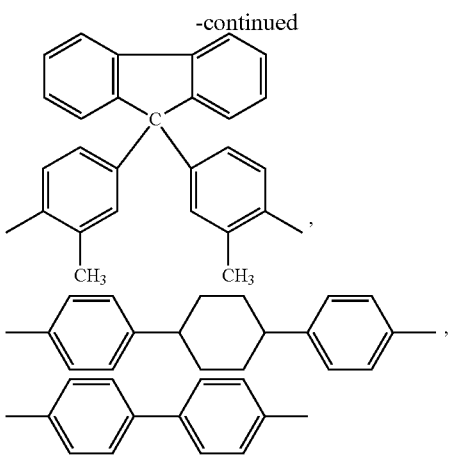

In Formula (IV-1), n represents the degree of polymerization that is specifically 5 to 1,000 and preferably 10 to 500. The polycyanoarylether used in the present invention may be composed of the same type or different types of repeating units in the constitutional unit represented by Formula (IV-1). In the latter case, such repeating unit may be a block or random polymer.

A method for producing the polycyanoarylether of the present invention is described in detail below. According to such description, the polycyanoarylether represented by Formula (IV-1) is considered to comprise a fluorine atom at the terminus at which a benzene ring containing a fluorine atom is present and a hydrogen atom at the terminus at which an oxygen atom ($R^{61}$) is present. That is, the polycyanoarylether represented by Formula (IV-1) is presumed to be a polymer represented by Formula (IV-4).

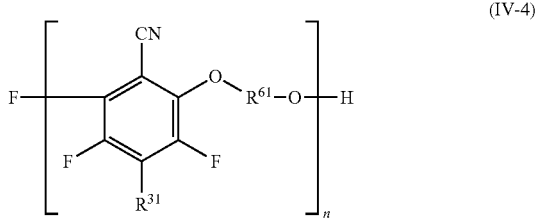

(IV-4)

The polycyanoarylether of the present invention is produced by polymerization of a tetrafluorobenzonitrile derivative represented by Formula (IV-2):

(IV-2)

with a dihydroxy compound represented by Formula (IV-3):

 (IV-3)

in the presence of a basic catalyst. In such a case, $R^{31}$ in Formula (IV-2) and $R^{61}$ in Formula (IV-3) are defined in the same manner as $R^{31}$ and $R^{61}$ in Formula (IV-1) above.

In the present invention, a tetrafluorobenzonitrile derivative represented by Formula (IV-2) can be produced in accordance with a conventional technique. For example, a compound represented by the formula $R^{31}H$, wherein $R^{31}$ is as defined in Formula (IV-1), may be allowed to react with 2,3,4,5,6-pentafluorobenzonitrile (which is also referred to as "PFBN" herein) in the presence of a basic compound in an organic solvent. Thus, such derivative can be produced.

In the reaction demonstrated above, the compounds represented by the formula $R^{31}H$ and PFBN may each independently be used as a single compound, or they may be used in the form of a mixture of two or more types of compounds represented by the formula $R^{31}H$ and/or PFBN. From the viewpoint of the step of purification and physical properties of a polymer, a single compound is preferably used. In the latter case, the total mole number of a plurality of types of or a single type of PFBN(s) used is preferably equivalent or substantially equivalent to the total mole number of a plurality of types of compounds or a single type of compound represented by the formula $R^{31}H$. Specifically, the amount of the compound represented by the formula $R^{31}H$ is preferably 0.1 to 5 moles, and more preferably 0.5 to 2 moles, relative to a mole of PFBN.

Examples of organic solvents that can be used in the reaction include: polar solvents, such as N-methyl-2-pyrrolidinone, N,N-dimethylacetamide, acetonitrile, benzonitrile, nitrobenzene, nitromethane, and methanol; and solvent mixtures of such polar solvents and non-polar solvents, such as toluene or xylene. Such organic solvents may be used alone or in combinations of two or more. PFBN concentration in the organic solvent is 1% to 40% by mass, and preferably 5% to 30% by mass. When toluene or another equivalent solvent is used at the initial stage of the reaction, water, which is a by-product when phenoxide is generated, can be removed as an azeotropic mixture of toluene, regardless of the type of polymerization solvent.

A basic compound used in the reaction preferably captures generated hydrogen fluoride, so as to promote the reaction. Examples of such basic compounds include potassium carbonate, calcium carbonate, potassium hydroxide, calcium hydroxide, potassium fluoride, triethylamine, tributylamine, and pyridine. In such a case, the amount of the basic compound used is 0.1 to 5 moles, and preferably 0.5 to 2 moles, relative to a mole of PFBN.

The reaction conditions are not particularly limited, provided that the reaction between a compound represented by $R^1H$ and PFBN can efficiently proceed. For example, the reaction is generally carried out at 20° C. to 180° C., and preferably 40° C. to 160° C., while agitating the reaction system. The duration of the reaction is generally 1 to 48 hours, and preferably 2 to 24 hours, although it varies depending on other reaction conditions or starting materials to be used. The reaction may be carried out under ordinary pressure or reduced pressure. From the viewpoint of equipment, the reaction is preferably carried out under ordinary pressure. The reaction product can be obtained by adding distilled water to a reaction mixture, extracting the reaction product with the aid of an extractant, such as dichloromethane, dichloroethane, or carbon tetrachloride, separating an organic layer from the extract, and removing the extractant via distillation. According to need, the resultant may be recrystallized with the aid of methanol or ethanol, and the resultant may be obtained in crystalline form.

The tetrafluorobenzonitrile derivative represented by Formula (IV-2) thus synthesized may be subjected to polymerization with the dihydroxy compound represented by Formula (IV-3) in the presence of a basic catalyst, as described above. Thus, the target polycyanoarylether represented by Formula (IV-1) is produced. In such a case, the tetrafluorobenzonitrile derivative represented by Formula (IV-2) may be used after the step of purification, such as extraction, recrystallization, chromatography, or distillation, as described above, or such derivative may be used without the step of purification. From the viewpoint of, for example, the yield of the next step, the derivative is preferably used after it is purified.

The dihydroxy compound represented by Formula (IV-3) used in the reaction is selected in accordance with the structure of the polycyanoarylether represented by Formula (IV-1), which is the target product. Examples of dihydroxy compounds represented by Formula (IV-3) that are preferably used include 2,2-bis(4-hydroxyphenyl)-1,1,1,3,3,3-hexafluoropropane (hereafter referred to as "6FBA"), 4,4'-dihydroxydiphenyl ether (hereafter referred to as "DPE"), hydroquinone (hereafter referred to as "HQ"), bisphenol A (hereafter referred to as "BA"), 9,9-bis(4-hydroxyphenyl) fluorene (hereafter referred to as "HF"), phenolphthalein (hereafter referred to as "PP"), 9,9-bis(3-methyl-4-hydroxyphenyl)fluorene (hereafter referred to as "MHF"), 1,4-bis (hydroxyphenyl)cyclohexane (hereafter referred to as "CHB"), and 4,4'-dihydroxybiphenyl (hereafter referred to as "BP").

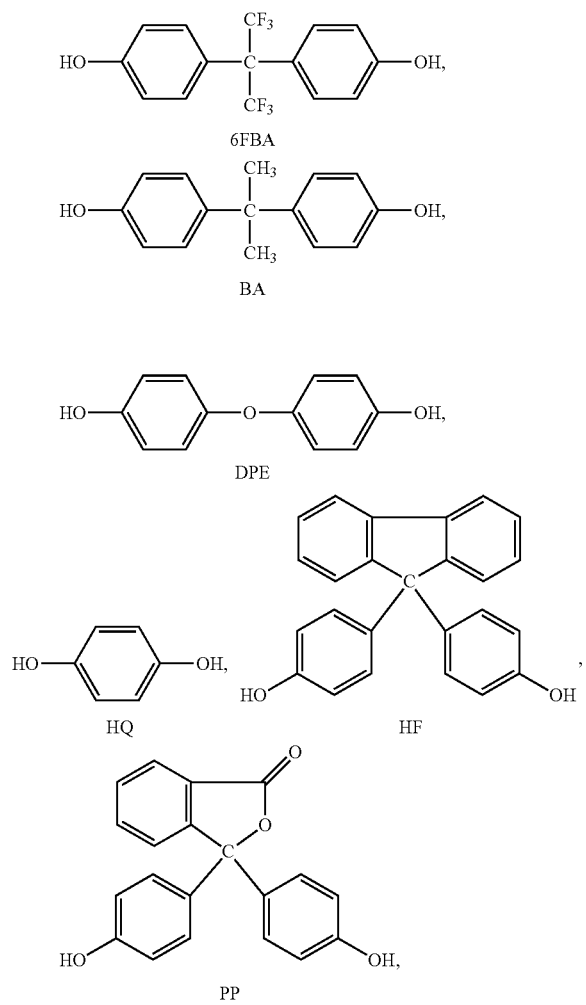

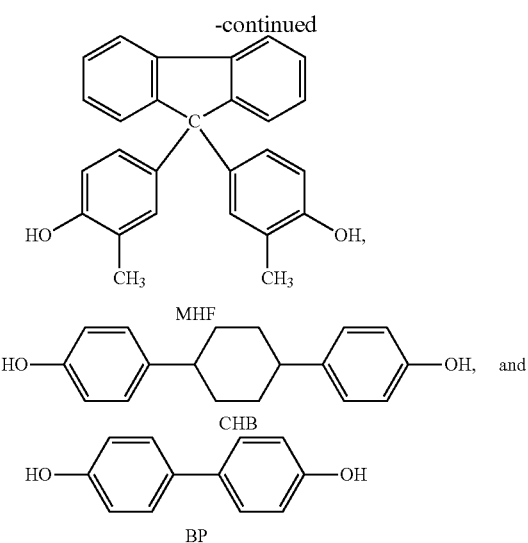

In the reaction demonstrated above, the tetrafluorobenzonitrile derivative represented by Formula (IV-2) and the dihydroxy compound represented by Formula (IV-3) may each independently be used as a single compound, or they may be used in the form of a mixture of two or more types of the tetrafluorobenzonitrile derivative represented by Formula (IV-2) and/or two or more types of the dihydroxy compound represented by Formula (IV-3). From the viewpoint of the step of purification and physical properties of a polymer, they are preferably used as a single compound respectively. In the latter case, the total mole number of a plurality of types of or a single type of the tetrafluorobenzonitrile derivative(s) represented by Formula (IV-2) is preferably equivalent or substantially equivalent to the total mole number of a plurality of types or a single type of the dihydroxy compound(s) represented by Formula (IV-3). Specifically, the amount of the dihydroxy compound represented by Formula (IV-3) is 0.1 to 5 moles, and preferably 1 to 2 moles, relative to a mole of the tetrafluorobenzonitrile derivative represented by Formula (IV-2).

The reaction may be carried out in an organic solvent or in the absence of a solvent, and the reaction is preferably carried out in an organic solvent. In the former case, examples of organic solvents that can be used include: polar solvents, such as N-methyl-2-pyrrolidinone, N,N-dimethylacetamide, acetonitrile, benzonitrile, nitrobenzene, nitromethane, and methanol; and solvent mixtures of such polar solvents and non-polar solvents, such as toluene or xylene. Such organic solvents may be used alone or in combinations of two or more. The concentration of the tetrafluorobenzonitrile derivative represented by Formula (IV-2) in the organic solvent is 1% to 50% by mass, and preferably 5% to 20% by mass. When toluene or another equivalent solvent is used at the initial stage of the reaction, water, which is a by-product when phenoxide is generated, can be removed as an azeotropic mixture of toluene, regardless of the type of polymerization solvent.

In the present invention, it is essential that the reaction of the tetrafluorobenzonitrile derivative represented by Formula (IV-2) and the dihydroxy compound represented by Formula (IV-3) be carried out in the presence of a basic catalyst. Such basic catalyst is preferably capable of converting the dihydroxy compound represented by Formula (IV-3) into an anion with higher reactivity, so as to promote the polycondensation carried out with the dihydroxy compound represented by Formula (IV-3). Specific examples thereof include potassium carbonate, calcium carbonate, potassium hydroxide, calcium hydroxide, and potassium fluoride. The amount of the basic catalyst used is not particularly limited, provided that the reaction between the tetrafluorobenzonitrile derivative represented by Formula (IV-2) and the dihydroxy compound represented by Formula (IV-3) can sufficiently proceed. It is generally 0.1 to 5 moles, and preferably 0.5 to 2 moles, relative to a mole of the tetrafluorobenzonitrile derivative represented by Formula (IV-2).

The reaction conditions for the polymerization are not particularly limited, provided that the reaction between the tetrafluorobenzonitrile derivative represented by Formula (IV-2) and the dihydroxy compound represented by Formula (IV-3) can efficiently proceed. For example, polymerization is carried out preferably at 200° C. or less, more preferably at 20° C. to 150° C., and most preferably at 40° C. to 100° C. By conducting the reaction at such low temperature, side reactions can be suppressed, and the polymer can be prevented from gelling without the need for special equipment. While the duration of polymerization varies depending on other reaction conditions and starting materials, it is preferably 1 to 48 hours, and more preferably 2 to 24 hours. While polymerization may be carried out under ordinary pressure or reduced pressure, it is preferably carried out under ordinary pressure from the viewpoint of equipment.

After the completion of the polymerization, a solvent is removed from the reaction solution via evaporation or other means, a distillate is washed, according to need, and a polymer of interest is thus obtained. Alternatively, the reaction solution is added to a solvent having a low degree of polymer solubility, so as to allow the polymer to precipitate as a solid, and the precipitate is separated via filtration. Thus, a polymer of interest may be obtained.

1.2.4. Chemical and Physical Properties of Polymer-Containing Resin Composition

1.2.4.1. Oxygen Gas Permeability Coefficient

In order to impart the cell culture substrate of the present invention with high oxygen gas permeability, use of a resin composition comprising a fluorine-containing polymer with a high oxygen gas permeability coefficient is preferable. Specifically, the oxygen gas permeability coefficient of the resin composition is preferably $0.10 \times 10^{-10}$ cm$^3$ (STP)·cm/(cm$^2$·s·cmHg) or higher, more preferably $0.50 \times 10^{-10}$ cm$^3$ (STP)·cm/(cm$^2$·s·cmHg) or higher, more preferably $1.0 \times 10^{-10}$ cm$^3$ (STP)·cm/(cm$^2$·s·cmHg) or higher, more preferably $1.5 \times 10^{-10}$ cm$^3$ (STP)·cm/(cm$^2$·s·cmHg) or higher, more preferably $2.0 \times 10^{-10}$ cm$^3$ (STP)·cm/(cm$^2$·s·cmHg) or higher, more preferably $2.5 \times 10^{-10}$ cm$^3$ (STP)·cm/(cm$^2$·s·cmHg) or higher, and more preferably $3.0 \times 10^{-10}$ cm$^3$ (STP)·cm/(cm$^2$·s·cmHg) or higher. As an oxygen gas permeability coefficient of a resin composition containing a fluorine-containing polymer increases, oxygen can be supplied to cultured cells more easily, and a higher oxygen gas permeability coefficient is thus preferable. While the upper limit of the oxygen gas permeability coefficient of such resin composition is not particularly limited, the oxygen gas permeability coefficient is generally $2.0 \times 10^{-8}$ cm$^3$ (STP)·cm/(cm$^2$·s·cmHg) or lower, and preferably $1.5 \times 10^{-8}$ cm$^3$ (STP)·cm/(cm$^2$·s·cmHg) or lower.

1.2.4.2. Water Contact Angle

On the cell culture substrate of the present invention, the water contact angle on the surface composed of a resin composition comprising a fluorine-containing polymer in the form of a film, membrane, plate, or the like is preferably 70° or more, more preferably 730 or more, further preferably 75° or more, preferably 115° or less, more preferably to 112° or less, and further preferably 110° or less. When the water contact angle is within such range, cells can easily adhere to the substrate surface with adequate strength, and cells can use the surface as the scaffold to form three-dimensional tissue. The contact angle can be determined by measuring the water contact angle at 25° C. with the use of an automated contact angle meter (DM-500, manufactured by Kyowa Interface Science Co., Ltd.).

1.2.4.3. Tensile Modulus of Elasticity

A resin composition comprising the fluorine-containing polymer is preferably excellent in flexibility. According to an embodiment, the resin composition comprising the fluorine-containing polymer is excellent in flexibility because the polymerization unit of the fluorine-containing polymer comprises ether bonds. The degree of flexibility can be evaluated in terms of the tensile modulus of elasticity. For example, the tensile modulus of elasticity can be 2 GPa or lower. The resin composition exhibiting the tensile modulus of elasticity of 2 GPa or lower is a preferable embodiment of the present invention. Cells can easily form three-dimensional tissue on the surface composed of a flexible resin composition exhibiting the tensile modulus of elasticity within such range. The tensile modulus of elasticity of the resin composition is more preferably 1.8 GPa or lower, and further preferably 1.5 GPa or lower. While the lower limit of the tensile modulus of elasticity is not particularly limited, the tensile modulus of elasticity is preferably 0.3 GPa or higher, and more preferably 0.5 GPa or higher. The tensile modulus of elasticity (GPa) can be determined by the method of dynamic viscoelasticity measurement known in the art.

2. Cell Culture Substrate

The cell culture substrate of the present invention comprises a surface at least a part of which is composed of the resin composition comprising the fluorine-containing polymer.

The form of a cell culture substrate is not particularly limited, provided that such substrate is a member having a surface serving as a scaffold for cell growth at the time of cell culture. For example, a cell culture substrate in the form of a film or plate is capable of being used to perform cell culture when a cell-containing medium is disposed on one of the surfaces. Alternatively, such substrate may be accommodated and fixed in any of various cell culture vessels, such as a culture plate (e.g., a single-well or multi-well plate), a culture petri dish, a culture dish, a flask, or a cell culture bag; a cell-containing medium may be added thereto; and cell culture may then be carried out. Also, a cell culture substrate may be in the form of any of a variety of cell culture vessels, such as a culture plate (e.g., a single-well or multi-well plate), a culture petri dish, a culture dish, a flask, or a cell culture bag. A cell culture bag can be used when, for example, subjecting suspended cells or stem cells to suspension culture.

A surface composed of the resin composition is a part of or the entire area of the cell culture substrate surface that is brought into contact with a cell-containing medium at the time of cell culture. It is preferably a part of or the entire area of the cell culture substrate surface that is positioned vertically below the cell-containing medium at the time of cell culture. The entire surface of the cell culture substrate may be composed of the resin composition. In a region on the cell culture substrate, the surface of which is composed of the resin composition, it is sufficient for the outermost layer serving as the scaffold for cell culture to be composed of the resin composition. A material in a position that is distant from the outermost layer in the thickness direction of such region is not particularly limited. Specifically, it is sufficient for the cell culture substrate of the present invention to comprise a layer composed of the resin composition in at least a part of or the entire area of the surface that is brought into contact with a cell-containing medium at the time of cell culture. As in the case of Embodiment 1 shown in FIG. 1, for example, the region of the cell culture substrate comprising the resin composition on a surface S may be composed of the resin composition in the through-thickness direction, in addition to on the surface. As in the case of Embodiment 2 shown in FIG. 2, alternatively, a film 1 composed of the resin composition may be formed on the outermost surface S serving as a scaffold for cell culture and in the vicinity thereof, and a support 2 composed of an arbitrary material may be provided on the surface opposite from the outermost surface S of the film 1.

Figure 2:
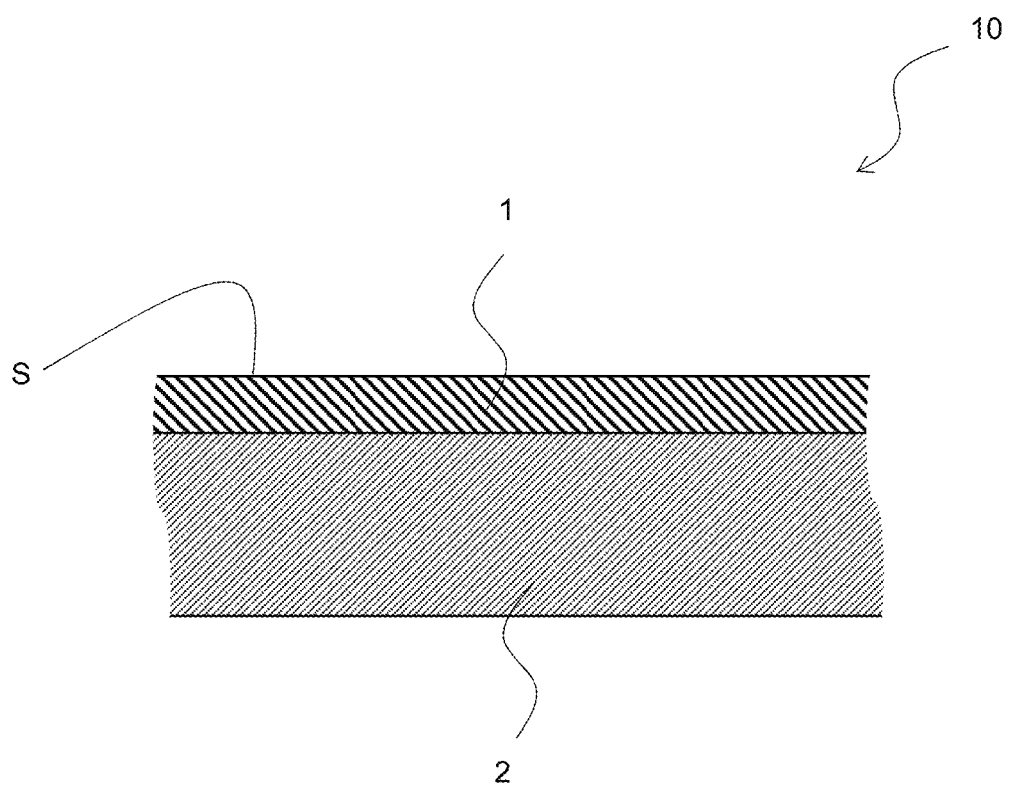
FIG. 2 schematically shows a cross section of a film 1 and a support 2 each composed of a resin composition of the cell culture substrate according to the second embodiment of the present invention, which is cut along the plane that is vertical to the main surface of the film 1.

The cell culture substrate according to a preferable embodiment of the present invention is a cell culture substrate in the form of a film, which is composed of the resin composition described above (Embodiment 1) or a cell culture substrate comprising a support and a film composed of the resin composition described above, which is integrated with the support and covers at least a part of the surface of the support (Embodiment 2). As shown in FIG. 1, specifically, a cell culture substrate 10 according to Embodiment 1 comprises a film 1 composed of the resin composition. As shown in FIG. 2, a cell culture substrate 10 according to Embodiment 2 comprises a film 1 composed of the resin composition and a support 2. A film composed of the resin composition according to Embodiment 1 and that according to Embodiment 2 can be formed in the same manner. According to Embodiment 2, a support may be in the form of, for example, a film, a porous support, or a mesh support, and such support can be in any form, so that it can be used for cell culture. For example, such support can be used for any of various cell culture vessels, such as a plate, culture dish, petri dish, single-well or multi-well plate, or flask.

According to an embodiment, the cell culture substrate of the present invention preferably comprises a film composed of a resin composition comprising a fluorine-containing polymer on at least a part of its surface.

The thickness (which does not include a thickness of the support) of a layer composed of a resin composition comprising a fluorine-containing polymer of the cell culture substrate of the present invention (such layer is also referred to as a "film" or "membrane") can be adequately adjusted, so that the entire substrate can have an adequate degree of oxygen gas permeability. Typically, such thickness is preferably 0.1 μm to 5 mm, more preferably 0.5 μm to 3 mm, further preferably 1 m to 2 mm, and particularly preferably 5 μm to 1 mm.

In the present invention, the "oxygen gas permeability coefficient" and the "oxygen gas permeability" are determined by the method in accordance with Annex 2 of JIS K7126-1 (the differential-pressure method). Both the "oxygen gas permeability coefficient" and the "oxygen gas permeability" are measured at 25° C. under dry conditions with relative humidity of substantially 0%, and the measured values are converted into the values that would be measured under the standard state of 0° C. and 1 atm. Specifically, the measurement conditions described below can be employed.
Test method: Differential-pressure method (in accordance with Annex 2, JIS K7126-1)
Detector: Gas chromatograph (thermal conductivity detector: TCD)
Test differential pressure: 1 atm
Test gas: Oxygen gas (dry conditions; relative humidity: substantially 0%)
Test conditions: 25° C.±2° C.
Permeation area: $1.52 \times 10^{-3}$ m$^2$
Apparatus: Differential pressure type gas/water vapor permeability measurement apparatus (GTR-30XAD2, G2700T·F, manufactured by GTR Tec Corporation-Yanaco Technical Science Corporation)

Figure 3:
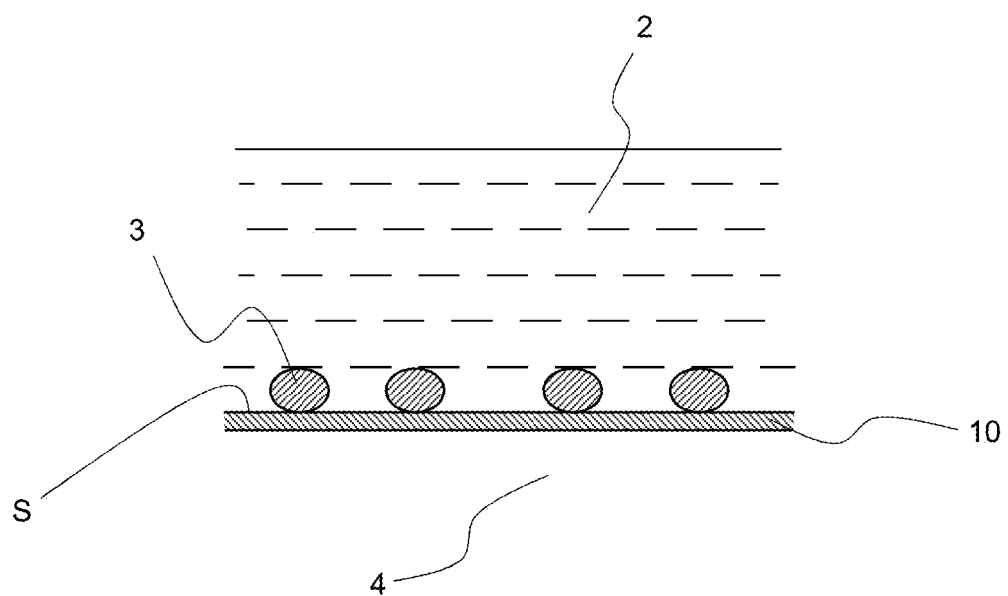
FIG. 3 schematically shows the positional relationship of the substrate 10, the medium 2, the cell 3, and the air (oxygen-containing gas) 4 in the method of cell culture according to the present invention.

When a cell culture substrate is composed of a plurality of layers as with the case shown in FIG. 3, the oxygen gas permeability of the entire cell culture substrate may be directly measured. Alternatively, the oxygen gas permeability of each layer may be determined, and the oxygen gas permeability of the entire substrate may then be determined based thereon.

The cell culture substrate used in the present invention has the oxygen gas permeability of 219 cm$^3$ (STP)/(m$^2 \cdot$24 h·atm) or higher. When the cell culture substrate of the present invention has the oxygen gas permeability as high as 219 cm$^3$ (STP)/(m$^2 \cdot$24 h·atm) or higher, oxygen is easily supplied when cells are cultured on the surface of the substrate comprising the resin composition. Thus, cell growth, three-dimensional tissue formation from cells, and tissue growth easily proceed. The oxygen gas permeability of the cell culture substrate of the present invention is more preferably 1,094 cm$^3$ (STP)/(m$^2 \cdot$0.24 h·atm) or higher, more preferably 2,189 cm$^3$ (STP)/(m$^2 \cdot$24 h·atm) or higher, more preferably 3,283 cm$^3$ (STP)/(m$^2 \cdot$0.24 h·atm) or higher, more preferably 4,378 cm$^3$ (STP)/(m$^2 \cdot$24 h·atm) or higher, more preferably 5,472 cm$^3$ (STP)/(m$^2 \cdot$24 h·atm) or higher, and more preferably 6,566 cm$^3$ (STP)/(m$^2 \cdot$24 h·atm) or higher. As the oxygen gas permeability of the cell culture substrate of the present invention increases, oxygen can be supplied to cultured cells more easily, and higher oxygen gas permeability is thus preferable. While the upper limit of the oxygen gas permeability of the cell culture substrate of the present invention is not particularly limited, the oxygen gas permeability is generally 437,760 cm$^3$ (STP)/(m$^2 \cdot$0.24 h·atm) or lower, and preferably 328,320 cm$^3$ (STP)/(m$^2 \cdot$0.24 h·atm) or lower.

The cell culture substrate of the present invention comprises a surface composed of a resin composition comprising a fluorine-containing polymer. In order to impart the cell culture substrate of the present invention with the oxygen gas permeability as described above, use of the resin composition with a high oxygen gas permeability coefficient is preferable. Specifically, the oxygen gas permeability coefficient of the resin composition is preferably $0.10 \times 10^{-10}$ cm$^3$ (STP)·cm/(cm$^2$·s·cmHg) or higher, more preferably $0.50 \times 10^{-10}$ cm$^3$ (STP)·cm/(cm$^2$·s·cmHg) or higher, more preferably $1.0 \times 10^{-10}$ cm$^3$ (STP)·cm/(cm$^2$·s·cmHg) or higher, more preferably $1.5 \times 10^{-10}$ cm$^3$ (STP)·cm/(cm$^2$·s·cmHg) or higher, more preferably $2.0 \times 10^{-10}$ cm$^3$ (STP)·cm/(cm$^2$·s·cmHg) or higher, more preferably $2.5 \times 10^{-10}$ cm$^3$ (STP)·cm/(cm$^2$·s·cmHg) or higher, and more preferably $3.0 \times 10^{-10}$ cm$^3$ (STP)·cm/(cm$^2$·s·cmHg) or higher. As an oxygen gas permeability coefficient of a resin composition containing a fluorine-containing polymer increases, oxygen can be supplied to cultured cells more easily, and a higher oxygen gas permeability coefficient is thus preferable. While the upper limit of the oxygen gas permeability coefficient of such resin composition is not particularly limited, the oxygen gas permeability coefficient is generally $2.0 \times 10^{-8}$ cm$^3$ (STP)·cm/(cm$^2$·s·cmHg) or lower, and preferably $1.5 \times 10^{-8}$ cm$^3$ (STP)·cm/(cm$^2$·s·cmHg) or lower.

When the cell culture substrate of the present invention is composed of a film 1 composed of the resin composition containing a fluorine-containing polymer and a support 2 as in the case of Embodiment 2 shown in FIG. 2, it is preferable that the support 2 be adequately selected, so as to adjust the oxygen gas permeability of the entire substrate 10 composed of the support 2 integrated with the film 1 within the range described above in the form. In particular, the use of a support 2 in the form of a porous support or a mesh support that does not have substantial adverse effects on the oxygen gas permeability of the film 1 is preferable.

Examples of methods of film formation include, but are not particularly limited to: solution film forming methods, such as solution casting; calendaring; and press molding. A solution film forming method is particularly preferable from the viewpoint of excellent productivity.

The fluorine-containing polyamide acid solution or the fluorine-containing polymer solution can be used for film formation. In an embodiment involving the use of fluorine-containing polyamide, the fluorine-containing polyamide acid solution is occasionally preferable. With the use of the polyamide acid solution, film formation can be simultaneously carried out with thermal imidization.

According to an embodiment involving the use of fluorine-containing polyamide acid, the cell culture vessel according to the present invention can be produced by the method comprising:

a step of forming a membrane of a solution comprising the fluorine-containing polyamide acid dissolved in a solvent; and a step of heating the membrane to imidize polyamide acid in the membrane, thereby forming the film.

In the present invention, a solution comprising the fluorine-containing polyamide acid dissolved in a solvent is referred to as a "polyamide acid solution." In a particular embodiment of the present invention, the solution comprising the fluorine-containing polyamide acid dissolved in a solvent, the solution comprising the fluorine-containing polyimide dissolved in a solvent, and the solution comprising the fluorine-containing polymer dissolved in a solvent are collectively referred to as "resin solutions."

As a solvent used for dissolving polyamide acid in a polyamide acid solution or a solvent used for dissolving a fluorine-containing polymer, the solvents described with respect to thermal imidization and amidation above are preferable. Examples thereof include: polar solvents, such as N-methylpyrrolidone, N-methyl-2-pyrrolidinone, N,N-dimethylacetamide, N,N-dimethylformamide, tetrahydrofuran, dimethylsulfoxide, sulfolane, methyl isobutyl ketone, acetonitrile, benzonitrile, nitrobenzene, nitromethane, dimethylsulfoxide, acetone, methyl ethyl ketone, isobutyl ketone, and methanol; and non-polar solvents, such as toluene and xylene. Use of a polar solvent is particularly preferable. Such organic solvents may be used alone or in combinations of two or more.

The concentration of the polyamide acid in the polyamide acid solution or that of a fluorine-containing polymer in the solution is preferably 5% by weight or more, and more preferably 10% by weight or more, preferably 50% by weight or less, and more preferably 40% by weight or less, from the viewpoint of the polymerizability and the post-polymerization viscosity of the resulting resin composition and ease of handling at the time of film formation or calcination after polymerization. Specific concentration may be determined on the basis of the results of the preliminary experiment.

Typically, a film is formed by coating the surface of the film-forming support with the resin solution in accordance with a conventional technique, such as spin coating, casting, roll coating, die coating, gravure coating, spray coating, bar coating, flexographic printing, or dip coating. When the resin solution is applied onto a film-forming support, it is applied to adjust a dry membrane thickness to preferably 0.1 μm to 5 mm (e.g., 1 mm or less), and more preferably 0.5 μm to 1 μm (e.g., 500 μm or less). Thereafter, the solvent is removed, and the film is calcined, according to need. Thus, a film comprising thermally or chemically imidized fluorine-containing polyimide or a film comprising a fluorine-containing polymer can be obtained.

According to a particular embodiment concerning thermal amidation, the conditions for heating the membrane of a polyamide acid solution are not particularly limited, provided that polyamide acid can be imidized. Heating is carried out in the air, preferably in an inert gas atmosphere, such as nitrogen, helium, or argon gas, or in a vacuum, at a temperature of preferably 50° C. to 400° C., and more preferably at 100° C. to 380° C., for preferably 0.1 to 10 hours, and more preferably 0.2 to 5 hours. Heating may be carried out gradually in separate steps, or it may be carried out continuously.

Examples of materials constituting a film-forming support include: quartz; inorganic glass, such as glass, borosilicate glass, soda glass; carbon; metals, such as gold, silver, copper, silicon, nickel, titanium, aluminum, and tungsten; polyolefins, such as polyethylene and polypropylene; polyesters, such as polybutylene terephthalate (PBT) and polyethylene terephthalate (PET); cyclic olefin resin, such as a cyclic olefin ring-opening polymer/hydride (COP) and a cyclic olefin copolymer (COC); acrylic resins, such as polymethyl methacrylate (PMMA); epoxy resins; resins, such as AS resin (acrylonitrile-styrene copolymer), polyvinyl chloride, polyvinylidene chloride, polystyrene (PST), polystyrene resin, polyvinyl acetate, ABS resin, polycarbonate resin, vinyl ether, polyacetal (POM), polyamide, polyphenylene ether (PPE), polyaryl ether, polyphenylene sulfide (PPS), polysulfone (PS), polyether sulfone (PES), polyether ether ketone (PEEK), polyaryl ether ketone (PEK), polyimide (PI), polyamide acid (PAA), polyamide-imide acrylic resin, phenol resin, polyether ketone resin, and polyether nitrile (PEN) resin; a glass, metal, or resin comprising any of the metals, oxides thereof, or mixed oxides on its surface; and wood. Examples of the mixed oxides include transparent conductive oxides such as ITO (i.e., indium tin oxide) and SiO$_2$. An example of a metal comprising a mixed oxide or the like on its surface is an SiO$_2$/Si substrate. A film-forming support can serve as the "support" according to Embodiment 2. In such a case, the cell culture substrate of the present invention is composed of a film in combination with the support. According to Embodiment 2, the support may be in any form, such as a plate or film, and it may be in the form of a cell culture vessel. A film formed on the film-forming support may be used in that state, the film may be peeled from the support after film formation, or the film may be used by itself as the cell culture substrate according to Embodiment 1. Alternatively, a film peeled from the film-forming support may be applied to and integrated with the surface of another support, so as to produce the cell culture substrate according to Embodiment 2 comprising the film and the support. The film can be integrated with the support via any means, such as the use of an adhesive agent. In such a case, materials constituting the support and the configuration of the support are the same as those of the film-forming support used in Embodiment 2.

In addition, the film made of the resin composition may be stretched. The film may be uniaxially or biaxially stretched. In the case of a uniaxially-stretched film, the film may be longitudinally stretched (i.e., in the film-wound direction) or horizontally stretched (i.e., in the film-width direction). In the case of longitudinal stretching, it may be free-end uniaxial stretching, so that a film can freely undergo width-direction changes, or it may be fixed-end uniaxial stretching, so that a film undergoes the fixed width-direction changes. Biaxial stretching may be sequential biaxial stretching comprising longitudinal stretching followed by horizontal stretching, or it may be simultaneous biaxial stretching comprising longitudinal stretching that is carried out simultaneously with horizontal stretching. Also, the film may be stretched in a film-thickness direction, or it may be stretched in a direction diagonal to a film roll. It is preferable that a stretching method, a stretching temperature, and a stretching ratio be adequately determined in accordance with optical properties, mechanical strength, and other properties of the target film made of a fluorine-containing polymer.

The thickness of the entire film composed of a resin composition comprising a fluorine-containing polymer (the thickness does not include the support) is preferably 0.1 µm to 1 mm, more preferably 0.5 µm to 500 µm, and further preferably 1 µm to 300 µm.

When the resin solution is a solution of polyimide obtained via chemical imidization, a film coated with such solution is preferably heated at a temperature for a duration that allows a solvent to be removed therefrom. For example, the film is calcined in a nitrogen atmosphere at preferably 50° C. to 400° C., and more preferably 100° C. to 300° C., for preferably 10 minutes to 5 hours, and more preferably 30 minutes to 3 hours. Thus, a film composed of the resin composition can be obtained.

The surface of the cell culture substrate of the present invention that is composed of the resin composition comprising a fluorine-containing polymer is preferably a smooth surface. For example, a smooth surface preferably has surface roughness of 0.5 µm or less (center line average roughness: Ra). Surface roughness is preferably 0.1 µm or less, and more preferably 0.01 µm or less. In the present invention, center line average roughness (Ra) is determined by the laser method. For example, surface roughness can be determined using a surface roughness meter (R5300GL-L-A100-AC; manufactured by Ryoka Systems Inc.). According to the present invention, three-dimensional cell culture can be carried out on a smooth surface that is easy to prepare. It should be noted that a surface of the cell culture substrate of the present invention that is composed of a polyimide-containing resin composition may be processed to have an adequate degree of roughness according to need. For example, fine concaves and convexes can be formed via rubbing treatment described in Non-Patent Document 1. Also, the cell culture substrate of the present invention may be provided with a cylindrical or conical hole (i.e., a cavity) with a diameter of 50 to 500 µm and a depth of 50 to 500 µm (e.g., 300 µm or less). Thus, spheroids and three-dimensional cell aggregates that are uniform in size can be formed. By providing the cavity structure, in addition, spheroids, three-dimensional cell aggregates, or the like can be prevented from being removed from the substrate together with the medium when the medium is removed.

In addition to the effects described above, the cell culture substrate of the present invention preferably has the effects described below. The substrate of the present invention preferably has high heat resistance. Thus, it can be subjected to high-pressure steam sterilization. By conducting high-pressure steam sterilization, the substrate can avoid quality changes that are observed at the time of γ-beam sterilization. Also, removal of remaining gas at the time of EOG sterilization becomes unnecessary. In addition, the risk of contamination at the time of cell culture and the risk of inclusion of a component that inhibits the growth of cultured cells can be reduced via simple sterilization treatment. A generally available cell culture substrate made of polystyrene has low heat resistance. Thus, it cannot be subjected to high-pressure steam sterilization. In addition to the sterilization techniques described above, the cell culture substrate of the present invention can be sterilized by a general sterilization technique, such as γ-beam sterilization, electron beam sterilization, alcohol sterilization such as ethanol sterilization, or EOG sterilization. It should be noted that such techniques are examples, and other sterilization techniques may be employed. The substrate of the present invention is preferably transparent, it does not exhibit autofluorescence at around the excitation wavelength and the fluorescent wavelength of a fluorescent pigment that is generally used for immunostaining, and, accordingly, it can be used for immunostaining that is carried out with the use of a fluorescent pigment. When the cell culture substrate of the present invention is in the form of a film composed of the resin composition, in general, such substrate exhibits the effects described herein.

3. Cell Culture Vessel

The present invention also provides a cell culture vessel comprising in at least in part, the cell culture substrate. Preferably, the present invention provides a cell culture vessel comprising in at least in part, the cell culture substrate having oxygen permeability. The cell culture vessel according to a preferable embodiment of the present invention comprises in at least in part, a cell culture substrate with one of its surfaces forming the bottom of a container portion for containing a cell and medium and the other surface being exposed to the outside of the vessel.

Figures 1, 4:
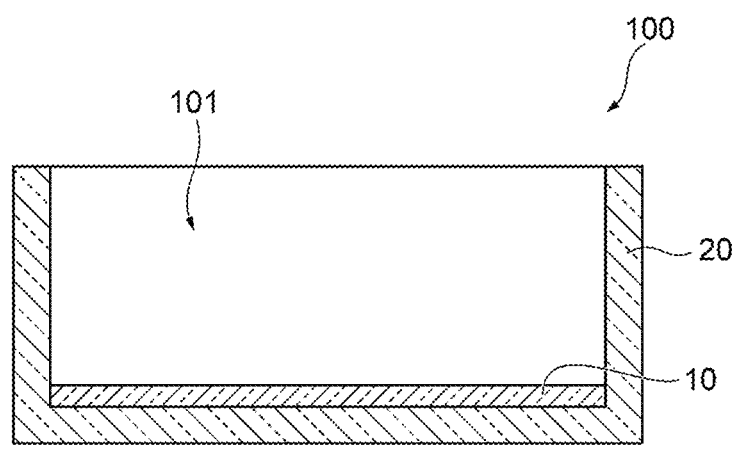
Figure 4:
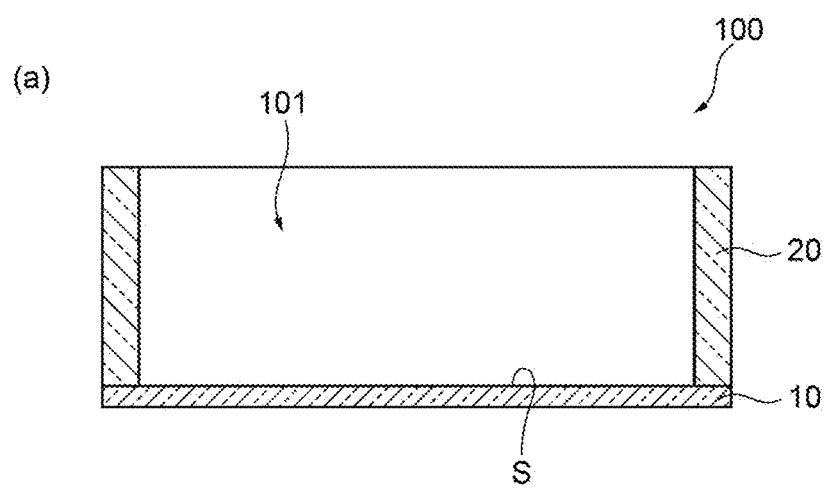
Figure 2:
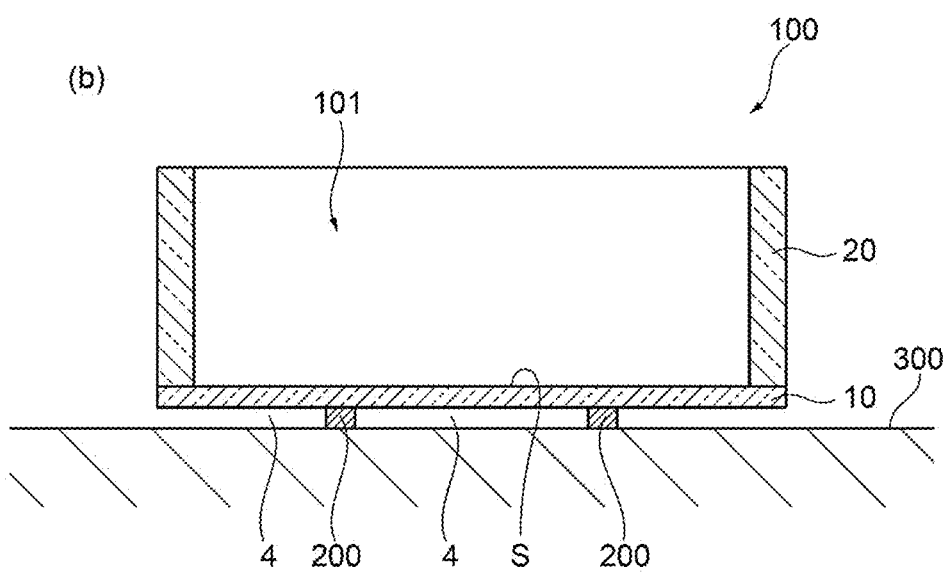

The cell culture vessel according to the present invention may comprise a cell culture substrate as shown in FIG. 4-1 or 4-2 inside or at the bottom of the vessel, or the cell culture vessel may comprise in at least in part, a cell culture substrate with one of its surfaces forming the bottom of a container portion for containing a cell and medium and the other surface being exposed to the outside of the vessel.

In the cell culture vessel according to the present invention, a surface composed of a resin composition comprising a fluorine-containing polymer serves as the scaffold for cells to be cultured. Thus, cell viability is high, and cell culture, and in particular three-dimensional cell culture, can be carried out while maintaining cellular functions at high levels.

It is sufficient if the cell culture vessel according to the present invention comprises the cell culture substrate of the present invention, and the cell culture vessel may be in any form as a whole. For example, it can be in a various form of culture vessel, and examples include a culture plate, such as a single-well or multi-well plate, a petri dish, a dish, a flask, and a bag. The cell culture vessel according to the present invention may be in the form of a cell culture vessel in a culture apparatus, such as a mass-culture apparatus or perfusion culture apparatus.

The cell culture vessel according to the present invention may be composed of the cell culture substrate of the present invention in combination with other members, the cell culture substrate of the present invention integrated with other members, or the cell culture substrate of the present invention alone. When the cell culture substrate of the present invention is a flexible substrate such as a film substrate, such substrate can form the bottom of a cell culture vessel while tightly stretching the substrate with the use of an adequate support membrane (e.g., a frame) with rigidity.

In the cell culture vessel according to a preferable embodiment of the present invention, the surface of the cell culture substrate composed of a resin composition comprising a fluorine-containing polymer forms the bottom of a container portion for containing a cell and medium and the other surface is positioned to be exposed to the outside of the vessel. When a cell culture substrate 10 consists of a film 1 composed of a resin composition comprising a fluorine-containing polymer as shown in FIG. 1, specifically, the cell culture substrate 10 is positioned in such a manner that one of the main surfaces defines the bottom of the portion accommodating cells and a medium and the other main surface is exposed to the outside of the vessel and brought into contact with the air. When a cell culture substrate 10 comprises a film 1 composed of a resin composition comprising a fluorine-containing polymer and a support 2, as shown in FIG. 2, the cell culture substrate 10 is positioned in such a manner that a surface S on which the film 1 is provided defines the bottom of the portion accommodating cells and a medium and the surface on which the support 2 is provided is exposed to the outside of the vessel and brought into contact with the air. In the cell culture vessel according to an embodiment of the present invention, the other surface of the cell culture substrate is exposed to the outside of the vessel and brought into contact with oxygen-containing gas, such as the air, that is present outside the vessel when it is used for cell culture.

In the cell culture vessel according to the embodiment described above, a surface composed of a resin composition comprising a fluorine-containing polymer serves as the scaffold for cells to be cultured. In addition, the substrate has oxygen permeability. Accordingly, oxygen is supplied to the cells and the medium from the surface of the substrate that is exposed to the outside the vessel and brought into contact with oxygen-containing gas such as air. Thus, cell viability is high, and cell culture, and in particular three-dimensional cell culture, can be carried out while maintaining cellular functions at high levels.

FIG. 4-1 shows a cell culture vessel 100, which is an embodiment of the cell culture vessel according to the present invention. The cell culture vessel 100 shown in FIG. 4-1 comprises: a bottom of the culture vessel; and a wall member 20 that forms a side wall of the culture vessel upright from the bottom rim, and the cell culture substrate 10 is provided at the bottom of the culture vessel to form a container portion 101. The constitution of the cell culture substrate 10 is as described above. In a planar view of the wall member 20 obtained from the open side, the inner wall and the outer wall can be in, for example, a circular, polygonal (e.g., quadrangular of triangular), or any other form.

FIG. 4-2(a) shows a cell culture vessel 100, which is an embodiment of the cell culture vessel according to the present invention. The cell culture vessel 100 shown in FIG. 4-2(a) comprises: a cell culture substrate 10 that forms the bottom of the culture vessel; and a wall member 20 that forms a side wall of the culture vessel upright from the rim of the cell culture substrate 10, and the container portion 101 is constituted by the cell culture substrate 10 and the wall member 20. The constitution of the cell culture substrate 10 is as described above, and a surface S composed of a resin composition comprising a fluorine-containing polymer is provided to face the inside of the container portion (the container portion 101). In a planar view of the wall member 20 obtained from the open side, the inner wall and the outer wall can be in, for example, a circular, polygonal (e.g., quadrangular of triangular), or any other form.

Figure 5:
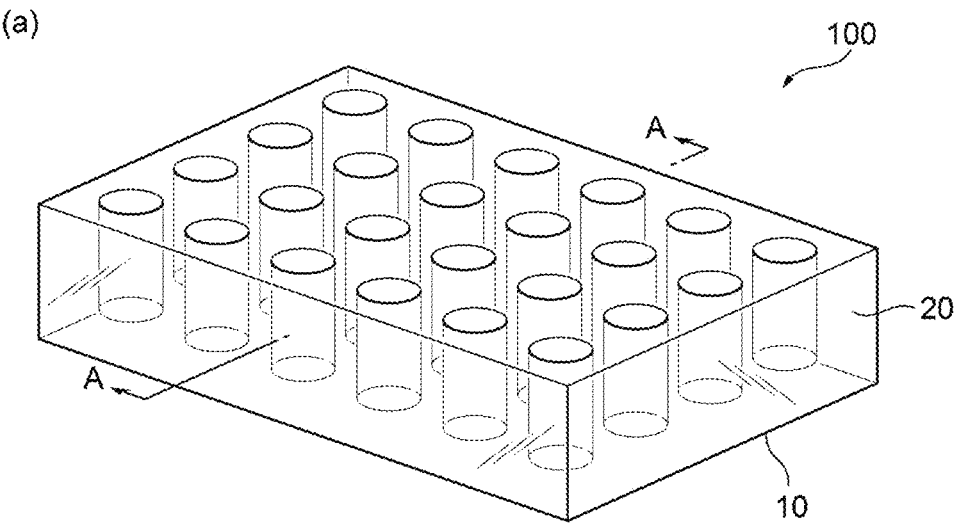
FIG. 5 shows another embodiment of the cell culture vessel according to the present invention: wherein (a) is a perspective view of the cell culture vessel 100; (b) is a schematic diagram of the A-A cross section of the cell culture vessel 100; and (c) is a schematic diagram of the A-A cross section of the cell culture vessel 100 according to another embodiment.
Figure 5:
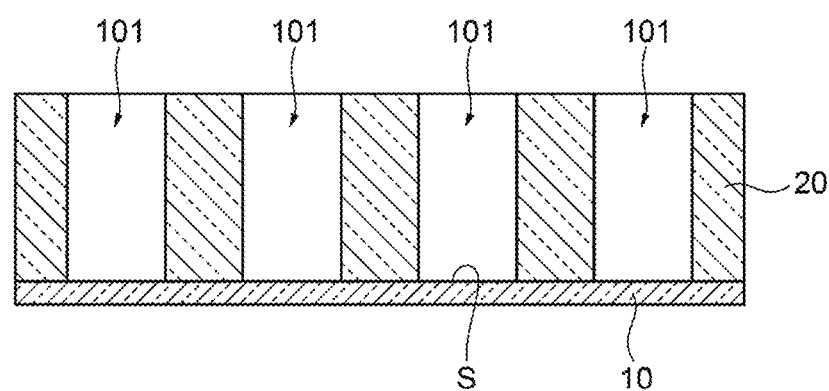
Figure 5:
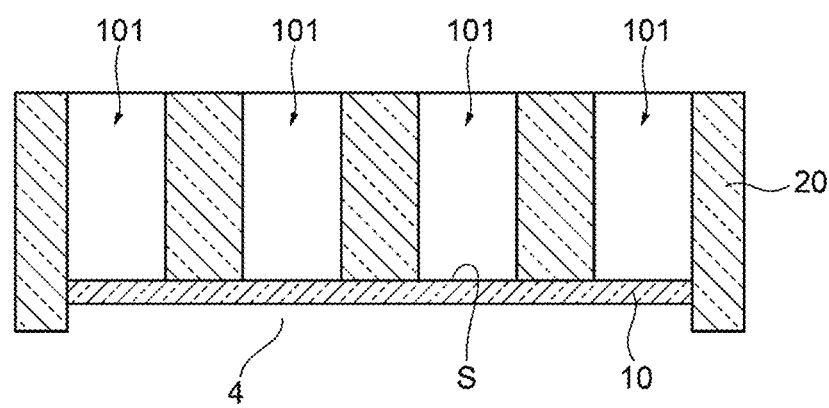

The cell culture vessel 100 shown in FIGS. 5(a), 5(b), and 5(c) is a multi-well plate, which is another embodiment of the cell culture vessel according to the present invention. The cell culture vessel 100 shown in FIGS. 5(a), 5(b), and 5(c) comprises: a cell culture substrate 10; and a plate wall member 20, which is provided to cover the surface S of the cell culture substrate 10 composed of a resin composition comprising a fluorine-containing polymer and is provided with a plurality of through-holes (24 holes in the figure) in a through-thickness direction. Regions surrounding the through-holes of the wall member 20 and the cell culture substrate 10 constitute a plurality of container portions 101 that accommodate cells and media. The constitution of the cell culture substrate 10 is as described above, and a surface S composed of a resin composition comprising a fluorine-containing polymer is provided to face the inside of the container portion (the container portion 101). In FIG. 5(c), the surface S composed of a resin composition comprising a fluorine-containing polymer is provided to face the inside of the container portion (the container portion 101), and the other surface of the cell culture substrate 10, which is opposite from the surface S, is connected to the wall member 20 in such a manner that, when the cell culture vessel 100 is disposed on a flat surface, such surface is not brought into contact with the flat surface, and a gap 4 is provided between the surface opposite from the surface S and the flat surface.

Figure 6:
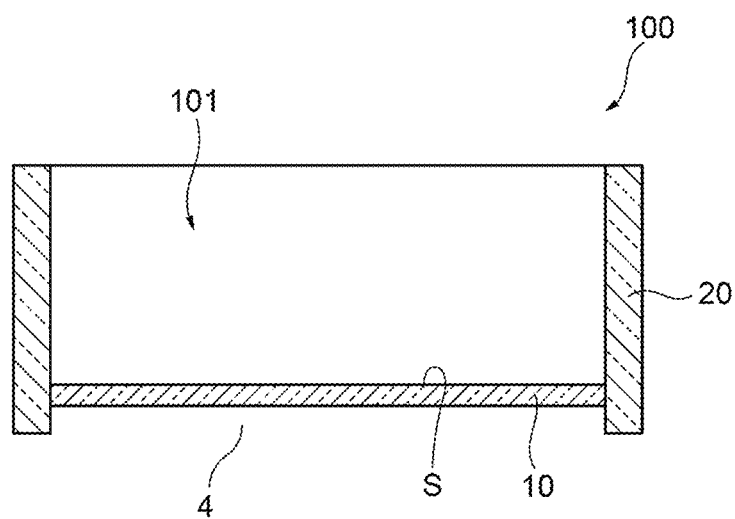
FIG. 6 shows a further embodiment of the cell culture vessel according to the present invention.

The cell culture vessel 100 shown in FIG. 6 is a further embodiment of the cell culture vessel according to the present invention. The cell culture vessel 100 shown in FIG. 6 comprises: a cell culture substrate 10 that forms the bottom of the culture vessel; and a wall member 20 that forms a side wall of the culture vessel, and the container portion 101 is constituted by the cell culture substrate 10 and the wall member 20. The surface S of the cell culture substrate 10 composed of a resin composition comprising a fluorine-containing polymer is provided to face the inside of the container portion (the container portion 101), and the cell culture substrate 10 is connected to the wall member 20 in such a manner that, when the cell culture vessel 100 is disposed on a flat surface, such surface is not brought into contact with the flat surface, and a gap 4 is provided between the surface opposite from the surface S and the flat surface.

In the cell culture vessel 100 according to any of the embodiments shown in FIGS. 4-1, 4-2(a), 5(a), 5(b), 5(c), and 6, the wall member 20 may be connected to the cell culture substrate 10 through any means. For example, they may be connected to each other through an adhesive material or member, such as a pressure-sensitive double-sided bonding tape.

Thus, a cell culture vessel comprising a surface S composed of a resin composition comprising a fluorine-containing polymer provided at the bottom can be produced. The configuration of the cell culture vessel according to the present invention is not limited to the above, and it can have an arbitrary configuration.

4. Culture Method

The present invention also provides a method of cell culture comprising a step of culturing cells on the surface of a cell culture substrate, which is composed of the resin composition comprising a fluorine-containing polymer.

Cells that can form three-dimensional tissue may be cultured for an adequate period of time on a surface of the cell culture substrate of the present invention, which is composed of the resin composition comprising a fluorine-containing polymer, so as to perform three-dimensional culture. However, the method of cell culture according to the present invention is not limited thereto. For example, a method for culturing cells that do not form three-dimensional tissue and a method for culturing cells that are capable of forming three-dimensional tissue to the phase prior to three-dimensional tissue formation are within the scope of the present invention.

According to another embodiment, the present invention also provides a method of cell culture comprising a step of cell culture while cells and a medium are in contact with one surface of the cell culture substrate, which is composed of a resin composition comprising a fluorine-containing polymer.

As shown in FIG. 4-1, specifically, the cell culture substrate 10 having the structure shown in FIG. 1 or FIG. 2 is introduced into the vessel, and cells may then be cultured while cells and a medium are in contact with a surface S (see FIG. 1 or FIG. 2), which is composed of a resin composition comprising a fluorine-containing polymer.

According to another embodiment, the present invention provides a method of cell culture comprising a step of conducting cell culture while cells and a medium are in contact with one surface of the cell culture substrate, which is composed of a resin composition comprising a fluorine-containing polymer, and the other surface of the cell culture substrate is in contact with oxygen-containing gas, such as air.

According to the embodiment above, specifically, cell culture is conducted while cells 3 and a medium 2 are in contact with the surface S (see FIG. 1 or 2) of the cell culture substrate 10 having the structure shown in FIG. 1 or FIG. 2, which is composed of a resin composition comprising a fluorine-containing polymer, as shown in FIG. 3, and the other surface of the cell culture substrate 10 is in contact with oxygen-containing gas 4, such as air. According to this method, the surface S of the substrate 10, which is composed of a resin composition comprising a fluorine-containing polymer, serves as a scaffold for cells to be cultured. In addition, the substrate 10 has oxygen permeability. Thus, oxygen is supplied to cells 3 and a medium 2 through the surface of the substrate 10 that is in contact with oxygen-containing gas 4, such as air. According to this method, cell viability is high, and cell culture, and in particular three-dimensional cell culture, can be carried out while maintaining cellular functions at high levels. When the cell culture vessel 100 as shown in FIG. 4-2(a) is used, for example, cell culture is conducted by providing the cell culture vessel 100 in such a manner that at least a part of the lower surface of the cell culture vessel 100 (i.e., the surface opposite from the surface S of the cell culture substrate 10) is brought into contact with oxygen-containing gas, such as air. Thus, the method of cell culture described above can be carried out. As shown in FIG. 4-2(b), for example, an adequate narrow spacer 200 is provided on a flat surface 300, and the cell culture vessel 100 is disposed on the spacer 200. Thus, the surface of the cell culture substrate 10 exposed to the outside of the culture vessel can be brought into contact with oxygen-containing gas (air) 4. With the use of the cell culture vessel 100 thus provided, cell culture as described above can be carried out. When the cell culture vessel 100 is disposed directly on the flat surface 300 without the use of the spacer 200, in general, oxygen-containing gas (air) is present in some spaces between the surface of the cell culture substrate 10 exposed to the outside of the culture vessel and the flat surface 300. Thus, the method of cell culture according to the present invention can be carried out. The cell culture vessel 100 shown in FIGS. 5(a), 5(b), and 5(c) can be used in the same manner. The cell culture vessel 100 shown in FIGS. 5(c) and 6 comprises the wall member 20, the edge at the bottom thereof is protruded downward from the cell culture substrate 10. When it is disposed on the flat surface, accordingly, the edge of the wall member 20 functions as a spacer, a gap 4 is formed between the surface opposite from the surface S of the cell culture substrate 10 and the flat surface, and oxygen-containing gas (e.g., air) can be present in the gap 4. Thus, the method of cell culture according to the present invention can be easily carried out.

The methods of culture described above are provided for illustrative purposes, and the method of cell culture according to the present invention is not limited thereto. The method is not particularly limited, provided that it comprises a step of performing cell culture while cells and a medium are in contact with one surface of the cell culture substrate, which is composed of a resin composition comprising a fluorine-containing polymer.

Cells to be cultured by the method of cell culture according to the present invention are not particularly limited. Examples thereof include: cells that are generally to be subjected to three-dimensional culture, such as human normal hepatic cells, rat normal hepatic cells, mouse normal hepatic cells, human hepatic cancer cells, human congenital hepatoma cells, rat hepatoma cells, mouse hepatoma cells, induced pluripotent stem (iPS) cells, embryonic stem (ES) cells, and mesenchymal stem cells; and other cells comprising various precursor cells and stem cells, such as adipocytes, hepatic cells, nephrocytes, pancreatic cells, mammary glandular cells, endothelial cells, epidermic cells, smooth muscle cells, sarcoblasts, cardiac muscle cells, nerve cells, glial cells, dendritic cells, cartilage cells, osteoblasts, osteoclasts, bone cells, fibroblasts, various blood cells, mesenchymal precursor cells, and various cancer cells.

Cells can be cultured in an adequate medium. While a type of a medium is not particularly limited, for example, any cell culture basal medium, differentiation medium, or primary culture-exclusive medium can be used. Specific examples thereof include, but are not limited to, Dulbecco's modified Eagle medium (DMEM), Glasgow's MEM (GMEM), RPMI 1640, Ham F12, MCDB medium, and William's E medium. Any medium can be used, provided that it contains components necessary for cell growth or differentiation. Also, a medium supplemented with sera, various growth factors, or differentiation inducers may be used.

5. Three-Dimensional Culture

The present invention also provides a method of three-dimensional cell culture comprising a step of performing three-dimensional cell culture on the surface of the cell culture substrate, which is composed of the resin composition comprising a fluorine-containing polymer. Specifically, cells can be subjected to three-dimensional culture by the method of cell culture according to the present invention.

Examples of tissues formed via three-dimensional culture include spheroids and three-dimensional cell aggregates. Spheroids or three-dimensional cell aggregates may be formed of single cells, such as rat normal hepatic cells or they may be formed of two or more different types of cells, such as various fibroblasts, vascular endothelial cells, and rat normal hepatic cells. Examples of cells that can be used include various cells described above.

A type of a medium used for three-dimensional culture is not particularly limited, and, for example, any cell culture basal medium, differentiation medium, or primary culture-exclusive medium can be used. Specific examples thereof include, but are not limited to, Dulbecco's modified Eagle medium (DMEM), Glasgow's MEM (GMEM), RPMI 1640, Ham F12, MCDB medium, and William's E medium. Any medium can be used, provided that it contains components necessary for cell growth or differentiation. Also, a medium supplemented with sera, various growth factors, or differentiation inducers may be used.

EXAMPLES

6. Examples

Hereafter, the present invention is described in greater detail with reference to the examples, although the present invention is not limited to these examples. Adequate modification can be made within the scope of the description above and below, and such modification is within the technical scope of the present invention. The units "part(s)" and "%" used hereinbelow refer to "part(s) by mass" and "% by mass," respectively, unless otherwise specified.

[Measurement of the Amount of Remaining Imidization Catalyst]
NMR Analysis
Apparatus: Magnetic Resonance Spectrometer (Unity Plus 400, Varian, Inc.)

$^1$H-NMR (400 MHz) was analyzed using a solvent (d-DMSO). As the internal standard, the position of H of tetramethylsilane (TMS) was designated as 0 ppm.

A known amount of an imidization catalyst (triethylamine, TEA) was added to polyamide acid, and the sample of a comparative example after imidization was subjected to $^1$H-NMR analysis (a sample before calcination). The polyimide film obtained via calcination of the imidized resin composition was dissolved in d-DMSO, and $^1$H-NMR was analyzed (a sample after calcination). In both the samples before and after calcination, a peak derived from H of polyimide (it is also derived from polyamide acid when polyamide acid remains) at around 8 ppm and peaks derived from H of TEA at around 1 ppm and 6 ppm were observed.

On the basis of the peak intensity derived from polyimide and the peak intensity derived from remaining polyamide acid of the samples before and after calcination observed at 8 ppm, relative intensity of the TEA-derived peak at 1 ppm was determined, and it was compared between the samples before and after calcination. On the basis of the results of comparison, with reference to the amount of TEA (the known amount) relative to the total amount of polyimide and remaining polyamide acid in the sample before calcination, the amount of TEA relative to the total amount of polyimide and remaining polyamide acid in the sample after calcination was determined.

[Method for Measurement of Fluorine Content]
With the use of an elemental analyzer (Micro Corder JM-10, J-Science Lab Co., Ltd.), fluorine content in the polyimide film was quantified.

[Method for Measurement of Degree of Imidization]
The polyimide film was analyzed via FT-IR (Nicolet Nexus 670, Thermo Fisher Scientific K. K.) to determine the degree of imidization of the polyimide film using the equation described below on the basis of the ratio (A: 1,370 cm$^{-1}$)/A: 1,500 cm$^{-1}$) of the absorbance at around 1,370 cm$^{-1}$ derived from the C—N stretching vibration of polyimide (A: 1,370 cm$^{-1}$) to the absorbance at around 1,500 cm$^{-1}$ derived from the skeletal vibration of the benzene ring (A: 1500 cm$^{-1}$).

Degree of imidization (%)=[(A:1,370 cm$^{-1}$)/A:1,500 cm$^{-1}$) of sample polyimide film]/[(A:1,370 cm$^{-1}$)/A:1,500 cm$^{-1}$) of sample polyimide film after thermal treatment]×100

The value "[(A: 1,370 cm$^{-1}$)/A: 1,500 cm$^{-1}$) of sample polyimide film after thermal treatment]" above is a value measured for a polyimide film, which is prepared by treating the sample polyimide film at temperature for a period of time (380° C. for 1 hour), so as to complete the imidization (i.e., the degree of imidization: 100%).

[Measurement of Weight Average Molecular Weight]
Apparatus: HCL-8220GPC, Tosoh Corporation
Column: TSKgel Super AWM-H
Eluate: (LiBr—H$_2$O, containing phosphoric acid, NMP): 0.01 mol/L
Method of measurement:
A 0.5% solution was prepared with the aid of an eluate, and the molecular weight was determined on the basis of the calibration curve prepared with polystyrene.

Polyamide acid and polyimide can be measured in the same manner.

[Measurement of Dynamic Viscoelasticity]
Apparatus: Dynamic viscoelastic analyzer (RSA III, TS Instruments)
Method of measurement:
A polyimide film (thickness: 20 µm) was cut into 5×40 mm-strips, and the stretching and stress at 25° C. was measured. Thus, tensile modulus of elasticity was determined.

[Measurement of Water Contact Angle]
Apparatus: Automated contact angle meter (DM-500, manufactured by Kyowa Interface Science Co., Ltd.)
Measurement Method:
Water (2 µl) was added dropwise at 25° C., and the angle of droplet deposition was measured immediately thereafter.

[Measurement of Oxygen Gas Permeability and Oxygen Gas Permeability Coefficient]
The oxygen gas permeability (unit: cm$^3$ (STP)/(m$^2$·0.24 h·atm)) and the oxygen gas permeability coefficient (unit: cm$^3$ (STP)·cm/(cm$^2$·s·cmHg)) were determined by the method in accordance with Annex 2 of JIS K7126-1 (the differential-pressure method). Specifically, measurement was carried out under the conditions described below.

Test method: Differential-pressure method (in accordance with Annex 2, JIS K7126-1)
Detector: Gas chromatograph (thermal conductivity detector: TCD)
Test differential pressure: 1 atm
Test gas: Oxygen gas (dry conditions (relative humidity: substantially 0%))
Test conditions: 25° C.±2° C.
Permeation area: 1.52×10$^{-3}$ m$^2$ Apparatus: Differential pressure type gas/water vapor permeability measurement apparatus (GTR-30XAD2, G2700T-F, manufactured by GTR Tec Corporation-Yanaco Technical Science Corporation)

[Measurement of Membrane Thickness]

Membrane thickness of the film was measured using a micrometer.

[Acid Dianhydride]

As acid dianhydride, 4,4'-[(2,3,5,6-tetrafluoro-1,4-phenylene)bis(oxy)]bis(3,5,6-trifluorophthalic anhydride) (10FEDAN) (synthesized by the applicant), 4,4'-(hexafluoroisopropylidene)diphthalic anhydride (6FDA) (synthesized by Nippon Shokubai Co., Ltd.), or pyromellitic dianhydride (manufactured by Kanto Chemical Co., Inc.) was used.

[Diamine]

As diamine, 1,4-bis(4-aminophenoxy)benzene (TPEQ) (manufactured by Wakayama Seika Kogyo Co., Ltd.), 2,6-bis(4-aminophenoxy)-3,5-difluoro-4-(1H,1H,2H,2H-heptadecafluoro-n-decanoxy)benzonitrile (AFDM) (synthesized by the applicant), 2,2-bis(4-(4-aminophenoxyl)phenyl)hexafluoropropane (HFBAPP) (manufactured by Wakayama Seika Kogyo Co., Ltd.), 2,2-bis(4-(4-aminophenoxy)phenyl)propane (BAPP) (manufactured by Wakayama Seika Kogyo Co., Ltd.), 4,4'-bis(4-aminophenoxy)biphenyl (BAPB) (manufactured by Wakayama Seika Kogyo Co., Ltd.), 4,4'-diaminodiphenyl ether (ODA) (manufactured by Wakayama Seika Kogyo Co., Ltd.), 1,3-bis(4-aminophenoxy)benzene (TPER) (manufactured by Wakayama Seika Kogyo Co., Ltd.), 1,3-diamino-2,4,5,6-tetrafluorobenzene (4FMPD) (synthesized by the applicant), 2,2-bis(4-aminophenyl)hexafluoropropane (6FAP) (manufactured by Tokyo Chemical Industry Co., Ltd.), or 2,2'-bis(trifluoromethyl)benzidine (TFMB) (manufactured by Tokyo Chemical Industry Co., Ltd.) was used.

Chemical structures of the compounds and the number of ether bonds and/or fluorine atoms in the molecules are as shown in Tables 1 to 4.

TABLE 1

| Abbreviation | Structure | —O— | F |
|---|---|---|---|
| 6FDA | 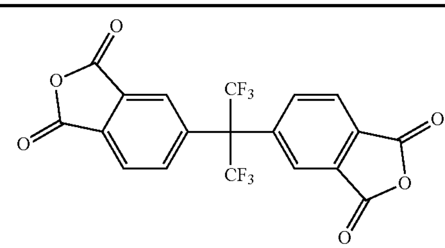 | 0 | 6 |
| Pyromellitic dianhydride | 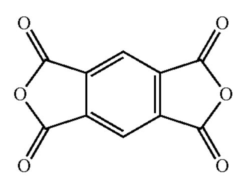 [SMILES: O=c1oc(=O)c2cc3c(=O)oc(=O)c3cc12] | 0 | 0 |
| TPEQ | 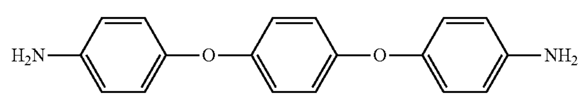 [SMILES: Nc1ccc(Oc2ccc(Oc3ccc(N)cc3)cc2)cc1] | 2 | 0 |
| AFDM | 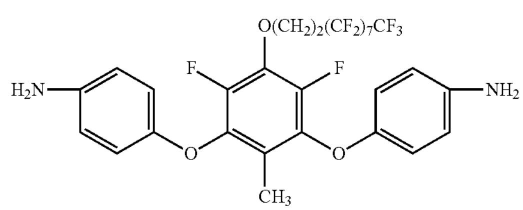 | 2 | 19 |
| HFBAPP | 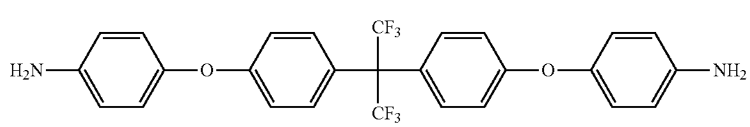 | 2 | 6 |
| BAPP | 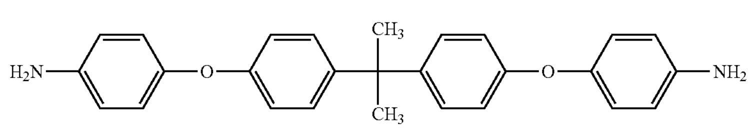 | 2 | 0 |
| BAPB | 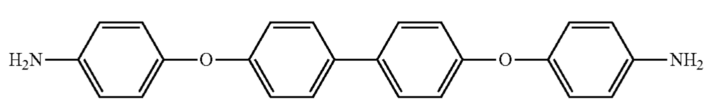 [SMILES: Nc1ccc(Oc2ccc(-c3ccc(Oc4ccc(N)cc4)cc3)cc2)cc1] | 2 | 0 |

TABLE 1-continued

| Abbreviation | Structure | —O— | F |
|---|---|---|---|
| ODA | H₂N—C₆H₄—O—C₆H₄—NH₂ | 1 | 0 |
| TPER | H₂N—C₆H₄—O—C₆H₄—O—C₆H₄—NH₂ | 2 | 0 |
| 4FMPD | tetrafluoro-phenylenediamine (F₄-C₆-(NH₂)₂) | 0 | 4 |

TABLE 2

| Abbreviation | Structure | F |
|---|---|---|
| 6FDA | 4,4'-(hexafluoroisopropylidene)diphthalic anhydride | 6 |
| TPEQ | H₂N—C₆H₄—O—C₆H₄—O—C₆H₄—NH₂ | 0 |
| AFDM | substituted benzene with O(CH₂)₂(CF₂)₇CF₃, F, F, OC₆H₄NH₂ (×2), CH₃ | 19 |
| HFBAPP | H₂N—C₆H₄—O—C₆H₄—C(CF₃)₂—C₆H₄—O—C₆H₄—NH₂ | 6 |
| BAPP | H₂N—C₆H₄—O—C₆H₄—C(CH₃)₂—C₆H₄—O—C₆H₄—NH₂ | 0 |
| BAPB | H₂N—C₆H₄—O—C₆H₄—C₆H₄—O—C₆H₄—NH₂ | 0 |
| ODA | H₂N—C₆H₄—O—C₆H₄—NH₂ | 0 |

TABLE 2-continued

| Abbreviation | Structure | F |
|---|---|---|
| TPER | H₂N–C₆H₄–O–C₆H₄–O–C₆H₄–NH₂ | 0 |
| 4FMPD | tetrafluoro-1,3-phenylenediamine | 4 |
| 6FAP | H₂N–C₆H₄–C(CF₃)₂–C₆H₄–NH₂ | 6 |
| TFMB | 2,2'-bis(trifluoromethyl)benzidine | 6 |

TABLE 3

| Abbreviation | Structure | F |
|---|---|---|
| 6FDA | 4,4'-(hexafluoroisopropylidene)diphthalic anhydride | 6 |
| 6FAP | H₂N–C₆H₄–C(CF₃)₂–C₆H₄–NH₂ | 6 |
| TFMB | 2,2'-bis(trifluoromethyl)benzidine | 6 |

TABLE 4

| Abbreviation | Structure | F |
|---|---|---|
| 6FDA | 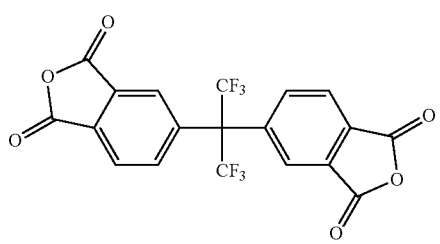 [SMILES: O=C1OC(=O)c2cc(C(c3ccc4c(c3)C(=O)OC4=O)(C(F)(F)F)C(F)(F)F)ccc21] | 6 |

TABLE 4-continued

| Abbreviation | Structure | F |
|---|---|---|
| Pyromellitic dianhydride | (structure) | 0 |
| TPEQ | H₂N–⌬–O–⌬–O–⌬–NH₂ | 0 |
| TFMB | (structure with F₃C and CF₃ groups) | 6 |
| ODA | H₂N–⌬–O–⌬–NH₂ | 0 |

6.1. Preparation of Fluorine-Containing Polyimide

Acid dianhydrides and diamines were used in combinations as shown in the tables below, so as to prepare polyimide films according to examples and comparative examples.

[Preparation Example 1] 6FDA/TPEQ

To a 100-ml three-necked flask, 2.976 g of 1,4-bis(aminophenoxy)benzene (10.2 mmol), 4.524 g of 4,4'-(hexafluoroisopropylidene)diphthalic anhydride (10.2 mmol), and 42.5 g of N,N-dimethylacetamide were introduced. Under the nitrogen atmosphere, the mixture was agitated at room temperature for 5 days. Thus, a fluorine-containing polyamide acid resin composition was obtained (solid density: 15.0% by mass). The weight average molecular weight of the polyamide acid was 180,000.

[Preparation Example 2] 6FDA/AFDM

To a 100-ml three-necked flask, 4.855 g of 2,6-bis(4-aminophenoxy)-3,5-difluoro-4-(1H,1H,2H,2H-heptadecafluoro-n-decanoxy)benzonitrile (5.95 mmol) and 42.5 g of N,N-dimethylacetamide were introduced and dissolved therein. 4,4'-(hexafluoroisopropylidene)diphthalic anhydride (2.645 g, 5.95 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 70,000.

[Preparation Example 3] 6FDA/HFBAPP

To a 100-ml three-necked flask, 2.693 g of 2,2-bis(4-(4-aminophenoxyl)phenyl)hexafluoropropane (5.19 mmol) and 42.5 g of N,N-dimethylacetamide were introduced and dissolved therein. 4,4'-(hexafluoroisopropylidene)diphthalic anhydride (2.307 g, 5.19 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 500,000.

[Preparation Example 4] 6FDA/BAPP

To a 100-ml three-necked flask, 3.602 g of 2,2-bis(4-(4-aminophenoxy)phenyl)propane (8.77 mmol) and 42.5 g of N,N-dimethylacetamide were introduced and dissolved therein. 4,4'-(hexafluoroisopropylidene)diphthalic anhydride (3.898 g, 8.77 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 280,000.

[Preparation Example 5] 6FDA/BAPB

To a 100-ml three-necked flask, 3.400 g of 4,4'-bis(4-aminophenoxy)biphenyl (9.23 mmol) and 42.5 g of N,N-dimethylacetamide were introduced and dissolved therein. 4,4'-(hexafluoroisopropylidene)diphthalic anhydride (4.100 g, 9.23 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 220,000.

[Preparation Example 6] 6FDA/ODA (DPE)

To a 100-ml three-necked flask, 2.330 g of 4,4'-diaminodiphenyl ether (11.64 mmol) and 42.5 g of N,N-dimethylacetamide were introduced and dissolved therein. 4,4'-(hexafluoroisopropylidene)diphthalic anhydride (5.170 g, 11.64 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 190,000.

[Preparation Example 7] 6FDA/TPER

To a 100-ml three-necked flask, 2.976 g of 1,3-bis(4-aminophenoxy)benzene (10.2 mmol) and 42.5 g of N,N-dimethylacetamide were introduced and dissolved therein. 4,4'-(hexafluoroisopropylidene)diphthalic anhydride (4.524 g, 10.2 mmol) was added thereto, and the mixture was agitated under the nitrogen atmosphere at room temperature for 5 days. Thus, a fluorine-containing polyamide acid resin composition was obtained (solid density: 15.0% by mass). The weight average molecular weight of the polyamide acid was 180,000.

[Preparation Example 8] 6FDA/6FAP

To a 100-ml three-necked flask, 3.220 g of 2,2-bis(4-aminophenyl)hexafluoropropane (9.63 mmol) and 42.5 g of N,N-dimethylacetamide were introduced and dissolved therein. 4,4'-(hexafluoroisopropylidene)diphthalic anhydride (4.280 g, 9.63 mmol) was added thereto, and the mixture was agitated under the nitrogen atmosphere at room temperature for 5 days. Thus, a fluorine-containing polyamide acid resin composition was obtained (solid density: 15% by mass). The weight average molecular weight of the polyamide acid was 80,000.

[Preparation Example 9] 6FDA/TFMB

To a 100-ml three-necked flask, 3.141 g of 2,2'-bis(trifluoromethyl)benzidine (9.81 mmol) and 42.5 g of N,N-dimethylacetamide were introduced and dissolved therein. 4,4'-(hexafluoroisopropylidene)diphthalic anhydride (4.359 g, 9.81 mmol) was added thereto, and the mixture was agitated under the nitrogen atmosphere at room temperature for 5 days. Thus, a fluorine-containing polyamide acid resin composition was obtained (solid density: 15% by mass). The weight average molecular weight of the polyamide acid was 250,000.

[Comparative Preparation Example 1] Pyromellitic Dianhydride/ODA

To a 100-ml three-necked flask, 2.393 g of 4,4'-diaminodiphenyl ether (12.0 mmol), 2.607 g of pyromellitic dianhydride (12.0 mmol), and 45.0 g of N,N-dimethylacetamide were introduced. Under the nitrogen atmosphere, the mixture was agitated at room temperature for 5 days. Thus, a polyamide acid resin composition that comprises ether bonds but does not comprise a fluorine atom was obtained (solid density: 10.0% by mass). The weight average molecular weight of the polyamide acid was 800,000.

[Example 1] 6FDA/TPEQ Membrane (Thermal Imidization)

The fluorine-containing polyamide acid resin composition obtained in Preparation Example 1 was applied onto a glass substrate using a die coater, so as to adjust the thickness of the calcined fluorine-containing polyimide film to 20 μm to 30 μm, the resulting film was calcined at 300° C. for 1 hour under the nitrogen atmosphere. Thereafter, the calcined film was separated from the glass, and a fluorine-containing polyimide film was thus obtained.

The fluorine-containing polyimide film exhibited the membrane thickness of 33 μm, the fluorine content of 17% by mass, the degree of imidization of 90%, the water contact angle of 88°, the tensile modulus of elasticity of 2.31 GPa, the oxygen gas permeability coefficient of $3.5 \times 10^{-10}$ $cm^3$ (STP)·cm/($cm^2$·s·cmHg), and the oxygen gas permeability of 7,030 $cm^3$ (STP)/($m^2$·0.24 h·atm). The tensile modulus of elasticity was initially measured to be 63.9 MPa, although it was erroneous, and it was corrected to be 2.31 GPa on the basis of the remeasurement.

[Example 2] 6FDA/TPEQ Membrane (Chemical Imidization)

The fluorine-containing polyamide acid resin composition obtained in Preparation Example 1 (20 g) was transferred to a 100-ml glass container, 0.013 g of 1,4-diazabicyclo[2.2.2]octane (0.01 mmol) and 0.8744 g of acetic anhydride (8.5 mmol) were added thereto, the mixture was agitated for 5 minutes, and the resultant was then allowed to stand for 24 hours. Thus, a fluorine-containing polyimide resin solution was obtained. The fluorine-containing polyimide resin solution was diluted with acetone, and the resultant was reprecipitated in water and methanol, followed by purification. The resulting powdered fluorine-containing polyimide resin was dissolved in a 2-butanone solution (15%), and a fluorine-containing polyimide resin composition was then obtained. The fluorine-containing polyimide resin composition was applied onto a glass substrate using a die coater, so as to adjust the thickness of the calcined fluorine-containing polyimide film to 30 μm, the resulting film was calcined at 200° C. for 1 hour under the nitrogen atmosphere. Thereafter, the calcined film was separated from the substrate, and a fluorine-containing polyimide film was obtained. The resulting fluorine-containing polyimide film exhibited the fluorine content of 17% by mass, the degree of imidization of 93%, the water contact angle of 88°, and the tensile modulus of elasticity of 2.02 GPa. The polyimide film was dissolved in a solvent, and the weight average molecular weight thereof was determined to be 250,000. The tensile modulus of elasticity was initially measured to be 64.5 MPa, although it was erroneous, and it was corrected to be 2.02 GPa on the basis of the remeasurement.

[Example 3] 6FDA/AFDM Membrane

The fluorine-containing polyimide film was obtained in the same manner as in Example 1, except that the fluorine-containing polyamide acid resin composition of Preparation Example 2 was used. The fluorine content, the degree of imidization, the water contact angle, and the tensile modulus of elasticity of the polyimide film were measured. The results are shown in Tables 5 to 8. The tensile modulus of elasticity was initially measured to be 20.8 MPa, although it was erroneous, and it was corrected to be 0.93 GPa on the basis of the remeasurement.

[Example 4] 6FDA/HFBAPP Membrane

The fluorine-containing polyimide film was obtained in the same manner as in Example 1, except that the fluorine-containing polyamide acid resin composition of Preparation Example 3 was used. The fluorine content, the degree of imidization, the water contact angle, the tensile modulus of elasticity, the membrane thickness, the oxygen gas permeability coefficient, and the oxygen gas permeability of the polyimide film were measured. The results are shown in Tables 5 to 8. The tensile modulus of elasticity was initially measured to be 42.6 MPa, although it was erroneous, and it was corrected to be 2.3 GPa on the basis of the remeasurement.

[Example 5] 6FDA/BAPP Membrane

The fluorine-containing polyimide film was obtained in the same manner as in Example 1, except that the fluorine-containing polyamide acid resin composition of Preparation Example 4 was used. The fluorine content, the degree of imidization, the water contact angle, and the tensile modulus of elasticity of the polyimide film were measured. The results are shown in Tables 5 to 8. The tensile modulus of elasticity was initially measured to be 48.4 MPa, although it was erroneous, and it was corrected to be 1.94 GPa on the basis of the remeasurement.

[Example 6] 6FDA/BAPB Membrane

The fluorine-containing polyimide film was obtained in the same manner as in Example 1, except that the fluorine-containing polyamide acid resin composition of Preparation Example 5 was used. The fluorine content, the degree of imidization, the water contact angle, the tensile modulus of elasticity, the membrane thickness, the oxygen gas permeability coefficient, and the oxygen gas permeability of the polyimide film were measured. The results are shown in Tables 5 to 8. The tensile modulus of elasticity was initially measured to be 44.6 MPa, although it was erroneous, and it was corrected to be 1.94 GPa on the basis of the remeasurement.

[Example 7] 6FDA/ODA Membrane

The fluorine-containing polyimide film was obtained in the same manner as in Example 1, except that the fluorine-containing polyamide acid resin composition of Preparation Example 6 was used. The fluorine content, the degree of imidization, the water contact angle, the tensile modulus of elasticity, the membrane thickness, the oxygen gas permeability coefficient, and the oxygen gas permeability of the polyimide film were measured. The results are shown in Tables 5 to 8. The tensile modulus of elasticity was initially measured to be 57.7 MPa, although it was erroneous, and it was corrected to be 2.62 GPa on the basis of the remeasurement.

[Example 8] 6FDA/TPER Membrane

The fluorine-containing polyimide film was obtained in the same manner as in Example 1, except that the fluorine-containing polyamide acid resin composition of Preparation Example 7 was used. The fluorine content, the degree of imidization, the water contact angle, and the tensile modulus of elasticity of the polyimide film were measured. The results are shown in Tables 5 to 8. The tensile modulus of elasticity was initially measured to be 23.9 MPa, although it was erroneous, and it was corrected to be 1.02 GPa on the basis of the remeasurement.

[Example 9] 6FDA/6FAP Membrane

The fluorine-containing polyimide film was obtained in the same manner as in Example 1, except that the fluorine-containing polyamide acid resin composition of Preparation Example 8 was used. The fluorine content, the degree of imidization, the water contact angle, the tensile modulus of elasticity, the membrane thickness, the oxygen gas permeability coefficient, and the oxygen gas permeability of the polyimide film were measured. The results are shown in Tables 5 to 8. The tensile modulus of elasticity was initially measured to be 27.6 MPa, although it was erroneous, and it was corrected to be 1.39 GPa on the basis of the remeasurement.

[Example 10] 6FDA/TFMB Membrane (Thermal Imidization)

The fluorine-containing polyimide film was obtained in the same manner as in Example 1, except that the fluorine-containing polyamide acid resin composition of Preparation Example 9 was used.

The resulting fluorine-containing polyimide film exhibited the membrane thickness of 26 μm, the fluorine content of 31% by mass, the degree of imidization of 92%, the water contact angle of 94°, the tensile modulus of elasticity of 1.68 GPa, the oxygen gas permeability coefficient of $1.9 \times 10^{-9}$ cm$^3$ (STP)·cm/(cm$^2$·s·cmHg), and the oxygen gas permeability of 48,900 cm$^3$ (STP)/(m$^2$·24 h·atm). The tensile modulus of elasticity was initially measured to be 50.8 MPa, although it was erroneous, and it was corrected to be 1.68 GPa on the basis of the remeasurement. The results are shown in Tables 5 to 8.

[Example 11] 6FDA/TFMB Membrane (Chemical Imidization)

The fluorine-containing polyamide acid resin composition obtained in Preparation Example 9 (20 g) was transferred to a 100-ml glass container, 0.013 g of 1,4-diazabicyclo[2.2.2]octane (0.1 mmol) and 0.84 g of acetic anhydride (8.2 mmol) were added thereto, the mixture was agitated for 5 minutes, and the resultant was then allowed to stand for 24 hours. Thus, a fluorine-containing polyimide resin solution was obtained. The fluorine-containing polyimide resin solution was diluted with acetone, and the resultant was reprecipitated in water and methanol, followed by purification. The resulting powdered fluorine-containing polyimide resin was dissolved in a 2-butanone solution (15%), and a fluorine-containing polyimide resin composition was then obtained. The fluorine-containing polyimide resin composition was applied onto a glass substrate using a die coater, so as to adjust the thickness of the calcined fluorine-containing polyimide film to 30 μm, and the resulting film was calcined at 200° C. for 1 hour under the nitrogen atmosphere. Thereafter, the calcined film was separated from the substrate, and a fluorine-containing polyimide film was obtained. The resulting fluorine-containing polyimide film exhibited the fluorine content of 31% by mass, the degree of imidization of 93%, the water contact angle of 94°, and the tensile modulus of elasticity of 1.45 GPa. The polyimide film was dissolved in a solvent, and the weight average molecular weight thereof was determined to be 250,000. The tensile modulus of elasticity was initially measured to be 51.2 MPa, although it was erroneous, and it was corrected to be 1.45 GPa on the basis of the remeasurement.

[Comparative Example 1] Pyromellitic Dianhydride/ODA

The polyamide acid resin composition obtained in Comparative Preparation Example 1 was applied onto a glass substrate using a die coater, so as to adjust the thickness of the calcined polyimide film to 30 µm, and the resulting film was calcined at 340° C. for 1 hour under the nitrogen atmosphere. Thereafter, the resulting film was separated from the glass substrate to obtain the polyimide film. The resulting polyimide film exhibited the fluorine content of 0% by mass, the degree of imidization of 95%, the water contact angle of 68°, and the tensile modulus of elasticity of 3.0 GPa. The tensile modulus of elasticity was initially measured to be larger than 100 MPa, although it was erroneous, and it was corrected to be 3.0 GPa on the basis of the remeasurement.

The oxygen gas permeability coefficient of the pyromellitic dianhydride/ODA polyimide film is $0.076 \times 10^{-10}$ cm$^3$ (STP)cm/(cm$^2$·s·cmHg) according to the literature (The Latest Polyimide: Fundamentals and Applications (in Japanese: Saishin Polyimide: Kiso to Ouyou), the modified edition, p. 369, Japan Polyimide & Aromatic Polymers Research Group (ed.), NTS Inc.). According to the literature, the oxygen gas permeability of the pyromellitic dianhydride/ODA polyimide film with a thickness of 30 µm is approximately 166 cm$^3$ (STP)/(m$^2$·0.24 h·atm).

Comparative Example 2

To a 100-ml three-necked flask, 1.330 g of 2,2-bis(4-aminophenyl)hexafluoropropane (3.98 mmol) and 21.10 g of N,N-dimethylacetamide were introduced and dissolved therein. 4,4'-(hexafluoroisopropylidene)diphthalic anhydride (1.768 g, 3.98 mmol) was added thereto, and the mixture was agitated at room temperature for 15 hours. Thus, a fluorine-containing polyamide acid resin composition was obtained (solid density: 12.8% by mass).

A 5-fold amount of the dehydration catalyst (i.e., acetic anhydride, 1.26 g) and 1.25 g of triethylamine were added dropwise to 15 g of the solution, and the mixture was agitated for 24 hours. The weight average molecular weight of the polyimide was 250,000. The solution was subjected to $^1$H-NMR analysis.

The resulting polymer solution was added dropwise to a poor solvent (i.e., methanol), it was allowed to reprecipitate, and it was naturally dried and then dried in a vacuum dryer at 150° C. for 15 hours. Tetrahydrofuran (10.3 g) was dissolved in 0.55 g of the dried polyimide grains, and the solution was agitated overnight to obtain a polyimide solution.

The resulting solution was introduced into a petri dish, the solvent was removed therefrom in a vacuum over a period of 10 hours, and the resultant was separated from the petri dish, followed by thermal treatment at 150° C. for 15 hours. The resulting film was subjected to $^1$H-NMR analysis, so as to quantify the amount of remaining triethylamine.

As a result of $^1$H-NMR analysis, the triethylamine content relative to the total amount of polyimide and remaining polyamide acid in the thermally treated polyimide membrane was found to be 0.039% by mass. The tensile modulus of elasticity was initially measured to be 28.5 MPa, although it was erroneous, and it was corrected to be 1.25 GPa on the basis of the remeasurement.

[Comparative Example 3] Polystyrene Multi-Well Plate

For comparison, a 24-well multi-well plate made of polystyrene having a plasma-treated surface (Falcon® Multi-well Cell Culture Plate; catalog No. 353047, Corning) was used.

The oxygen gas permeability coefficient of polystyrene is $2.6 \times 10^{-10}$ cm$^3$ (STP)·cm/(cm$^2$·s·cmHg) according to the literature (The Latest Polyimide: Fundamentals and Applications (in Japanese: Saishin Polyimide: Kiso to Ouyou), the modified edition, p. 369, Japan Polyimide & Aromatic Polymers Research Group (ed.), NTS Inc.). According to the literature, the oxygen gas permeability of the polystyrene film with a thickness of 30 µm is 5,691 cm$^3$ (STP)/(m$^2$·0.24 h·atm).

TABLE 5

| Ex. Comp. Ex. No. | Polyamide acid preparation | Acid dianhydride | Diamine | —O—/ unit | F/ unit | Water contact angle (°) | Elastic modulus (GPa) | Weight average molecular weight[1] ×10$^4$ Mw | Degree of imidization (%) | Fluorine Content (%) | Spheroid formation |
|---|---|---|---|---|---|---|---|---|---|---|---|
| Ex. 1 | Prep. Ex. 1 | 6FDA | TPEQ | 2 | 6 | 88 | 2.31 | 18 | 90 | 17 | ◯ |
| Ex. 2 | Prep. Ex. 1 | 6FDA | TPEQ | 2 | 6 | 88 | 2.02 | 25 | 93 | 17 | ◯ |
| Ex. 3 | Prep. Ex. 2 | 6FDA | AFDM | 2 | 25 | 97 | 0.93 | 7 | 91 | 39 | ◯ |
| Ex. 4 | Prep. Ex. 3 | 6FDA | HFBAPP | 2 | 12 | 89 | 2.3 | 50 | 90 | 25 | ◯ |
| Ex. 5 | Prep. Ex. 4 | 6FDA | BAPP | 2 | 6 | 90 | 1.94 | 28 | 92 | 14 | ◯ |
| Ex. 6 | Prep. Ex. 5 | 6FDA | BAPB | 2 | 6 | 98 | 1.94 | 22 | 92 | 15 | ◯ |
| Ex. 7 | Prep. Ex. 6 | 6FDA | ODA | 1 | 6 | 97 | 2.62 | 19 | 93 | 19 | ◯ |
| Ex. 8 | Prep. Ex. 7 | 6FDA | TPER | 2 | 6 | 85 | 1.02 | 18 | 90 | 17 | ◯ |
| Comp. Ex. 1 | Comp. Prep. Ex. 1 | Pyromellitic dianhydride | ODA | 1 | 0 | 68 | 3.0 | 80 | 95 | 0 | X |
| Non-Patent Document 1[2] | | 6FDA | 6FAP | 0 | 12 | | | | | | X |

[1] Ex. 2: weight average molecular weight of polyimide of polyimide film, other Examples and Comparative Examples: weight average molecular weight of polyamide acid

[2] Non-Patent Document 1 (N. Matsumoto et al., Polymers for Advanced Technologies, 19, 1002, 2008) describes that spheroids were not formed on a film of polyimide (free of ether bonds or thioether bonds) resulting from polymerization of 2,2'-bis(3,4-dicarboxyphenyl)hexafluoropropane dianhydride (6FDA) with a diamine compound (i.e., 2,2'-bis(4-aminophenyl) hexafluoropropane (6FAP)) when it is not subjected to rubbing.

◯: Spheroid formation succeeded;

X: Spheroid formation failed

TABLE 6

| Ex. Comp. Ex. No. | Polyamide acid preparation | Acid dianhydride | Diamine | Imidization method | F/unit | Water contact angle (°) | Elastic modulus (GPa) | Weight average molecular weight[1] ×10⁴ Mw | Degree of imidization (%) | Fluorine content (%) | Spheroid formation |
|---|---|---|---|---|---|---|---|---|---|---|---|
| Ex. 1 | Prep. Ex. 1 | 6FDA | TPEQ | Thermal imidization | 6 | 88 | 2.31 | 18 | 90 | 17 | ○ |
| Ex. 3 | Prep. Ex. 2 | 6FDA | AFDM | Thermal imidization | 25 | 97 | 0.93 | 7 | 91 | 39 | ○ |
| Ex. 4 | Prep. Ex. 3 | 6FDA | HFBAPP | Thermal imidization | 12 | 89 | 2.3 | 50 | 90 | 25 | ○ |
| Ex. 5 | Prep. Ex. 4 | 6FDA | BAPP | Thermal imidization | 6 | 90 | 1.94 | 28 | 92 | 14 | ○ |
| Ex. 6 | Prep. Ex. 5 | 6FDA | BAPB | Thermal imidization | 6 | 98 | 1.94 | 22 | 92 | 15 | ○ |
| Ex. 7 | Prep. Ex. 6 | 6FDA | ODA | Thermal imidization | 6 | 97 | 2.62 | 19 | 93 | 19 | ○ |
| Ex. 8 | Prep. Ex. 7 | 6FDA | TPER | Thermal imidization | 6 | 85 | 1.02 | 18 | 90 | 17 | ○ |
| Ex. 9 | Prep. Ex. 8 | 6FDA | 6FAP | Thermal imidization | 12 | 93 | 1.39 | 8 | 91 | 31 | ○ |
| Ex. 10 | Prep. Ex. 9 | 6FDA | TFMB | Thermal imidization | 12 | 94 | 1.68 | 25 | 92 | 31 | ○ |
| Comp. Ex. 2 | | 6FDA | 6FAP | Thermal imidization | 12 | 93 | 1.25 | 25 | 95 | 31 | X |

Examples 1 and 3 to 10 weight average molecular weight of polyamide acid;
Comparative examples: weight average molecular weight of polyimide
○: Spheroid formation succeeded;
X: Spheroid formation failed

TABLE 7

| Ex. No. | Acid dianhydride | Diamine | Imidization method | F/unit | Water contact angle (°) | Elastic modulus (GPa) | Weight average molecular weight[1] ×10⁴ Mw | Degree of imidization (%) | Fluorine Content (%) | Spheroid formation |
|---|---|---|---|---|---|---|---|---|---|---|
| Ex. 10 | 6FDA | TFMB | Thermal imidization | 12 | 94 | 1.68 | 25 | 92 | 31 | ○ |
| Ex. 11 | 6FDA | TFMB | Chemical imidization | 12 | 94 | 1.45 | 25 | 93 | 31 | ○ |
| Non-Patent Document 1[2] | 6FDA | 6FAP | Chemical imidization | 12 | | | | | | X |

[1] Examples 10 and 11: weight average molecular weight of polyamide acid: Comparative Examples: weight average molecular weight of polyimide
[2] Non-Patent Document 1 (N. Matsumoto et al., Polymers for Advanced Technologies, 19, 1002, 2008) describes that spheroids were not formed on a film of polyimide (free of biphenyl groups) resulting from polymerization of 2,2'-bis(3,4-dicarboxyphenyl)hexafluoropropane dianhydride (6FDA) with a diamine compound (i.e., 2,2'-bis(4-aminophenyl)hexafluoropropane (6FAP)) when it is not subjected to rubbing.
○: Spheroid formation succeeded;
X: Spheroid formation failed

TABLE 8

| Experiment No. | Polyamide acid preparation | Acid dianhydride | Diamine | —O—/unit | F/unit | Water contact angle (°) | Elastic modulus (GPa) | Weight average molecular weight ×10⁴ Mw |
|---|---|---|---|---|---|---|---|---|
| Ex. 3 | Prep. Ex. 2 | 6FDA | AFDM | 2 | 25 | 97 | 0.93 | 7 |
| Ex. 4 | Prep. Ex. 3 | 6FDA | HFBAPP | 2 | 12 | 89 | 2.3 | 50 |
| Ex. 5 | Prep. Ex. 4 | 6FDA | BAPP | 2 | 6 | 90 | 1.94 | 28 |
| Ex. 6 | Prep. Ex. 5 | 6FDA | BAPB | 2 | 6 | 98 | 1.94 | 22 |
| Ex. 7 | Prep. Ex. 6 | 6FDA | ODA | 1 | 6 | 97 | 2.62 | 19 |
| Ex. 8 | Prep. Ex. 7 | 6FDA | TPER | 2 | 6 | 85 | 1.02 | 18 |
| Ex. 9 | Prep. Ex. 8 | 6FDA | 6FAP | 0 | 12 | 93 | 1.39 | 8 |

| Experiment No. | Degree of imidization (%) | Fluorine Content (%) | Membrane thickness (μm) | Oxygen gas permeability* | Oxygen gas permeability coefficient** | Spheroid formation |
|---|---|---|---|---|---|---|
| Ex. 3 | 91 | 39 | | | | ○ |
| Ex. 4 | 90 | 25 | 25 | 14800 | $5.64 \times 10^{-10}$ | ○ |
| Ex. 5 | 92 | 14 | | | | ○ |
| Ex. 6 | 92 | 15 | 25 | 8320 | $3.17 \times 10^{-10}$ | ○ |
| Ex. 7 | 93 | 19 | 23 | 9060 | $3.17 \times 10^{-10}$ | ○ |
| Ex. 8 | 90 | 17 | | | | ○ |
| Ex. 9 | 91 | 31 | 21 | 34300 | $1.10 \times 10^{-9}$ | ○ |

*Oxygen gas permeability unit: $cm^3(STP)/(m^2 \cdot 24\ h \cdot atm)$
**Oxygen gas permeability coefficient unit: $cm^3(STP) \cdot cm/(cm^2 \cdot s \cdot cmHg)$
○: Spheroid formation succeeded;
X: Spheroid formation failed

6.2. Spheroid Formation Via Cell Culture Using Fluorine-Containing Polyimide Membrane-1

1: Fibroblast-Like Cell Culture

Figure 7:
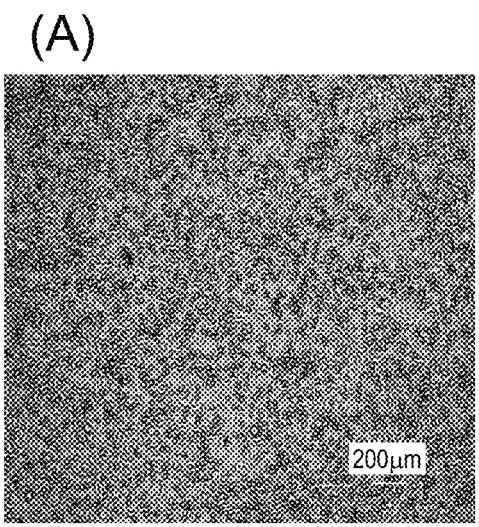
FIG. 7 shows photographs demonstrating the results of culture of fibroblast-like cells: wherein (A) shows the results of culture conducted with the use of a 24-well multi-well cell culture plate (BD Falcon); (B) shows the results of culture conducted with the use of the 6FDA/TPEQ membrane of the present invention; (C) shows the results of culture conducted with the use of a petri dish for suspension cell culture (Nunc); and (D) shows the results of culture conducted with the use of a 24-well plate with a ultra-low attachment surface (Corning).
Figure 7:
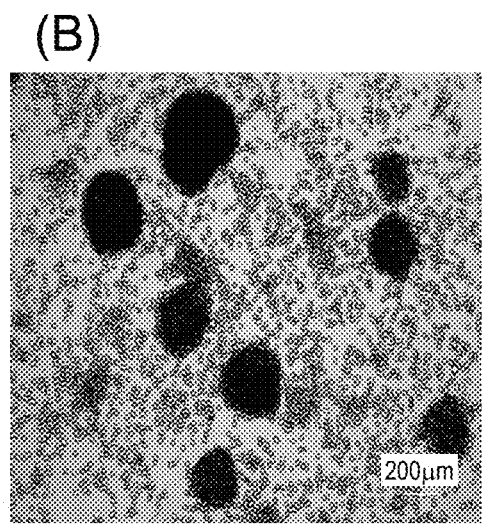
Figure 7:
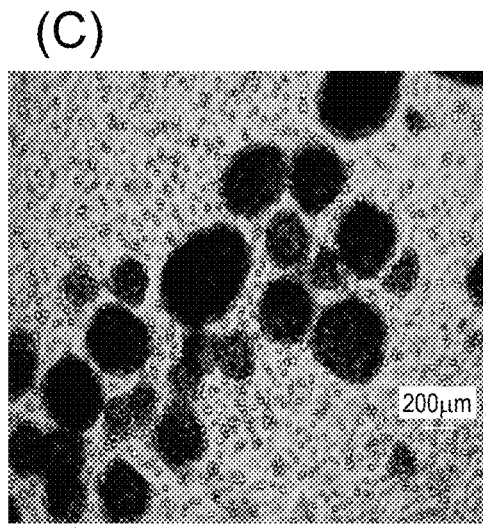
Figure 7:
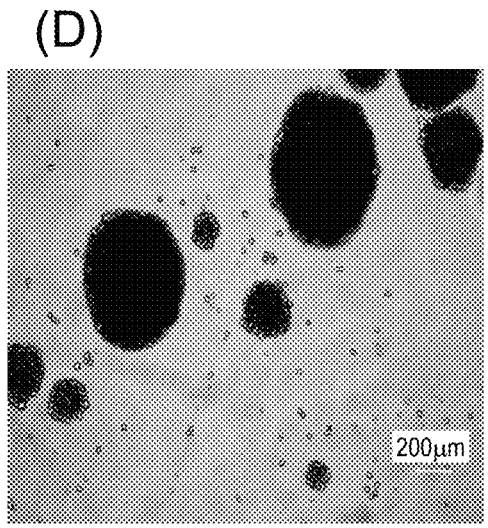

Fibroblast-like cells (L929 cells) were purchased from DS Pharma Biomedical Co., Ltd. L929 cells were suspended in a DMEM medium (DS Pharma Biomedical Co., Ltd.) comprising a fetal bovine serum (FBS) (DS Pharma Biomedical Co., Ltd.) to a final concentration of 10 vol %, the suspension was seeded in a 100-mm cell culture dish (BD Falcon), and culture was conducted at 37° C. in the presence of 5% $CO_2$. After culture was continued to reach 90% confluence, the culture product was treated with a 0.25% trypsin/50 mM EDTA solution, a DMEM medium supplemented with 10% FBS was added to terminate the trypsin reaction, and a suspension of L929 cells was obtained. The L929 cell count in the cell suspension was determined using a 0.4 w/v % trypan blue solution (Wako Pure Chemical Industries, Ltd.) and a blood cell counting chamber. The cells were seeded on the 24-well multi-well cell culture plate (BD Falcon), the 6FDA/TPEQ membrane obtained in Example 1, a petri dish for suspension cell culture (Nunc), and the 24-well plate with a ultra-low attachment surface (Corning) to a density of $5.3 \times 10^4$ cells/cm$^2$, and culture was conducted at 37° C. in the presence of 5% $CO_2$. The 6FDA/TPEQ membrane was first subjected to high pressure steam sterilization and then used for cell culture. FIG. 7 shows a phase-contrast microscope photograph 5 days after the initiation of culture.

On the 24-well multi-well cell culture plate (BD Falcon) that is generally used for adherent cell culture, cells grew as monolayers, and the formation of cell aggregates was not observed. In the case of the 6FDA/TPEQ membrane, the petri dish for suspension cell culture (Nunc), and the 24-well plate with a ultra-low attachment surface (Corning), the formation of cell aggregates having a three-dimensional structure was observed. These cell aggregates were uniform in size, they were of adequate sizes, and spheroids were evenly distributed all over the substrate.

The cells of the test groups were treated with a 0.25% trypsin/50 mM EDTA solution 5 days after the initiation of culture, and the viable cell count was then determined by the trypan blue dye-exclusion assay using a 0.4 w/v % trypan blue solution (Wako Pure Chemical Industries, Ltd.) and a blood cell counting chamber. The cell viability of the test groups 5 days after the initiation of culture is shown below.

TABLE 9

|  | Viability |
|---|---|
| 24-well multi-well cell culture plate (BD Falcon) | 86.4 |
| 6FDA/6FAP membrane | 87.2 |
| Petri dish for suspension cell culture (Nunc) | 64.8 |
| 24-well plate with ultra-low attachment surface (Corning) | 52.9 |

On the 6FDA/TPEQ membrane according to the present invention, the viability as high as that attained on a cell culture plate that is generally used for adherent cell culture was attained; however, many dead cells were observed on a petri dish for suspension cell culture (Nunc) and the 24-well plate with a ultra-low attachment surface (Corning). This indicates that a cell aggregate with high viability can be formed on the 6FDA/TPEQ membrane.

2: Preparation of Primary Rat Hepatocytes

Wistar rats (male, 6-week-old, body weight: 130 g) were purchased from Japan SLC, Inc. Primary rat hepatocytes were obtained with reference to the method described in Experiment Handbook for Cultured Cells, Yodosha Co., Ltd., Chapter 10, Hepatic cells. Specifically, the abdominal cavity of Wistar rats was opened under pentobarbital anesthesia, and a catheter was inserted into the portal vein to inject the preperfusate (an EGTA solution that does not contain $Ca^{2+}$ or $Mg^{2+}$) thereinto. At the same time, the postcaval vein in the lower part of the liver was incised to release the blood. Subsequently, the thoracic cavity was opened, the postcaval vein entering into the right atrium was incised, and the postcaval vein in the lower part of the liver was ligated using forceps to perform perfusion. After sufficient removal of the blood from the liver was confirmed, perfusion was terminated, and the perfusate was replaced with a collagenase solution to perform perfusion. After the intercellular tissue was confirmed to have been digested with collagenase, perfusion was terminated. The liver was resected and transferred to a glass petri dish, a cooled Hanks' solution was added thereto, and cells were dispersed via pipetting. Subsequently, undigested tissue was removed with the use of a 150-mm strainer. A cell suspension was repeatedly subjected to centrifugation at 50 G for 1 minute several times to remove nonparenchymal cells. The viability of the obtained hepatic cells was determined via trypan blue exclusion, and the hepatic cells exhibiting 70% or higher viability were used for the culture test as primary rat hepatocytes.

3-1: Culture of Primary Rat Hepatocytes (1)

The primary rat hepatocytes obtained by the method described above were suspended in the medium of the composition described below, the cell suspension was seeded on the 24-well multi-well cell culture plate (BD Falcon), the 6FDA/TPEQ membrane obtained in Example 1, the high-binding 24-well NanoCulture® plate with MS pattern (SCIVAX Corporation), and the 24-well, PrimeSurface multi-well plate (Sumitomo Bakelite Co., Ltd.) to the cell density of $5.3 \times 10^4$ cells/cm$^2$, and culture was conducted at 37° C. in the presence of 5% $CO_2$. The 6FDA/TPEQ membrane was first subjected to high pressure steam sterilization and then used for cell culture. The medium was exchanged with a fresh medium every day. Since the high-binding 24-well NanoCulture® plate with MS pattern (SCIVAX Corporation) comprises fine concaves and convexes on its surface, the plate was subjected to the following deaeration treatment before the cell suspension was seeded thereon, and air bubbles were removed from the concaves and convexes.

The thermally-imidized 6FDA/6FAP membrane obtained in Example 9 was tested by suspending the primary rat hepatocytes obtained by the method described above in a medium of the following composition, seeding the cell suspension on the 24-well multi-well cell culture plate (BD Falcon) and the thermally-imidized 6FDA/6FAP membrane obtained by the method described in Example 8 to the cell density of $5.3 \times 10^4$ cells/cm$^2$, and conducting culture at 37° C. in the presence of 5% $CO_2$. The 6FDA/6FAP membrane was first subjected to high pressure steam sterilization and then used for cell culture. The medium was exchanged with a fresh medium every day.

The 6FDA/TFMB membrane obtained in Example 10 was tested by suspending the primary rat hepatocytes obtained by the method described above in a medium of the following composition, seeding the cell suspension on a polystyrene 24-well multi-well cell culture plate (BD Falcon), the 6FDA/TFMB membrane (obtained in Example 10), and the high-binding 24-well NanoCulture® plate with MS pattern (SCIVAX Corporation) to the cell density of $5.3 \times 10^4$ cells/cm², and conducting culture at 37° C. in the presence of 5% $CO_2$. The 6FDA/TFMB membrane was first subjected to high pressure steam sterilization and then used for cell culture. The medium was exchanged with a fresh medium every day. Since the high-binding 24-well NanoCulture® plate with MS pattern (SCIVAX Corporation) comprises fine concaves and convexes on its surface, the plate was subjected to the following deairation treatment before the cell suspension was seeded thereon, and air bubbles were removed from the concaves and convexes.

Deairation

William's E medium (Wako Pure Chemical Industries, Ltd.) was fractionated at 500 μl/well.

Centrifugation was carried out at 300 to 500×g for 3 minutes.

The resultant was allowed to stand at room temperature for 30 minutes.

Medium Composition

William's E medium (Wako Pure Chemical Industries, Ltd.)+10% FBS (Wako Pure Chemical Industries, Ltd.)+8.6 nM insulin+255 nM dexamethazone+50 ng/mL EGF+5 KIU/mL aprotinin+antibiotics (penicillin (100 units/mL)/streptomycin (100 μg/mL)/amphotericin B (0.25 μg/mL))

Figure 8:
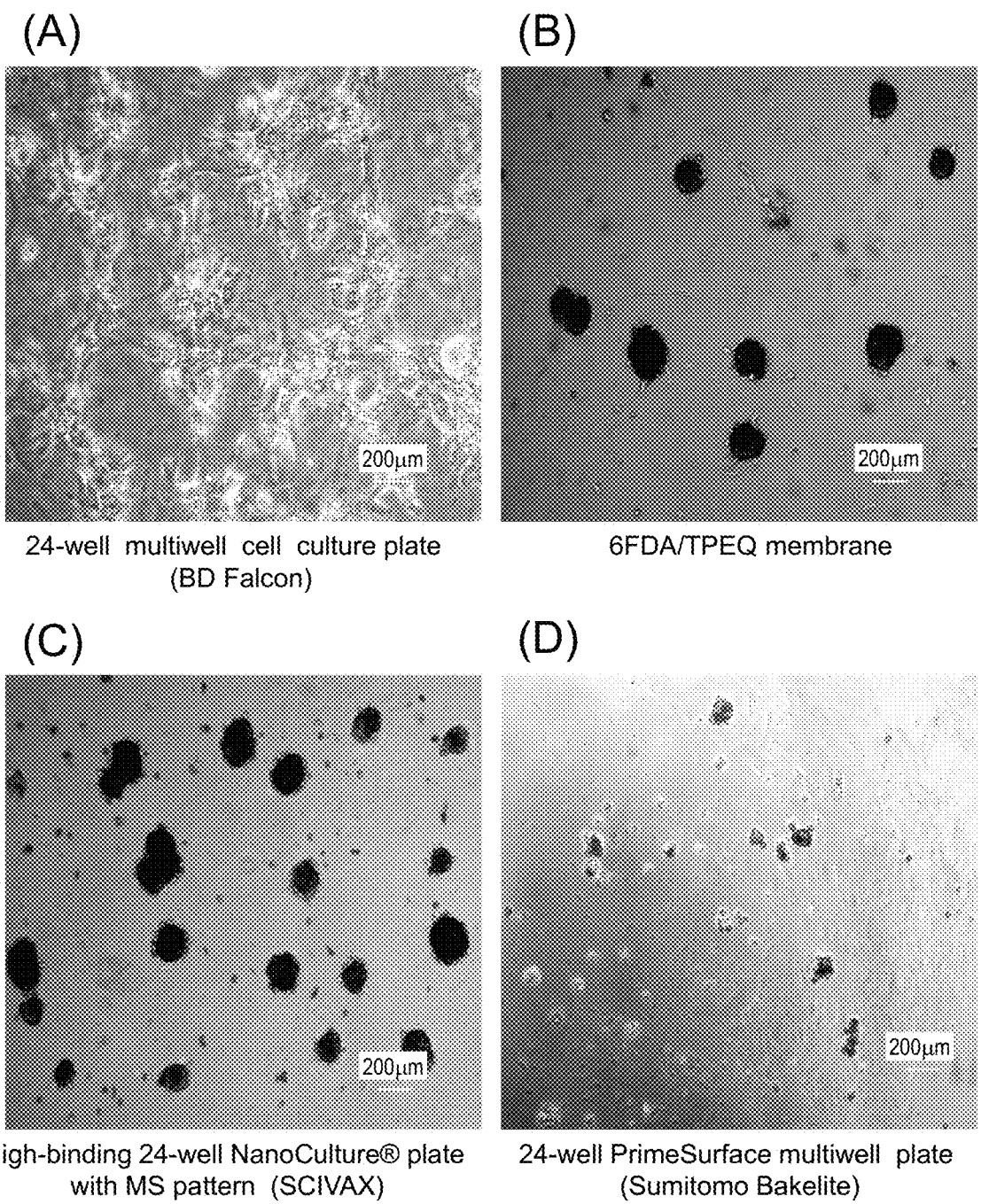
FIG. 8 shows photographs demonstrating the results of culture of primary rat hepatocytes: wherein (A) shows the results of culture conducted with the use of a 24-well multi-well cell culture plate (BD Falcon); (B) shows the results of culture conducted with the use of the 6FDA/TPEQ membrane of the present invention; (C) shows the results of culture conducted with the use of the high-binding 24-well NanoCulture® plate with MS pattern (SCIVAX Corporation); and (D) shows the results of culture conducted with the use of the 24-well PrimeSurface multi-well plate (Sumitomo Bakelite Co., Ltd.).
Figure 9:
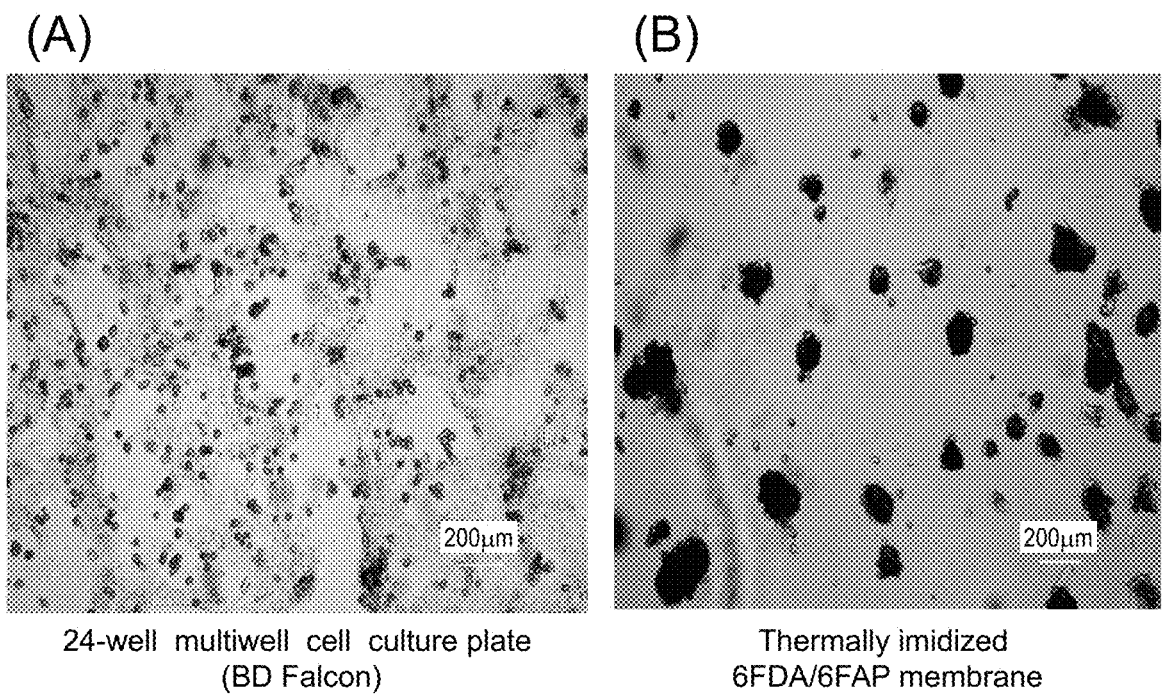
FIG. 9 shows photographs demonstrating the results of culture of primary rat hepatocytes: wherein (A) shows the results of culture conducted with the use of a 24-well multi-well cell culture plate (BD Falcon); and (B) shows the results of culture conducted with the use of the 6FDA/6FAP membrane of the present invention.
Figure 10:
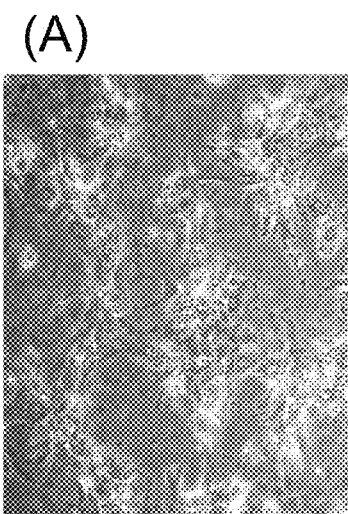
FIG. 10 shows photographs demonstrating the results of culture of primary rat hepatocytes: wherein (A) shows the results of culture conducted with the use of a 24-well multi-well cell culture plate (BD Falcon); (B) shows the results of culture conducted with the use of the 6FDA/TFMB membrane of the present invention; and (C) shows the results of culture conducted with the use of the high-binding 24-well NanoCulture® plate with MS pattern (SCIVAX Corporation).
Figure 10:
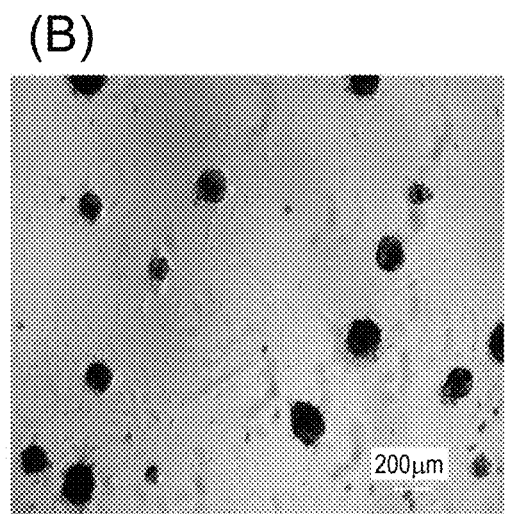
Figure 10:
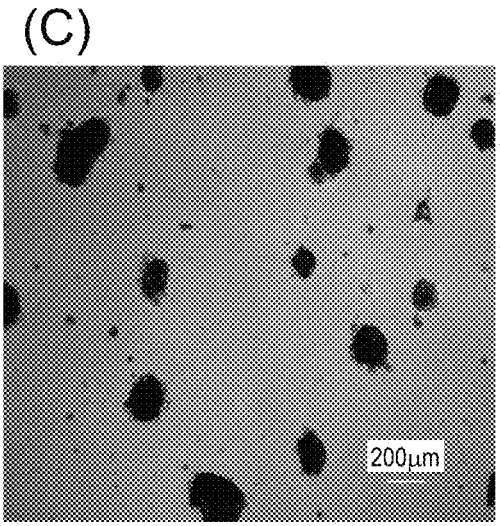

FIG. 8 (Example 1), FIG. 9 (Example 9), and FIG. 10 (Example 10) show phase-contrast microscope photographs 5 days after the initiation of culture.

On the 24-well multi-well cell culture plate (BD Falcon) that is generally used for adherent cell culture, cells grew as monolayers, and the formation of cell aggregates was not observed. In the case of the 6FDA/TPEQ membrane, the high-binding 24-well NanoCulture® plate with MS pattern (SCIVAX Corporation), and the 24-well PrimeSurface multi-well plate (Sumitomo Bakelite Co., Ltd.), the formation of cell aggregates having a three-dimensional structure was confirmed (FIG. 8). While the formation of cell aggregates was observed on the 24-well PrimeSurface multi-well plate (Sumitomo Bakelite Co., Ltd.), the number thereof was very small. It is considered that cells are removed together with the medium at the time of medium exchange. In addition, cell aggregates formed on the high-binding 24-well plate with MS pattern (SCIVAX Corporation) and the 24-well PrimeSurface multi-well plate (Sumitomo Bakelite Co., Ltd.) were not uniform in size, and most cell aggregates were concentrated in the center of the wells. In contrast, cell aggregates cultured on the culture substrate according to the present invention were uniform in size, they were of adequate sizes, and spheroids were evenly distributed all over the substrate.

In relation to the thermally-imidized 6FDA/6FAP membrane, a similar result was also observed. On the 24-well multi-well cell culture plate (BD Falcon) that is generally used for adherent cell culture, cells grew as monolayers, and the formation of cell aggregates was not observed. In the case of the thermally-imidized 6FDA/6FAP membrane, and the high-binding 24-well NanoCulture® plate with MS pattern (SCIVAX Corporation), in contrast, the formation of cell aggregates having a three-dimensional structure was observed (FIG. 9). These cell aggregates were uniform in size, they were of adequate sizes, and spheroids were evenly distributed all over the substrate.

In relation to the 6FDA/TFMB membrane obtained in Example 10, a similar result was also observed. On the 24-well multi-well cell culture plate (BD Falcon) that is generally used for adherent cell culture, cells grew as monolayers, and the formation of cell aggregates was not observed. In the case of the 6FDA/TFMB membrane, and the high-binding 24-well NanoCulture® plate with MS pattern (SCIVAX Corporation), in contrast, the formation of cell aggregates was observed (FIG. 10). Cell aggregates formed on the high-binding 24-well plate with MS pattern (SCIVAX Corporation) were not uniform in size, and most cell aggregates were concentrated in the center of the wells. In contrast, cell aggregates cultured on the culture substrate according to the present invention were uniform in size, they were of adequate sizes, and spheroids were evenly distributed all over the substrate.

The cultured cells were treated with a 0.25% trypsin/50 mM EDTA solution every 24 hours, and the total cell count was determined with the use of a 0.4 w/v % trypan blue solution (Wako Pure Chemical Industries, Ltd.) and a blood cell counting chamber. Also, the culture solution was sampled every 24 hours and stored at −20° C.

[Culture on Polyimide Film Prepared Via Chemical Imidization (Comparative Examples)]

Primary rat hepatocytes were subjected to the culture test on the chemically imidized 6FDA/6FAP membrane prepared by the method described in Comparative Example 2. Primary rat hepatocytes were obtained from Wistar rats (male, 6-week-old, body weight: 130 g) in the same manner as described above and subjected to the culture test under the same culture conditions with the use of the medium as described above. Cultured cells were observed under the phase-contrast microscope 5 days after the initiation of culture. As a result, the formation of cell aggregates was not observed on the chemically imidized 6FDA/6FAP membrane.

3-2: Culture of Primary Rat Hepatocytes (2)

The primary rat hepatocytes obtained by the method described above were suspended in a medium of the following composition, and the cell suspension was seeded on the polystyrene multi-well cell culture plate according to Comparative Example 3, the 6FDA/TPEQ membrane of Example 1, and the 6FDA/TFMB membrane of Example 10 to the cell density of $5.3 \times 10^4$ cells/cm², and culture was conducted at 37° C. in the presence of 5% $CO_2$. The 6FDA/TPEQ membrane and the 6FDA/TFMB membrane were first subjected to high pressure steam sterilization and then used for cell culture. The medium was exchanged with a fresh medium every day.

Cell culture on the 6FDA/TPEQ membrane or the 6FDA/TFMB membrane was carried out with the use of a cell culture vessel in which a part of the bottom wall constituting the bottom of the container portion that accommodates cells and a liquid medium was made only of the 6FDA/TPEQ membrane or the 6FDA/TFMB membrane. When such vessel is disposed on the surface of an experiment table, the surface of the experiment table is not brought into contact with the lower surface of the membrane (i.e., the surface exposed to the outside of the vessel), and the air is present therebetween. With the use of such culture vessel, as shown in FIG. 3, cell culture can be carried out in a manner such that a surface of the membrane (substrate) 10 serves as a scaffold for cells 3 while being in contact with a liquid medium 2 containing cells 3 and the other surface of the membrane 10 is exposed to the air 4 outside the vessel.

Medium Composition

William's E medium (Wako Pure Chemical Industries, Ltd.)+10% FBS (Wako Pure Chemical Industries, Ltd.)+8.6 nM insulin+255 nM dexamethazone+50 ng/mL EGF+5

KIU/mL aprotinin+antibiotics (penicillin (100 units/mL)/ streptomycin (100 μg/mL)/amphotericin B (0.25 μg/mL))

Figure 11:
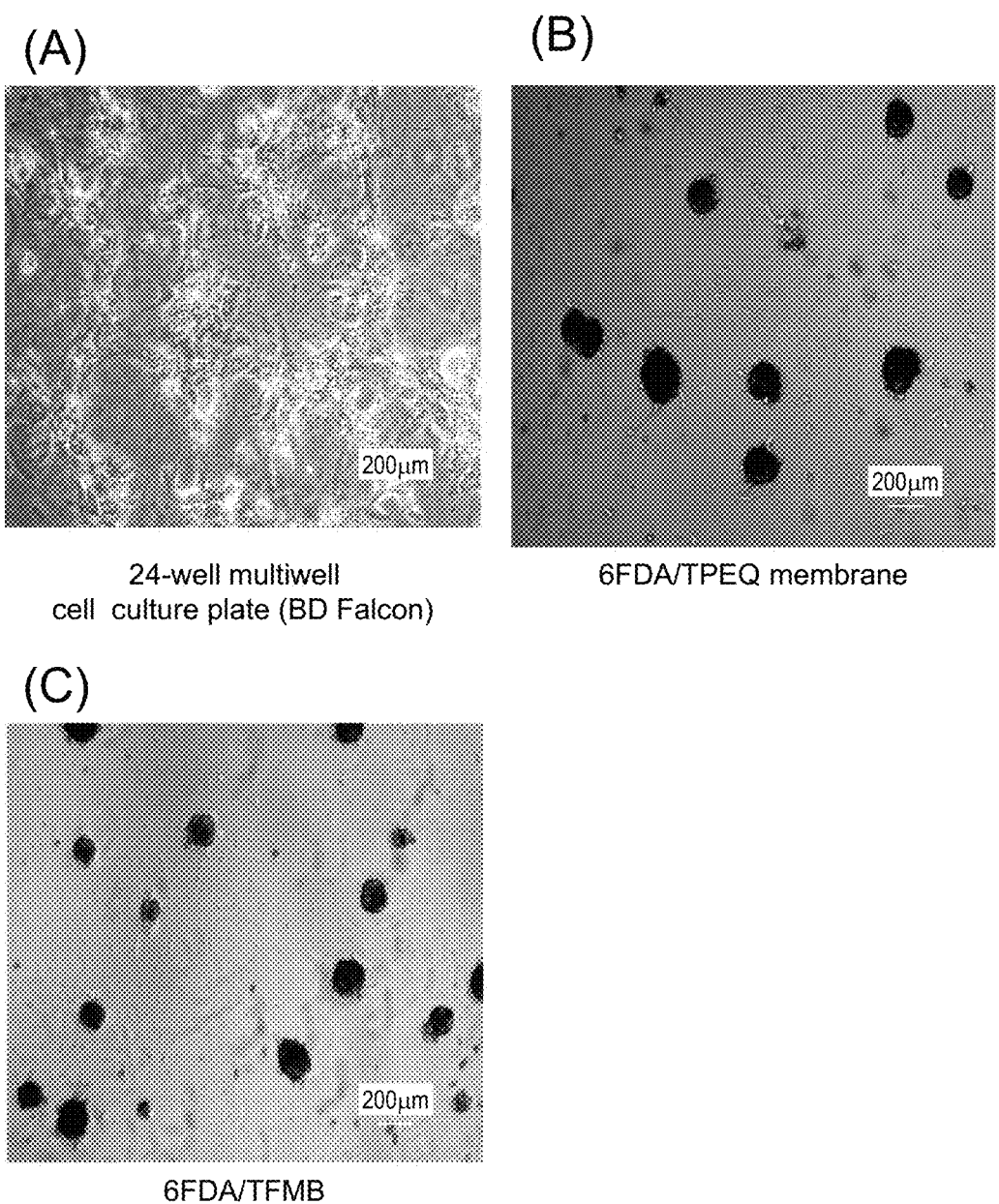
FIG. 11 shows photographs demonstrating the results attained 5 days after the initiation of culture of primary rat hepatocytes: wherein (A) shows the results of culture conducted with the use of a 24-well multi-well cell culture plate (BD Falcon) made of polystyrene; (B) shows the results of culture conducted with the use of the 6FDA/TPEQ membrane of the present invention; and (C) shows the results of culture conducted with the use of the 6FDA/TFMB membrane of the present invention.

FIG. 11 shows a phase-contrast microscope photograph 5 days after the initiation of culture.

On the multi-well cell culture plate of Comparative Example 3 that is generally used for adherent cell culture, cells grew as monolayers, and the formation of cell aggregates was not observed. On the 6FDA/TPEQ membrane and the 6FDA/TFMB membrane, the formation of cell aggregates having a three-dimensional structure was observed. In addition, these cell aggregates were uniform in size, they were of adequate sizes, and spheroids were evenly distributed all over the substrate.

The cultured cells were treated with a 0.25% trypsin/50 mM EDTA solution every 24 hours, and the total cell count was determined with the use of a 0.4 w/v % trypan blue solution (Wako Pure Chemical Industries, Ltd.) and a blood cell counting chamber. Also, the culture solution was sampled every 24 hours and stored at −20° C.

4: Immunostaining

Figure 12:
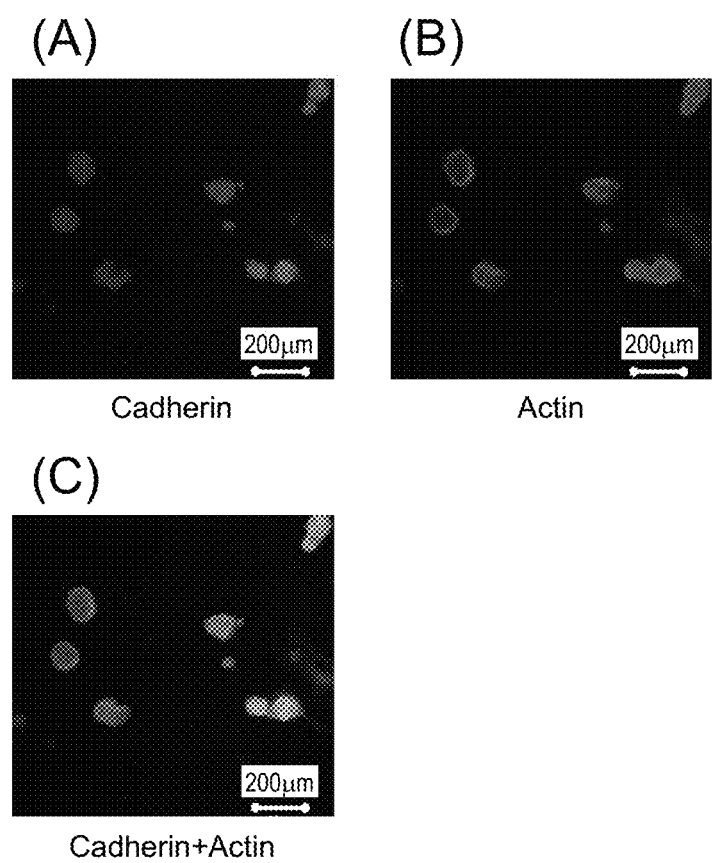
FIG. 12 shows photographs demonstrating the results of cadherin and actin immunostaining of the cell aggregate formed on the 6FDA/TPEQ membrane 5 days after the initiation of culture of primary rat hepatocytes (fluorescence microscopy images): wherein (A) shows the results of cadherin staining; (B) shows the results of actin staining; and (C) shows the fluorescence microscopy image of cadherin staining and the fluorescence microscopy image of actin staining superposed on top of each other.

The cell aggregates formed on the 6FDA/TPEQ membrane or the 6FDA/TFMB membrane were subjected to cadherin and actin immunostaining 5 days after the initiation of culture. Specifically, a 4% paraformaldehyde/PBS(−) solution was used as a fixing solution, a 0.1% BSA-supplemented PBS(−) solution was used as a blocking solution, and a 0.05% Triton-X/PBS(−) solution was used as a wash solution. The rabbit E-cadherin polyclonal antibody (Santa Cruz), the biotinylated anti-rabbit IgG antibody (Vector Laboratories), the streptavidin-fluorescein antibody (Perkin Elmer), and the rhodamine phalloidin antibody (Invitrogen) were used. Fluorescence microscope photographs were obtained with the use of a confocal laser scanning microscope LSM700 (ZEISS). FIG. 12 (the 6FDA/TPEQ membrane: Example 1) and FIG. 13 (the 6FDA/TFMB membrane: Example 10) show fluorescence microscopy images. Green indicates cadherin (A) and red indicates actin (B). (C) shows images (A) and (B) superposed on top of each other.

Thus, cell aggregates formed on the 6FDA/TPEQ membrane were confirmed to be cadherin-expressing spheroids (FIG. 12).

Figure 13:
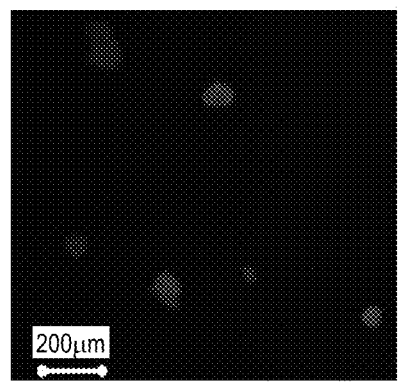
FIG. 13 shows photographs demonstrating the results of cadherin and actin immunostaining of the cell aggregate formed on the 6FDA/TFMB membrane 5 days after the initiation of culture of primary rat hepatocytes (fluorescence microscopy images): wherein (A) shows the results of cadherin staining; (B) shows the results of actin staining; and (C) shows the fluorescence microscopy image of cadherin staining and the fluorescence microscopy image of actin staining superposed on top of each other.
Figure 13:
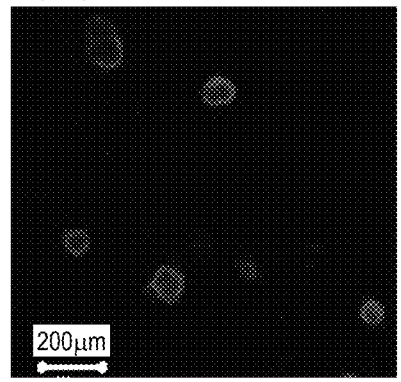
Figure 13:
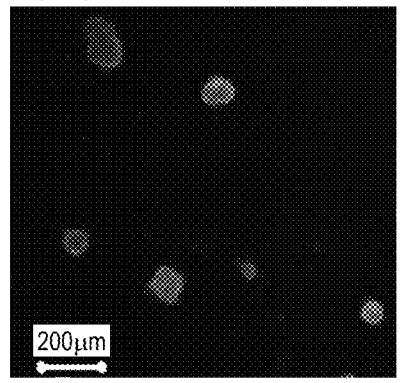

Also, cell aggregates formed on the 6FDA/TFMB membrane were confirmed to be cadherin-expressing spheroids (FIG. 13).

5: Albumin Quantification

Figure 14:
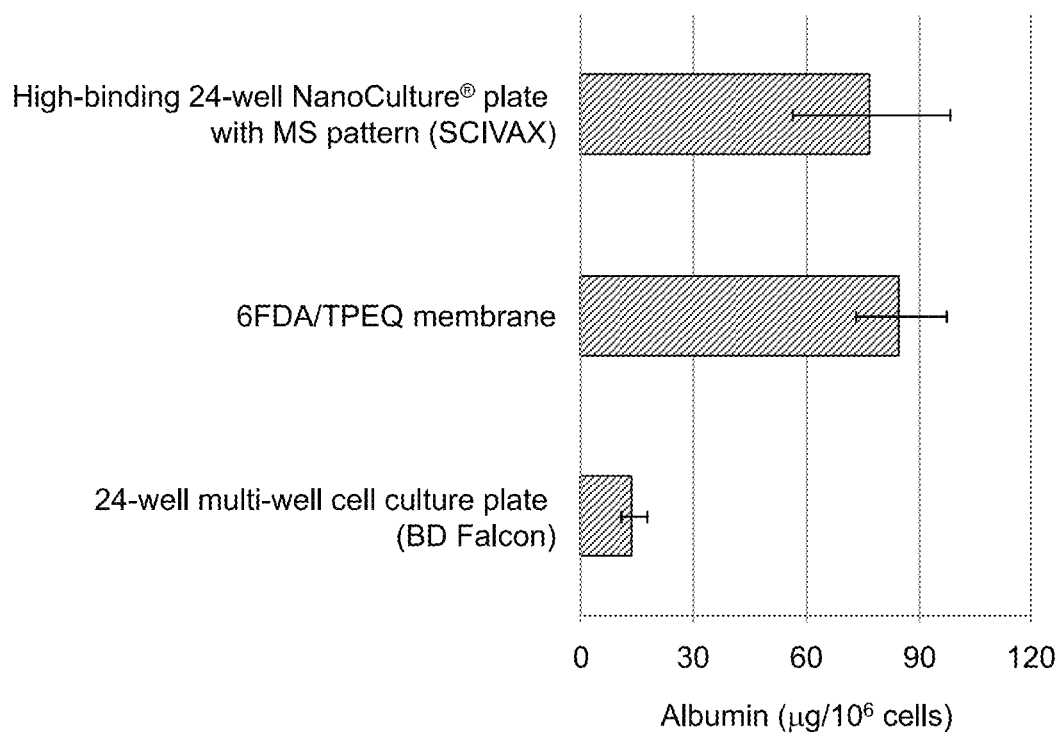
FIG. 14 shows the results of albumin quantification of the culture solution 5 days after the initiation of culture of primary rat hepatocytes on the 6FDA/TPEQ membrane.
Figure 15:
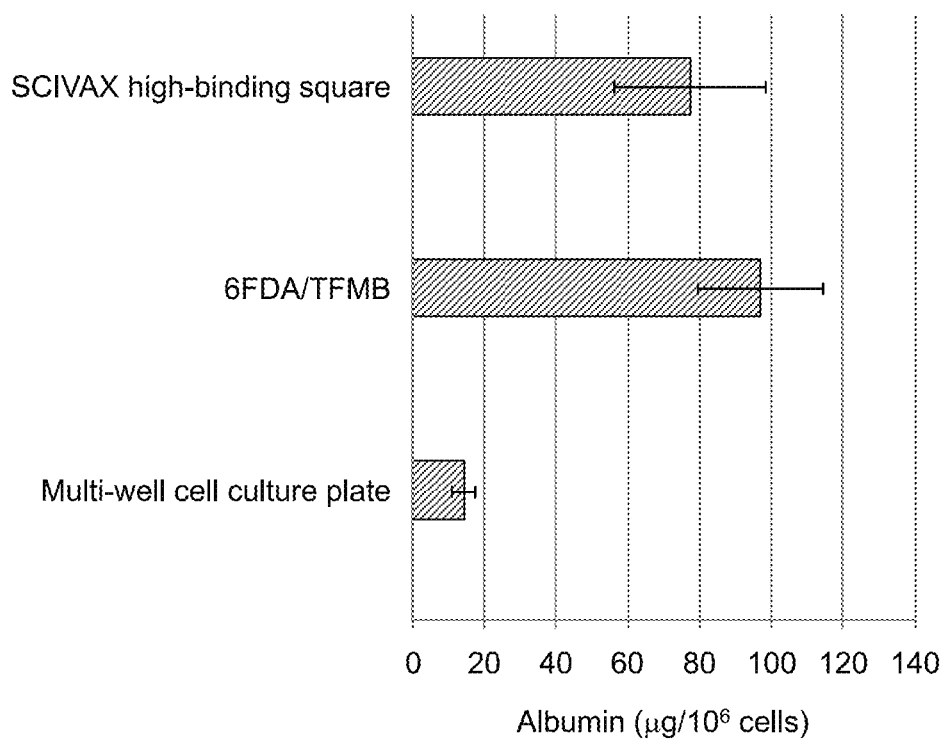
FIG. 15 shows the results of albumin quantification of the culture solution 5 days after the initiation of culture of primary rat hepatocytes on the 6FDA/TFMB membrane.
Figure 16:
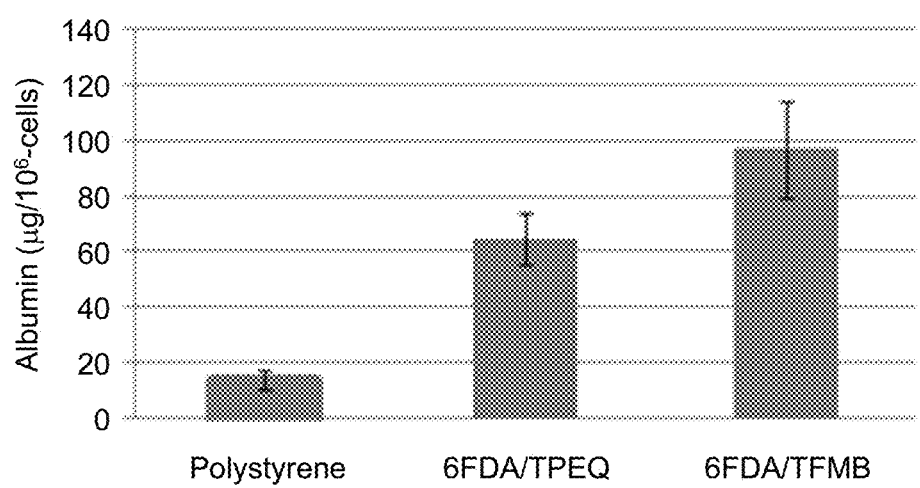
FIG. 16 shows the results of albumin quantification of the culture solution 5 days after the initiation of culture of primary rat hepatocytes on the 6FDA/TPEQ membrane and on the 6FDA/TFMB membrane.

The culture solutions of the test groups were subjected to albumin quantification 5 days after the initiation of culture. Albumin quantification was carried out with the use of the rat albumin ELISA quantitation set (Bethyl Laboratories) in accordance with the protocols included therein. FIGS. 14 and 16 (the 6FDA/TPEQ membrane) and FIGS. 15 and 16 (the 6FDA/TFMB membrane) show the results of albumin quantification of the test groups. Albumin was not detected on the 24-well PrimeSurface multi-well plate (Sumitomo Bakelite Co., Ltd.).

It was found that albumin production achieved with the use of the 6FDA/TPEQ membrane without concaves or convexes would be equivalent to that achieved with the use of the high-binding NanoCulture plate with MS pattern.

The amount of albumin produced with the use of the 6FDA/TFMB membrane was the highest, which is followed by the 6FDA/TPEQ membrane and the 24-well multi-well cell culture plate (BD Falcon) in that order. That is, the use of a material with higher oxygen permeability was found to enable the maintenance of hepatic cell functions at higher levels.

6: Spheroid Formation Via Cell Culture Using Other Substrate

Culture tests were carried out with the use of the 6FDA/TPEQ membrane (Example 2), the 6FDA/AFDM membrane (Example 3), the 6FDA/HFBAPP membrane (Example 4), the 6FDA/BAPP membrane (Example 5), the 6FDA/BAPB membrane (Example 6), the 6FDA/ODA membrane (Example 7), the 6FDA/TPER membrane (Example 8), the 6FDA/TFMB (Example 11), and the pyromellitic acid/ODA membrane (Comparative Example 1). The test membranes were first subjected to high pressure steam sterilization and then used for culture tests. Primary rat hepatocytes were obtained from Wistar rats (male, 6-week-old, body weight: 130 g) in the same manner as described above and subjected to the culture test under the same culture conditions with the use of the medium as described above. Cultured cells of the test groups were observed under the phase-contrast microscope 5 days after the initiation of culture. As a result, the formation of cell aggregates was observed in the test groups except for the test group of Comparative Example 1. The size of the cell aggregates formed on the 6FDA/TPEQ membrane obtained in Example 2 was smaller than that of the cell aggregates formed on the membranes obtained in Examples 3 to 8, and the number of aggregates was also smaller.

7: Culture on Fluorine-Free Polyimide Membrane

Culture of primary rat hepatocytes was carried out on the pyromellitic dianhydride/ODA polyimide membrane (containing no fluorine atoms) of Comparative Example 1 in the same manner as in culture of primary rat hepatocytes on the 6FDA/TPEQ membrane or the 6FDA/TFMB membrane described in 3-2 above. As shown in FIG. 3, specifically, primary rat hepatocytes were cultured in a manner such that a surface of the pyromellitic dianhydride/ODA polyimide membrane 10 serves as a scaffold for cells 3 while being in contact with a liquid medium 2 containing cells 3 and the other surface of the membrane 10 is exposed to the air 4 outside the vessel. Also, primary rat hepatocytes were obtained in the manner described in 1 above.

Cultured cells were observed under the phase-contrast microscope 5 days after the initiation of culture. As a result, the formation of cell aggregates was not observed.

6.3: Spheroid Formation Via Cell Culture Using Fluorine-Containing Polyimide Membrane-2

1: Preparation of Primary Rat Hepatocytes

Specific viral pathogen-free Wistar rats (male, 9-week-old, body weight: 200 g) were purchased from Japan SLC, Inc. Primary rat hepatocytes were obtained with reference to the method described in Experiment Handbook for Cultured Cells, Yodosha Co., Ltd., Chapter 10, Hepatic cells. Specifically, the abdominal cavity of Wistar rats was opened under isoflurane anesthesia, and a catheter was inserted into the portal vein to inject the preperfusate having the composition shown in Table 10. At the same time, the postcaval vein in the lower part of the liver was incised to release the blood. Subsequently, the thoracic cavity was opened, the postcaval vein entering into the right atrium was incised, and the postcaval vein in the lower part of the liver was ligated using forceps to perform perfusion. After sufficient removal of the blood from the liver was confirmed, perfusion was terminated, and the perfusate was replaced with a collagenase solution having the composition shown in Table 10 to perform perfusion. After the intercellular tissue was confirmed to have been digested with collagenase, perfusion was terminated. The liver was resected and transferred to a glass petri dish, a cooled Hanks' solution was added thereto, and cells were dispersed via pipetting. Subsequently, undigested tissue was removed with the use of a 150-mm strainer. A cell suspension was repeatedly subjected to centrifugation at 50 G for minutes several times to remove nonparenchymal cells. The viability of the obtained hepatic cells was determined via trypan blue exclusion, and the hepatic cells exhibiting 85% or higher viability were used for the culture test as primary rat hepatocytes.

TABLE 10

|  | Preperfusate g/L | Collagenase solution g/L |
| --- | --- | --- |
| NaCl | 8 | 8 |
| KCl | 0.4 | 0.4 |
| $Na_2HPO_4$ | 0.04796 | 0.04796 |
| $KH_2PO_4$ | 0.06 | 0.06 |
| $MgSO_4 \cdot 7H_2O$ | — | 0.2 |
| $CaCl_2 \cdot 2H_2O$ | — | 0.735 |
| $NaHCO_3$ | 0.35 | 0.35 |
| Glucose | 1 | 1 |
| Phenol red | 0.006 | 0.006 |
| HEPES | 2.383 | 2.383 |
| EGTA | 0.19 | — |
| Collagenase | — | 0.5 |

2: Culture of Primary Rat Hepatocytes with the Use of Serum-Free Medium

The primary rat hepatocytes obtained by the method described above were suspended in a serum-free medium having the composition shown in Table 11, 0.4 ml of a suspension comprising primary rat hepatocytes at $6.25 \times 10^5$ cells/mL was applied to the high-binding 24-well NanoCulture® plate with MS pattern (SCIVAX Corporation), the 24-well PrimeSurface multi-well plate (Sumitomo Bakelite Co., Ltd.), and the 24-well 6FDA/TPEQ plate (Example 1) to the cell density of $1.33 \times 10^4$ cells/cm$^2$, and culture was conducted at 37° C. in the presence of 5% $CO_2$. The medium was exchanged with a fresh medium by removing the total amount of the medium 4 hours after seeding and 1 day, 3 days, and 5 days after the initiation of culture and then adding 0.4 ml of the serum-free medium. Since the high-binding 24-well NanoCulture® plate with MS pattern (SCIVAX Corporation) comprises fine concaves and convexes on its surface, the plate was subjected to the following deairation treatment before the cell suspension was seeded thereon, and air bubbles were removed from the concaves and convexes.

TABLE 11

| Composition of serum-free medium | |
| --- | --- |
| Dulbecco's modified Eagle medium-low glucose (Sigma-Aldrich) | 10 g/L |
| $CuSO_4 \cdot 5H_2O$ | 0.025 mg/L |
| $H_2SeO_3$ | 3 µg/L |
| $ZnSO_4 \cdot H_2O$ | 50 pM |

TABLE 11-continued

| Composition of serum-free medium | |
| --- | --- |
| Linolic acid | 50 mg/L |
| HEPES | 1.19 g/L |
| L-proline | 60 mg/L |
| Hydrocortisone | 7.5 mg/L |
| Penicillin | 58.8 mg/L |
| Streptomycin | 100 mg/L |
| EGF | 50 µg/L |
| Insulin | 10 mg/L |
| $NaHCO_3$ | 1.05 g/L |

Figure 17:
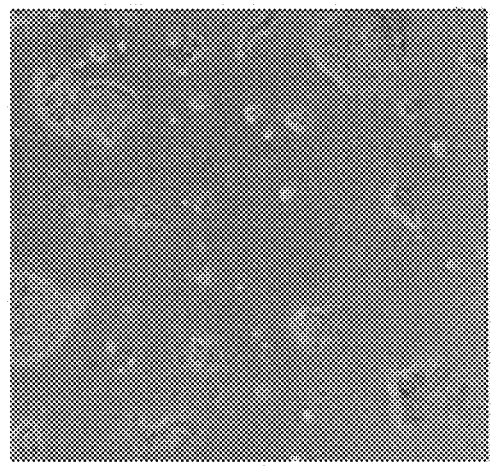
FIG. 17 shows photographs demonstrating the results of culture of primary rat hepatocytes conducted with the use of a serum-free medium: (A) shows the results of culture conducted with the use of the high-binding 24-well NanoCulture® plate with MS pattern (SCIVAX Corporation); (B) shows the results of culture conducted with the use of the 24-well PrimeSurface multi-well plate (Sumitomo Bakelite Co., Ltd.); and (C) shows the results of culture conducted with the use of the 24-well 6FDA/TPEQ plate of the present invention.
Figure 17:
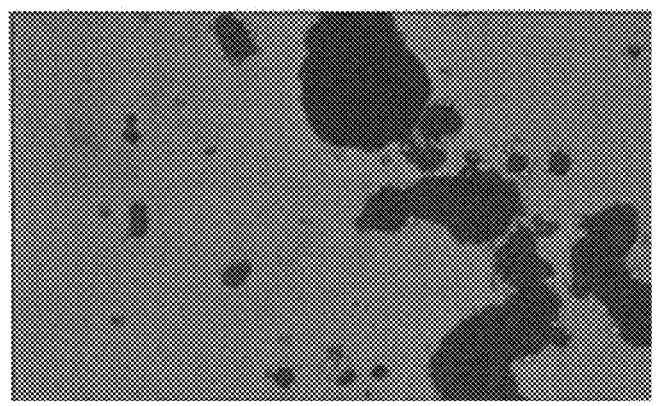
Figure 17:
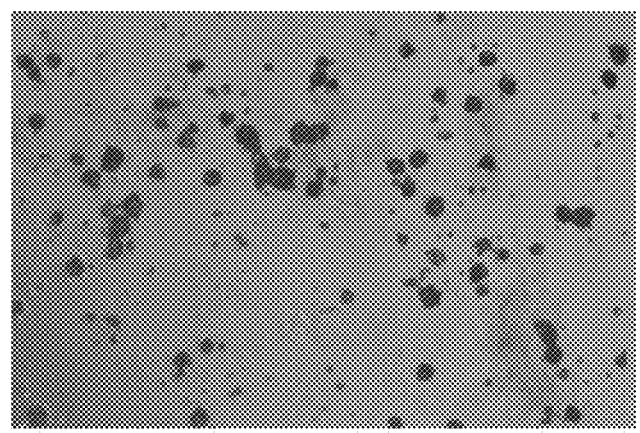

FIG. 17 shows phase-contrast microscope photographs of the high-binding 24-well NanoCulture® plate with MS pattern (SCIVAX Corporation) (FIG. 17A), the 24-well PrimeSurface multi-well plate (Sumitomo Bakelite Co., Ltd.) (FIG. 17B), and the 24-well 6FDA/TPEQ plate (Example 1) (FIG. 17C) 5 days after the initiation of culture.

While cell aggregates were formed on the 24-well PrimeSurface multi-well plate (Sumitomo Bakelite Co., Ltd.), the aggregates were floated in the medium, and large masses were formed (FIG. 17B). In addition, the number of cells is small. This is considered to have occurred because the cells floated in the medium were removed together with the medium at the time of medium exchange. On the high-binding 24-well NanoCulture® plate with MS pattern (SCIVAX Corporation), formation of some aggregates was observed, but most cells grew as monolayers and adhered to the substrate (FIG. 17A). In contrast, the number of cells adhered to the substrate as monolayers was small on the 24-well FDA/TPEQ plate (Example 1), and cell aggregates having a three-dimensional structure were formed (FIG. 17C).

3: Measurement of CYP1A Activity

Figure 18:
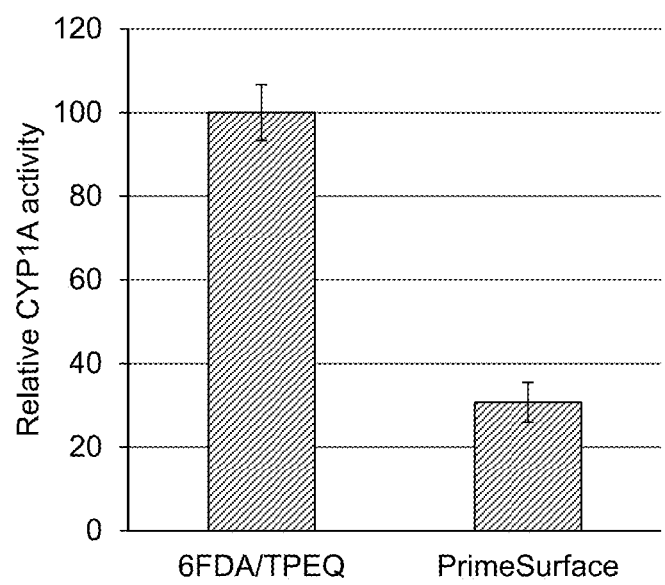
FIG. 18 shows a chart demonstrating the results of CYP1A activity assay of the culture solution 5 days after the initiation of culture of primary rat hepatocytes with the use of a serum-free medium on the 6FDA/TPEQ membrane.

The cells on the 24-well PrimeSurface multi-well plate (Sumitomo Bakelite Co., Ltd.) and the 24-well 6FDA/TPEQ plate (Example 1) were subjected to measurement of CYP1A activity 5 days after the initiation of culture. The medium was removed and the serum-free medium supplemented with 3-methylcholanthrene at the final concentration of 2 µM was added. The medium was removed 24 hours after it was added. Subsequently, the serum-free medium supplemented with ethoxyresorufin at the final concentration of 10 µM was added, and incubation was carried out at 37° C. in the presence of $CO_2$ for 75 minutes. After incubation, the fluorescence intensity of each well was measured using a fluorometer. The results are shown in FIG. 18.

Compared with the cells on the 24-well 6FDA/TPEQ plate (Example 1), the cells on the 24-well PrimeSurface multi-well plate (Sumitomo Bakelite Co., Ltd.) exhibited lower CYP1A activity. This is considered to have occurred for the following reasons. That is, cells formed a large mass on the 24-well PrimeSurface multi-well plate (Sumitomo Bakelite Co., Ltd.), components of the medium and oxygen were not sufficiently supplied to the cells in the center of the cell mass, and cellular functions were lowered as a consequence. In addition, 3-methylcholanthrene and ethoxyresorufin could not be efficiently introduced into the cells in the case of a large cell mass on the 24-well PrimeSurface multi-well plate (Sumitomo Bakelite Co., Ltd.), and the expression level of the CYP1A gene was lowered.

4: Culture of Primary Rat Hepatocytes with the Use of Serum Medium

The primary rat hepatocytes obtained by the method described above were suspended in a serum medium having the composition shown below, 0.4 ml of a suspension comprising primary rat hepatocytes at $6.25 \times 10^5$ cells/mL was applied to the 24-well collagen type I-coated microplate (Asahi Glass Co. Ltd.), the high-binding 24-well NanoCulture® plate with MS pattern (SCIVAX Corporation), the 24-well PrimeSurface multi-well plate (Sumitomo Bakelite Co., Ltd.), the 24-well Lumox multi-well plate (Greiner), and the 24-well 6FDA/TPEQ plate (Example 1) to the cell density of $1.33 \times 10^4$ cells/cm$^2$, and culture was conducted at 37° C. in the presence of 5% $CO_2$. The medium was exchanged with a fresh medium by removing the total amount of the medium 4 hours after seeding and 1 day, 3 days, and 5 days after the initiation of culture and then adding 0.4 ml of the serum medium.

Serum Medium Composition

William's E medium (Wako Pure Chemical Industries, Ltd.)+10% FBS (Wako Pure Chemical Industries, Ltd.)+8.6 nM insulin+255 nM dexamethazone+50 ng/mL EGF+5 KIU/mL aprotinin+antibiotics (penicillin (100 units/mL)/streptomycin (100 μg/mL)/amphotericin B (0.25 μg/mL))

Figure 19:
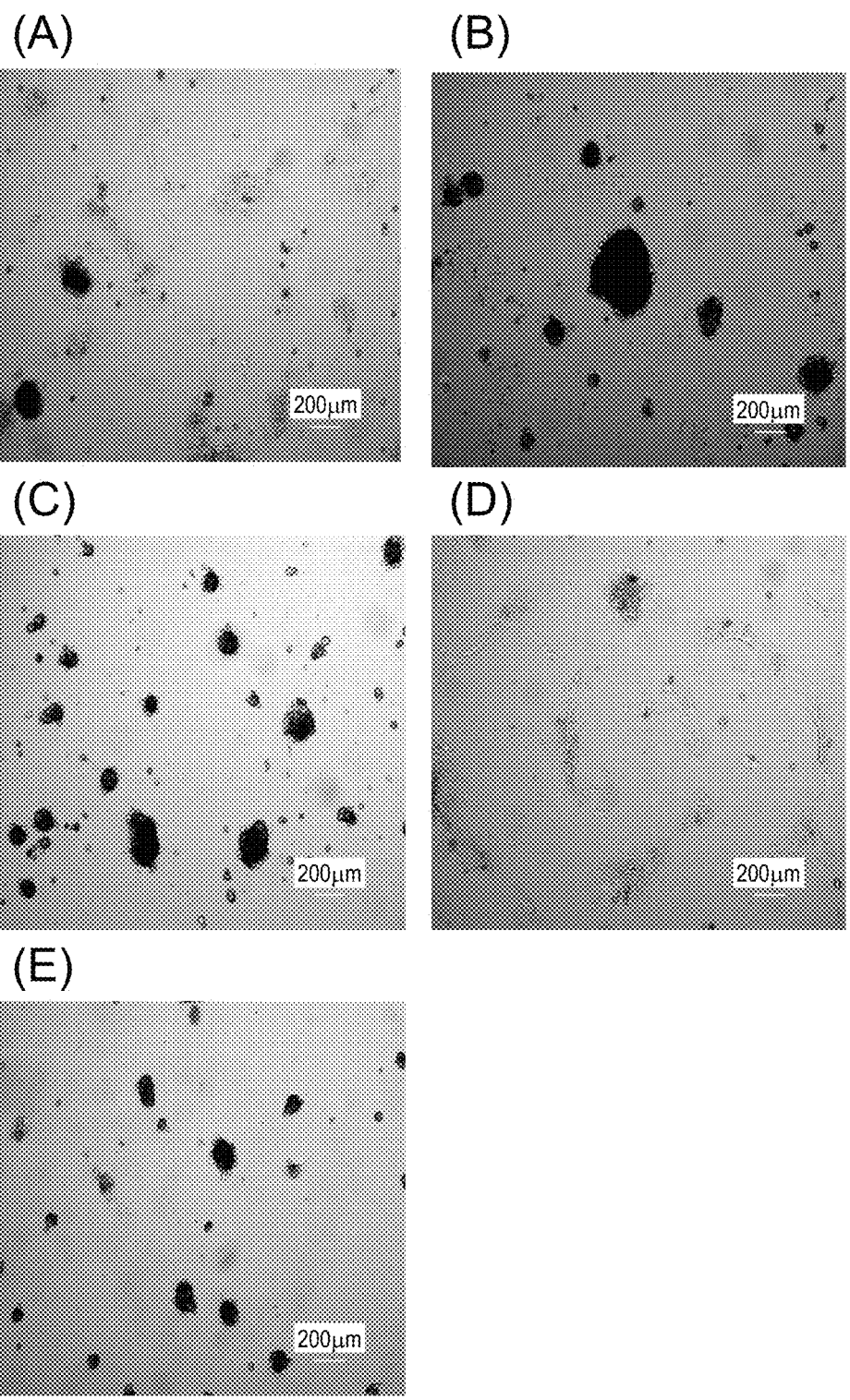
FIG. 19 shows photographs demonstrating the results of culture of primary rat hepatocytes with the use of a serum medium: (A) shows the results of culture conducted with the use of a 24-well collagen type I-coated microplate (Asahi Glass Co. Ltd.); (B) shows the results of culture conducted with the use of the high-binding 24-well NanoCulture® plate with MS pattern (SCIVAX Corporation); (C) shows the results of culture conducted with the use of the 24-well PrimeSurface multi-well plate (Sumitomo Bakelite Co., Ltd.); (D) shows the results of culture conducted with the use of the 24-well Lumox multi-well plate (Greiner); and (E) shows the results of culture conducted with the use of the 24-well 6FDA/TPEQ plate of the present invention.

FIG. 19 shows a phase-contrast microscope photograph of cells on wells 5 days after the initiation of culture.

On the 24-well collagen type I-coated microplate (Asahi Glass Co. Ltd.) (FIG. 19A) and the 24-well Lumox multi-well plate (Greiner) (FIG. 19D), many cells grew as monolayers, and the formation of cell aggregates was not substantially observed. On the high-binding 24-well NanoCulture® plate with MS pattern (SCIVAX Corporation) (FIG. 19B) and the 24-well PrimeSurface multi-well plate (Sumitomo Bakelite Co., Ltd.) (FIG. 19C), in addition, cell aggregates were formed, cell aggregates did not adhere to the substrate but floated in the medium, and the floating cell aggregates further formed larger masses. When cell aggregates are excessively large, components of the medium and oxygen are not sufficiently supplied to the cells in the center of the cell aggregates. Thus, cells in the center would undergo necrosis. On the 24-well 6FDA/TPEQ plate (Example 1), in contrast, cell aggregates of adequate sizes were formed while they adhered to the substrate and were evenly distributed all over the wells (FIG. 19E). Because the cell aggregates had adhered to the substrate, cell aggregates were prevented from being further aggregated with each other, and the cell aggregates could maintain adequate sizes. Because the cell aggregates had adhered to the substrate, in addition, the cells were prevented from being removed together with the medium at the time of medium exchange.

5: Albumin Quantification

Figure 20:
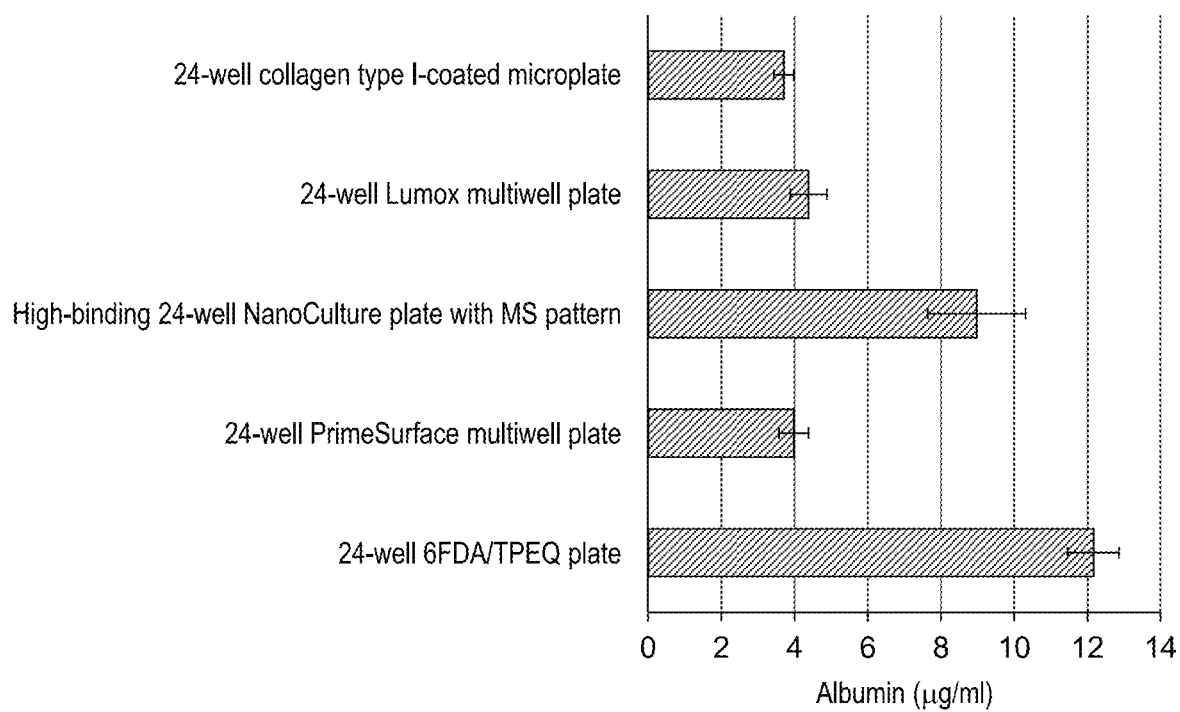
FIG. 20 shows a chart demonstrating the results of albumin quantification of the culture solution 5 days after the initiation of culture of primary rat hepatocytes with the use of a serum medium on the 6FDA/TPEQ membrane.

The culture solutions of the test groups were subjected to albumin quantification 5 days after the initiation of culture. Albumin quantification was carried out with the use of the rat albumin ELISA quantitation set (Bethyl Laboratories) in accordance with the protocols included therein. FIG. 20 shows the results of albumin quantification of the test groups.

The highest level of albumin production was observed on the 24-well 6FDA/TPEQ plate (Example 1). This indicates that components of the medium and oxygen are efficiently supplied to the cell aggregates of adequate sizes formed on the 24-well 6FDA/TPEQ plate (Example 1), and high hepatic functions are expressed as a consequence.

6: Culture of HepG2 Cells

HepG2 cells were purchased from DS Pharma Biomedical Co., Ltd. HepG2 cells were suspended in EMEM medium (DS Pharma Biomedical Co., Ltd.) supplemented with fetal bovine serum (FBS) at the final concentration of 10% (DS Pharma Biomedical Co., Ltd.), non-essential amino acids for 100×MEM (DS Pharma Biomedical Co., Ltd.), and a glutamine solution at the final concentration of 2 mM (DS Pharma Biomedical Co., Ltd.), the cell suspension was seeded on a 100-mm cell culture dish (BD Falcon), and culture was conducted at 37° C. in the presence of 5% $CO_2$. After culture was continued to reach 70% confluence, the culture product was treated with a 0.25% trypsin/50 mM EDTA solution, the medium described above was added to terminate the trypsin reaction, and a suspension of HepG2 cells was obtained. The HepG2 cell count in the cell suspension was determined using a 0.4 w/v % trypan blue solution (Wako Pure Chemical Industries, Ltd.), the cell suspension was seeded on the 24-well multi-well cell culture plate (BD Falcon), the 6FDA/TPEQ membrane (Example 1), and the 24-well PrimeSurface multi-well plate (Sumitomo Bakelite Co., Ltd.) to the cell density of $3.13 \times 10^4$ cells/cm$^2$, and culture was conducted at 37° C. in the presence of 5% $CO_2$. The medium was exchanged with a fresh medium by removing the total amount of the medium 4 days after the initiation of culture and then adding 1 ml of the medium described above. The 6FDA/TPEQ membrane was first subjected to high pressure steam sterilization and then used for cell culture.

Figure 21:
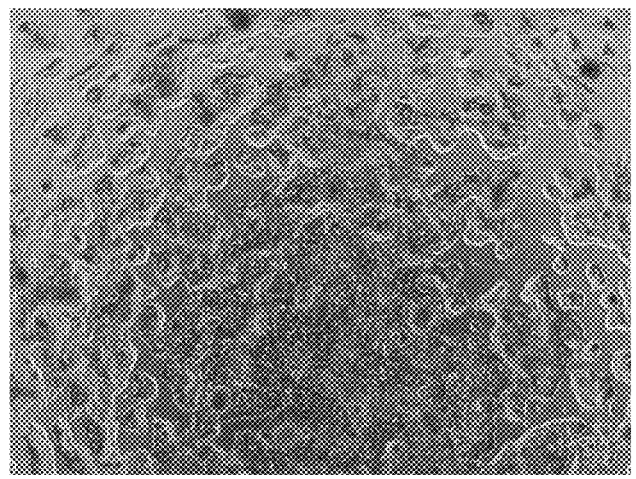
FIG. 21 shows photographs demonstrating the results of culture of HepG2 cells: wherein (A) shows the results of culture conducted with the use of a 24-well multi-well cell culture plate (BD Falcon); (B) shows the results of culture conducted with the use of the 24-well PrimeSurface multi-well plate (Sumitomo Bakelite Co., Ltd.); and (C) shows the results of culture conducted with the use of the 6FDA/TPEQ membrane of the present invention.
Figure 21:
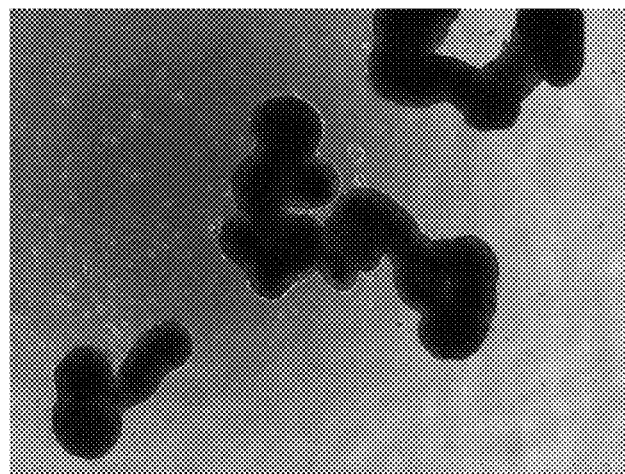
Figure 21:
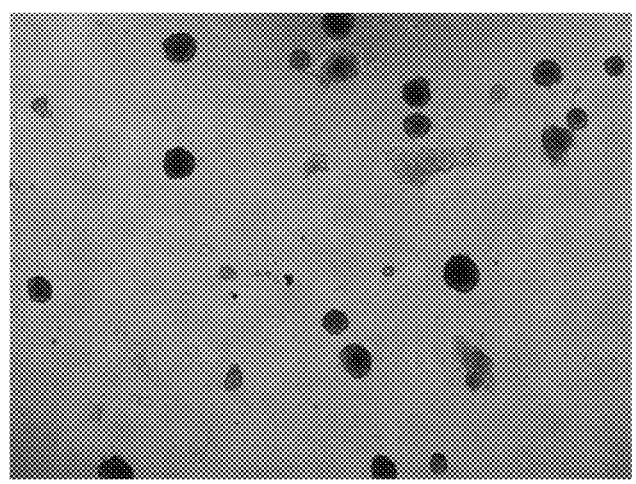

FIG. 21 shows a phase-contrast microscope photograph 7 days after the initiation of culture.

On the 24-well multi-well cell culture plate (BD Falcon) that is generally used for adherent cell culture, cells grew as monolayers, and the formation of cell aggregates was not observed (FIG. 21A). On the 24-well PrimeSurface multi-well plate (Sumitomo Bakelite Co., Ltd.), cell aggregates were formed, cell aggregates did not adhere to the substrate but floated in the medium, and the floating cell aggregates further formed larger masses (FIG. 21B). When cell aggregates are excessively large, components of the medium and oxygen are not sufficiently supplied to the cells in the center of the cell aggregates. Thus, cells in the center would undergo necrosis. On the 6FDA/TPEQ membrane (Example 1), in contrast, cell aggregates of adequate sizes were formed while they adhered to the substrate and were evenly distributed all over the wells (FIG. 21C). Because the cell aggregates had adhered to the substrate, cell aggregates were prevented from being further aggregated with each other, and the cell aggregates could maintain adequate sizes. Because the cell aggregates had adhered to the substrate, in addition, the cells were prevented from being removed together with the medium at the time of medium exchange.

6.4: Preparation of Fluorine-Containing Polymer

[Preparation Example 1] Fluorine-Containing Polyaryl Ether Ketone Resin (FPEK)

To a 225-ml three-necked flask, 16.74 g of 4,4'-bis(2,3,4,5,6-pentafluorobenzoyl)diphenyl ether (it is abbreviated as "p,p-BPDE"), 10.14 g of 2,2-bis(4-hydroxyphenyl) hexafluoropropane (6FBA), 4.14 g of potassium carbonate ($K_2CO_3$), and 90 g of N-methylpyrrolidinone were introduced. The mixture was heated to 60° C. for 5 hours. After the completion of the reaction, the reaction product was cooled, and the solution was added to an aqueous solution of 1% acetic acid while vigorously agitating the solution with a blender. The precipitated polymer was separated via filtration, washed with distilled water and methanol, and then dried under reduced pressure.

The powdery fluorine-containing polyaryl ether ketone obtained was dissolved in a 2-butanone solution to a concentration of 15% therein, and a solution of fluorine-containing polyaryl ether ketone (FPEK) having the structure shown below was obtained.

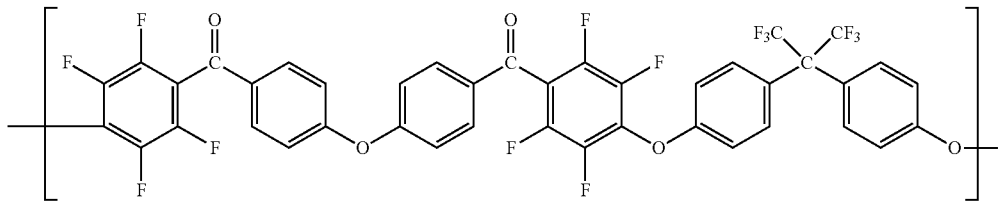

[Example 1] FPEK Membrane

The FPEK solution obtained in Preparation Example 1 was applied onto a glass substrate using a die coater, so as to adjust the thickness of the calcined polymer film to 60 µm, and the resulting film was calcined via heating at 150° C. for 1 hour. Thereafter, the calcined film was separated from the glass, and a fluorine-containing polyaryl ether ketone membrane (FPEK membrane) was thus obtained.

The FPEK membrane exhibited the membrane thickness of 60 µm, the water contact angle of 89°, the tensile modulus of elasticity of 1.2 GPa, and the oxygen gas permeability coefficient of $3.21 \times 10^{-10}$ cm$^3$ (STP)·cm/(cm$^2$·s·cmHg).

6.5: Spheroid Formation Via Cell Culture Using Fluorine-Containing Polymer Membrane 1: Preparation of Primary Rat Hepatocytes Specific viral pathogen-free Wistar rats (male, 9-week-old, body weight: 200 g) were purchased from Japan SLC, Inc. Primary rat hepatocytes were obtained with reference to the method described in Experiment Handbook for Cultured Cells, Yodosha Co., Ltd., Chapter 10, Hepatic cells. Specifically, the abdominal cavity of Wistar rats was opened under isoflurane anesthesia, and a catheter was inserted into the portal vein to inject the preperfusate having the composition shown in Table 10. At the same time, the postcaval vein in the lower part of the liver was incised to release the blood. Subsequently, the thoracic cavity was opened, and the postcaval vein entering into the right atrium was incised, and the postcaval vein in the lower part of the liver was ligated using forceps to perform perfusion. After sufficient removal of the blood from the liver was confirmed, perfusion was terminated, and the perfusate was replaced with a collagenase solution having the composition shown in Table 10 to perform perfusion. After the intercellular tissue was confirmed to have been digested with collagenase, perfusion was terminated. The liver was resected and transferred to a glass petri dish, a cooled Hanks' solution was added thereto, and cells were dispersed via pipetting. Subsequently, undigested tissue was removed with the use of a 150-mm strainer. A cell suspension was repeatedly subjected to centrifugation at 50 G for 1 minute to remove nonparenchymal cells. The viability of the obtained hepatic cells was determined via trypan blue exclusion, and the hepatic cells exhibiting 70% or higher viability were used for the culture test as primary rat hepatocytes.

2: Culture of Primary Rat Hepatocytes

The primary rat hepatocytes obtained by the method described above were suspended in a medium of the following composition, 0.4 ml of a suspension comprising primary rat hepatocytes at $1.25 \times 10^5$ cells/mL was applied to the 24-well collagen type I-coated microplate with a cover (Asahi Glass Co. Ltd.) and the FPEK membrane to the cell density of $2.66 \times 10^4$ cells/cm$^2$, and culture was conducted at 37° C. in the presence of 5% CO$_2$. The FPEK membrane prepared in Example 1 was first subjected to high pressure steam sterilization and then used for cell culture. The medium was exchanged with a fresh medium 3 hours after seeding and 1 day, 3 days, and 5 days after the initiation of culture.

Medium Composition

William's E medium (Wako Pure Chemical Industries, Ltd.)+10% FBS (Wako Pure Chemical Industries, Ltd.)+8.6 nM insulin+255 nM dexamethazone+50 ng/mL EGF+5 KIU/mL aprotinin+antibiotics (penicillin (100 units/mL)/streptomycin (100 µg/mL)/amphotericin B (0.25 g/mL))

Figure 22:
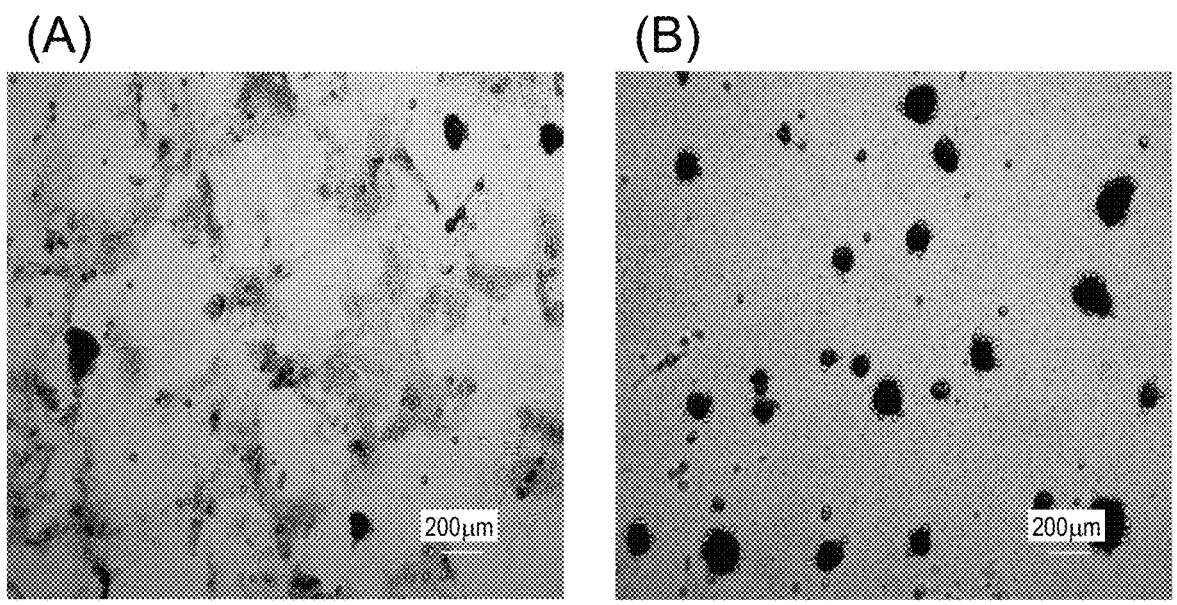
FIG. 22 shows photographs demonstrating the results of culture of primary rat hepatocytes: wherein (A) shows the results of culture conducted with the use of a 24-well collagen type I-coated microplate with a cover (Asahi Glass Co. Ltd.); and (B) shows the results of culture conducted on the FPEK membrane of the present invention.

FIGS. 22(A) and 22(B) show phase-contrast microscope photographs of the 24-well collagen type I-coated microplate with a cover (Asahi Glass Co. Ltd.) and the FPEK membrane 5 days after the initiation of culture.

On the 24-well collagen type I-coated microplate (Asahi Glass Co. Ltd.) that is generally used for adherent cell culture, cells adhered to the substrate as monolayers, and formation of cell aggregates was not substantially observed. On the FPEK membrane, in contrast, cells adhered thereto as monolayers were not observed, and cell aggregates having a three-dimensional structure were formed. These cell aggregates were uniform in size, they were of adequate sizes, and spheroids were evenly distributed all over the substrate.

The cultured cells were treated with a 0.25% trypsin/50 mM EDTA solution every 24 hours, and the total cell count was determined with the use of a 0.4 w/v % trypan blue solution (Wako Pure Chemical Industries, Ltd.) and a blood cell counting chamber. Also, the culture solution was sampled every 24 hours and stored at −20° C.

3: Albumin Quantification

Figure 23:
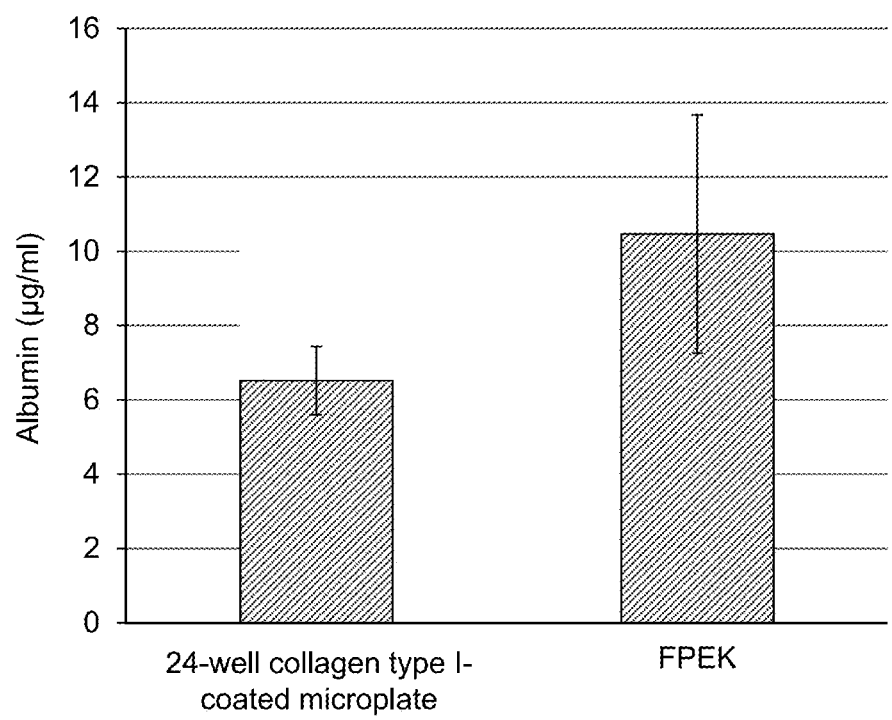
FIG. 23 shows the results of albumin quantification of the culture solution 5 days after the initiation of culture of primary rat hepatocytes on the FPEK membrane.

The culture solutions of the test groups were subjected to albumin quantification 5 days after the initiation of culture. Albumin quantification was carried out with the use of the rat albumin ELISA quantitation set (Bethyl Laboratories) in accordance with the protocols included therein. FIG. 23 shows the results of albumin quantification of the test groups.

As shown in FIG. 23, a larger amount of albumin was produced on the FPEK membrane than on the 24-well collagen type I-coated microplate with a cover (Asahi Glass Co. Ltd.). Components of the medium and oxygen were efficiently supplied to the cell aggregates of adequate sizes formed on the FPEK membrane, and high hepatic functions were expressed as a consequence.

The invention claimed is:

1. A cell culture substrate having a smooth surface at least a part of which is composed of a resin composition comprising a fluorine-containing polymer having one or more fluorine atoms in a repeating unit, wherein the oxygen gas permeability of the cell culture substrate is 219 cm³ (STP)/(m²·24 h·atm) or higher, and wherein the smooth surface has a center line average roughness of 0.5 μm or less,
  wherein the fluorine-containing polymer comprises:
    (I) at least one type of fluorine-containing polyimide selected from the group consisting of:
      (a) an aromatic polyimide comprising a repeating unit represented by formula (V):

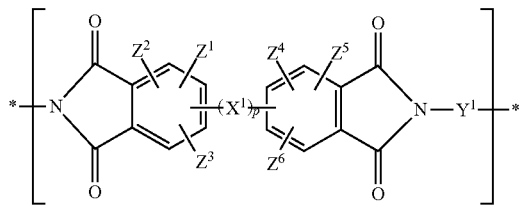

wherein
  p is 0 or 1;
  X¹ is —C(CF₃)₂—,

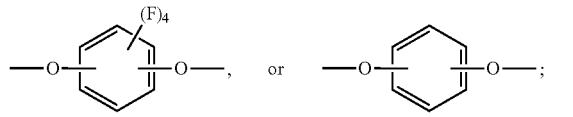

all of Z¹, Z², Z³, Z⁴, Z⁵, and Z⁶ are hydrogen atoms or fluorine atoms;
Y¹ comprises at least one of:

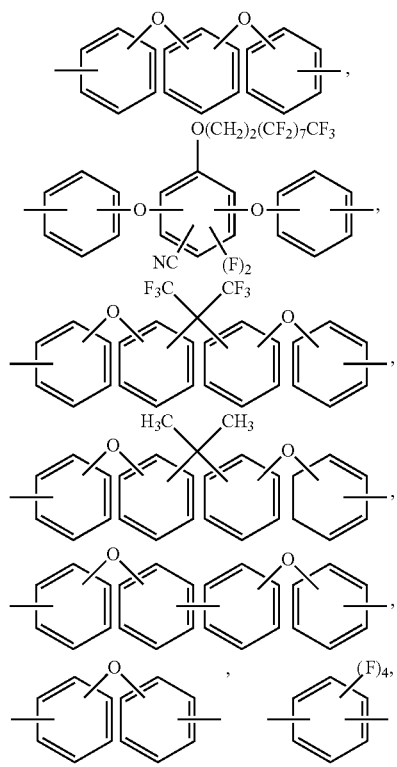

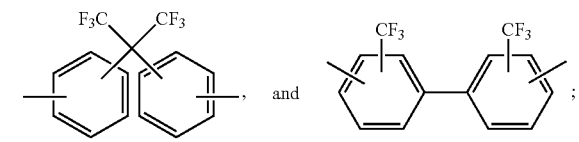

and
at least one of X¹, Y¹, Z¹, Z², Z³, Z⁴, Z⁵, and Z⁶ comprises a fluorine atom;
provided
  if X¹ is —C(CF₃)₂—, then Y¹ is

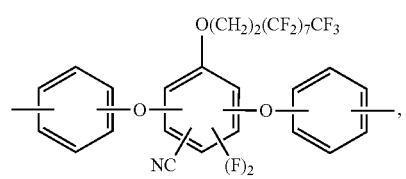

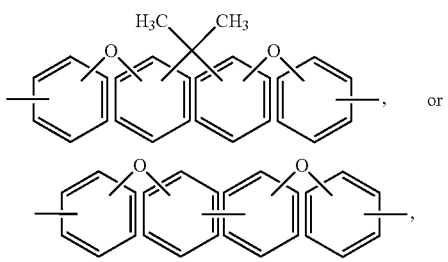

if p is 0, then Y¹ is

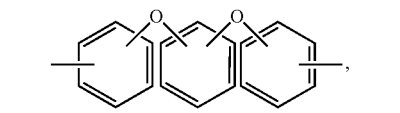

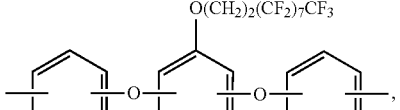

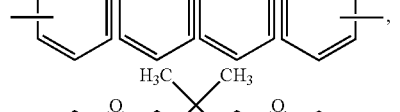

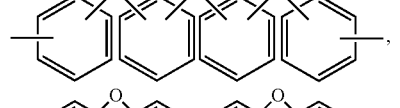

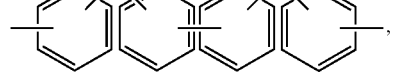

-continued

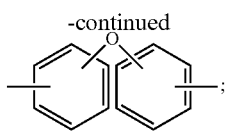

(b) an aromatic polyimide comprising a repeating unit represented by formula (V):

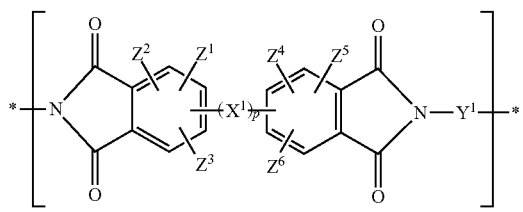

(V)

wherein
p is 0 or 1;
$X^1$ is —S—,

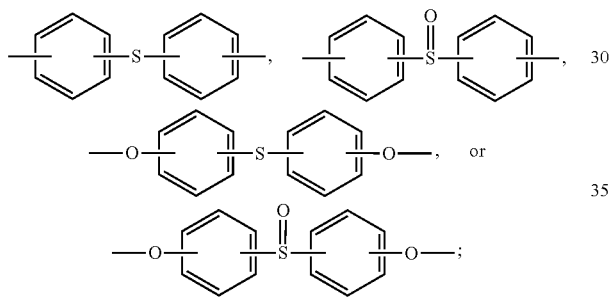

all of $Z^1$, $Z^2$, $Z^3$, $Z^4$, $Z^5$, and $Z^6$ are hydrogen atoms or fluorine atoms;
$Y^1$ comprises at least one of:

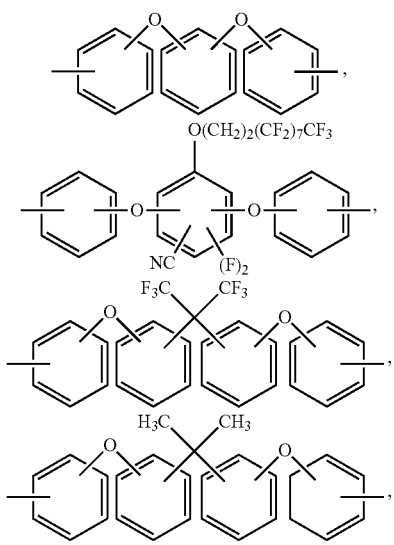

-continued

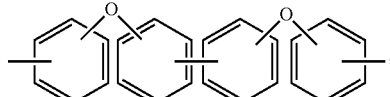

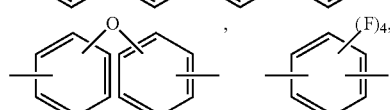

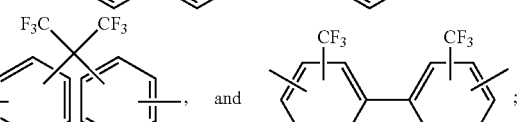

and
at least one of $X^1$, $Y^1$, $Z^1$, $Z^2$, $Z^3$, $Z^4$, $Z^5$, and $Z^6$ comprises a fluorine atom;
and
(c) a fluorine-containing polyimide comprising in its main chain a repeating unit represented by Formula (3):

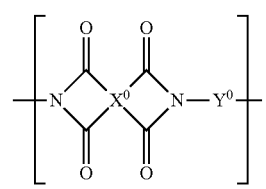

(3)

wherein
$X^0$ represents a tetravalent organic group;
$Y^0$ represents a divalent organic group;
$X^0$ and $Y^0$ contain one or more fluorine atoms in total; and
$Y^0$ is a group represented by Formula (D):

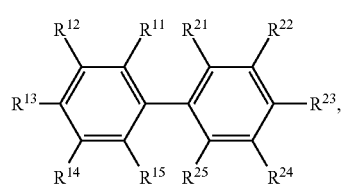

(D)

wherein one of $R^{11}$, $R^{12}$, $R^{13}$, $R^{14}$, and $R^{15}$ represents a single bond to a nitrogen atom, and 4 other members each independently represent a group selected from the group consisting of a hydrogen atom, an alkyl group having 1 to 6 carbon atoms, an alkoxy group having 1 to 6 carbon atoms, —SO$_3$H, and —OH; and
wherein one of $R^{21}$, $R^{22}$, $R^{23}$, $R^{24}$, and $R^{25}$ represents a single bond to a nitrogen atom, and 4 other members each independently represent a group selected from the group consisting of a hydrogen atom, an alkyl group having 1 to 6 carbon atoms, an alkoxy group having 1 to 6 carbon atoms, —SO$_3$H, and —OH; or $R^{11}$ and $R^{21}$ and/or $R^{15}$ and $R^{25}$ may together form —S(=O)$_2$—; or
(II) a polymer having a fluorine-containing aromatic ring and having an ether bond in its main chain represented by Formula (II-2):

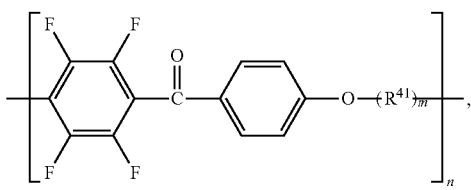

(II-2)

wherein n represents the degree of polymerization, m is 0 or 1, and $R^{41}$ is a group represented by Formula (II-3):

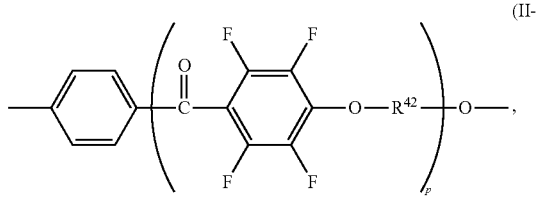

(II-3)

wherein p is the integer 0 or 1, and $R^{42}$ represents a structure represented by any of the formulae shown below:

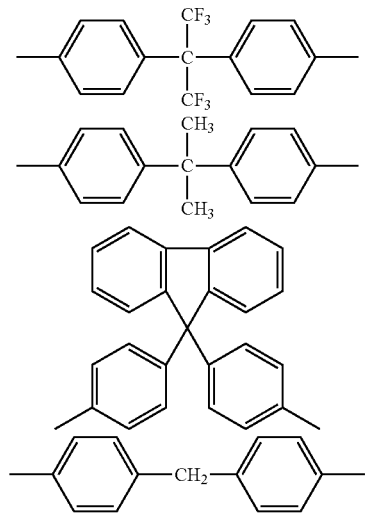

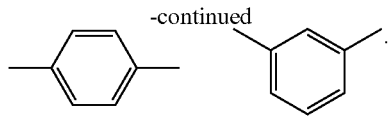

2. The cell culture substrate according to claim 1, wherein the fluorine content in the resin composition is 1% to 60% by mass, and the degree of imidization is 20% or higher.

3. The cell culture substrate according to claim 1, wherein the oxygen gas permeability coefficient of the resin composition is $0.10 \times 10^{-10}$ cm$^3$ (STP)·cm/(cm$^2$·s·cmHg) or higher.

4. A cell culture vessel at least a part of which is composed of the cell culture substrate according to claim 1.

5. A cell culture vessel comprising, in at least in part, a substrate that is provided in a manner such that one surface of the substrate constitutes the bottom of a container portion for containing a cell and medium and the other surface is exposed to the outside of the vessel, wherein the substrate is the cell culture substrate according to claim 1 and at least a part of the one surface is composed of the resin composition.

6. The cell culture substrate according to claim 1, wherein the substrate is a film composed of the resin composition.

7. The cell culture substrate according to claim 1, wherein the fluorine-containing polymer is the at least one type of the fluorine-containing polyimide.

8. The cell culture substrate according to claim 7, wherein the fluorine-containing polyimide is obtained via thermal imidization.

9. The cell culture substrate according to claim 7, wherein the fluorine-containing polyimide comprises 0 to 0.030% by mass of a tertiary amine compound relative to total amount of the polyimide and remaining polyamide acid.

10. The cell culture substrate according to claim 1, wherein the smooth surface composed of the resin composition exhibits a water contact angle of 700 or more.

11. The cell culture substrate according to claim 1, wherein the resin composition exhibits a tensile modulus of elasticity of 2 GPa or lower.

12. The cell culture substrate according to claim 1, wherein the substrate comprises a cylindrical or conical cavity.

13. The cell culture substrate according to claim 12, wherein the cylindrical or conical cavity has a diameter of 50 to 500 μm and a depth of 50 to 500 μm.

\* \* \* \* \*